US007414110B2

(12) United States Patent
Harpold et al.

(10) Patent No.: US 7,414,110 B2
(45) Date of Patent: Aug. 19, 2008

(54) HUMAN CALCIUM CHANNEL COMPOSITIONS AND METHODS

(75) Inventors: Michael M. Harpold, El Cajon, CA (US); Steven B. Ellis, San Diego, CA (US); Mark E. Williams, Carlsbad, CA (US); Ann F. McCue, La Mesa, CA (US); Alison Gillespie, San Diego, CA (US); Daniel H. Feldman, Gainesville, FL (US); Robert Brenner, Austin, TX (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/702,388

(22) Filed: Feb. 5, 2007

(65) Prior Publication Data

US 2007/0244297 A1 Oct. 18, 2007

Related U.S. Application Data

(60) Continuation of application No. 10/375,253, filed on Feb. 27, 2003, now abandoned, which is a division of application No. 08/450,273, filed on May 25, 1995, now Pat. No. 6,653,097, which is a continuation-in-part of application No. 08/404,354, filed on Feb. 15, 1995, now Pat. No. 5,618,720, which is a continuation of application No. 07/914,231, filed on Jul. 13, 1992, now Pat. No. 5,407,820, and a continuation of application No. 08/314,083, filed on Sep. 28, 1994, now Pat. No. 5,686,241, which is a division of application No. 07/914,231, filed on Jul. 13, 1992, now Pat. No. 5,407,820, which is a continuation-in-part of application No. 07/603,751, filed on Nov. 8, 1990, now abandoned, application No. 11/702,388, and a continuation-in-part of application No. 08/290,012, filed on Aug. 11, 1994, now abandoned, which is a continuation-in-part of application No. 08/149,097, filed on Nov. 5, 1993, now Pat. No. 5,874,236, and a continuation-in-part of application No. 08/105,536, filed on Aug. 11, 1993, now abandoned, said application No. 08/149,097 and a continuation-in-part of application No. 08/105,536, filed on Aug. 11, 1993, now abandoned, is a continuation-in-part of application No. 07/603,751, filed on Nov. 8, 1990, now abandoned, application No. 11/702,388, and a continuation-in-part of application No. 08/223,305, filed on Apr. 4, 1994, now Pat. No. 5,851,824, which is a continuation of application No. 07/868,354, filed on Apr. 10, 1992, now abandoned, which is a continuation-in-part of application No. 07/745,206, filed on Aug. 15, 1991, now Pat. No. 5,429,921, which is a continuation-in-part of application No. 07/603,751, filed on Nov. 8, 1990, now abandoned, and a continuation-in-part of application No. 07/620,250, filed on Nov. 30, 1990, now abandoned, application No. 11/702,388, and a continuation-in-part of application No. 08/149,097, filed on Nov. 5, 1993, now Pat. No. 5,874,236, and a continuation-in-part of application No. 08/105,536, filed on Aug. 11, 1993, now abandoned, and a continuation-in-part of application No. 07/914,231, filed on Jul. 13, 1992, now Pat. No. 5,407,820, and a continuation-in-part of application No. 07/868,354, filed on Apr. 10, 1992, now abandoned, and a continuation-in-part of application No. 07/745,206, filed on Aug. 15, 1991, now Pat. No. 5,429,921, and a continuation-in-part of application No. 08/311,363, filed on Sep. 23, 1994, now Pat. No. 5,876,958, which is a continuation of application No. 07/745,206, filed on Aug. 15, 1991, now Pat. No. 5,429,921, and application No. 11/702,388, and a continuation-in-part of application No. 08/193,078, filed as application No. PCT/US92/06903 on Aug. 14, 1992, now Pat. No. 5,846,757, and a continuation-in-part of application No. 07/868,354, filed on Apr. 10, 1992, now abandoned, and a continuation-in-part of application No. 07/745,206, filed on Aug. 15, 1991, now Pat. No. 5,429,921, and a continuation-in-part of application No. 07/603,751, filed on Nov. 8, 1990, now abandoned, and a continuation-in-part of application No. 07/176,899, filed on Apr. 4, 1988, now abandoned, and a continuation-in-part of application No. 07/620,250, filed on Nov. 30, 1990, now abandoned, and a continuation-in-part of application No. 07/482,384, filed on Feb. 20, 1990, now Pat. No. 5,386,025, application No. 11/702,388, and a continuation-in-part of application No. 08/336,257, filed on Nov. 7, 1994, now Pat. No. 5,726,035, which is a continuation of application No. 07/482,384, filed on Feb. 20, 1990, now Pat. No. 5,386,025.

(51) Int. Cl.

| | |
|---|---|
| ***C07K 14/435*** | (2006.01) |
| ***C07K 14/705*** | (2006.01) |
| *C12P 21/02* | (2006.01) |
| *A61K 38/17* | (2006.01) |

(52) U.S. Cl. ............................ 530/350; 514/2; 514/12; 536/23.5; 435/69.1

(58) Field of Classification Search ....................... None
See application file for complete search history.

(56) References Cited

U.S. PATENT DOCUMENTS

| | | | | |
|---|---|---|---|---|
| 4,788,135 | A | 11/1988 | Davis et al. | 435/6 |
| 4,912,202 | A | 3/1990 | Campbell et al. | 530/387 |
| 4,954,436 | A | 9/1990 | Froehner et al. | 435/7 |
| 5,024,939 | A | 6/1991 | Gorman et al. | 435/69.1 |
| 5,051,403 | A | 9/1991 | Miljanich et al. | 514/12 |
| 5,189,020 | A | 2/1993 | Miljanich et al. | 514/12 |
| 5,264,371 | A | 11/1993 | Miljanich et al. | 436/503 |
| 5,386,025 | A | 1/1995 | Jay et al. | 536/23.5 |
| 5,401,629 | A | 3/1995 | Harpold et al. | 435/6 |
| 5,407,820 | A | 4/1995 | Ellis et al. | 435/240.2 |
| 5,424,218 | A | 6/1995 | Miljanich et al. | 436/503 |

FOREIGN PATENT DOCUMENTS

| | | |
|---|---|---|
| CA | 2085502 | 2/1993 |
| EP | 0507170 | 3/1992 |
| EP | 0556651 | 4/1993 |
| WO | 8907608 | 8/1989 |
| WO | 8909834 | 10/1989 |
| WO | 9113077 | 9/1991 |
| WO | 9202639 | 2/1992 |

| | | |
|---|---|---|
| WO | 9308469 | 4/1993 |
| WO | 9402511 | 2/1994 |
| WO | 9504144 | 2/1995 |

OTHER PUBLICATIONS

Lu et al. (2004). Arrhythmia in isolated prenatal hearts after ablation of the Cav2.3 (α1E) subunit of voltage-gated Ca2+ channels. Cellular Physiology and Biochemistry. 14:11-22.*

Weiergräber et al. (2005). Ablation of Cav2.3/E-type voltage-gated calcium channel results in cardiac arrhythmia and altered autonomic control within the murine cardiovascular system. Basic Research in Cardiology. 100:1-13.*

Jing et al. (2005). Cav2.3 calcium channels control second-phase insulin release. The Journal of Clinical Investigation. 115(1):146-154.*

Miljanich and Ramachandran, "Antagonists of neuronal calcium channels: structure, function, and therapeutic implication," *Ann. Rev. Pharm. and Toxicol*. 35:707-734 (1995).

Adams, et al., "Intramembrane charge movement restored in dysgenic skeletal muscle by injection of dihydropyridine receptor cDNAs," *Nature*, 346:569-572 (1990).

Ahlijanian, et al., "Subunit structure and localization of dihydropyridine-sensitive calcium channels in mammalian brain, spinal cord, and retina," *Neuron*, 4:819-832 (1990).

Ahlijanian, et al., "Phosphorylation of an α1-like subunit of an *w*-conotoxin-sensitive brain calcium channel by cAMP-dependent protein kinase and protein kinase C," *J.Biol.Chem.*, 266:20192 (1991).

Artalejo, et al., "*w*-Conotoxin GVIA blocks a $Ca^{2+}$ current in bovine chromaffin cells that is not of the 'classic' N type," *Neuron*, 8:85-95 (1992).

Barhanin, et al., "The calcium channel antagonists receptor from rabbit skeletal muscle: reconstitution after purification and subunit characterization," *Eur.J.Biochem.*, 164:525-531 (1987).

Bean, et al., "Classes of calcium channels in vertebrate cells," *Annu. Rev. Physiol.*, 51:367-384 (1989).

Biel, et al., "Primary structure and functional expression of a high voltage activiated calcium channel from rabbit lung," *FEBS Letters*, 269(2):409-412 (1990).

Blount, et al., "Assembly intermediates of the mouse muscle nicotinic Acetylcholine receptor in stably transfected fibroblasts," *J.Cell. Biol.*, 111:2601 (1990).

Borsotto, et al., "The 1,4-dihydropyridine receptor associated with the skeletal muscle voltage-dependent $Ca^{2+}$ channel," *J.Biol.Chem.*, 260(26):14255-14263 (1985).

Bosse, et al., "The cDNA and deduced amino acid sequence of the γ subunit of the L-type calcium channel from rabbit skeletal muscle," *FEBS*, 267(1):153-156 (1990).

Breitbart, et al., "Alternative Splicing: A Ubiquitous Mechanism for the Generation of Multiple Protein Isoforms From Single Genes," *Ann. Rev. Biochem*. 56:467-495 (1987).

Brust, et al., "Human Neuronal Voltage-Dependent Calcium Channels: Studies on Subunit Structure and Role in Channel Assembly," *Neuropharmacology* 32(11):1089-1102 (1993).

Burns, et al., "Calcium channel activity of purified human synexin and structure of the human synexin gene," *Proc.Natl.Acad.Sci.*, 86:3798-3802 (1989).

Campbell, et al., "The biochemistry and molecular biology of the dihydropyridine-sensitive calcium channel," *TINS*, 11(10):425-430 (1988).

Campbell, et al., "32,000-Dalton subunit of the 1,4-dihydropyridine receptor," *Ann.N.Y.Acad.Sci.*, 560:251-257 (1989).

Carbone, et al., "Ca currents in human neuroblastoma IMR32 cells: kinetics, permeability and pharmacology," *Pfluegers Arch*. 416:170-179 (1990) (best available copy submitted).

Catterall, et al., "Molecular properties of dihydropyridine-sensitive calcium channels in skeletal muscle," *J.Biol.Chem.*, 263(8):3535-3538 (1988).

Claudio, T., "Stable expression of transfected *Torpedo* acetylcholine receptor α subunits in mouse fibroblast L cells," *Proc.Natl.Acad.Sci.*, 84:5967-5971 (1987).

Claudio, et al., "Genetic reconstitution of functional acetylcholine receptor channels in mouse fibroblasts," *Science*, 238:1688-1694 (1987).

Cohen, et al., "Distribution of $Ca^{2+}$ channels on frog motor nerve terminals revealed by fluorescent *w*-conotoxin," *J. of Neuroscience*, 11(4):1032-1039 (1991).

Collin, et al., "Cloning, chromosomal Location and Functional Expression of the Human Voltage-dependent Calcium Channel β3 Subunit," *Eur. J. Biochem*. 220:257-262 (1994).

Cooper, et al., "Purification and characterization of the dihydropyridine-sensitive voltage-dependent calcium channel from cardiac tissue," *J.Biol.Chem.*, 262(2):509-512 (1987).

Cruz et al., "Characterization of ω-Conotoxin Target. Evidence for Tissue-Specific Heterogeneity ion Calcium Channel Types," *Biochem. J.* 26:820 (1987).

Curran and Morgan, "Barium modules *c-fos* expression and post-translational modification," *Proc.Natl.Acad.Sci.*, 83:3521-8524 (1986).

Curtis, et al., "Reconstitution of the voltage-sensitive calcium channel purified from skeletal muscle transverse tubules," *Biochemistry*, 25:3077-3083 (1986).

Curtis, et al., "Purification to the calcium antagonist receptor of the voltage-sensitive calcium channel from skeletal muscle transverse tubules," *Biochemistry*, 23(10):2113-2118 (1984).

Dascal, et al., "Expression of modulation of voltage-gated calcium channels after RNA injection in *Xenopus oocytes*," *Science*, 231:1147-1150 (1986).

Dascal, N., "The use of *Xenopus oocytes* for the study of ion channels," *CRC Critical Rev.Biochem.*, 22(4):317-387 (1987).

DeJongh, et al., "Subunits of purified calcium channels," *J.Biol. Chem.*, 265(25):14738-14741 (1990).

Dubel, et al., "Molecular cloning of the α-1 subunit of an ω-conotoxin-sensitive calcium channel," *Proc.Natl.Acad.Sci.* 89:5058-5062 (1992).

Elinor, et al., "Functional expression of a rapidly inactivating neuronal calcium channel," *Nature* 363:455-458 (1993).

Ellis, et al., "Sequence and Expression of mRNAs Encoding the $\alpha_1$ and $\alpha_2$ Subunits of a DHP-Sensitive Calcium Channel," *Science*, 241:1661-1664. (1988).

Feramisco, et al., "Optical spatial requirements for the location of basic residues in peptide substrates for the cyclic AMP-dependent protein kinase," *J.Biol.Chem.*, 255(9):4240-4245 (1980).

Fisch, et al., "*c-fos* sequences necessary for basal expression and induction by epidermal growth factor, 12-*0*-tetradecanoyl phorbol-13-acetate, and the calcium inophore," *Mol.Cell.Biol.*, 7(10):3490-3502 (1987).

Froehner, "New insights into the molecular structure of the dihydropyridine-sensitive calcium channel," *TINS*, 11(3):90-92 (1988).

Gustin, et al., "Ion channels in yeast," *Science*, 233:1195-1197 (1986).

Hamill, et al., "Improved patch-clamp techniques for high-resolution current recording from cells and cell-free membrane patches," *Pfluger Archiv.European Journal of Physiology*, 391:85-100 (1981).

Hamilton, et al., "Subunit composition of the purified dihydropyridine binding protein from skeletal muscle," *Biochemistry*, 28:7820-7828 (1989).

Hess, et al., "Calcium channels in vertebrate cells," *Ann.Rev. Neurosci.*, 13:337-356 (1990).

Hess, et al., "Different modes of Ca channel gating behavior favored by dihydropyridine Ca agonist and antagonists," *Nature*, 311:538-544 (1984).

Hofmann, et al., "Regulation of the L-type calcium channel," *TINS*, 8:393-398 (1987).

Horne, et al., "Molecular diversity of $Ca^{2+}$ channel $\alpha_1$ subunits from the marine ray *Discopyge ommata,*" *Proc.Natl.Acad.Sci.* 90:3787-3791 (1993).

Hubbard, et al., "Synthesis and processing of asparagine-linked oligosaccharides[1,2]," *Ann.Rev.Biochem.*, 50:555-583 (1981).

Hui, et al., "Molecular cloning of multiple sybtypes of a novel rat brain isoform of the $a_1$ subunit of the voltage-dependent calcium channel," *Neuron*, 7:35-44 (1991).

Hullin, et al., "Calcium channel β subunit heterogeneity: functional expression of cloned cDNA from heart, aorta and brain," *EMBO J.*, 11:885 (1992).
Ichida, et al., "Photoaffinity labeling with dihydropyridine derivatives of crude membranes from rat skeletal, cardiac, ileal, and uterine muscles and whole brain," *J.Biochem.*, 105:767-774 (1989).
Imagawa, et al., "Phosphorylation of the 1,4-dihydropyridine receptor of the voltage-dependent $Ca^{2+}$ channel by an intrinsic protein kinase in isolated triads from rabbit skeletal muscle," *J.Biol.Chem.*, 262(17):8333-8339 (1987).
Jay, et al., "Primary Structure of the γ subunit of the DHP-sensitive calcium channel from skeletal muscle," *Science*, 248:490-492 (1990).
Jay, et al., "Structural characterization of the dihydropyridine-sensitive calcium channel $\alpha_2$-subunit and the associated δ peptides," *J.Biol.Chem.*, 266(5):3287-3293 (1991).
Jongh, et al., "Subunits of purified calcium channels: a 212-kDa form of $\alpha_1$ and partial amino acid sequence of a phosphorylation site of an independent β-subunit," *Proc.Natl.Acad.Sci. USA*, 86:8585-8589 (1989).
Kasai, H., "Tonic inhibition and rebound facilitation of a neuronal calcium channel by a GTP-binding protein," *Proc. Natl.Acad.Sci. USA*, 88:8855-8859 (1991).
Kim, et al., "Studies on the structural requirements for the activity of the skeletal muscle dihydropyridine receptor/slow $Ca^{2+}$ channel," *J.Biol.Chem.*, 11858-11863 (1990).
Kim, et al., "IgG from patients with Lambert-Eaton syndrome blocks voltage-dependent calcium channels," *Science*, 239:405-408 (1988).
Kim, et al., "Rat brain expresses an alternatively spliced form of the dihydropyridine-sensitive L-type calcium channel α2 subunit," *Proc. Natl.Acad.Sci.*, 89:3251 (1992).
Koch, et al., "cDNA cloning of a dihydropyridine-sensitive calcium channel from rat aorta," *J. Biol. Chem.*, 265(29):17786-17791 (1990).
Koch, et al., "Characterization of cDNA clones encoding two putative isoforms of the $\alpha_1$-subunit of the dihydropyridine-sensitive voltage-dependent calcium channel isolated from rat brain and rat aorta," *FEBS Letters*, 250(2):386-388 (1989).
Kozak, "An analysis of 5'-noncoding sequences from 699 vertebrate messenger RNAs," *Nucleic Acids Research*, 15(20):8125-8148 (1987).
Lang, et al., "The effect of myasthenic syndrome antibody on presynaptic calcium channels in the mouse," *J.Physiol.*, 390:257-270 (1987).
Leung, et al., "Biochemical and ultrastructural characterization of the 1,4-dihydropyridine receptor from rabbit skeletal muscle," *J.Biol. Chem.*, 263(2):994-1001 (1988).
Leung, et al., "Monoclonal antibody characterization of the 1,4-dihydropyridine receptor of rabbit skeletal muscle," *Ann.N.Y.Acad. Sci.*, 522:43-46 (1988).
Leung, et al., "Structural characterization of the 1,4-dihydropyridine receptor of the voltage-dependent $Ca^{2+}$ channel from rabbit skeletal muscle," *J.Biol.Chem.*, 262(17):7943-7946 (1987).
Leveque, et al., "The synaptic vesicle protein synaptotagmim associates with calcium channels and is a putative Lambert-Eaton myasthenic syndrome antigen," *Proc.Natl.Acad.Sci.* 89:3625-3629 (1992).
Lotan, et al., "Specific block of calcium channel expression by a fragment of dihydropyridine receptor cDNA, " *Science*, 243:666-669 (1989).
Meshi, et al., "Nucleotide sequence of the 30K protein cistron of cowpea strain of tobacco mosaic virus," *Nucleic Acids Research*, 10(19):6111-6117 (1982).
Mierendorf, et al., "Gene isolation by screening kgtll libraries with antibodies," *Methods in Enz.*, 152:458-469 (1986).
Mikami, et al., "Primary structure and functional expression of the cardiac dihydropridine-sensitive calcium channel," *Nature*, 340:230-233 (1989).
Miller, "Multiple calcium channels and neuronal function," *Science*, 235:46-52 (1987).
Miller, R., "Voltage-sensitive $Ca^{2+}$ channels," *J.Biol.Chem.*, 267(3):1403-1406 (1992).
Mishina, et al., "Location of functional regions of acetylcholine receptor α-subunit by site-directed mutagenesis," *Nature*, 313:364-369 (1985).
Mori, et al., "Primary structure and functional expression from complementary DNA of a brain calcium channel," *Nature*, 350:398-402 (1991).
Morton et al. "Monoclonal antibody identifies a 200-kDA subunit of the dihydropyridine-sensitive calcium channel," *J.Biol.Chem.*, 262(25):11904-11907 (1987).
Nakayama, et al., "Purification of a putative $Ca^{2+}$ channel protein from rabbit skeletal muscle," *J.Biol.Chem.*, 262:6572-6576 (1987).
Niidome, et al., "Molecular cloning and characterization of a novel calcium channel from rabbit brain," *FEBS LTTRS* 308:7-13 (1992).
Nikaido, et al., "Molecular cloning of cDNA encoding human interleukin-2 receptor," *Nature*, 311:631-636 (1984).
Noda, et al., "Existence of distinct sodium channel messenger RNAs in rat brain," *Nature*, 320:188-192 (1986).
Noda, et al., "Expression of functional sodium channels from cloned cDNA," *Nature*, 322:826-828 (1986).
Nunoki, et al., "Activation of purified calcium channels by stoichiometric protein phosphorylation," *Proc.Natl.Acad.Sci. USA*, 86:6816-6820 (1989).
Olivera, et al., "Conotoxins," *J.Biol.Chem.*, 266(33):22067-22070 (1991).
Pelzer, et al., "Properties and regulation of calcium channels in muscle cells," *Rev.Physiol.Biochem.Pharmacol.*, 114:107-207 (1990).
Perez-Reyes, et al., "Induction of calcium currents by the expression of the $\alpha_1$-subunit of the dihydropyridine receptor from skeletal muscle," *Nature*, 340:233-236 (1989).
Perez-Reyes, et al., "Cloning and expression of a cardiac/brain β subunit of the L-type calcium channel," *J.Biol.Chem.*, 267(3):1792-1797 (1992).
Perez-Reyes, et al., "Molecular diversity of L-type calcium channels," *J.Biol.Chem.*, 265(33):20430-20436 (1990).
Powers et al., "Skeletal Muscle and Brain Isoforms of a β-Subunit of Human Voltage-dependent Calcium Channels Are Encoded by a Single Gene," *J.Biol.Chem.* 267:22967-22972 (1992).
Powers, et al., "Assignment of the human gene for the $\alpha_1$ subunit of the cardiac DHP-sensitive $Ca^{2+}$ channel (CCHL1A1) to Chromosome 12p12-pter," *Genomics*, 10:835-839 (1991).
Pragnell, et al., "Cloning and tissue-specific expression of the brain calcium channel β-subunit," *FEBS Letters*, 291:253 (1991).
Rampe, et al., "[$^3$H]Pn200-110 binding in a fibroblast cell line transformed with the $\alpha_1$ subunit of the skeletal muscle L-type $Ca^{2+}$ channel," *Biochem. and Biophys.Research Communications*, 169(3):825-831 (1990).
Regulla, et al., "Identification of the site of interaction of the dihydropyridine channel blockers nitrendipine and azidopine with the calcium-channel $\alpha_1$ subunit," *EMBO Journal*, 10(1):45-49 (1991).
Roberts, et al., "Paraneoplastic myasthenic syndrome IgG inhibits $^{45}Ca^{2+}$ flux in a human small cell carcinoma line," *Nature*, 317:737-739 (1985).
Rosenfield, et al., "Cloning and Characterization of a Lambert-Eaton Myasthenic Syndrome Antigen," *Annals of Neurology* 33:113-120 (1993).
Ruth, et al., "Primary structure of the α-subunit of the DHP-sensitive calcium channel from skeletal muscle," *Science*, 245:1115-1118 (1989).
Sakamoto, et al., "A monoclonal antibody to the β subunit of the skeletal muscle dihydropyridine receptor immunoprecipitates the brain w-conotoxin GVIA receptor," *J.Biol.Chem.*, 266:18914 (1991).
Schmid, et al., "Immunochemical analysis of subunit structure of 1,4-dihydropyridine receptors associated with voltage-dependent $Ca^{2+}$ channels in skeletal, cardiac, and smooth muscles," *Biochemistry*, 25:3492-3495 (1986).
Seagar, et al., "Molecular properties of dehydropyrine-sensitive calcium channels," *Ann.N.Y.Acad.Sci.*, 552:162-175 (1988).
Seino, et al., "Cloning of $\alpha_1$ subunit of a voltage-dependent calcium channel expressed in pancreatic β cells," *Proc.Natl.Acad.Sci. USA*, 89:584-588 (1992).

Sharp, et al., "Identification and characterization of the dihydropyridine-binding subunit of the skeletal muscle dihydropridine receptor," *J.Biol.Chem.*, 62(25):12309-12315 (1987).
Sharp and Campbell, "Characterization of the 1,4-dihydropyridine receptor using subunit-specific polyclonal antibodies," *J.Biol.Chem.*, 264(5):2816-2825 (1989).
Sher, et al., "w-Conotoxin binding and effects on calcium channel function in human neuroblastoma and rat pheochromocytoma cell lines," *FEBS Letters*, 235:(1,2): 178-182 (1988).
Sher, et al., "Voltage-operated calcium channels in small lung carcinoma cell lines: pharmacological, functional, and immunological properties," *Cancer Research*, 5:3892-3896 (1990).
Sieber, et al., "The 165-kDa peptide of the purified skeletal muscle dihydropyridine receptor contains the known regulatory sites of the calcium channel," *Eur.J.Biochem.*, 167:117-122 (1987).
Slish, et al., "Evidence for the existence of a cardiac specific isoform of the $\alpha_1$-subunit of the voltage dependent calcium channel," *FEBS Letters*, 250(2):509-514 (1989).
Smith, et al., "Calcium channel activity in a purified dihydropyridine-receptor preparation of skeletal muscle," *Biochemistry*, 26:7182-7188 (1987).
Snutch, et al., "Rat brain expresses a heterogeneous family of calcium channels," *Proc.Natl.Acad.Sci. USA*, 87:3391-3395 (1990).
Snutch, et al., "Distinct calcium channels are generated by alternative splicing and are differentially expressed in the mammalian CNS," *Neuron*, 7:45-57 (1991).
Soldatov, "Molecular diversity of L-type $Ca^{2+}$ channel transcripts in human fibroblasts," *Proc.Natl.Acad.Sci.* 89:4628-4632 (1992).
Soong, et al., "Structure and Functional Expression of a Member of the Low Voltage-Activated Calcium Channel Family," *Science* 260:1133-1136 (1993).
Spedding, et al., 'Calcium Antgonists': A Class of Drugs with a Bright Future. Part II. Determination of Basic Pharmacological Properties, *Life Sciences* 35:575-587 (1984).
Stanley, et al., "Characterization of a calcium current in a vertebrate cholinergic presynaptic nerve terminal," *J. Neurosci.*, 11:985 (1991).
Starr, et al., "Primary structure of a calcium channel that is highly expressed in the rat cerebellum," *Proc.Natl.Acad.Sci.*, 88:5621-5625 (1991).
Striessnig, et al., "Photoaffinity labelling of the phenylalkylamine receptor of the skeletal muscle transverse-tubule calcium channel," *FEBS Letters*, 212(2):247-253 (1987).
Swandulla, et al., "Do calcium channel classifications account for neuronal calcium channel diversity?" *TINS*, 14(2):46-51 (1991).
Takahashi, et al., "Identification of an $\alpha$ subunit of dihydropyridine-sensitive brain calcium channels," *Science*, 236:88-91 (1987).
Takahashi and Catterall, "Dihydropyridine-sensitive calcium channels in cardiac and skeletal muscle membranes: studies with antibodies against $\alpha$-subunits," *Biochemistry*, 26(17):1518-1526 (1987).
Takahashi, et al., "Subunit structure of dihydropyridine-sensitive calcium channels from skeletal muscle," *Proc.Natl.Acad.Sci.* (USA), 84:5478-5482 (1987).
Tanabe, et al., "Primary structure of the receptor for calcium channel blockers from skeletal muscle," *Nature*, 328:313-318 (1987).
Tanabe, et al., "Cardiac-type excitation-contraction coupling in dysgenic skeletal muscle injected with cardiac dihydropyridine receptor cDNA," *Nature*, 344:451-453 (1990).
Tanabe, et al., "Regions of the skeletal muscle dihydropyridine receptor critical for excitation-contraction coupling," *Nature*, 346:567-569 (1991).
Tsien, et al., "Molecular diversity of voltage-dependent $Ca^{2+}$ channels," *Trends in Pharmacol.Sci.*, 12:349 (1991).
Vaghy, et al., "Identification of a novel 1,4-dihydropyridine- and phenylalkylamine-binding polypeptide in calcium channel preparations," *J.Biol.Chem.*, 262(29):14337-14342 (1987).
Vaghy, et al., "Mechanism of action of calcium channel modulator drugs," *Ann.N.Y.Acad.Sci.*, 522:176-186 (1988).
Varadi, et al., "Development regulation of expression of the $\alpha_1$ and $\alpha_2$ subunits mRNAs of the voltage-dependent calcium channel in a differentiating myogenic cell line," *FEBS Letters*, 250(2)CE:515-518 (1989).
von Heijne, "Signal sequences: the limits of variation," *Jour. of Mol. Biol.*, 184:99-105 (1985).
Wah, et al., "Structure and Functional Expression of a Member of the Low-Voltage-Activated Calcium channel Family," *Science* 260:1133-1136. (1993).
Wei, et al., "Heterologous regulation of the cardiac $Ca^{2+}$ channel $\alpha_1$ subunit by skeletal muscle $\beta$ and $\gamma$ subunits," *J.Biol.Chem.*, 266:21943-21947 (1991).
Williams, et al., "Structure and Functional Expression of $\alpha_1$, $\alpha_2$ and $\beta$ subunits of a novel human neuronal calcium channel subtype," *Neuron*, 8:71-84 (1992).
Williams, et al., "Structure and Functional Expression of an w-Conotoxin-Sensitive Human N-Type Calcium Channel," *Science* 257:389-395 (1992).
Williams, et al., Structure and Functional Characterization of Neuronal $\alpha_{1E}$ Calcium Channel Subtypes, *J. Biol. Chem.* 269(35):22347-22357 (1994).
Wood, "Gene cloning based on long oligonucleotide probes," *Methods on Enzymology*, 152:443-447 (1987).
Yu, et al., "Molecular characterization and nephron distribution of a family of transcripts encoding the pore-forming subunit of $Ca^{2+}$ channels in the kidney," *Proc.Natl.Acad.Sci.* 89:10494-10498 (1992).

* cited by examiner

*Primary Examiner*—Christine J Saoud
*Assistant Examiner*—Jon M Lockard
(74) *Attorney, Agent, or Firm*—Vineet Kohli; Joan E. Switzer; William Krovatin

(57) ABSTRACT

Isolated DNA encoding each of human calcium channel $\alpha_1$-, $\alpha_2$-, $\beta$- and $\gamma$-subunits, including subunits that arise as splice variants of primary transcripts, is provided. Cells and vectors containing the DNA and methods for identifying compounds that modulate the activity of human calcium channels are also provided.

2 Claims, No Drawings

HUMAN CALCIUM CHANNEL COMPOSITIONS AND METHODS

This application is a continuation-in-part of U.S. application Ser. No. 08/404,354, filed Feb. 15, 1995 now U.S. Pat. No. 5,618,720, which is a continuation of U.S. application Ser. No. 07/914,231, filed Jul. 13, 1992 now U.S. Pat. No. 5,407,820, now U.S Patent No. 5,407,820, and also of U.S. application Ser. No. 08/314,083, filed Sep. 28, 1994 now U.S. Pat. No. 5,686,241, which is a divisional of U.S. application Ser. No. 07/914,231. U.S. application Ser. No. 07/914,231 is a continuation of U.S. application Ser. No. 07/603,751, filed Nov. 8, 1990now abandoned, which is the national stage of International PCT Application PCT/US89/01408, filed Apr. 4, 1989, which is a continuation-in-part of U.S. application Ser. No. 07/176,899, filed Apr. 4, 1988, now abandoned.

This application is also a continuation-in-part of U.S. application Ser. No. 08/290,012, filed Aug. 11, 1994 now abandoned, which is a continuation-in-part of U.S. application Ser. No. 08/149,097, filed Nov. 5, 1993 now U.S. Pat. No. 5,874,236, and a continuation-in-part of U.S. application Ser. No. 08/105,536, filed Aug. 11, 1993now abandoned. U.S. application Ser. No. 08/149,097 is a continuation-in-part of U.S. application Ser. No. 08/105,536, which is a continuation-in-part of the above-mentioned U.S. application Ser. No. 07/603,751, filed Nov. 8, 1990 now abandoned.

This application is also a continuation-in-part of U.S. application Ser. No. 08/223,305, filed Apr. 4, 1994, now U.S. Pat. No. 5,851,824 which is a continuation of U.S. application Ser. No. 07/868,354; filed Apr. 10, 1992 now abandoned which is a continuation-in-part of allowed U.S. application Ser. No. 07/745,206, filed Aug. 15, 1991, now U.S. Pat. No. 5,429,921 which is a continuation-in-part of the above-mentioned U.S. application Ser. No. 07/603,751, filed Nov. 8, 1990, now abandoned and a continuation-in-part of U.S. application Ser. No. 07/620,250, filed Nov. 30, 1990, now abandoned. This application is, thus, also a continuation-in-part of U.S. application Ser. Nos. 08/149,097, 08/105,536, 07/914,231 07/868,354, and 07/745,206.

This application is also a continuation-in-part of U.S. application Ser. No. 08/311,363, filed Sep. 23, 1994, now U.S. Pat. No. 5,876,958 which is a continuation of allowed U.S. application Ser. No. 07/745,206, filed Aug. 15, 1991. now U.S. Pat. No. 5,429,921.

This application is also a continuation-in-part of U.S. application Ser. No. 08/193,078, filed Feb. 7, 1994, now U.S. Pat. No. 5,846,757 which is the National Stage of International PCT Application No. PCT/US92/06903, filed Aug. 14, 1992 and which is a continuation-in-part of U.S. application Ser. Nos. 07/868,354, 07/745,206, 07/603,751, 07/176,899, 07/620,250, filed Nov. 30, 1990, now abandoned, and Ser. No. 07/482,384, now U.S. Pat. No. 5,386,025, filed Feb. 2, 1990.

This application is also a continuation-in-part of U.S. application Ser. No. 08/336,257, filed Nov. 7, 1994, now U.S. Pat. No. 5,726,035 which is a continuation of Ser. No. 07/482,384, now U.S. Pat. No. 5,386,025, filed Feb. 2, 1990.

The subject matter of each of U.S. application Ser. No. 08/404,354, U.S. application Ser. No. 08/336,257, U.S. application Ser. No. 08/314,083, U.S. application Ser. No. 08/311,363, U.S. application Ser. No. 08/290,012, U.S. application Ser. No. 08/193,078, U.S. application Ser. No. 08/149,097, U.S. application Ser. No. 08/105,536, U.S. application Ser. No. 07/914,231, U.S. application Ser. No. 07/620,250, U.S. application Ser. No. 07/603,751, U.S. application Ser. No. 07/482,384, and U.S. application Ser. No. 07/176,899 is incorporated herein in its entirety.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels. "Opening" of a voltage-dependent channel to allow an influx of $Ca^{2+}$ ions into the cells requires a depolarization to a certain level of the potential difference between the inside of the cell bearing the channel and the extracellular environment bathing the cell. The rate of influx of $Ca^{2+}$ into the cell depends on this potential difference.

Multiple types of calcium channels have been identified in mammalian cells from various tissues, including skeletal muscle, cardiac muscle, lung, smooth muscle and brain, [see, e.g., Bean, B. P. (1989) *Ann. Rev. Physiol.* 51:367-384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins that contain two large subunits, designated $\alpha_1$ and $\alpha_2$, which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethyl-maleimide), the $\alpha_2$ subunit migrates in SDS-PAGE as a band corresponding to a molecular weight of about 160-190 kD. Upon reduction, a large fragment and smaller fragments are released. The β subunit of the rabbit skeletal muscle calcium channel is a phosphorylated protein that has a molecular weight of 52-65 kD as determined by SDS-PAGE analysis. This subunit is insensitive to reducing conditions. The γ subunit of the calcium channel appears to be a glycoprotein with an apparent molecular weight of 30-33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo.

In order to conduct this examination and to fully understand calcium channel structure and function, it is critical to identify and characterize as many calcium channel subunits as possible. Also in order to prepare recombinant cells for use in identifying compounds that interact with calcium channels, it is necessary to be able to produce cells that express uniform populations of calcium channels containing defined subunits.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding specific calcium channel subunits and to provide eukaryotic cells bearing recombinant tissue-specific or subtype-specific calcium channels. It is also an object to provide assays for identification of potentially therapeutic compounds that act as calcium channel antagonists and agonists.

SUMMARY OF THE INVENTION

Isolated and purified nucleic acid fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels (VDCCs) type A, type B (also referred to as VDCC IV), type C (also referred to as VDCC II) type D (also referred to as VDCC III) and type E are provided.

DNA encoding $\alpha_{1A}$, $\alpha_{1B}$, $\alpha_{1C}$, $\alpha_{1D}$ and $\alpha_{1E}$ subunits is provided. DNA encoding an $\alpha_{1D}$ subunit that includes the amino acids substantially as set forth as residues 10-2161 of SEQ ID No. 1 is provided. DNA encoding an $\alpha_{1D}$ subunit that includes substantially the amino acids set forth as amino acids 1-34 in SEQ ID No. 2 in place of amino acids 373-406 of SEQ ID No. 1 is also provided. DNA encoding an $\alpha_{1C}$ subunit that includes the amino acids substantially-as set forth in SEQ ID No. 3 or SEQ ID No. 6 and DNA encoding an $\alpha_{1B}$ subunit that includes an amino acid sequence substantially as set forth in SEQ ID No. 7 or in SEQ ID No. 8 is also provided.

DNA encoding $\alpha_{1A}$ subunits is also provided. Such DNA includes DNA encoding an $\alpha_{1A}$ subunit that has substantially the same sequence of amino acids as encoded by the DNA set forth in SEQ ID No. 22 or No. 23 or other splice variants of $\alpha_{1A}$ that include all or part of the sequence set forth in SEQ ID No. 22 or 23. The sequence set forth in SEQ ID NO. 22 is a splice variant designated $\alpha_{1A-1}$; and the sequence set forth in SEQ ID NO. 23 is a splice variant designated $\alpha_{1A-2}$. DNA encoding $\alpha_{1A}$ subunits also include DNA encoding subunits that can be isolated using all or a portion of the DNA having SEQ ID NO. 21, 22 or 23 or DNA obtained from the phage lysate of an *E. coli* host containing DNA encoding an $\alpha_{1A}$ subunit that has been deposited in the American Type Culture Collection, 12301 Parklawn Drive, Rockville, Md. 20852 U.S.A. under Accession No. 75293 in accord with the Budapest Treaty. The DNA in such phage includes a DNA fragment having the sequence set forth in SEQ ID No. 21. This fragment selectively hybridizes under conditions of high stringency to DNA encoding $\alpha_{1A}$ but not to DNA encoding $\alpha_{1B}$ and, thus, can be used to isolate DNA that encodes $\alpha_{1A}$ subunits.

DNA encoding $\alpha_{1E}$ subunits of a human calcium channel is also provided. This DNA includes DNA that encodes an $\alpha_{1E}$ splice variant designated $\alpha_{1E-1}$ encoded by the DNA set forth in SEQ ID No. 24, and a variant designated $\alpha_{1E-3}$ encoded by SEQ ID No. 25. This DNA also includes other splice variants thereof that encodes sequences of amino acids encoded by all or a portion of the sequences of nucleotides set forth in SEQ ID Nos. 24 and 25 and DNA that hybridizes under conditions of high stringency to the DNA of SEQ ID. No. 24 or 25 and that encodes an $\alpha_{1E}$ splice variant.

DNA encoding $\alpha_2$ subunits of a human calcium channel, and RNA encoding such subunits, made upon transcription of such a DNA are provided. DNA encoding splice variants of the $\alpha_2$ subunit, including tissue-specific splice variants, are also provided. In particular, DNA encoding the $\alpha_{2a}$-$\alpha_{2e}$ subunit subtypes is provided. In particularly preferred embodiments, the DNA encoding the $\alpha_2$ subunit that is produced by alternative processing of a primary transcript that includes DNA encoding the amino acids set forth in SEQ ID 11 and the DNA of SEQ ID No. 13 inserted between nucleotides 1624 and 1625 of SEQ ID No. 11 is provided. The DNA and amino acid sequences of $\alpha_{2a}$-$\alpha_{2e}$ are set forth in SEQ ID Nos. 11 ($\alpha_{2b}$), 29 ($\alpha_{2a}$) and 30-32 ($\alpha_{2c}$-$\alpha_{2e}$, respectively), respectively.

Isolated and purified DNA fragments encoding human calcium channel β subunits, including DNA encoding $\beta_1$, $\beta_2$, $\beta_3$ and $\beta_4$ subunits, and splice variants of the β subunits are provided. RNA encoding β subunits, made upon transcription of the DNA is also provided.

DNA encoding a $\beta_1$ subunit that is produced by alternative processing of a primary transcript that includes DNA encoding the amino acids set forth in SEQ ID No. 9, but including the DNA set forth in SEQ ID No. 12 inserted in place of nucleotides 615-781 of SEQ ID No. 9 is also provided. DNA encoding $\beta_1$ subunits that are encoded by transcripts that have the sequence set forth in SEQ ID No. 9 including the DNA set forth in SEQ ID No. 12 inserted in place of nucleotides 615-781 of SEQ ID No. 9, but that lack one or more of the following sequences of nucleotides: nucleotides 14-34 of SEQ ID No. 12, nucleotides 13-34 of SEQ ID No. 12, nucleotides 35-55 of SEQ ID No 12, nucleotides 56-190 of SEQ ID No. 12 and nucleotides 191-271 of SEQ ID No. 12 are also provided. In particular, $\beta_1$ subunit splice variants $\beta_{1-1}$-$\beta_{1-5}$ (see, SEQ ID Nos. 9, 10 and 33-35) described below, are provided.

$B_2$ subunit splice variants $\beta_{2c}$-$\beta_{2e}$, that include all or a portion of SEQ ID Nos. 26, 37 and 38 are provided; $\beta_3$ subunit splice variants, including $\beta_3$ subunit splice variants that have the sequences set forth in SEQ ID Nos 19 and 20, and DNA encoding the $\beta_4$ subunit that includes DNA having the sequence set forth in SEQ ID No. 27 and the amino acid sequence set forth in SEQ ID No. 28 are provided.

Also *Escherichia coli* (*E. coli*) host cells harboring plasmids containing DNA encoding $\beta_3$ have been deposited in accord with the Budapest Treaty under Accession No. 69048 at the American Type Culture Collection. The deposited clone encompasses nucleotides 122-457 in SEQ ID No. 19 and 112-447 in SEQ ID No. 20.

DNA encoding β subunits that are produced by alternative processing of a primary transcript encoding a β subunit, including a transcript that includes DNA encoding the amino acids set forth in SEQ ID No. 9 or including a primary transcript that encodes $\beta_3$ as deposited under ATCC Accession No. 69048, but lacking and including alternative exons are provided or may be constructed from the DNA provided herein.

DNA encoding γ subunits of human calcium channels is also provided. RNA, encoding γ subunits, made upon transcription of the DNA are also provided. In particular, DNA containing the sequence of nucleotides set forth in SEQ ID No. 14 is provided.

Full-length DNA clones and corresponding RNA transcripts, encoding $\alpha_1$, including splice variants of $\alpha_{1A}$, $\alpha_{1D}$, $\alpha_{1B}$, $\alpha_{1C}$, and $\alpha_{1E}$, $\alpha_2$ and β subunits, including $\beta_{1-1}$-$\beta_{1-5}$, $\beta_{2C}$, $\beta_{2D}$, $\beta_{2E}$, $\beta_{3-1}$ and $\beta_4$ of human calcium channels are provided. Also provided are DNA clones encoding substantial portions of the certain $\alpha_{1C}$ subtype subunits and γ subunits of voltage-dependent human calcium channels for the preparation of full-length DNA clones encoding the corresponding full-length subunits. Full-length clones may be readily obtained using the disclosed DNA as a probe as described herein.

The $\alpha_{1A}$ subunit, $\alpha_{1C}$ subunit, $\alpha_{1E}$ subunit and splice variants thereof, the $\beta_{2D}$, $\beta_{2C}$ and $\beta_{2E}$ subunits and $\beta_4$ subunits and nucleic acids encoding these subunits are of particular interest herein.

Eukaryotic cells containing heterologous DNA encoding one or more calcium channel subunits, particularly human calcium channel subunits, or containing RNA transcripts of DNA clones encoding one or more of the subunits are provided. A single $\alpha_1$ subunit can form a channel. The requisite combination of subunits for formation of active channels in selected cells, however, can be determined empirically using the methods herein. For example, if a selected $\alpha_1$ subtype or variant does not form an active channel in a selected cell line, an additional subunit or subunits can be added until an active channel is formed.

In preferred embodiments, the cells contain DNA or RNA encoding a human $\beta_1$ subunit, preferably at least an $\beta_{1D}$, $\beta_{1B}$, $\beta_{1A}$ or $\beta_{1E}$ subunit. In more preferred embodiments, the cells contain DNA or RNA encoding additional heterologous subunits, including at least one β, $\alpha_2$ or γ subunit. In such embodiments, eukaryotic cells stably or transiently transfected with any combination of one, two, three or four of the subunit-encoding DNA clones, such as DNA encoding any of $\alpha_1$, $\alpha_1$+β, $\alpha_1$+β+$\alpha_2$, are provided.

The eukaryotic cells provided herein contain heterologous DNA that encodes an $\alpha_1$ subunit or heterologous DNA that encodes an $\alpha_1$ subunit and heterologous DNA that encodes a β subunit. At least one subunit is selected from among and $\alpha_{1A-1}$, $\alpha_{1A-2}$, $\alpha_{1C-2}$, $\alpha_{1E-1}$, $\alpha_{1E-3}$, $\beta_{2C}$, $\beta_{2D}$, $\beta_{2F}$, a $\beta_{3-1}$, $\beta_{3-2}$ subunit or a $\beta_4$ subunit.

In preferred embodiments, the cells express such heterologous calcium channel subunits and include one or more of the subunits in membrane-spanning heterologous calcium channels. In more preferred embodiments, the eukaryotic cells express functional, heterologous calcium channels that are capable of gating the passage of calcium channel-selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell. Such cells provide a means to obtain homogeneous populations of calcium channels. Typically, the cells contain the selected calcium channel as the only heterologous ion channel expressed by the cell.

In certain embodiments the recombinant eukaryotic cells that contain the heterologous DNA encoding the calcium channel subunits are produced by transfection with DNA encoding one or more of the subunits or are injected with RNA transcripts of DNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions. Because the cells constitute homogeneous populations of calcium channels, they provide a means to identify agonists or antagonists of calcium channel activity that are specific for each such population.

The assays that use the eukaryotic cells for identifying compounds that modulate calcium channel activity are also provided. In practicing these assays the eukaryotic cell that expresses a heterologous calcium channel, containing at least one subunit encoded by the DNA provided herein, is in a solution containing a test compound and a calcium channel selective ion, the cell membrane is depolarized, and current flowing into the cell is detected. If the test compound is one that modulates calcium channel activity, the current that is detected is different from that produced by depolarizing the same or a substantially identical cell in the presence of the same calcium channel-selective ion but in the absence of the compound. In preferred embodiments, prior to the depolarization step, the cell is maintained at a holding potential which substantially inactivates calcium channels which are endogenous to the cell. Also in preferred embodiments, the cells are mammalian cells, most preferably HEK cells, or amphibian obcytes.

Nucleic acid probes, typically labeled for detection, containing at least about 14, preferably 16, or, if desired, 20 or 30 or more, contiguous nucleotides of $\alpha_{1D}$, $\alpha_{1C}$, $\alpha_{1B}$, $\alpha_{1A}$ and $\alpha_{1E}$, $\alpha_2$, β, including $\beta_1$, $\beta_2$, $\beta_3$ and $\beta_4$ splice variants and γ subunit-encoding DNA are provided. Methods using the probes for the isolation and cloning of calcium channel subunit-encoding DNA, including splice variants within tissues and inter-tissue variants are also provided.

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. *E. coli* fusion proteins including a fragment of a human calcium channel subunit may also be used as immunogen. Such fusion proteins may contain a bacterial protein or portion thereof, such as the *E. coli* TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample. Such antibodies may also be used to selectively isolate cells that express calcium channels that contain the subunit for which the antibodies are specific.

Methods for modulating the activity of ion channels by contacting the calcium channels with an effective amount of the above-described antibodies are also provided.

A diagnostic method for determining the presence of Lambert Eaton Syndrome (LES) in a human based on immunological reactivity of LES immunoglobulin G (IgG) with a human calcium channel subunit or a eukaryotic cell which expresses a recombinant human calcium channel or a subunit thereof is also provided. In particular, an immunoassay method for diagnosing Lambert-Eaton Syndrome in a person by combining serum or an IgG fraction from the person (test serum) with calcium channel proteins, including the α and β subunits, and ascertaining whether antibodies in the test serum react with one or more of the subunits, or a recombinant cell which expresses one or more of the subunits to a greater extent than antibodies in control serum, obtained from a person or group of persons known to be free of the Syndrome, is provided. Any immunoassay procedure known in the art for detecting antibodies against a given antigen in serum can be employed in the method.

DETAILED DESCRIPTION OF THE INVENTION

Definitions:

Unless defined otherwise, all technical and scientific terms used herein have the same meaning as is commonly understood by one of skill in the art to which this invention belongs. All patents and publications referred to herein are incorporated by reference herein.

Reference to each of the calcium channel subunits includes the subunits that are specifically disclosed herein and human calcium channel subunits encoded by DNA that can be isolated by using the DNA disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

The subunits and DNA fragments encoding such subunits provided herein include any $\alpha_1$, $\alpha_2$, β or γ subunits of a human calcium channel. In particular, such DNA fragments include any isolated DNA fragment that (encodes a subunit of a human calcium channel, that (1) contains a sequence of nucleotides that encodes the subunit, and (2) is selected from among:

(a) a sequence of nucleotides that encodes a human calcium channel subunit and includes a sequence of nucleotides set forth in any of the SEQ ID's herein (i.e., SEQ ID Nos. 1-38) that encodes such subunit;

(b) a sequence of nucleotides that encodes the subunit and hybridizes under conditions of high stringency to DNA that is complementary to an mRNA transcript present in a human cell that encodes a subunit that includes the sequence of nucleotides set forth in any of SEQ ID No. 1-38;

(c) a sequence of nucleotides that encodes the subunit that includes a sequence of amino acids encoded by any of SEQ ID Nos. 1-38; and (d) a sequence of nucleotides that encodes a subunit that includes a sequence of amino acids encoded by a sequence of nucleotides that encodes such subunit and hybridizes under conditions of high stringency to DNA that is complementary to an mRNA transcript present in a human cell that encodes the subunit that includes the sequence of nucleotides set forth in any of SEQ ID Nos. 1-38.

As used herein, the $\alpha_1$ subunits types, encoded by different genes, are designated as type $\alpha_{1A}$, $\alpha_{1B}$, $\alpha_{1C}$, $\alpha_{1D}$ and $\alpha_{1E}$. These types have also been referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has at least about 40% homology to protein encoded by DNA disclosed herein that encodes an $\alpha_1$ subunit of a human calcium channel. In particular, a splice variant of any of the $\alpha_1$ subunits (or any of the subunits particularly disclosed herein) will contain regions (at least one exon) of divergence and one or more regions (at least one exon, typically more than about 16 nucleotides, and generally substantially more) that have 100% homology with one or more of the $\alpha_1$ subunit subtypes provided herein, and will also contain a region that has substantially less homology, since it is derived from a different exon. It is well within the skill of those in this art to identify exons and splice variants. Thus, for example, an $\alpha_{1A}$ subunit will be readily identifiable, because it will share at least about 40% protein homology with one of the $\alpha_{1A}$ subunits disclosed herein, and will include at least one region (one exon) that is 100% homologous. It will also have activity, as discussed below, that indicates that it is an $\alpha_1$ subunit.

An $\alpha_1$ subunit may be identified by its ability to form a calcium channel. Typically, $\alpha_1$ subunits have molecular masses greater than at least about 120 kD. Also, hydropathy plots of deduced $\alpha_1$ subunit amino acid sequences indicate that the $\alpha_1$ subunits contain four internal repeats, each containing six putative transmembrane domains.

The activity of a calcium channel may be assessed in vitro by methods known to those of skill in the art, including the electrophysiological and other methods described herein. Typically, $\alpha_1$ subunits include regions with which one or more modulators of calcium channel activity, such as a 1,4-DHP or ω-CgTx, interact directly or indirectly. Types of $\alpha_1$ subunits may be distinguished by any method known to those of skill in the art, including on the basis of binding specificity. For example, it has been found herein that $\alpha_{1B}$ subunits participate in the formation of channels that have previously been referred to as N-type channels, $\alpha_{1D}$ subunits participate in the formation of channels that had previously been referred to as L-type channels, and $\alpha_{1A}$ subunits appear to participate in the formation of channels that exhibit characteristics typical of channels that had previously been designated P-type channels. Thus, for example, the activity of channels that contain the $\alpha_{1B}$ subunit are insensitive to 1,4-DHPs; whereas the activity of channels that contain the $\alpha_{1D}$ subunit are modulated or altered by a 1,4-DHP. It is presently preferable to refer to calcium channels based on pharmacological characteristics and current kinetics and to avoid historical designations. Types and subtypes of $\alpha_1$ subunits may be characterized on the basis of the effects of such modulators on the subunit or a channel containing the subunit as well as differences in currents and current kinetics produced by calcium channels containing the subunit.

As used herein, an $\alpha_2$ subunit is encoded by DNA that hybridizes to the DNA provided herein under conditions of low stringency or encodes a protein that has at least about 40% homology with that disclosed herein. Such DNA encodes a protein that typically has a molecular mass greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}$, . . . $\alpha_{2e}$. In addition, the $\alpha_2$ subunit and-the large fragment produced when the protein is subjected to reducing conditions appear to be glycosylated with at least N-linked sugars and do not specifically bind to the 1,4-DHPs and phenylalkylamines that specifically bind to the a subunit. The smaller fragment, the C-terminal fragment, is referred to as the δ subunit and includes amino acids from about 946 (SEQ ID No. 11) through about the C-terminus. This fragment may dissociate from the remaining portion of $\alpha_2$ when the $\alpha_2$ subunit is exposed to reducing conditions.

As used herein, a β subunit is encoded by DNA that hybridizes to the DNA provided herein under conditions of low stringency or encodes a protein that has at least about 40% homology with that disclosed herein and is a protein that typically has a molecular mass lower than the α subunits and on the order of about 50-80 kD, does not form a detectable calcium channel in the absence of an $\alpha_1$ subunit, but may alter the activity of a calcium channel that contains an $\alpha_1$ subunit or that contains an $\alpha_1$ and $\alpha_2$ subunit.

Types of the β subunit that are encoded by different genes are designated with subscripts, such as $\beta_1$, $\beta_2$, $\beta_3$ and $\beta_4$. Subtypes of β subunits that arise as splice variants of a particular type are designated with a numerical subscript referring to the type and to the variant. Such subtypes include, but are not limited to the $\beta_1$ splice variants, including $\beta_{1-1}$-$\beta_{1-5}$ and $\beta_2$ variants, including $\beta_{2C}$-$\beta_{2E}$.

As used herein, a γ subunit is a subunit encoded by DNA disclosed herein as encoding the γ subunit and may be isolated and identified using the DNA disclosed herein as a probe by hybridization or other such method known to those of skill in the art, whereby full-length clones encoding a γ subunit may be isolated or constructed. A γ subunit will be encoded by DNA that hybridizes to the DNA provided herein under conditions of low stringency or exhibits sufficient sequence homology to encode a protein that has at least about 40% homology with the γ subunit described herein.

Thus, one of skill in the art, in light of the disclosure herein, can identify DNA encoding $\alpha_1$, $\alpha_2$, β, δ and γ calcium channel subunits, including types encoded by different genes and subtypes that represent splice variants. For example, DNA probes based on the DNA disclosed herein may be used to screen an appropriate library, including a genomic or cDNA library, for hybridization to the probe and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1$, $\alpha_2$ etc. subunit. Functional assays may, if necessary, be used to determine whether the subunit is an $\alpha_1$, $\alpha_2$ subunit or β subunit.

For example, DNA encoding an $\alpha_{1A}$ subunit may be isolated by screening an appropriate library with DNA, encoding all or a portion of the human $\alpha_{1A}$ subunit. Such DNA includes the DNA in the phage deposited under ATCC Accession No. 75293 that encodes a portion of an $\alpha_1$ subunit. DNA encoding an $\alpha_{1A}$ subunit may be obtained from an appropriate library by screening with an oligonucleotide having all or a portion of the sequence set forth in SEQ ID No. 21, 22 and/or 23 or with the DNA in the deposited phage. Alternatively, such DNA may have a sequence that encodes an $\alpha_{1A}$ subunit that is encoded by SEQ ID NO. 22 or 23.

Similarly, DNA encoding $\beta_3$ may be isolated by screening a human cDNA library with DNA probes prepared from the plasmid β1.42 deposited under ATCC Accession No. 69048 or may be obtained from an appropriate library using probes having sequences prepared according to the sequences set forth in SEQ ID Nos. 19 and/or 20. Also, DNA encoding $\beta_4$ may be isolated by screening a human cDNA library with DNA probes prepared according to DNA set forth in SEQ ID No. 27, which sets forth the DNA sequence of a clone encoding a $\beta_4$ subunit. The amino acid sequence is set forth in SEQ ID No. 28. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the subunits provided herein. Splice variants share extensive regions of homology, but include non-homologous regions, subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel-selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel-selective ion.

As used herein, a compound that modulates calcium channel activity is one that affects the ability of the calcium channel to pass calcium channel-selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, selectively hybridize means that a DNA fragment hybridizes to a second fragment with sufficient specificity to permit the second fragment to be identified or isolated from among a plurality of fragments. In general, selective hybridization occurs at conditions of high stringency.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding a calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologqus DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cell that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel-selective ions, including, but not limited to, $Ca^{2+}$ or $Ba^{2+}$, in response to a stimulus and/or bind ligands with affinity for the channel. Preferably such calcium channel activity is distinguishable, such as by electro-physiological, pharmacological and other means known to those of skill in the art, from any endogenous calcium channel activity that is in the host cell.

As used herein, a peptide having an amino acid sequence substantially as set forth in a particular SEQ ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel-selective ion is a concentration of the calcium channel-selective ion necessary and sufficient to provide an inward current when the channels open.

As used herein, activity of a calcium channel refers to the movement of a calcium channel-selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally require comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound is compared to the response (or lack of response) of the calcium channel-negative cell to the test compound, when cells or cultures of each type of cell are exposed to substantially the same reaction conditions in the presence of the compound being assayed.

For example, in methods that use patch clamp electrophysiological procedures, the same cell can be tested in the presence and absence of the test compound, by changing the external solution bathing the cell as known in the art.

It is also understood that each of the subunits disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Such substitutions are preferably, although not exclusively, made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art. Mutation may be effected by any method known to those of skill in the art, including site-specific or site-directed mutagenesis of DNA encoding the protein and the use of DNA amplification methods using primers to introduce and amplify alterations in the DNA template.

Identification and Isolation of DNA Encoding Human Calcium Channel Subunits

Methods for identifying and isolating DNA encoding $\alpha_1$, $\alpha_2$, $\beta$ and $\gamma$ subunits of human calcium channels are provided.

Identification and isolation of such DNA may be accomplished by hybridizing, under appropriate conditions, at least low stringency whereby DNA that encodes the desired subunit is isolated, restriction enzyme-digested human DNA with a labeled probe having at least 14, preferably 16 or more nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel-forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences of the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA. Splice variants share regions of 100% homology.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably 16 or more, generally at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning: A Laboratory Manual,* 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, β and γ subunits of voltage-dependent human calcium channels has been cloned herein by nucleic acid amplication of cDNA from selected tissues or by screening human cDNA libraries prepared from isolated poly A+ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

Preferred regions from which to construct probes include 5' and/or 3' coding sequences, sequences predicted to encode transmembrane domains, sequences predicted to encode cytoplasmic loops, signal sequences, ligand-binding sites, and other functionally significant sequences (see Table, below). Either the full-length subunit-encoding DNA or fragments thereof can be used as probes, preferably labeled with suitable label means for ready detection. When fragments are used as probes, preferably the DNA sequences will be typically from the carboxyl-end-encoding portion of the DNA, and most preferably will include predicted transmembrane domain-encoding portions based on hydropathy analysis of the deduced amino acid sequence [see, e.g., Kyte and Doolittle [(1982) *J. Mol. Biol.* 167:105].

Riboprobes that are specific for human calcium channel subunit types or subtypes have been prepared. These probes are useful for identifying expression of particular subunits in selected tissues and cells. The regions from which the probes were prepared were identified by comparing the DNA and amino acid sequences of all known α or β subunit subtypes. Regions of least homology, preferably human-derived sequences, and generally about 250 to about 600 nucleotides were selected. Numerous riboprobes for α and β subunits have been prepared; some of these are listed in the following Table.

TABLE 2

SUMMARY OF RNA PROBES

| SUBUNIT SPECIFICITY | NUCLEOTIDE POSITION | PROBE NAME | PROBE TYPE | ORIENTATION |
|---|---|---|---|---|
| α1A generic | 3357-3840 | pGEM7Zα1A* | riboprobe | n/a |
| | 761-790 | SE700 | oligo | antisense |
| | 3440-3464 | SE71B | oligo | antisense |
| | 3542-3565 | SE724 | oligo | sense |
| α1B generic | 3091-3463 | pGEM7Zα1B$_{cyt}$ | riboprobe | n/a |
| | 6635-6858 | pGEM7Zα1B$_{cooh}$ | riboprobe | n/a |
| α1B-1 specific | 6490-6676 | pCRII α1B-1/187 | riboprobe | n/a |
| α1E generic | 3114-3462 | pGEM7Zα1E | riboprobe | n/a |
| α2b | 1321-1603 | pCRIIα2b | riboprobe | n/a |
| β generic(?) | 212-236 | SE300 | oligo | antisense |
| β1 generic | 1267-1291 | SE301 | oligo | antisense |

TABLE 2-continued

SUMMARY OF RNA PROBES

| SUBUNIT SPECIFICITY | NUCLEOTIDE POSITION | PROBE NAME | PROBE TYPE | ORIENTATION |
|---|---|---|---|---|
| β1-2 specific | 1333-1362 | SE17 | oligo | antisense |
| | 1682-1706 | SE23 | oligo | sense |
| | 2742-2766 | SE43 | oligo | antisense |
| | 27-56 | SE208 | oligo | antisense |
| | 340-364 | SE274 | oligo | antisense |
| | 340-364 | SE275 | oligo | sense |
| β3 specific | 1309-1509 | | riboprobe | n/a |
| β4 specific | 1228-1560 | | riboprobe | n/a |

*The pGEM series are available from Promega, Madison WI; see also, U.S. Pat. No. 4,766,072.

The above-noted nucleotide regions are also useful in selecting regions of the protein for preparation of subunit-specific antibodies, discussed below.

The DNA clones and fragments thereof provided herein thus can be used to isolate genomic clones encoding each subunit and to isolate any splice variants by hybridization screening of libraries prepared from different human tissues. Nucleic acid amplification techniques, which are well known in the art, can also be used to locate DNA encoding splice variants of human calcium channel subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human calcium channel subunits.

Once DNA encoding a calcium channel subunit is isolated, ribonuclease (RNase) protection assays can be employed to determine which tissues express mRNA encoding a particular calcium channel subunit or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. In situ hybridization techniques can also be used to determine which tissues express mRNA encoding a particular calcium channel subunit. The labeled subunit DNAs are hybridized to different tissue slices to visualize subunit mRNA expression.

With respect to each of the respective subunits ($\alpha_1$, $\alpha_2$, β or γ) of human calcium channels, once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Other modifications of the 5' end, known to those of skill in the art, that may be required to optimize translation and/or transcription efficiency may also be effected, if deemed necessary.

Examples II-VIII, below, describe in detail the cloning of each of the various subunits of a human calcium channel as well as subtypes and splice variants, including tissue-specific variants thereof. In the few instances in which partial sequences of a subunit are disclosed, it is well within the skill of the art, in view of the teaching herein, to obtain the corresponding full-length clones and sequence thereof encoding the subunit, subtype or splice variant thereof using the methods described above and exemplified below.

Identification and Isolation of DNA Encoding $\alpha_1$ Subunits

A number of voltage-dependent calcium channel $\alpha_1$ subunit genes, which are expressed in the human CNS and in other tissues, have been identified and have been designated as $\alpha_{1A}$, $\alpha_{1B}$, (or VDCC IV), $\alpha_{1C}$ (or VDCC II), $\alpha_{1D}$ (or VDCC III) and $\alpha_{1E}$. DNA, isolated from a human neural cDNA library, that encodes each of the subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunit types A, B, C, D and E of voltage-dependent calcium channels, and subtypes thereof, differ with respect to sensitivity to known classes of calcium channel agonists and antagonists, such as DHPs, phenylalkylamines, omega conotoxin (ω-CgTx), the funnel web spider toxin ω-Aga-IV, and pyrazonoylguanidines. These subunit types also appear to differ in the holding potential and in the kinetics of currents produced upon depolarization of cell membranes containing calcium channels that include different types of $\alpha_1$ subunits.

DNA that encodes an $\alpha_1$ subunit that binds to at least one compound selected from among dihydropyridines, phenylalkylamines, ω-CgTx, components of funnel web spider toxin, and pyrazonoylguanidines is provided. For example, the $\alpha_{1B}$ subunit provided herein appears to specifically interact with ω-CgTx in N-type channels, and the $\alpha_{1D}$ subunit provided herein specifically interacts with DHPs in L-type channels.

Identification and Isolation of DNA Encoding the $\alpha_{1D}$ Human Calcium Channel Subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone α1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit was obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) *Nature* 328:313-318 for a description of transmembrane domain terminology] of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to mediate DHP-sensitive, high-voltage-activated, long-lasting calcium channel activity. This calcium channel activity was detected when oöcytes were co-injected with RNA transcripts encoding an $\alpha_{1D}$ and $\beta_{1-2}$ or $\alpha_{1D}$, $\alpha_{2b}$ and $\beta_{1-2}$ subunits. This activity was distinguished from $Ba^{2+}$ currents detected when oöcytes were injected with RNA transcripts encoding the $\beta_{1-2}\pm\alpha_{2b}$ subunits. These currents pharmacologically and biophysically resembled $Ca^{2+}$ currents reported for uninjected oöcytes.

Identification and Isolation of DNA Encoding the $\alpha_{1A}$ Human Calcium Channel Subunit Biological material containing DNA encoding a portion of the $\alpha_{1A}$ subunit had been deposited in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

A portion of an $\alpha_{1A}$ subunit is encoded by an approximately 3 kb insert in λgt10 phage designated α1.254 in *E. coli* host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:

```
5' CTCAGTACCATCTCTGATACCAGCCCCA 3'.
```

$\alpha_{1A}$ splice variants have been obtained. The sequences of two $\alpha_{1A}$ splice variants, $\alpha_{1a-1}$ and $\alpha_{1a-2}$ are set forth in SEQ. ID Nos. 22 and 23. Other splice variants may be obtained by screening a human library as described above or using all or a portion of the sequences set forth in SEQ ID Nos. 22 and 23.

Identification and Isolation of DNA Encoding the $\alpha_{1B}$ Human Calcium Channel Subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. Nucleic acid amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit, $\alpha_{1B-2}$, encoded by the nucleotide sequence shown as SEQ ID No. 8, which is derived from alternative splicing of the $\alpha_{1B}$ subunit transcript.

Nucleic acid amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because,they contain divergent coding sequences.

Identification and Isolation of DNA Encoding the $\alpha_{1C}$ Human Calcium Channel Subunit Numerous $\alpha_{1C}$-specific DNA clones were isolated. Characterization of the sequence revealed the $\alpha_{1C}$ coding sequences, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding a substantial protion of an $\alpha_{1C}$ subunit. The DNA sequences set forth in SEQ ID No. 4 and No. 5 encode two possible amino terminal ends of the $\alpha_{1C}$ protein. SEQ ID No. 6 encodes an alternative exon for the IV S3 transmembrane domain. The sequences of substantial portions of two $\alpha_{1C}$ splice variants, designated $\alpha_{1C-1}$ and $\alpha_{1C}$-2 are set forth in SEQ ID NOs. 3 and 36, respectively.

The isolation and identification of DNA clones encoding portions of the $\alpha_{1C}$ subunit is described in detail in Example II.

Identification and Isolation of DNA Encoding the $\alpha_{1E}$ Human Calcium Channel Subunit DNA encoding a $\alpha_{1E}$ human calcium channel subunits have been isolated from an oligo dT-primed human hippocampus library. The resulting clones, which are splice variants, were designated $\alpha_{1E-1}$ and $\alpha_{1E-3}$. The subunit designated $\alpha_{1E-1}$ has the amino acid sequence set forth in SEQ ID No. 24, and a subunit designated $\alpha_{1E-3}$ has the amino acid sequence set forth in SEQ ID No. 25. These splice variants differ by virtue of a 57 base pair insert between nucleotides 2405 and 2406 of SEQ. ID No. 24.

The $\alpha_{1E}$ subunits provided herein appear to participate in the formation of calcium channels that have properties of high-voltage activated calcium channels and low-voltage activated channels. These channels are rapidly inactivating compared to other high voltage-activated calcium channels. In addition these channels exhibit pharmacological profiles that are similar to voltage-activated channels, but are also sensitive to DHPs and ω-Aga-IVA, which block certain high voltage activated channels. Additional details regarding the electrophysiology and pharmacology of channels containing $\alpha_{1E}$ subunits is provided in Example VII. F.

Identification and Isolation of DNA Encoding Encoding Additional $\alpha_1$ Human Calcium Channel Subunit Types and Subtypes DNA encoding additional $\alpha_1$ subunits can be isolated and identified using the DNA provided herein as described for the $\alpha_{1A}$, $\alpha_{1B}$, $\alpha_{1C}$, $\alpha_{1D}$ and $\alpha_{1E}$ subunits or using other methods known to those of skill in the art. In particular, the DNA provided herein may be used to screen appropriate libraries to isolate related DNA. Full-length clones can be constructed using methods, such as those described herein, and the resulting subunits characterized by comparison of their sequences and electrophysiological and pharmacological properties with the subunits exemplified herein.

Identification and Isolation of DNA Encoding β Human Calcium Channel Subunits DNA Encoding $\beta_1$ To isolate DNA encoding the $\beta_1$ subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire human calcium channel β subunit were isolated and sequenced.

Five alternatively spliced forms of the human calcium channel $\beta_1$ subunit have been identified and DNA encoding a number of forms have been isolated. These forms are designated $\beta_{1-1}$, expressed in skeletal muscle, $\beta_{1-2}$, expressed in the CNS, $\beta_{1-3}$, also expressed in the in the CNS, $\beta_{1-4}$, expressed in aorta tissue and HEK 293 cells, and $\beta_{1-5}$, expressed in HEK 293 cells. Full-length DNA clones encoding the $\beta_{1-2}$ and $\beta_{1-3}$ subunits have been constructed. The subunits $\beta_{1-1}$, $\beta_{1-2}$, $\beta_{1-4}$ and $\beta_{1-5}$ have been identified by nucleic acid amplification analysis as alternatively spliced forms of the β subunit. Sequences of the $\beta_1$ splice variants are set forth in SEQ ID Nos. 9, 10 and 33-35.

DNA Encoding $\beta_2$

DNA encoding the $\beta_2$ splice variants has been obtained. These splice variants include $\beta_{2C}$-$\beta_{2E}$. Splice variants $\beta_{2C}$-$\beta_{2E}$ include all of sequence set forth in SEQ ID No. 26, except for the portion at the 5' end (up to nucleotide 182), which differs among splice variants. The sequence set forth in SEQ ID No. 26 encodes $\beta_{2D}$. Additional splice variants may be isolated using the methods described herein and oligonucleotides including all or portions of the DNA set forth in SEQ ID. No. 26 or may be prepared or obtained as described in the Examples. The sequences of $\beta_2$ splice variants $\beta_{2C}$ and $\beta_{2E}$ are set forth in SEQ ID Nos. 37 and 38, respectively.

DNA Encoding $\beta_3$

DNA encoding the $\beta_3$ subunit and any splice variants thereof may be isolated by screening a library, as described above for the $\beta_1$ subunit, using DNA probes prepared according to SEQ ID Nos. 19, 20 or using all or a portion of the deposited $\beta_3$ clone plasmid β1.42 (ATCC Accession No. 69048).

The *E. coli* host containing plasmid β1.42 that includes DNA encoding a $\beta_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

The $\beta_3$ encoding plasmid is designated β1.42. The plasmid contains a 2.5 kb EcoRI fragment encoding $\beta_3$ inserted into vector pGem 7zF(+) and has been deposited in *E. coli* host strain DH5α. The sequences of $\beta_3$ splice variants, designated $\beta_{3-1}$ and $\beta_{3-2}$ are set forth in SEQ ID Nos. 19 and 20, respectively.

Identification and Isolation of DNA Encoding the $\beta_2$ Human Calcium Channel Subunit DNA encoding a human neuronal calcium channel $\alpha_2$ subunit was isolated in a manner substantially similar to that used for isolating DNA encoding an $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520 (now allowed U.S. application Ser. No. 07/914,231), which is a continuation-in-part of U.S. Ser. No. 176,899, filed Apr. 4, 1988, which applications have been incorporated herein by reference.

Example IV describes the isolation of DNA clones encoding $\alpha_2$ subunits of a human calcium channel from a human DNA library using genomic DNA and cDNA clones, identified by hybridization to the genomic DNA, as probes.

SEQ ID Nos. 11 and 29-32 show the sequence of DNA encoding $\alpha_2$ subunits. As described in Example V, nucleic acid amplification analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and Isolation of DNA Encoding γ Human Calcium Channel Subunits

DNA encoding a portion of a human neuronal calcium channel γ subunit has been isolated as described in detail in Example VI. SEQ ID No. 14 shows the nucleotide sequence at the 3'-end of this DNA which includes a reading frame encoding a sequence of 43 amino acid residues. Since the portion that has been obtained is homologous to the rabbit clone, described in allowed co-owned U.S. application Ser. No. 07/482,384, the remainder of the clone can be obtained using routine methods.

Antibodies

Antibodies, monoclonal or polyclonal, specific for calcium channel subunit subtypes or for calcium channel types can be prepared employing standard techniques, known to those of skill in the art, using the subunit proteins or portions thereof as antigens. Anti-peptide and anti-fusion protein antibodies can be used [see, for example, Bahouth et al. (1991) *Trends Pharmacol. Sci.* 12:338-343; *Current Protocols in Molecular Biology* (Ausubel et al., eds.) John Wiley and Sons, New York (1984)]. Factors to consider in selecting portions of the calcium channel subunits for use as immunogens (as either a synthetic peptide or a recombinantly produced bacterial fusion protein) include antigenicity accessibility (i.e., extracellular and cytoplasmic domains), uniqueness to the particular subunit, and other factors known to those of skill in this art.

The availability of subunit-specific antibodies makes possible the application of the technique of immunohistochemistry to monitor the distribution and expression density of various subunits (e.g., in normal vs diseased brain tissue). Such antibodies could also be employed in diagnostic, such as LES diagnosis, and therapeutic applications, such as using antibodies that modulate activities of calcium channels.

The antibodies can be administered to a subject employing standard methods, such as, for example, by intraperitoneal, intramuscular, intravenous, or subcutaneous injection, implant or transdermal modes of administration. One of skill in the art can empirically determine dosage forms, treatment regiments, and other parameters, depending on the mode of administration employed.

Subunit-specific monoclonal antibodies and polyclonal antisera have been prepared. The regions from which the antigens were derived were identified by comparing the DNA and amino acid sequences of all known α or β subunit subtypes. Regions of least homology, preferably human-derived sequences were selected. The selected regions or fusion proteins containing the selected regions are used as immunogens. Hydrophobicity analyses of residues in selected protein regions and fusion proteins are also performed; regions of high hydrophobicity are avoided. Also, and more importantly, when preparing fusion proteins in bacterial hosts, rare codons are avoided. In particular, inclusion of 3 or more successive rare codons in a selected host is avoided. Numerous antibodies, polyclonal and monoclonal, specific for α or β subunit types or subtypes have been prepared; some of these are listed in the following Table. Exemplary antibodies and peptide antigens used to prepare the antibodies are set forth Table 3:

TABLE 3

| SPECIFICITY | AMINO ACID NUMBER | ANTIGEN NAME | ANTIBODY TYPE |
|---|---|---|---|
| α1 generic | 112-140 | peptide 1A#1 | polyclonal |
| α1 generic | 1420-1447 | peptide 1A#2 | polyclonal |
| α1A generic | 1048-1208 | α1A#2(b)GST fusion* | polyclonal<br>monoclonal |
| α1B generic | 983-1106 | α1B#2(b) GST fusion | polyclonal<br>monoclonal |
| α1B-1 | 2164-2339 | α1B-1#3 GST fusion | polyclonal |
| α1B-2 | 2164-2237 | α1B-2#4 GST fusion | polyclonal |
| α1E generic | 985-1004<br>(α1E-3) | α1E#2(a) GST fusion | polyclonal |

*GST gene fusion system is available from Pharmacia; see also, Smith et al. (1988) Gene 67: 31. The system provides pGEX plasmids that are designed for inducible, high-level expression of genes or gene fragments as fusions with *Schistosoma japonicum* GST. Upon expression in a bacterial host, the resulting fusion proteins are purified from bacterial lysates by affinity chromatography.

The GST fusion proteins are each specific for the cytoplasmic loop region IIS6-IIS1, which is a region of low subtype homology for all subtypes, including $\alpha_{1C}$ and $\alpha_{1D}$, for which similar fusions and antisera can be prepared.

Preparation of Recombinant Eukaryotic Cells Containing DNA Encoding Heterologous Calcium Channel Subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual, Second Edition*, Cold Spring Harbor Laboratory Press].

Cloned full-length DNA encoding any of the subunits of a human calcium channel may be introduced into a plasmid vector for expression in a eukaryotic cell. Such DNA may be genomic DNA or cDNA. Host cells may be transfected with one or a combination of the plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* [see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCDNA1, or pcDNA-amp and MMTV promoter-based vectors. DNA encoding the human calcium channel subunits has been inserted in the vector pCDNA1 at a position immediately following the CMV promoter. The vector pCDNA1 is presently preferred.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene.

Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan.

Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to, cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts or cDNA include *Xenopus laevis* oöcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that can be frozen in liquid nitrogen and then thawed and regrown. Such HEK 293 cells are described, for example in U.S. Pat. No. 5,024,939 to Gorman [see, also Stillman et al. (1985) *Mol. Cell. Biol.* 5:2051-2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium-channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, β subunits of a human calcium channel and γ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In other embodiments, eukaryotic cells that contain heterologous DNA encoding at least one of an $\alpha_1$ subunit of a human calcium channel, an $\alpha_2$ subunit of a human calcium channel, a β subunit of a human calcium channel and a γ subunit of a human calcium channel are provided. In accordance with one preferred embodiment, the heterologous DNA is expressed in the eukaryotic cell and preferably encodes a human calcium channel $\alpha_1$ subunit.

Expression of Heterologous Calcium Channels: Electrophysiology and Pharmacology Electrophysiological methods for measuring calcium channel activity are known to those of skill in the art and are exemplified herein. Any such methods may be used in order to detect the formation of functional calcium channels and to characterize the kinetics and other characteristics of the resulting currents. Pharmacological studies may be combined with the electrophysiological measurements in order to further characterize the calcium channels.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Thus, various combinations of subunits encoded by the DNA provided herein are introduced into eukaryotic cells. The resulting cells can be examined to ascertain whether functional channels are expressed and to determine the properties of the channels. In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude and/or pharmacological properties or exhibits biophysical properties not exhibited in the untransfected cell.

The eukaryotic cells can be transfected with various combinations of the subunit subtypes provided herein. The resulting cells will provide a uniform population of calcium channels for study of calcium channel activity and for use in the drug screening assays provided herein. Experiments that have been performed have demonstrated the inadequacy of prior classification schemes.

Preferred among transfected cells is a recombinant eukaryotic cell with a functional heterologous calcium channel. The recombinant cell can be produced by introduction of and expression of heterologous DNA or RNA transcripts encoding an $\alpha_1$ subunit of a human calcium channel, more preferably also expressing, a heterologous DNA encoding a β subunit of a human calcium channel and/or heterologous DNA encoding an $\alpha_2$ subunit of a human calcium channel. Especially preferred is the expression in such a recombinant cell of each of the $\alpha_1$, β and $\alpha_2$ subunits encoded by such heterologous DNA or RNA transcripts, and optionally expression of heterologous DNA or an RNA transcript encoding a γ subunit of a human calcium channel.

The functional calcium channels may preferably include at least an $\alpha_1$ subunit and a β subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a β subunit have been shown to exhibit increased calcium selective ion flow across the cellular membrane in response to depolarization, indicating that the $\alpha_2$ subunit may potentiate calcium channel function. Cells that have been co-transfected with increasing ratios of $\alpha_2$ to $\alpha_1$ and the activity of the resulting calcium channels has been measured. The results indicate that increasing the amount of $\alpha_2$-encoding DNA relative to the other transfected subunits increases calcium channel activity.

Eukaryotic cells which express heterologous calcium channels containing at least a human $\alpha_1$ subunit, a human β subunit and a human $\alpha_2$ subunit are preferred. Eukaryotic cells transformed with a composition containing cDNA or an RNA transcript that encodes an $\alpha_1$ subunit alone or in combination with a β and/or an $\alpha_2$ subunit may be used to produce cells that express functional calcium channels. Since recombinant cells expressing human calcium channels containing all of the human subunits encoded by the heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

In particular, mammalian cells have been transiently and stably tranfected with DNA encoding one or more human calcium channel subunits. Such cells express heterologous calcium channels that exhibit pharmacological and electrophysiological properties that can be ascribed to human calcium channels. Such cells, however, represent homogeneous populations and the pharmacological and electrophysiological data provides insights into human calcium channel activity heretofore unattainable. For example, HEK cells that have been transiently transfected with DNA encoding the $\alpha_{1E-1}$, $\alpha_{2b}$, and $\beta_{1-3}$ subunits. The resulting cells transiently express these subunits, which form calcium channels that have properties that appear to be a pharmacologically distinct class of voltage-activated calcium channels distinct from those of L-, N-, T- and P-type channels. The observed $\alpha_{1E}$ currents were insensitive to drugs and toxins previously used to define other classes of voltage-activated calcium channels.

HEK cells that have been transiently transfected with DNA encoding $\alpha_{1B-1}$, $\alpha_{2b}$, and $\beta_{1-2}$ express heterologous calcium channels that exhibit sensitivity to ω-conotoxin and currents typical of N-type channels. It has been found that alteration of the molar ratios of $\alpha_{1B-1}$, $\alpha_{2b}$ and $\beta_{1-2}$ introduced into the cells to achieve equivalent mRNA levels significantly increased the number of receptors per cell, the current density, and affected the $K_d$ for ω-conotoxin.

The electrophysiological properties of these channels produced from $\alpha_{1B-1}$, $\alpha_{2b}$, and $\beta_{1-2}$ was compared with those of channels produced by transiently transfecting HEK cells with DNA encoding $\alpha_{1B-1}$, $\alpha_{2b}$ and $\beta_{1-3}$. The channels exhibited similar voltage dependence of activation, substantially identical voltage dependence, similar kinetics of activation and tail currents that could be fit by a single exponential. The voltage dependence of the kinetics of inactivation was significantly different at all voltages examined.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an a subunit of a human calcium channel. More preferably, the composition that is introduced contains an RNA transcript which encodes an $\alpha_1$ subunit of a human calcium channel and also contains (1) an RNA transcript which encodes a β subunit of a human calcium channel and/or (2) an RNA transcript which encodes an $\alpha_2$ subunit of a human calcium channel. Especially preferred is the introduction of RNA encoding an $\alpha_1$, a β and an $\alpha_2$ human calcium channel subunit, and, optionally, a γ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oöcytes are particularly preferred for expression of in vitro transcripts of the human calcium channel subunit cDNA clones provided herein. Amphibian oocytes that express functional heterologous calcium channels have been produced by this method.

Assays and Clinical Uses of the Cells and Calcium Channels Assays

Assays for Identifying Compounds that Modulate Calcium Channel Activity

Among the uses for eukaryotic cells which recombinantly express one or more subunits are assays for determining whether a test compound has calcium channel agonist or antagonist activity. These eukaryotic cells may also be used to select from among known calcium channel agonists and antagonists those exhibiting a particular calcium channel subtype specificity and to thereby select compounds that have potential as disease- or tissue-specific therapeutic agents.

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities.

These assays should accurately predict the relative therapeutic efficacy of a compound for the treatment of certain disorders in humans. In addition, since subtype- and tissue-specific calcium channel subunits are provided, cells with tissue-specific or subtype-specific recombinant calcium channels may be prepared and used in assays for identification of human calcium channel tissue- or subtype-specific drugs.

Desirably, the host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays. Also, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically bind to heterologous calcium channels by, for example, evaluating the ability of the test compound to inhibit the interaction of a labeled compound known to specifically interact with calcium channels. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

The assays involve contacting the cell membrane of a recombinant eukarybtic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell that has a calcium channel containing an $\alpha_1$ subunit of a human calcium channel in combination with a β subunit of a human calcium channel and/or an $\alpha_2$ subunit of a human calcium channel. Recombinant cells expressing heterologous calcium channels containing each of the $\alpha_1$, β and $\alpha_2$ human subunits, and, optionally, a γ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel-selective ion and comparing the measured calcium channel activity to the calcium channel activity of the same cell or a substantially identical control cell in a solution not containing the test compound. The cell is maintained in a solution having a concentration of calcium channel-selective ions sufficient to provide an inward current when the channels open. Rcombinant cells expressing calcium channels that include each of the $\alpha_1$, β and $\alpha_2$ human subunits, and, optionally, a γ subunit of a human calcium channel, are especially preferred for use in such assays. Methods for practicing such assays are known to those of skill in the art. For example, for similar methods applied with *Xenopus laevis* oöcytes and acetylcholine receptors, see, Mishina et al. [(1985) *Nature* 313:364] and, with such oöcytes and sodium channels [see, Noda et al. (1986) *Nature* 322:826-828]. For similar studies which have been carried out with the acetylcholine receptor, see, e.g., Claudio et al. [(1987) *Science* 238:1688-1694].

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium-selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) *Nature* 311:538-544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium ions or other ions through a human calcium channel can be accomplished by (a) maintaining a eukaryotic cell which is transfected or injected to express a heterologous functional calcium channel capable of regulating the flow of calcium channel-selective ions into the cell in a medium containing calcium channel-selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel-selective ions; and (d) comparing the amount and duration of current flow into the cell in the presence of the test compound to that of the current flow into the cell, or a substantially similar cell, in the absence of the test compound.

The assays thus use cells, provided herein, that express heterologous functional calcium channels and measure functionally, such as electrophysiologically, the ability of a test compound to potentiate, antagonize or otherwise modulate the magnitude and duration of the flow of calcium channel-selective ions, such as $Ca^{2+}$ or $Ba^{2+}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel-selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel-selective ion, such as $Ca^{2+}$ and $Ba^{2+}$. The details of such transcriptional based assays are described in commonly owned PCT International Patent Application No. PCT/US91/5625, filed Aug. 7, 1991, which claims priority to copending commonly owned allowed U.S. application Ser. No. 07/563,751, filed Aug. 7, 1990; see also, commonly owned published PCT International Patent Application PCT US92/11090, which corresponds to co-pending U.S. applications Ser. Nos. 08/229,150 and 08/244,985. The contents of these applications are herein incorporated by reference thereto.

Assays for Diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405-408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

Clinical Applications

In relation to therapeutic treatment of various disease states, the availability of DNA encoding human calcium channel subunits permits identification of any alterations in such genes (e.g., mutations) which may correlate with the occurrence of certain disease states. In addition, the creation of animal models of such disease states becomes possible, by specifically introducing such mutations into synthetic DNA fragments that can then be introduced into laboratory animals or in vitro assay systems to determine the effects thereof.

Also, genetic screening can be carried out using the nucleotide sequences as probes. Thus, nucleic acid samples from subjects having pathological conditions suspected of involving alteration/modification of any one or more of the calcium channel subunits can be screened with appropriate probes to determine if any abnormalities exist with respect to any of the endogenous calcium channels. Similarly, subjects having a family history of disease states related to calcium channel dysfunction can be screened to determine if they are also predisposed to such disease states.

EXAMPLES

The following examples are included for illustrative purposes only and are not intended to limit the scope of the invention.

Example I

Preparation of Libraries Used for Isolation of DNA Encoding Human Neuronal Voltage-Dependent Calcium Channel Subunits A. RNA Isolation 1. IMR32 Cells IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [(1988) *Nucleic Acids Research* 16:1487-1497]. Poly($A^+$) RNA was selected according to standard procedures [see, e.g., Sambrook et al. (1989) *Molecular Cloning, A Laboratory Manual*, Cold Spring Harbor Laboratory Press; pg. 7.26-7.29].

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5 M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4; and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7 M CsCl, 0.1 M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25 M NaCl and two volumes of 95 ethanol.

The precipitate was collected by centrifugation and resuspended in 4 ml PK buffer (0.05 M TRIS, pH 8.4, 0.14 M NaCl, 0.01 M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform:isoamylalcohol (24:1). The RNA was precipitated with ethanol and NaCl. The precipitate was resuspended in 400 μl of ETS buffer. The yield of total RNA was approximately 1.0 mg. Poly $A^+$ RNA (30 μg) was isolated from the total RNA according to standard methods as stated in Example I.A.1.

B. Library Construction

Double-stranded cDNA was synthesized according to standard methods [see, e.g., Sambrook et al. (1989) IN: *Molecular Cloning, A Laboratory Manual*, Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA Library #1

Single-stranded cDNA was synthesized using IMR32 poly ($A^+$) RNA (Example I.A.1.) as a template and was primed using oligo $(dT)_{12-18}$ (Collaborative Research Inc., Bedford, Mass.). The single-stranded cDNA was converted to double-stranded cDNA and the yield was approximately 2 μg. EcoI adapters:

```
                                  (SEQ ID No.15)
5'-AATTCGGTACGTACACTCGAGC-3' = 22-mer
                                  (SEQ ID No.16)
3'-    GCCATGCATGTGAGCTCG-5' = 18-mer
```

also containing SnaBI and XhoI restriction sites were then added to the double-stranded cDNA according to the following procedure.

a. Phosphorylation of 18-mer

The 18-mer was phosphorylated using standard methods [see, e.g., Sambrook et al. (1989) IN: *Molecular Cloning, A Laboratory Manual*, Cold Spring Harbor Laboratory Press, Chapter 8] by combining in a 10 μl total volume the 18-mer (225 pmoles) with $[^{32}P]\gamma$-ATP (7000 Ci/mmole; 1.0 μl) and kinase (2 U) and incubating at 37° C. for 15 minutes. After incubation, 1 μl 10 mM ATP and an additional 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

C. Ligation of Adapters to cDNA

After the EcoRI, SnaBI, XhoI adapters were ligated to the double-stranded cDNA using a standard protocol [see, e.g., Sambrook et al. (1989) IN: *Molecular Cloning, A Laboratory Manual*, Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 μl), water (24 μl), 10× kinase buffer (3 μl), 10 mM ATP (1 μl) and kinase (2 μl of 2 U/μl). The reaction was stopped by the addition of 2 μl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA Library #2

This library was prepared as described (Example I.B.1.) with the exception that 3 to 9 kb cDNA fragments were ligated into the λgt11 phage vector rather than the 1 to 3 kb fragments.

3. IMR32 cDNA Library #3

IMR32 cell poly($A^+$) RNA. (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized, EcoRI, SnaBI, XhoI adapters were added to the cDNA, the unligated adapters were removed, and the double-stranded cDNA with the ligated adapters was fractionated on an agarose gel, as described in Example I.B.1. The cDNA fraction-greater than 1.8 kb was eluted from the agarose, ligated into λgt11, packaged, and plated into a bacterial lawn of Y1088 (as described in Example I.B.1.).

4. IMR32 cDNA Library #4

IMR32 cell poly($A^+$) RNA (Example I.A.1.) was used as a template to synthesize single-stranded cDNA. The primers for the first strand cDNA synthesis were oligonucleotides: 89-365a specific for the ctD (VDCC III) type $\alpha_1$-subunit (see Example II.A.) coding sequence (the complementary sequence of nt 2927 to 2956, SEQ ID No. 1), 89-495 specific for the ($\alpha_{1C}$ (VDCC II) type $\alpha_1$-subunit (see Example. II.B.) coding sequence (the complementary sequence of nt 852 to 873, SEQ ID No. 3), and 90-12 specific for the $\alpha_{1C}$-subunit coding sequence (the complementary sequence of nt. 2496 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA Library #5

The cDNA library was constructed as described (Example I.B.3.) with the exception that the size-fraction greater than 1.2 kb was eluted from the agarose rather than the greater than 1.8 kb fraction.

6. Human Thalamus cDNA Library #6

Human thalamus poly ($A^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

```
                              (SEQ ID NO.17)
5' CCATGGTACCTTCGTTGACG 3' = 20-mer

                              (SEQ ID NO.18)
3' GGTACCATGGAAGCAACTGCTTAA 5' = 24-mer
```

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [hybridization: 50%; deionized formamide, 200 μg/ml sonicated herring sperm DNA (Cat #223646, Boehringer Mannheim Biochemicals, Indianapolis, Ind.), 5×SSPE, 5× Denhardt's, 42° C.; wash:0.2×SSPE, 0.1% SDS, 65° C.]. The recipes for SSPE and Denhardt's and the preparation of deionized formamide are described, for example, in Sambrook et al. (1989) *Molecular Cloning, A Laboratory Manual*, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C..

It is understood that equivalent stringencies may be achieved using alternative buffers, salts and temperatures.

Example II

Isolation of DNA Encoding the Human Neuronal Calcium Channel $\alpha_1$ Subunit A. Isolation of DNA Encoding the $\alpha_{1D}$ Subunit 1. Reference List of Partial $\alpha_{1D}$ cDNA Clones Numerous $\alpha_{1D}$-specific cDNA clones were isolated in order to characterize the complete $\alpha_{1D}$ coding sequence plus portions of the 5' and 3' untranslated sequences. SEQ ID No. 1 shows the complete aED DNA coding sequence, plus 510 nucleotides of $\alpha_{1D}$ 5' untranslated sequence ending in the guanidine nucleotide adjacent to the adenine nucleotide of the proposed initiation of translation as well as 642 nucleotides of 3' untranslated sequence. Also shown in SEQ ID No. 1 is the deduced amino acid sequence. A list of partial cDNA clones used to characterize the $\alpha_{1D}$ sequence and the nucleotide position of each clone relative to the full-length $\alpha_{1D}$ cDNA sequence, which is set forth in SEQ ID No. 1, is shown below. The isolation and characterization of these clones are described below (Example II.A.2.).

| | | |
|---|---|---|
| IMR32 | 1.144 | nt 1 to 510 of SEQ ID No. 1<br>5' untranslated sequence,<br>nt 511 to 2431, SEQ ID No. 1 |
| IMR32* | 1.136 | nt 1627 to 2988, SEQ ID No. 1<br>nt 1 to 104 of SEQ ID No. 2<br>additional exon, |
| IMR32@ | 1.80 | nt 2083 to 6468, SEQ ID No. 1 |
| IMR32# | 1.36 | nt 2857 to 4281, SEQ ID No. 1 |
| IMR32 | 1.163 | nt 5200 to 7635, SEQ ID No. 1 |

*5' of nt 1627, IMR32 1.136 encodes an intron and an additional exon described in Example II.A.2.d.
@IMR32 1.80 contains two deletions, nt 2984 to 3131 and nt 5303 to 5349 (SEQ ID No. 1). The 148 nt deletion (nt 2984 to 3131) was corrected by performing a polymerase chain reaction described in Example II.A.3.b.
#IMR32 1.36 contains a 132 nt deletion (nt 3081 to 3212).

2. Isolation and Characterization of Individual Clones Listed in Example II.A.1.

a. IMR32 1.36

Two million recombinants of the IMR32 cDNA library #1 (Example I.E.1.) were screened in duplicate at a density of approximately. 200,000 plaques per 150 mm plate using a mixture of radiolabelled fragments of the coding region of the rabbit skeletal muscle calcium channel $\alpha_1$ cDNA [for the sequence of the rabbit skeletal muscle calcium channel $\alpha_1$ subunit cDNA, see, Tanabe et al. (1987). *Nature* 328:313-318]:

| Fragment | Nucleotides |
|---|---|
| KpnI-EcoRI | −78 to 1006 |
| EcoRI-XhoI | 1006 to 2653 |
| ApaI-ApaI | 3093 to 4182 |
| BglII-SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the $2\times10^6$ screened was identified. IMR32 1.36 was plaque purified by standard methods (J. Sambrook et al. (1989) *Molecular Cloning, A Laboratory Manual*, Cold Spring Harbor Laboratory Press, Chapter 8) subcloned into pGEM3 (Promega, Madison, Wis.) and characterized by DNA sequencing.

b. IMR32 1.80

Approximately $1\times10^6$ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used, and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

C. IMR32 1.144

Approximately $1\times10^6$ recombinants of the IMR32 cDNA library #3 (Example I.B.3) were screened with the EcoRI-PvuII fragment (nt 2083 to 2518, SEQ ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, SEQ ID No. 1). Nucleic acid amplification analysis, and DNA sequencing of cloned nucleic acid amplification analysis products encoding these seven ATG codons confirmed that this sequence is present in the $\alpha_{1D}$ transcript expressed in dbcAMP-induced IMR32 cells.

d. IMR32 1.136

Approximately $1\times10^6$ recombinants of the IMR32 cDNA library #4 (Example I.B.4) were screened with the EcoRI-PvuII fragment (nt 2083 to 2518, SEQ ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of SEQ ID No. 1 preceded by an approximate 640 bp intron. This intron is then preceded by a 104 nt exon (SEQ ID No. 2) which is an alternative exon encoding the IS6 transmembrane domain [see, e.g., Tanabe et al. (1987) *Nature* 328:313-318 for a description of the IS1 to IVS6 transmembrane terminology] of the $\alpha_{1D}$ subunit and can replace nt 1627 to 1730, SEQ ID No. 1, to produce a completely spliced $\alpha_{1D}$ transcript.

e. IMR32 1.163

Approximately $1\times10^6$ recombinants of the IMR32 cDNA library #3 (Example I.B.3.) were screened with the NcoI-XhoI fragment of IMR32 1.80 (Example II.A.1.) containing nt 5811 to 6468 (SEQ ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, pSP72 (Promega, Madison, Wis.), and characterized by DNA sequencing. This characterization revealed that IMR32 1.163 contains the $\alpha_{1d}$ termination codon, nt 6994 to 6996 (SEQ ID No. 1).

3. Construction of a Full-Length $\alpha_{1D}$ cDNA [pVDCCIII (A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (SEQ ID No. 1), with the exception of a 148 bp deletion, nt 2984 to 3131 (SEQ ID No. 1). Portions of these partial cDNA clones were ligated to generate a full-length $\alpha_{1D}$ cDNA in a eukaryotic expression vector. The resulting vector was called pVDCCIII (A). The construction of PVDCCTII (A) was performed in four steps described in detail below: (1) the construction of pVDCCIII/5' using portions of IMR32 1.144, IMR32 1.136, and IMR32 1.80, (2) the construction of PVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII (A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0 M NaCl, 10 mM TRIS, pH 8.0, 1 mM EDTA. The ligations typically were performed in a 10 μl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (SEQ ID No. 1), and $\alpha_{1D}$ nt 511 to 1732 (SEQ ID No. 1) was isolated by gel electrophoresis. The EcoRI-ApaI fragment of IMR32 1.136 (Example II.A.2.d.) nucleotides 1733 to 2671 (SEQ ID No. 1) was isolated, and the ApaI-HindIII fragment of IMR32 1.80 (Example II.A.2.b.), nucleotides 2672 to 4492 (SEQ ID No. 1) was isolated. The three DNA clones were ligated to form pVDCCIII/5' containing nt 1 to 510 (5' untranslated sequence; SEQ ID No. 1) and nt 511 to 4492 (SEQ ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. nucleic acid amplification analysis of IMR32 1.80 and dbcAMP-induced (1.0 mM, 10 days) IMR32 cytoplasmic RNA (isolated according to Ausubel, F. M. et al. (Eds) (1988) *Current Protocols in Molecular Biology*, John Wiley and Sons, New York) revealed that IMR32 1.80 had a 148 nt deletion, nt 2984 to 3131 (SEQ ID No. 1), and that IMR32 1.36 had a 132 nt deletion, nt 3081 to 3212. To perform the nucleic acid amplification analysis, the amplification reaction was primed with $\alpha_{1D}$-specific oligonucleotides 112 (nt 2548 to 2572, SEQ ID No. 1) and 311 (the complementary sequence of nt 3928 to 3957, SEQ ID No. 1). These products were then reamplified using $\alpha_{1D}$-specific oligonucleotides 310 (nt 2583 to 2608 SEQ ID No. 1) and 312 (the complementary sequence of nt 3883 to 3909). This reamplified product, which contains AccI and BglII restriction sites, was digested with AccI and BglII and the AccI-BglII fragment, nt 2765 to 3890 (SEQ ID No. 1) was cloned into AccI-BglII digested pVDCCIII/5' to replace the AccI-BglII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (Example I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacZ gene. This plasmid was then digested with HindIII and BglII and the HindIII-BglII fragment (the HindIII site comes from the vector and the BglII site is at nt 6220, SEQ ID No. 1) was eliminated, thus deleting nt 5200 to 6220 (SEQ ID No. 1) of the IMR32 1.163 clone and removing this sequence from the remainder of the plasmid which contained the 3' BglII-XhoI fragment, nt 6221 to 7635 (SEQ ID No. 1). pVDCCIII/3'.1 was then made by splicing together the HindIII-PvuII fragment from IMR32 1.80 (nucleotides 4493-5296, SEQ ID No. 1), the PvuII-BglII fragment of IMR32 1.163 (nucleotides 5294 to 6220, SEQ ID No. 1) and the HindIII-BglII-digested pBluescript plasmid containing the 3' BglII/XhoI IMR32 1.163 fragment (nt 6221 to 7635, SEQ ID No. 1).

d. pVDCCIII(A): the Full-Length $\alpha_{1D}$ Construct

To construct pVDCCIII(A), the DraI-HindIII fragment (5' untranslated sequence nt 330 to 510, SEQ ID No. 1 and coding sequence nt 511 to 4492, SEQ ID No. 1) of pVDCCIII/5'.3 (Example II.A.3.b.) was isolated; the HindIII-XhoI fragment of pVDCCIII/3'.1 (containing nt 4493 to 7635, SEQ ID No. 1, plus the XhoI site of the adapter) (Example II.A.3.c.) was isolated; and the plasmid vector, pcDNA1, was digested with EcoRV and XhoI and isolated on an agarose gel. The three DNA fragments were ligated and MC1061-P3 (Invitrogen, San Diego, Calif.) was transformed. Isolated clones were analyzed by restriction mapping and DNA sequencing and pVDCCIII (A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, SEQ ID No. 1). This 5' portion plus nt 532 to 537, encoding two lysine residues, were deleted from pVDCCIII (A) and replaced with an efficient ribosomal binding site (5'-ACCACC-3') to form pVDCCIII.RBS(A). Expression experiments in which transcripts of this construct were injected into *Xenopus laevis* oöcytes did not result in an enhancement in the recombinant voltage-dependent calcium channel expression level relative to the level of expression in oöcytes injected with transcripts of pVDCCIII(A).

B. Isolation of DNA Encoding the $\alpha_{1C}$ Subunit

1. Reference List of Partial $\alpha_{1C}$ cDNA Clones

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. SEQ ID No. 3 sets forth one $\alpha_{1C}$ coding sequence ($\alpha_{1C-1}$) and deduced amino acid sequence; SEQ ID No. 36 sets forth another splice variant designated $\alpha_{1C-2}$. SEQ ID No. 4 and No. 5 encode two possible amino terminal ends of an $\alpha_{1C}$ splice variant. SEQ ID No. 6 encodes an alternative exon for the IV S3 transmembrane domain. Other $\alpha_{1C}$ variants can be constructed by selecting the alternative amino terminal ends in place of the ends in SEQ ID No. 3 or 36 and/or inserting the alternative exon (SEQ ID No. 6) in the appropriate location, such as in SEQ ID NO. 3 in place of nucleotides 3904-3987. In addition, the 75 nucleotide sequence (nucleotides 1391-1465 in SEQ ID No. 3) can be deleted or inserted to produce an alternative $\alpha_{1C}$ splice variant.

Shown below is a list of clones used to characterize the $\alpha_{1C}$ sequence and the nucleotide position of each clone relative to the characterized $\alpha_{1C}$ sequence (SEQ ID No. 3). The isolation and characterization of these cDNA clones are described below (Example II.B.2).

| | | |
|---|---|---|
| IMR32 | 1.66 | nt 1 to 916, SEQ ID No. 3<br>nt 1 to 132, SEQ ID No. 4 |
| IMR32 | 1.157 | nt 1 to 873, SEQ ID No. 3<br>nt 1 to 89, SEQ ID No. 5 |
| IMR32 | 1.67 | nt 50 to 1717, SEQ ID No. 3 |
| *IMR32 | 1.86 | nt 1366 to 2583, SEQ ID No. 3 |
| @1.16G | | nt 758 to 867, SEQ ID No. 3 |
| IMR32 | 1.37 | nt 2804 to 5904, SEQ ID No. 3 |
| CNS | 1.30 | nt 2199 to 3903, SEQ ID No. 3<br>nt 1 to 84 of alternative exon,<br>SEQ ID No. 6 |
| IMR32 | 1.38 | nt 2448 to 4702, SEQ ID No. 3<br>nt 1 to 84 of alternative exon,<br>SEQ ID No. 6 |

*IMR32 1.86 has a 73 nt deletion compared to the rabbit cardiac muscle calcium channel $\alpha_1$ subunit cDNA sequence.
@1.16G is an $\alpha_{1C}$ genomic clone.

2. Isolation and Characterization of Clones Described in Example II.B.1.

a. CNS 1.30

Approximately $1\times10^6$ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes $\alpha_{1C}$-specific sequence nt 2199 to 3903 (SEQ ID No. 3) followed by nt 1 to 84 of one of two identified alternative $\alpha_{1C}$ exons (SEQ ID No. 6). 3' of SEQ ID No. 6, CNS 1.30 contains an intron and, thus, CNS 1.30 encodes a partially spliced $\alpha_{1C}$ transcript.

b. 1.16G

Approximately $1\times10^6$ recombinants of a λEMBL3-based human genomic DNA library (Cat # HL1006d Clontech Corp., Palo Alto, Calif.) were screened using a rabbit skeletal muscle cDNA fragment (nt −78 to 1006, Example II.A.2.a.). The hybridization was performed using standard hybridization conditions (Example I.C.) and-the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.B.1.

c. IMR32 1.66 and IMR32 1.67

Approximately $1\times10^6$ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, SEQ ID No. 3). The hybridization was performed using standard hybridization conditions (Example I.C.). The filters were then washed in 0.5×SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced. $\alpha_{1C}$ transcript marked by a GT splice donor dinucleotide beginning at the nucleotide 3' of nt 916 (SEQ ID No. 3). The intron sequence within 1.66 is 101 nt long. IMR32 1.66 encodes the $\alpha_{1C}$ initiation of translation, nt 1 to 3 (SEQ ID No. 3) and 132 nt of 5' untranslated sequence (SEQ ID No. 4) precede the start codon in IMR32 1.66.

d. IMR32 1.37 and IMR32 1.38

Approximately $2\times10^6$ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (SEQ ID No. 3) and IMR32 1.38 appears to be anomalously spliced to contain both exons juxtaposed, nt 3904 to 3987 (SEQ ID No. 3) followed by nt 1 to 84 (SEQ ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 contains nt 1 to 84 (SEQ ID No. 6) preceded by the identical sequence contained in IMR32 1.37 for nt 2199 to 3903 (SEQ ID No. 3). As described in. Example II.B.2.a., an intron follows nt 1 to 84 (SEQ ID No. 6). Two alternative exons have been spliced adjacent to nt 3903 (SEQ ID No. 3) represented by CNS 1.30 and IMR32 1.37.

e. IMR32 1.86

IMR32 cDNA library #1 (Example I.B.1.) was screened in duplicate using oligonucleotide probes 90-9 (nt 1462 to 1491, SEQ ID No. 3) and 90-12 (nt 2496 to 2520, SEQ ID No. 3). These oligonucleotide probes were chosen in order to isolate a clone that encodes the $\alpha_{1C}$ subunit between the 3' end of IMR32 1.67 (nt 1717, SEQ ID No. 3) and the 5' end of CNS 1.30 (nt 2199, SEQ ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) *Nature* 340:230], nt 2191 to 2263. These missing nucleotides correspond to nt 2176-2248 of SEQ ID No. 3. Because the 5'-end of CNS 1.30 overlaps the 3'-end of IMR32 1.86, some of these missing nucleotides, i.e., nt 2205-2248 of SEQ ID No. 3, are accounted for by CNS 1.30. The remaining missing nucleotides of the 73 nucleotide deletion in IMR32 1.86 (i.e., nt 2176-2204 SEQ ID No. 3) were determined by nucleic acid amplification analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and nucleic acid amplification analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (SEQ ID No. 3). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector pGEM7Z (Promega, Madison, Wis.). The DNA was characterized by sequencing. IMR32 1.157 appears to encodes an alternative 5' portion of the $\alpha_{1C}$ sequence beginning with nt 1 to 89 (SEQ ID No. 5) and followed by nt 1 to 873 (SEQ ID No. 3). Analysis of the 1.66 and 1.157 5' sequence is described below (Example II.B.3.).

3. Characterization of the $\alpha_{1C}$ Initiation of Translation Site

Portions of the sequences of IMR32 1.157 (nt 57 to 89, SEQ ID No. 5; nt 1 to 67, SEQ ID No. 3), IMR32 1.66 (nt 100 to 132, SEQ ID No. 4; nt 1 to 67, SEQ ID No. 3), were compared to the rabbit lung CaCB-receptor cDNA sequence, nt −33 to 67 [Biel et al. (1990) *FEBS Lett.* 269:409]. The human sequences are possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (SEQ ID No. 4). The start codon identified in the CaCB receptor cDNA sequence is the same start codon used to describe the $\alpha_{1C}$ coding sequence, nt 1 to 3 (SEQ ID No. 3).

The sequences of $\alpha_{1C}$ splice variants, designated $\alpha_{1C\text{-}1}$ and $\alpha_{1C\text{-}2}$ are set forth in SEQ ID NOs. 3 and 36.

C. Isolation of Partial cDNA Clones Encoding the $\alpha_{1B}$ Subunit and Construction of a Full-Length Clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of nucleic acid amplification analysis of IMR32 cell RNA to determine the accuracy of the cDNA sequences.

Nucleic acid amplification analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1B}$ subunit transcript to include another exon that is not present in the mRNA corresponding to the other 3' $\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B\text{-}1}$ (SEQ ID No. 7), whereas the subunit encoded by a DNA sequence corresponding to the form lacking the additional exon is referred to as $\alpha_{1B\text{-}2}$ (SEQ ID No. 8). The sequence of $\alpha_{1B\text{-}1}$ diverges from that of $\alpha_{1B\text{-}2}$ beginning at nt 6633 (SEQ ID No. 7). Following the sequence of the additional exon in $\alpha_{1B\text{-}1}$ (nt 6633-6819; SEQ ID No. 7), the $\alpha_{1B\text{-}1}$ and $\alpha_{1B\text{-}2}$ sequences are identical (i.e., nt 6820-7362 in SEQ ID No. 7 and nt 6633-7175 in SEQ ID No. 8). SEQ ID No. 7 and No. 8 set forth 143 nt of 5' untranslated sequence (nt 1-143) as well as 202 nt of 3' untranslated sequence (nt 7161-7362, SEQ ID No. 7) of the DNA encoding $\alpha_{1B\text{-}1}$ and 321 nt of 3' untranslated sequence (nt 6855-7175, SEQ ID No. 8) of the DNA encoding $\alpha_{1B\text{-}2}$.

Nucleic acid amplification analysis of the IS6 region of the $\alpha_{1B}$ transcript revealed what appear to be additional splice variants based on multiple fragment sizes seen on an ethidium bromide-stained agarose gel containing the products of the amplification reaction.

A full-length $\alpha_{1B\text{-}1}$ cDNA clone designated pcDNA-$\alpha_{1B\text{-}1}$ was prepared in an eight-step process as follows.

STEP 1: The SacI restriction site of pGEM3 (Promega, Madison, Wis.) was destroyed by digestion at the SacI site, producing blunt ends by treatment with T4 DNA polymerase, and religation. The new vector was designated pGEMΔSac.

STEP 2: Fragment 1 (HindIII/KpnI; nt 2337 to 4303 of SEQ ID No. 7) was ligated into HindIII/KpnI digested pGEM3ΔSac to produce pα1.177HK.

STEP 3: Fragment 1 has a 2 nucleotide deletion (nt 3852 and 3853 of SEQ ID No. 7). The deletion was repaired by inserting an amplfied fragment (fragment 2) of IMR32 RNA into pα1.177HK. Thus, fragment 2 (NarI/KpnI; nt 3828 to 4303 of SEQ ID No. 7) was inserted into NarI/KpnI digested pα1.177HK replacing the NarI/KpnI portion of fragment 1 and producing pα1.177HK/PCR.

STEP 4: Fragment 3 (KpnI/KpnI; nt 4303 to 5663 of SEQ ID No. 7) was ligated into KpnI digested pα1.177HK/PCR to produce pα1B5'K.

STEP 5: Fragment 4 (EcoRI/HindIII; EcoRI adaptor plus nt 1 to 2337 of SEQ ID No. 7) and fragment 5 (HindIII/XhoI fragment of pα1B5'K; nt 2337 to 5446 of SEQ ID No. 7) were ligated together into EcoRI/XhoI digested pcDNA1 (Invitrogen, San Diego, Calif.) to produce pα1B5'.

STEP 6: Fragment 6 (EcoRI/EcoRI; EcoRI adapters on both ends plus nt 5749 to 7362 of SEQ ID No. 7) was ligated into EcoRI digested pBluescript II KS (Stratagene, La Jolla, Calif.) with the 5' end of the fragment proximal to the KpnI site in the polylinker to produce pα1.230.

STEP 7: Fragment 7 (KpnI/XhoI; nt 4303 to 5446 of SEQ ID No. 7), and fragment 8 (XhoI/CspI; nt 5446 to 6259 of SEQ ID No. 7) were ligated into KpnI/CspI digested pα1.230 (removes nt 5749 to 6259 of SEQ ID No. 7 that was encoded in pα1.230 and maintains nt 6259 to 7362 of SEQ ID No. 7) to produce pα1B3'.

STEP 8: Fragment 9 (SphI/XhoI; nt 4993 to 5446 of SEQ ID No. 7) and fragment 10 (XhoI/XbaI of pα1B3α; nt 5446 to 7319 of SEQ ID No. 7) were ligated into SphI/XbaI digested pα1B5' (removes nt 4993 to 5446 of SEQ ID No. 7 that were encoded in pα1B5' and maintains nt 1 to 4850 of SEQ ID No. 7) to produce PcDNA$\alpha_{1B\text{-}1}$.

The resulting construct, pcDNA$\alpha_{1B\text{-}1}$, contains, in pcDNA1, a full-length coding region encoding $\alpha_{1B\text{-}1}$ (nt 144-7362, SEQ ID No. 7), plus 5' untranslated sequence (nt 1-143, SEQ ID No. 7) and 3' untranslated sequence (nt 7161-7319, SEQ ID No. 7) under the transcriptional control of the CMV promoter.

D. Isolation of DNA Encoding Human Calcium Channel $\alpha_{1A}$ Subunits

1. Isolation of Partial Clones

DNA clones encoding portions of human calcium channel $\alpha_{1A}$ subunits were obtained by hybridization screening of human cerebellum cDNA libraries and nucleic acid amplification of human cerebellum RNA. Clones corresponding to the 3' end of the $\alpha_{1A}$ coding sequence were isolated by screening $1\times10^6$ recombinants of a randomly primed cerebellum cDNA library (size-selected for inserts greater than 2.8 kb in length) under low stringency conditions (6×SSPE, 5× Denhart's solution, 0.2% SDS, 200 μg/ml sonicated herring sperm DNA, 42° C.) with oligonucleotide 704 containing nt 6190-6217 of the rat $\alpha_{1A}$ coding sequence [Starr et al. (1992) *Proc. Natl. Acad. Sci. U.S.A.* 88:5621-5625]. Washes were performed under low stringency conditions. Several clones that hybridized to the probe (clones $\alpha$1.251-$\alpha$1.259 and $\alpha$1.244) were purified and characterized by restriction enzyme mapping and DNA sequence analysis. At least two of the clones, $\alpha$1.244 and $\alpha$1.254, contained a translation termination codon. Although clones $\alpha$1.244 and $\alpha$1.254 are different lengths, they both contain a sequence of nucleotides that corresponds to the extreme 3' end of the $\alpha_{1A}$ transcript, i.e., the two clones overlap. These two clones are identical in the region of overlap, except, clone $\alpha$1.244 contains a sequence of 5 and a sequence of 12 nucleotides that are not present in $\alpha$1.254.

To obtain additional $\alpha_{1A}$-encoding clones, $1\times10^6$ recombinants of a randomly primed cerebellum cDNA library (size-selected for inserts ranging from 1.0 to 2.8 kb in length) was screened for hybridization to three oligonucleotides: oligonucleotide 701 (containing nucleotides 2288-2315 of the rat $\alpha_{1A}$ coding sequence), oligonucleotide 702 (containing nucleotides 3559-3585 of the rat $\alpha_{1A}$ coding sequence) and oligonucleotide 703 (containing nucleotides 4798-4827 of the rat $\alpha_{1A}$ coding sequence). Hybridization and washes were performed using the same conditions as used for the first screening with oligonucleotide 704, except that washes were conducted at 45° C. Twenty clones (clones $\alpha$1.269-$\alpha$1.288) hybridized to the probe. Several clones were plaque-purified and characterized by restriction enzyme mapping and DNA sequence analysis. One clone, $\alpha$1.279, contained a sequence of about 170 nucleotides that is not present in other clones corresponding to the same region of the coding sequence. This region may be present in other splice variants. None of the clones contained a translation intiation codon.

To obtain clones corresponding to the 5' end of the human $\alpha_{1A}$ coding sequence, another cerebellum cDNA library was prepared using oligonucleotide 720 (containing nucleotides 2485-2510 of SEQ ID No. 22) to specifically prime first-strand cDNA synthesis. The library ($8\times10^5$ recombinants) was screened for hybridization to three oligonucleotides: oligonucleotide 701, oligonucleotide 726 (containing nucleotides 2333-2360 of the rat $\alpha_{1A}$ coding sequence) and oligonucleotide 700 (containing nucleotides 767-796 of the rat $\alpha_{1A}$ coding sequence) under low stringency hybridization and washing conditions. Approximately 50 plaques hybridized to the probe. Hybridizing clones $\alpha$1.381-$\alpha$1.390 were plaque-purified and characterized by restriction enzyme maping and DNA sequence analysis. At least one of the clones, $\alpha$1.381, contained a translation initiation codon.

Alignment of the sequences of the purified clones revealed that the sequences overlapped to comprise the entire $\alpha_{1A}$ coding sequence. However, not all the overlapping sequences of partial clones contained convenient enzyme restriction sites for use in ligating partial clones to construct a full-length $\alpha_{1A}$ coding sequence. To obtain DNA fragments containing convenient restriction enzyme sites that could be used in constructing a full-length $\alpha_{1A}$ DNA, cDNA was synthesized from RNA isolated from human cerebellum tissue and subjected to nucleic acid amplification. The oligonucleotides used as primers corresponded to human $\alpha_{1A}$ coding sequence located 5' and 3' of selected restriction enzyme sites. Thus, in the first amplification reaction, oligonucleotides 753 (containing nucleotides 2368-2391 of SEQ ID No. 22) and 728 (containing nucleotides 3179-3202 of SEQ ID No. 22) were used as the primer pair. To provide a sufficient amount of the desired DNA fragment, the product of this amplification was reamplified using oligonucleotides 753 and 754 (containing nucleotides 3112-3135 of SEQ ID No. 22 as the primer pair. The resulting product was 768 bp in length. In the second amplification reaction, oligonucleotides 719 (containing nucleotides 4950-4975 of SEQ ID No. 22 and 752 (containing nucleotides 5647-5670 of SEQ ID No. 22) were used as the primer pair. To provide a sufficient amount of the desired second DNA fragment, the product of this amplification was reamplified using oligonucleotides 756 (containing nucleotides 5112-5135 of SEQ ID No. 22) and 752 as the primer pair. The resulting product was 559 bp in length.

2. Construction of Full-Length $\alpha_{1A}$ Coding Sequences

Portions of clone $\alpha$1.381, the 768-bp nucleic acid amplification product, clone $\alpha$1.278, the 559-bp nucleic acid amplification product, and clone $\alpha$1.244 were ligated at convenient restriction sites to generate a full-length $\alpha_{1A}$ coding sequence referred to as $\alpha_{1A-1}$.

Comparison of the results of sequence analysis of clones $\alpha$1.244 and $\alpha$1.254 indicated that the primary transcript of the $\alpha_{1A}$ subunit gene is alternatively spliced to yield at least two variant mRNAs encoding different forms of the $\alpha_{1A}$ subunit. One form, $\alpha_{1A-1}$, is encoded by the sequence shown in SEQ ID No. 22. The sequence encoding a second form, $\alpha_{1A-2}$, differs from the $\alpha_{1A-1}$-encoding sequence at the 3' end in that it lacks a 5-nt sequence found in clone $\alpha$1.244 (nucleotides 7035-7039 of SEQ ID No. 22). This deletion shifts the reading frame and introduces a translation termination codon resulting in an $\alpha_{1A-2}$ coding sequence that encodes a shorter $\alpha_{1A}$ subunit than that encoded by the $\alpha_{1A-1}$ splice variant. Consequently, a portion of the 3' end of the $\alpha_{1A-2}$ coding sequence is actually 3' untranslated sequence in the $\alpha_{1A-2}$ DNA. The complete sequence of $\alpha_{1A-2}$, which can be constructed by ligating portions of clone $\alpha$1.381, the 768-bp nucleic acid amplification product, clone $\alpha$1.278, the 559-bp nucleic acid amplification product and clone $\alpha$1.254, is set forth in SEQ ID No. 23.

E. Isolation of DNA Encoding the $\alpha_{1E}$ Subunit

DNA encoding $\alpha_{1E}$ subunits of the human calcium channel were isolated from human hippocampus libraries. The selected clones sequenced. DNA sequence analysis of DNA clones encoding the $\alpha_{1E}$ subunit indicated that at least two alternatively spliced forms of the same $\alpha_{1E}$ subunit primary transcript are expressed. One form has the sequence set forth in SEQ ID No. 24 and was designated $\alpha_{1E-1}$ and the other was designated $\alpha_{1E-3}$, which has the sequence obtained by inserting a 57 base pair fragment between nucleotides 2405 and 2406 of SEQ ID No. 24. The resulting sequence is set forth in SEQ ID No. 25.

The subunit designated $\alpha_{1E-1}$ has a calculated molecular weight of 254,836 and the subunit designated $\alpha_{1E-3}$ has a calculated molecular weight of 257,348. $\alpha_{1E-3}$ has a 19 amino acid insertion (encoded by SEQ ID No. 25) relative to $\alpha_{1E-1}$ in the region that appears to be the cytoplasmic loop between transmembrane domains IIS6 and IIIS1.

Example III

Isolation of cDNA Clones Encoding the Human Neuronal Calcium Channel $\beta_1$ Subunit A. Isolation of Partial cDNA Clones Encoding the $\beta$ Subunit and Construction of a Full-Length Clone Encoding the $\beta_1$ Subunit A human hippocampus cDNA library was screened with the rabbit skeletal muscle calcium channel $\beta_1$ subunit cDNA fragment (nt 441 to 1379) [for isolation and sequence of the rabbit skeletal muscle calcium channel $\beta_1$ subunit cDNA, see U.S. patent application Ser. No. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel $\beta_1$ subunit cDNA sequence.

Portions of the partial $\beta_1$ subunit cDNA clones were ligated to generate a full-length clone encoding the entire $\beta_1$ subunit. SEQ ID No. 9 shows the $\beta_1$ subunit coding sequence (nt 1-1434) as well as a portion of the 3' untranslated sequence (nt 1435-1546). The deduced amino acid sequence is also provided in SEQ ID No. 9. In order to perform expression experiments, full-length $\beta_1$ subunit cDNA clones were constructed as follows.

Step 1: DNA fragment 1 (~800 bp of 5' untranslated sequence plus nt 1-277 of SEQ ID No. 9) was ligated to DNA fragment 2 (nt 277-1546 of SEQ ID No. 9 plus 448 bp of intron sequence) and cloned into pGEM7Z. The resulting plasmid, p$\beta$1-1.18, contained a full-length $\beta_1$ subunit clone that included a 448-bp intron.

Step 2: To replace the 5' untranslated sequence of p$\beta$1-1.18 with a ribosome binding site, a double-stranded adapter was synthesized that contains an EcoRI site, sequence encoding a ribosome binding site (5'-ACCACC-3') and nt 1-25 of SEQ ID No. 9. The adapter was ligated to SmaI-digested p$\beta$1-1.18, and the products of the ligation reaction were digested with EcoRI.

Step 3: The EcoRI fragment from step 2 containing the EcoRI adapter, efficient ribosome binding site and nt 1-1546 of SEQ ID No. 9 plus intron sequence was cloned into a plasmid vector and designated p$\beta$1-1.18RBS. The EcoRI fragment of p$\beta$1-1.18RBS was subcloned into EcoRI-digested pcDNA1 with the initiation codon proximal to CMV promoter to form pHBCaCH$\beta_{1a}$RBS(A).

Step 4: To generate a full-length clone encoding the $\beta_1$ subunit lacking intron sequence, DNA fragment 3 (nt 69-1146 of SEQ ID No. 9 plus 448 bp of intron sequence followed by nt 1147-1546 of SEQ ID No. 9), was subjected to site-directed mutagenesis to delete the intron sequence, thereby yielding p$\beta$1(−). The EcoRI-XhoI fragment of p$\beta$1-1.18RBS (containing of the ribosome binding site and nt 1-277 of SEQ ID No. 9) was ligated to the XhoI-EcoRI fragment of p$\beta$1(−) (containing of nt 277-1546 of SEQ ID No. 9) and cloned into pcDNA1 with the initiation of translation proximal to the CMV promoter. The resulting expression plasmid was designated pHBCaCH$\beta_{1b}$RBS(A).

B. Splice Variant $\beta_{1-3}$

DNA sequence analysis of the DNA clones encoding the $\beta_1$ subunit indicated that in the CNS at least two alternatively spliced forms of the same human $\beta_1$ subunit primary transcript are expressed. One form is represented by the sequence shown in SEQ ID No. 9 and is referred to as $\beta_{1-2}$. The sequences of $\beta_{1-2}$ and the alternative form, $\beta_{1-3}$, diverge at nt 1334 (SEQ ID No. 9). The complete $\beta_{1-3}$ sequence (nt 1-1851), including 3' untranslated sequence (nt 1795-1851), is set forth in SEQ ID No. 10.

Example IV

Isolation of cDNA Clones Encoding the Human Neuronal Calcium Channel $\alpha_2$-Subunit A. Isolation of cDNA Clones The complete human neuronal $\alpha_2$ coding sequence (nt 35-3310) plus a portion of the 5' untranslated sequence (nt 1 to 34) as well as a portion of the 3' untranslated sequence (nt 3311-3600) is set forth in SEQ ID No. 11.

To isolate DNA encoding the human neuronal $\alpha_2$ subunit, human $\alpha_2$ genomic clones first were isolated by probing human genomic Southern blots using a rabbit skeletal muscle calcium channel $\alpha_2$ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRI fragments ranging from 2.2 kb to 4.3 kb. The library was screened as described above using the rabbit $\alpha_2$ probe, hybridizing clones were isolated and characterized by DNA sequencing. HGCaCH$\alpha$2.20 contained the 3.5 kb fragment and HGCaCH$\alpha$2.9 contained the 3.0 kb fragment.

Restriction mapping and DNA sequencing revealed that HGCaCH$\alpha$2.20 contains an 82 bp exon (nt 130 to 211 of the human $\alpha_2$ coding sequence, SEQ ID No. 11) on a 650 bp PstI-XbaI restriction fragment and that HGCaCH$\alpha$2.9 contains 105 bp of an exon (nt 212 to 316 of the coding sequence, SEQ ID No. 11) on a 750 bp XbaI-BglII restriction fragment. These restriction fragments were used to screen the human basal ganglia cDNA library (Example II.C.2.a.). HBCaCH$\alpha$2.1 was isolated (nt 29 to 1163, SEQ ID No. 11) and used to screen a human brain stem cDNA library (ATCC Accession No. 37432) obtained from the American Type Culture Collection, 12301 Parklawn Drive, Rockville, Md. 20852. Two clones were isolated, HBCaCH$\alpha$2.5 (nt 1 to 1162, SEQ ID No. 11) and HBCaCH$\alpha$2.8 (nt 714 to 1562, SEQ ID No. 11, followed by 1600 nt of intervening sequence). A 2400 bp fragment of HBCaCH$\alpha$2.8 (beginning at nt 759 of SEQ ID No. 11 and ending at a SmaI site in the intron) was used to rescreen the brain stem library and to isolate HBCaCH$\alpha$2.11 (nt 879 to 3600, SEQ ID No. 11). Clones HBCaCH$\alpha$2.5 and HBCaCH$\alpha$2.11 overlap to encode an entire human brain $\alpha_2$ protein.

B. Construction of pHBCaCH$\alpha_2$A

To construct pHBCaCH$\alpha_2$A containing DNA encoding a full-length human calcium channel $\alpha_2$ subunit, an (EcoRI)-PvuII fragment of HBCaCH$\alpha$2.5 (nt 1 to 1061, SEQ ID No. 11, EcoRI adapter, PvuII partial digest) and a PvuII-PstI fragment of HBCaCH$\alpha$2.11 (nt 1061 to 2424 SEQ ID No. 11; PvuII partial digest) were ligated into EcoRI-PstI-digested pIBI24 (Stratagene, La Jolla, Calif.). Subsequently, an (EcoRI)-PstI fragment (nt 1 to 2424 SEQ ID No. 11) was isolated and ligated to a PstI-(EcoRI) fragment (nt 2424 to 3600 SEQ ID No. 11) of HBCaCH$\alpha$2.11 in EcoRI-digested pIBI24 to produce DNA, HBCaCH$\alpha$2, encoding a full-length human brain $\alpha_2$ subunit. The 3600 bp EcoRI insert of HBCaCH$\alpha$2 (nt 1 to 3600, SEQ ID No. 11) was subcloned into pcDNA1 (pHBCaCH$\alpha$2A) with the methionine initiating codon proximal to the CMV promoter. The 3600 bp EcoRI insert of HBCaCH$\alpha$2 was also subcloned into pSV2dHFR [Subramani et al. (1981). *Mol. Cell. Biol.* 1:854-864] which contains the SV40 early promoter, mouse dihydrofolate reductase (dhfr) gene, SV40 polyadenylation and splice sites and sequences required for maintenance of the vector in bacteria.

Example V

Differential Processing of the Human $\beta_1$ Transcript and the Human $\alpha_2$ Transcript A. Differential Processing of the $\beta_1$ Transcript Nucleic acid amplification analysis of the human $\beta_1$ transcript present in skeletal muscle, aorta, hippocampus and basal ganglia, and HEK 293 cells revealed differential processing of the region corresponding to nt 615-781 of SEQ ID No. 9 in each of the tissues. Four different sequences that result in five different processed $\beta_1$ transcripts through this region were identified. The $\beta_1$ transcripts from the different tissues contained different combinations of the four sequences, except for one of the $\beta_1$ transcripts expressed in HEK 293 cells ($\beta_{1-5}$) which lacked all four sequences.

None of the $\beta_1$ transcripts contained each of the four sequences; however, for ease of reference, all four sequences are set forth end-to-end as a single long sequence in SEQ ID No. 12. The four sequences that are differentially processed are sequence 1 (nt 14-34 in SEQ ID No. 12), sequence 2 (nt 35-55 in SEQ ID No. 12), sequence 3 (nt 56-190 in SEQ ID No. 12) and sequence 4 (nt 191-271 in SEQ ID No. 12). The forms of the $\beta_1$ transcript that have been identified include: (1) a form that lacks sequence 1 called $\beta_{1-1}$ (expressed in skeletal muscle), (2) a form that lacks sequences 2 and 3 called $\beta_{1-2}$ (expressed in CNS), (3) a form that lacks sequences 1, 2 and 3 called $\beta_{1-4}$ (expressed in aorta and HEK cells) and (4) a form that lacks sequences 1-4 called $\beta_{1-5}$ (expressed in HEK cells). Additionally, the $\beta_{1-4}$ and $\beta_{1-5}$ contain a guanine nucleotide (nt 13 in SEQ ID No. 12) that is absent in the $\beta_{1-1}$ and $\beta_{1-2}$ forms. The sequences of $\beta_1$ splice variants are set forth in SEQ ID Nos. 9, 10 and 33-35.

B. Differential Processing of Transcripts Encoding the $\alpha_2$ Subunit.

The complete human neuronal $\alpha_2$ coding sequence (nt 35-3307) plus a portion of the 5' untranslated sequence (nt 1 to 34) as well as a portion of the 3' untranslated sequence (nt 3308-3600) is set forth as SEQ ID No. 11.

Nucleic acid amplification analysis of the human $\alpha_2$ transcript present in skeletal muscle, aorta, and CNS revealed differential processing of the region corresponding to nt 1595-1942 of SEQ ID No. 11 in each of the tissues.

The analysis indicated that the primary transcript of the genomic DNA that includes the nucleotides corresponding to nt 1595-1942 also includes an additional sequence (SEQ ID No. 13: 5' CCTATTGGTGTAGGTATACCAACAATTAATTT AAGAAAAAGGAGACCCAATATCCAG 3') inserted between nt 1624 and 1625 of SEQ ID No. 11. Five alternatively spliced variant transcripts that differ in the presence or absence of one to three different portions of the region of the primary transcript that includes the region of nt 1595-1942 of SEQ ID No. 11 plus SEQ ID No. 13 inserted between nt 1624 and 1625 have been identified. The five $\alpha_2$-encoding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (SEQ ID No. 13), sequence 2 (5' AACCCCAAATCTCAG 3', which is nt 1625-1639 of SEQ ID No. 11), and sequence 3 (5' CAAAAAAGGGCAAAATGAAGG 3', which is nt 1908-1928 of SEQ ID No. 11). The five; $\alpha_2$ forms identified are (1) a form that lacks sequence 3 called $\alpha_{2a}$ (expressed in skeletal muscle), (2) a form that lacks sequence 1 called $\alpha_{2b}$ (expressed in CNS), (3) a form that lacks sequences 1 and 2 called $\alpha_{2c}$ expressed in aorta), (4) a form that lacks sequences 1, 2 and 3 called $\alpha_{2d}$ (expressed in aorta) and (5) a form that lacks sequences 1 and 3 called $\alpha_{2e}$ (expressed in aorta).

The sequences of $\alpha_{2a}$-$\alpha_{2e}$ are set forth in SEQ ID Nos. 11 ($\alpha_{2b}$), 29 ($\alpha_{2a}$) and 30-32 ($\alpha_{2c}$-$\alpha_{2e}$, respectively), respectively.

Example VI

Isolation of DNA Encoding a Calcium channel $\gamma$ Subunit from a Human Brain cDNA Library A. Isolation of DNA Encoding the $\gamma$ Subunit Approximately $1\times10^6$ recombinants from a $\lambda$gt11-based human hippocampus cDNA library (Clontech catalog #HL1088b, Palo Alto, Calif.) were screened by hybridization to a 484 bp sequence of the rabbit skeletal muscle calcium channel $\gamma$ subunit cDNA (nucleotides 621-626 of the coding sequence plus 438 nucleotides of 3'-untranslated sequence) contained in vector $\gamma$J10 [Jay, S. et al. (1990). *Science* 248: 490-492]. Hybridization was performed using moderate stringency conditions (20% deionized formamide, 5× Denhardt's, 6×SSPE, 0.2% SDS, 20 μg/ml herring sperm DNA, 42° C.) and the filters were washed under low stringency (see Example I.C.). A plaque that hybridized to this probe was purified and insert DNA was subcloned into pGEM7Z. This cDNA insert was designated $\gamma$1.4.

B. Characterization of $\gamma$1.4

$\gamma$1.4 was confirmed by DNA hybridization and characterized by DNA sequencing. The 1500 bp SstI fragment of $\gamma$1.4 hybridized to the rabbit skeletal muscle calcium channel $\gamma$ subunit cDNA $\gamma$J10 on a Southern blot. SEQ analysis of this fragment revealed that it contains of approximately 500 nt of human DNA sequence and −1000 nt of $\lambda$gt11 sequence (included due to apparent destruction of one of the EcoRI cloning sites in $\lambda$gt11). The human DNA sequence contains of 129 nt of coding sequence followed immediately by a translational STOP codon and 3' untranslated sequence (SEQ ID No. 14).

To isolate the remaining 5' sequence of the human $\gamma$ subunit cDNA, human CNS cDNA libraries and/or preparations of mRNA from human CNS tissues can first be assayed by nucleic acid amplification analysis methods using oligonucleotide primers based on the $\gamma$ cDNA-specific sequence of $\gamma$1.4. Additional human neuronal $\gamma$ subunit-encoding DNA can be isolated from cDNA libraries that, based on the results of the nucleic acid amplification analysis assay, contain $\gamma$-specific amplifiable cDNA. Alternatively, cDNA libraries can be constructed from mRNA preparations that, based on the results of the nucleic acid amplification analysis assays, contain $\gamma$-specific amplifiable transcripts. Such libraries are constructed by standard methods using oligo dT to prime first-strand cDNA synthesis from poly $A^+$ RNA (see Example I.B.). Alternatively, first-strand cDNA can be specified by priming first-strand cDNA synthesis with a $\gamma$ cDNA-specific oligonucleotide based on the human DNA sequence in $\gamma$1.4. A cDNA library can then be constructed based on this first-strand synthesis and screened with the $\gamma$-specific portion of $\gamma$1.4.

Example VII

Isolation of cDNA Clones Encoding the Human Calcium $\beta_2$ Subunit

Sequencing of clones isolated as described in Example III revealed a clone encoding a human neuronal calcium channel $\beta_2$ subunit (designated $\beta_{2D}$ see, SEQ ID No. 26). An oligonucleotide based on the 5' end of this clone was used to prime a human hippocampus cDNA library. The library was screened with this $\beta_2$ clone under conditions of low to medium stringency (final wash 0.5×SSPE, 50° C.). Several hybridizing clones were isolated and sequenced. Among these clones were those that encode $\beta_{2C}$, $\beta_{2D}$ and $\beta_{2E}$. For example, the sequence of $\beta_{2C}$ is set forth in SEQ ID NO. 37, and the sequeence of $\beta_{2E}$ is set forth in SEQ ID No. 38.

A randomly primed hippocampus library was then screened using a combination of the clone encoding $\beta_{2D}$ and a portion of the $\beta_3$ clone deposited under ATCC Accession No. 69048. Multiple hybridizing clones were isolated. Among these were clones designated β101, β102 and β104. β101 appears to encodes the 5' end of a splice variant of $\beta_2$, designated $\beta_{2E}$. β102 and β104 encode portions of the 3' end of $\beta_2$.

It appears that the $\beta_2$ splice variants include nucleotides 182-2294 of SEQ ID No. 26 and differ only between the start codon and nucleotides that correspond to 212 of SEQ. ID No. 26.

Example VIII

Isolation of cDNA Clones Encoding Human Calcium Channel $\beta_4$ and $\beta_3$ Subunits A. Isolation of cDNA Clones Encoding a Human $\beta_4$ Subunit A clone containing a translation initiation codon and approximately 60% of the $\beta_4$ coding sequence was obtained from a human cerebellum cDNA library (see nucleotides 1-894 of Sequence ID No. 27). To obtain DNA encoding the remaining 3' portion of the $\beta_4$ coding sequence, a human cerebellum cDNA library was screened for hybridization a nucleic acid amplification product under high stringency hybridization and wash conditions. Hybridizing clones are purified and characterized by restriction enzyme mapping and DNA sequence analysis to identify those that contain sequence corresponding to the 3' end of the $\beta_4$ subunit coding sequence and a termination codon. Selected clones are ligated to the clone containing the 5' half of the $\beta_4$ coding sequence at convenient restriction sites to generate a full-length cDNA encoding a $\beta_4$ subunit. The sequence of a full-length $\beta_4$ clone is set forth in SEQ ID No. 27; the amino acid sequence is set forth in SEQ ID No. 28.

B. Isolation of cDNA Clones Encoding a Human $\beta_3$ Subunit

Sequencing of clones isolated as described in Example III also revealed a clone encoding a human neuronal calcium channel $\beta_3$ subunit. This clone has been deposited as plasmid β1.42 (ATCC Accession No. 69048).

To isolate a full-length cDNA clone encoding a complete $\beta_3$ subunit, a human hippocampus cDNA library (Stratagene, La Jolla, Calif.) was screened for hybridization to a 5' EcoRI-PstI fragment of the cDNA encoding $\beta_{1-2}$ using lower stringency hybridization conditions (20% deionized formamide, 200 μg/ml sonicated herring sperm DNA, 5×SSPE, 5× Denhardt's solution, 42° C.) and wash conditions. One of the hybridizing clones contained both translation initiation and termination codons and encodes a complete $\beta_3$ subunit designated $\beta_{3-1}$ (Sequence ID No. 19). In vitro transcripts of the cDNA were prepared and injected into *Xenopus* oocytes along with transcripts of the $\alpha_{1B-1}$ and $\alpha_{2b}$ cDNAs using methods similiar to those described in Example IX.D. Two-electrode voltage clamp recordings of the oocytes revealed significant voltage-dependent inward $Ba^{2+}$ currents.

An additional $\beta_3$ subunit-encoding clone, designated $\beta_{3-2}$, was obtained by screening a human cerebellum cDNA library for hybridization to the nucleic acid amplification, product referred to in Example VIII.A. under lower stringency (20% deionized formamide, 200 μg/ml sonicated herring sperm DNA, 5×SSPE, 5× Denhardt's solution, 42° C.) hybridization and wash conditions. The 5' ends of this clone (Sequence. ID No. 20, $\beta_{3-2}$) and the first $\beta_3$ subunit, designated $\beta_{3-1}$, (Sequence ID No. 19). differ at their 5' ends and are splice variants of the $\beta_3$ gene.

Example IX

Recombinant Expression of Human Neuronal Calcium Channel Subunit-Encoding cDNA and RNA Transcripts in Mammalian Cells A. Recombinant Expression of the Human Neuronal Calcium Channel $\alpha_2$ Subunit cDNA in DG44 Cells 1. Stable Transfection of DG44 Cells DG44 cells [dhfr$^-$ Chinese hamster ovary cells; see, e.g., Urlaub, G. et al. (1986) *Som. Cell Molec. Genet.* 12:555-566] obtained from Lawrence Chasin at Columbia University were stably transfected by $CaPO_4$ precipitation methods [Wigler et al. (1979) *Proc. Natl. Acad. Sci. USA* 76:1373-1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ Subunit cDNA Expression in Transfected DG44 Cells

Total RNA was extracted according to the method of Birnboim [(1988) *Nuc. Acids Res.* 16:1487-1497] from four of the DG44 cell lines that had been stably transfected with pSV2dhfr containing the human neuronal calcium channel $\alpha_2$ subunit cDNA. RNA (~15 μg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5× Denhardt's, 42° C.; wash :0.2×SSPE, 0.1% SDS, 65° C). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter Gorman, C. and Howard, B. (1983) *Nucleic Acids Res.* 11:1631). This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 μl of a solution containing 50 mM HEPES, 1 mM EDTA, 1 mM PMSF. An equal volume of 2× loading dye [Laemmli, U. K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$ subunit of the human neuronal calcium channel (130-150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110 kD immunoreactive protein that may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA Encoding Human Neuronal Calcium Channel $\alpha_1$, $\alpha_2$ and $\beta_1$ Subunits in HEK Cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were.

1. Transfection of HEK 293 Cells

Separate expression vectors containing DNA encoding human neuronal calcium channel $\alpha_{1D}$, $\alpha_2$ and $\beta_1$ subunits, plasmids pVDCCIII(A), pHBCaCH$\alpha_2$A, and pHBCaCH$\beta_{1a}$RBS(A), respectively, were constructed as described in Examples II.A.3, IV.B. and III.B.3., respectively. These three vectors were used to transiently co-transfect HEK 293 cells. For stable transfection of HEK 293 cells, vector pHBCaCH$\beta_{2b}$RBS(A) (Example III.B.3.) was used in place of pHBCaCH$\beta_{1a}$RBS(A) to introduce the DNA encoding the $\beta_1$ subunit into the cells along with PVDCCIII (A) and pHBCaCH$\alpha_2$A.

a. Transient Transfection

Expression vectors pVDCCIII(A), pHBCaCH$\alpha_2$A and pHBCaCH$\beta_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMV$\beta$gal (Clontech Laboratories, Palo Alto, Calif.). Plasmid pCMV$\beta$gal contains the lacZ gene (encoding *E. coli* $\beta$-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII (A) and pCMV$\beta$gal. In both transfections, 2-4×$10^6$ HEK 293 cells in a 10-cm tissue culture plate were transiently co-transfected with 5 µg of each of the plasmids included in the experiment according to standard $CaPO_4$ precipitation transfection-procedures (Wigler et al. (1979) *Proc. Natl. Acad. Sci. USA* 76:1373-1376). The transfectants were analyzed for $\beta$-galactosidase expression by direct staining of the product of a reaction involving $\beta$-galactosidase and the X-gal substrate [Jones, J. R. (1986) *EMBO* 5:3133-3142] and by measurement of $\beta$-galactosidase activity [Miller, J. H. (1972) Experiments in Molecular Genetics, pp. 352-355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis)

b. Stable Transfection

HEK 293 cells were transfected using the calcium phosphate transfection procedure [*Current Protocols in Molecular Biology*, Vol. 1, Wiley Inter-Science, Supplement 14, Unit 9.1.1-9.1.9 (1990)]. Ten-cm plates, each containing one-to-two million HEK 293 cells, were transfected with 1 ml of DNA/calcium phosphate precipitate containing 5 µg pVD.C-CIII(A), 5 µg pHBCaCH$\alpha_2$A, 5 µg PHBCaCH$\beta_{1b}$RBS(A), 5 µg pCMVBgal and 1 µg pSV2neo (as a selectable marker). After 10-20 days of growth in media containing 500 µg G418, colonies had formed and were isolated using cloning cylinders.

2. Analysis of HEK 293 Cells Transiently Transfected with DNA Encoding Human Neuronal Calcium Channel Subunits a. Analysis of $\beta$-Galactosidase Expression Transient transfectants were assayed for $\beta$-galactosidase expression by $\beta$-galactosidase activity assays (Miller, J. H., (1972) Experiments in Molecular Genetics, pp. 352-355, Cold Spring Harbor Press) of cell lysates (prepared as described in Example VII.A.2) and staining of fixed cells (Jones, J. R. (1986) *EMBO* 5:3133-3142). The results of these assays indicated that approximately 30% of the HEK 293 cells had been transfected.

b. Northern Analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and $\beta_1$ subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and $\beta_1$ subunit-encoding cDNA and the lacZ gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple $\beta$ subunit transcripts of varying sizes were produced since the $\beta$ subunit cDNA expression vector contains two potential polyA$^+$ addition sites.

c. Electrophysiological Analysis

Individual transiently transfected HEK 293 cells were assayed for the presence of voltage-dependent barium currents using the whole-cell variant of the patch clamp technique [Hamill et al. (1981). *Pflugers Arch.* 391:85-100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1-4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMvβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (~160 pA) was recorded when the membrane was depolarized to 0 mV in the presence of 1 μM Bay K 8644. A comparison of the I-V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a ~50 pA current when the membrane was depolarized from −90 mv. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 Cells Stably Transfected with DNA Encoding Human Neuronal Calcium Channel Subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107-207], cAMP (Na salt, 250 μM) was added to the pipet solution and forskolin (10 μM) was added to the bath solution in some of the recordings. Qualitatively similar results were obtained whether these compounds were present or not.

Barium currents were recorded from stably transfected cells in the absence and presence of Bay K 8644 (1 μM) When the cell was depolarized to −10 mV from a holding potential of −90 mv in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

c. Use of pCMV-Based Vectors and pcDNA1-Based Vectors for Expression of DNA Encoding Human Neuronal Calcium Channel Subunits 1. Preparation of Constructs Additional expression vectors were constructed using pCMV. The full-length $\alpha_{1D}$ cDNA from pVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta_1$ subunit cDNA from pHBCaCH$\beta_{1b}$RBS(A) (see Example III.B.3) were separately subcloned into plasmid pCMVβgal. Plasmid pCMVβgal was digested with NotI to remove the lacZ gene. The remaining vector portion of the plasmid, referred to as pCMV, was blunt-ended at the NotI sites. The full-length $a_2$-encoding DNA and $\beta_1$-encoding DNA, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence of restriction enzyme recognition sites:

| | | | | | | | |
|---|---|---|---|---|---|---|---|
| GGCCGC CG | EcoRI site | SalI site | PstI site | EcoRV site | HindIII site | XbaII site | GT CACCGG ↑ |
| NotI | | | | | | | Destroys Not |

The $\alpha_{1D}$-encoding DNA, isolated as a BamHI/XhoI fragment from pVDCCIII(A), was then ligated to XbaII/SalI-digested pCMV to place it between the CMV promoter and SV40 polyadenylation site.

Plasmid pCMV contains the CMV promoter as does pcDNA1, but differs from pcDNAl in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 Cells

HEK 293 cells were transiently co-transfected with the $\alpha_{1D}$, $\alpha_2$ and $\beta_1$ subunit-encoding DNA in pCMV or with the $\alpha_{1D}$, $\alpha_2$ and $\beta$ subunit-encoding DNA in pcDNA1 (vectors pVDCCIII(A), pHBCaCH$\alpha_2$A and pHBCaCH$\beta_{1b}$RBS(A), respectively), as described in Example VII.B.1.a. Plasmid pCMV$\beta$gal was included in each transfection as a measure of transfection efficiency. The results of $\beta$-galactosidase assays of the transfectants (see Example VII.B.2.), indicated that HEK 293 cells were transfected equally efficiently with pCMV- and pcDNA1-based plasmids. The pcDNA1-based plasmids, however, are presently preferred for expression of calcium channel receptors.

D. Expression in *Xenopus laevis* Oöcytes of RNA Encoding Human Neuronal Calcium Channel Subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included $a_{1D}$ exhibited voltage-activated barium currents.

1. Preparation of Transcripts

Transcripts encoding the human neuronal calcium channel $\alpha_{1d}$, $\alpha_2$ and $\beta_1$ subunits were synthesized according to the instructions of the mCAP mRNA CAPPING-KIT (Strategene, La Jolla, Calif. catalog #200350). Plasmids pVDCC III.RBS(A), containing pcDNA1 and the $\alpha_{1D}$ cDNA that begins with a ribosome binding site and the eighth ATG codon of the coding sequence (see Example III.A.3.d), plasmid pHBCaCH$\alpha_1$A containing pcDNA1 and an $\alpha_2$ subunit cDNA (see Example IV) and plasmid pHBCaCH$\beta_{1b}$RBS(A) containing pcDNA1 and the $\beta_1$ DNA lacking intron sequence and containing a ribosome binding site (see Example III), were linearized by restriction digestion. The $\alpha_{1D}$ cDNA- and $\alpha_2$ subunit-encoding plasmids were digested with XhoI, and the $\beta_1$ subunit-encoding plasmid was digested with EcoRV. The DNA insert was transcribed with T7 RNA polymerase.

2. Injection of Oöcytes

*Xenopus laevis* oöcytes were isolated and defolliculated by collagenase treatment and maintained in 100 mM NaCl, 2 mM KCl, 1.8 mM $CaCl_2$, 1 mM $MgCl_2$, 5 mM HEPES, pH 7.6, 20 µg/ml ampicillin and 25 µg/ml streptomycin at 19-25° C. for 2 to 5 days after injection and prior to recording. For each transcript that was injected into the oöcyte, 6 ng of the specific mRNA was injected per cell in a total volume of 50 nl.

3. Intracellular Voltage Recordings

Injected oocytes were examined for voltage-dependent barium currents using two-electrode voltage clamp methods [Dascal, N. (1987) *CRC Crit. Rev. Biochem.* 22:317]. The pclamp (Axon Instruments) software package was used in conjunction with a Labmaster 125 kHz data acquisition interface to generate voltage commands and to acquire and analyze data. Quattro Professional was also used in this analysis. Current signals were digitized at 1-5 kHz, and filtered appropriately. The bath solution contained of the following: 40 mM $BaCl_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological Analysis of Oöcytes Injected with Transcripts Encoding the Human Neuronal Calcium Channel $\alpha_1$, $\alpha_2$ and $\beta_1$-Subunits Uninjected oöcytes were examined by two-electrode voltage clamp methods and a very small (25 nA) endogenous inward $Ba^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec. were administered. Depolarization to a series of voltages revealed currents that first appeared at approximately −30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10× concentrate directly into the 60 µl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\alpha_2$ and $\beta_1$ subunits. A residual inactivating component of the inward barium current typically remained after nifedipine application. The inward barium current was blocked completely by 50 µM $Cd^{2+}$, but only approximately 15% by 100 µM $Ni^{2+}$.

The effect of ωCgTX on the inward barium currents in oöcytes co-injected with transcripts of the $\alpha_{1D}$, $\alpha_2$ and $\beta_2$ subunits was investigated, ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10-15 μM) of ωCgTX. The test currents and the accompanying tail currents were blocked progressively within two to three minutes after application of ωCgTX, but both recovered partially as the ωCgTX was flushed from the bath.

b. Analysis of Oöcytes Injected with Transcripts Encoding the Human Neuronal Calcium Channel $\alpha_{1D}$ or Transcripts Encoding an $\alpha_{1D}$ and other Subunits The contribution of the ($\alpha_2$ and $\beta_1$ subunits to the inward barium current in oöcytes injected with transcripts encoding the $\alpha_{1D}$, $\alpha_2$ and $\beta_1$ subunits was assessed by expression of the $\alpha_{1D}$ subunit alone or in combination with either the $\alpha_1$ subunit or the $\alpha_2$ subunit. In oöcytes injected with only the transcript of a $\alpha_{1D}$ cDNA, no $Ba^{2+}$ currents were detected (n=3). In oöcytes injected with transcripts of $\alpha_{1D}$ and $\beta_1$ cDNAs, small (108±39 nA) $Ba^{2+}$ currents were detected upon depolarization of the membrane from a holding potential of −90 mV that resembled the currents observed in cells injected with transcripts of $\alpha_{1D}$, $\alpha_2$ and $\beta_1$ cDNAs, although the magnitude of the current was less. In two of the four oöcytes injected with transcripts of the $\alpha_{1D}$-encoding and $\beta_1$-encoding DNA, the $Ba^{2+}$ currents exhibited a sensitivity to Bay K 8644 that was similar to the Bay K 8644 sensitivity of $Ba^{2+}$ currents expressed in oöcytes injected with transcripts encoding the $\alpha_{1D}$ $\alpha_1$-, $\alpha_2$- and $\beta_1$ subunits.

Three of five oöcytes injected with transcripts encoding the $\alpha_{1D}$ and $\alpha_2$ subunits exhibited very small $Ba^{2+}$ currents (15-30 nA) upon depolarization of the membrane from a holding potential of −90 mV. These barium currents showed little or no response to Bay K 8644.

c. Analysis of Oöcytes Injected with Transcripts Encoding the Human Neuronal Calcium Channel $\alpha_2$ and/or $\beta_{1\ Subunit}$ To evaluate the contribution of the $\alpha_{1D}$ $\alpha_1$-subunit to the inward barium currents detected in oöcytes co-injected with transcripts encoding the $\alpha_{1D}$, $\alpha_2$ and $\beta_1$ subunits, oöcytes injected with transcripts encoding the human neuronal calcium channel $\alpha_2$ and/or $\beta_1$ subunits were assayed for barium currents. Oöcytes injected with transcripts encoding the $\alpha_2$ subunit displayed no detectable inward barium currents (n=5). Oöcytes injected with transcripts encoding a $\beta_1$ subunit displayed measurable (54±23 nA, n=5) inward barium currents upon depolarization and oöcytes injected with transcripts encoding the $\alpha_2$ and $\beta_1$ subunits displayed inward barium currents that were approximately 50% larger (80±61 nA, n=18) than those detected in oöcytes injected with transcripts of the $\beta_1$-encoding DNA only.

The inward barium currents in oöcytes injected with transcripts encoding the $\beta_1$ subunit or $\alpha_2$ and $\beta_1$ subunits typically were first observed when the membrane was depolarized to −30 mV from a holding potential of −90 mV and peaked when the membrane was depolarized to 10 to 20 mV. Macroscopically, the currents in oöcytes injected with transcripts encoding the $\alpha_2$ and $\beta_1$ subunits or with transcripts encoding the $\beta_1$ subunit were indistinguishable. In contrast to the currents in oöcytes co-injected with transcripts of $\alpha_{1D}$, $\alpha_2$ and $\beta_1$ subunit cDNAs, these currents showed a significant inactivation during the test pulse and a strong sensitivity to the holding potential. The inward barium currents in oöcytes co-injected with transcripts encoding the $\alpha_2$ and $\beta_1$ subunits usually inactivated to 10-60% of the peak magnitude during a 140-msec pulse and were significantly more sensitive to holding potential than those in oöcytes co-injected with transcripts encoding the $\alpha_{1D}$, $\alpha_2$ and $\beta_1$ subunits. Changing the holding potential of the membranes of oöcytes co-injected with transcripts encoding the $\alpha_2$ and $\beta_1$ subunits from −90 to −50 mV resulted in an approximately 81% (n=11) reduction in the magnitude of the inward barium current of these cells. In contrast, the inward barium current measured in oöcytes co-injected with transcripts encoding the $\alpha_{1D}$, $\alpha_2$ and $\beta_1$ subunits were reduced approximately 24% (n=11) when the holding potential was changed from −90 to −50 mV.

The inward barium currents detected in oöcytes injected with transcripts encoding the $\alpha_2$ and $\beta_1$ subunits were pharmacologically distinct from those observed in oöcytes co-injected with transcripts encoding the $\alpha_{1D}$, $\alpha_2$ and $\beta_1$ subunits. Oöcytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oöcytes injected with transcripts encoding the $\alpha_2$ and $\beta_1$ subunits. Nevertheless, two oöcytes that were co-injected with transcripts encoding the $\alpha_2$ and $\beta_1$ subunits displayed measurable (25 to 45 nA) inward barium currents that were insensitive to nifedipine (5 to 10 μM), when iS depolarized from a holding potential of −50 mV. The inward barium currents in oöcytes injected with transcripts encoding the $\alpha_2$ and $\beta_1$ subunits showed the same sensitivity to heavy metals as the currents detected in oöcytes injected with transcripts encoding the $\alpha_{1D}$, $\alpha_2$ and $\beta_1$ subunits.

The inward barium current detected in oöcytes injected with transcripts encoding the human neuronal $\alpha_2$ and $\beta_1$ subunits has pharmacological and biophysical properties that resemble calcium currents in uninjected *Xenopus* oöcytes. Because the amino acids of this human neuronal calcium channel $\beta_1$ subunit lack hydrophobic segments capable of forming transmembrane domains. It is unlikely that recombinant $\beta_1$ subunits alone form an ion channel, but rather that an endogenous $\alpha_1$ subunit exists in oöcytes and that the activity mediated by such an $\alpha_1$ subunit is enhanced by expression of a human neuronal $\beta_1$ subunit.

E. Expression of DNA Encoding Human Neuronal Calcium Channel $\alpha_{1B}$, $\alpha_{2B}$ and $\beta_{1-2}$ Subunits in HEK Cells 1. Transfection of HEK Cells The transient expression of the human neuronal $\alpha_{1B-1}$, $\alpha_{2b}$ and $\beta_{1-2}$ subunits was studied in HEK293 cells. The HEK293 cells were grown as a monolayer in Dulbecco's modified Eagle's medium :(Gibco) containing 5% defined-supplemented bovine calf serum (Hyclone) plus penicillin G (100 U/ml) and steptomycin sulfate (100 μg/ml). HEK293 cell transfections were mediated by calcium phosphate as described above. Transfected cells were examined for inward $Ba^{2+}$ currents ($I_{Ba}$) mediated by voltage-dependent $Ca^{2+}$ channels.

Cells were transfected (2×10$^6$ per polylysine-coated plate). Standard transfections (10-cm dish) contained 8 μg of pcDNA$\alpha_{1B-1}$, 5 μg of pHBCaCH$\alpha_2$A, 2 μg pHBCaCH$\beta_{1b}$RBS(A) (see, Examples II.A.3, IV.B. and III), 2 μg of CMVβ (Clontech) β-galactosidase expression plasmid, and pUC18 to maintain a constant mass of 20 μg/ml. Cells were analyzed 48 to 72 hours after transfection. Transfection efficiencies (±10%), which were determined by in situ histochemical staining for β-galactosidase activity (Sanes et al. (1986) *EMBO J.,* 5:3133), generally were greater than 50%.

2. Electrophysiological Analysis of Transfectant Currents a. Materials and Methods Properties of recombinantly expressed $Ca^{2+}$ channels were studied by whole cell patch-clamp techniques. Recordings were performed on transfected HEK293 cells 2 to 3 days after transfection. Cells were plated at 100,000 to 300,000 cells per polylysine-coated, 35-mm tissue culture dishes (Falcon, Oxnard, Calif.) 24 hours before recordings. Cells were perfused with 15 mM $BaCl_2$, 125 mM choline chloride, 1 mM $MgCl_2$, and 10 mM Hepes (pH=7.3) adjusted with tetraethylammonium hydroxide (bath solution). Pipettes were filled with 135 mM CsCl, 10 mM EGTA, 10 mM Hepes, 4 mM Mg-adenosine triphosphate (pH=7.5) adjusted with tetraethylammonium hydroxide. Sylgard (Dow-Corning, Midland, Mich.)—coated, fire-polished, and filled pipettes had resistances of 1 to 2 megohm before gigohm seals were established to cells.

Bay K 8644 and nifedipine (Research Biochemicals, Natick, Mass.) were prepared from stock solutions (in dimethyl sulfoxide) and diluted into the bath solution. The dimethyl sulfoxide concentration in the final drug solutions in contact with the cells never exceeded 0.1%. Control experiments showed that 0.1% dimethyl sulfoxide had no efect on membrane currents. ωCgTX (Bachem, Inc., Torrance Calif.) was prepared in the 15 mM $BaCl_2$ bath solution plus 0.1% cytochrome C (Sigma, St. Louis Mo.) to serve as a carrier protein. Control experiments showed that cytochrome C had no effect on currents. These drugs were dissolved in bath solution, and continuously applied by means of puffer pipettes as required for a given experiment. Recordings were performed at room temperature (22° to 25° C.). Series resistance compensation (70 to 85%) was employed to minimize voltage error that resulted from pipette access resistance, typically 2 to 3.5 megohm. Current signals were-filtered (−3 dB, 4-pole Bessel) at a frequency of 1/4 to 1/5 the sampling rate, which ranged from 0.5 to 3 kHz. Voltage commands were generated and data were acquired with CLAMPEX (pClamp, Axon Instruments, Foster City, Calif.). All reported data are corrected for linear leak and capacitive components. Exponential fitting of currents was performed with CLAMPFIT (Axon Instruments, Foster City, Calif.).

b. Results

Transfectants were examined for inward $Ba^{2+}$ currents ($I_{Ba}$). Cells cotransfected with DNA encoding $\alpha_{1B-1}$, $\alpha_{2b}$ and $\beta_{1-2}$ subunits expressed high-voltage-activated $Ca^{2+}$ channels. $I_{Ba}$ first appeared when the membrane was depolarized from a holding potential of −90 mV to −20 mV and peaked in magnitude at 10 mV. Thirty-nine of 95 cells (12 independent transfections) had $I_{Ba}$ that ranged from 30 to 2700 pA, with a mean of 433 pA. The mean current density was 26 pA/pF, and the highest density was 150 pA/pF. The $I_{Ba}$ typically increased by 2- to 20-fold during the first 5 minutes of recording. Repeated depolarizations during long records often revealed rundown of $I_{Ba}$ usually not exceeding 20% within 10. min. $I_{Ba}$ typically activated within 10 ms and inactivated with both a fast time constant ranging from 46 to 105 ms and a slow time constant ranging from 291 to 453 ms (n=3) Inactivation showed a complex voltage dependence, such that $I_{Ba}$ elicited at ≧20 mV inactivated more slowly than $I_{Ba}$ elicited at lower test voltages, possibly a result of an increase in the magnitude of slow compared to fast inactivation components at higher test voltages.

Recombinant $\alpha_{1B-1}\alpha_{2b}\beta_{1-2}$ channels were sensitive to holding potential. Steady-state inactivation of $I_{Ba}$, measured after a 30- to 60-s conditioning at various holding potentials, was approximately 50% at holding potential between −60 and −70 mV and approximately 90% at −40 mV. Recovery of $I_{Ba}$ from inactivation was usually incomplete, measuring 55 to 75% of the original magnitude within 1 min. after the holding potential was returned to more negative potentials, possibly indicating some rundown or a slow recovery rate.

Recombinant $\alpha_{1B-1}\alpha_{2b}\beta_{1-2}$ channels were also blocked irreversibly by ω-CgTx concentrations ranging from 0.5 to 10 μM during the time scale of the experiments. Application of 5 μM toxin (n=7) blocked the activity completely within 2 min., and no recovery of $I_{Ba}$ was observed after washing ω-CgTx from the bath for up to 15 min. $d^{2+}$ blockage (50 μM) was rapid, complete, and reversible; the DHPs Bay K 8644 (1 μM; n=4) or nifedipine (5 μM; n=-3) had no discernable effect.

Cells cotransfected with DNA encoding $\alpha_{1B-1}$, $\alpha_{2b}$ and $\beta_{1-2}$ subunits predominantly displayed a single class of saturable, high-affinity ω-CgTx binding sites. The determined dissociation constant ($K_d$) value was 54.6±14.5 pM (n=4). Cells transfected with the vector containing only β-galactosidase-encoding DNA or $\alpha_{2b}\beta$-encoding DNA showed no specific binding. The binding capacity ($B_{max}$) of the $\alpha_{1B-1}\alpha_{2b}\beta$-transfected cells was 28,710±11,950 sites per cell (n=4).

These results demonstrate that $\alpha_{1B-1}\alpha_{2b}\beta_{1-2}$-transfected cells express high-voltage-activated, inactivating $Ca^{2+}$ channel activity that is irreversibly blocked by ω-CgTx, insensitive to DHPs, and sensitive to holding potential. The activation and inactivation kinetics and voltage sensitivity of the channel formed in these cells are generally consistent with previous characterizations of neuronal N-type $Ca^{2+}$ channels.

F. Expression of DNA Encoding Human Neuronal Calcium Channel $\alpha_{1B-1}$, $\alpha_{1B-2}$, $\alpha_{2B}$, $\beta_{1-2}$ and $\beta_{1-3}$ Subunits in HEK Cells Significant $Ba^{2+}$ currents were not detected in untransfected HEK293 cells. Furthermore, untransfected HEK293 cells do not express detectable ω-CgTx GVIA binding sites. In order to approximate the expression of a homogeneous population of trimeric $\alpha_{1B}$, $\alpha_{2b}$ and $\beta_1$ protein complexes in transfected HEK293 cells, the $\alpha_{1B}$, $\alpha_{2b}$ and $\beta_1$ expression levels were altered. The efficiency of expression and assembly of channel complexes at the cell surface were optimized by adjusting the molar ratio of $\alpha_{1B}$, $\alpha_{2b}$ and $\beta_1$ expression plasmids used in the transfections. The transfectants were analyzed for mRNA levels, ω-CgTx GVIA binding and $Ca^{2+}$ channel current density in order to determine near optimal channel expression in the absence of immunological reagents for evaluating protein expression. Higher molar ratios of $\alpha_{2b}$ appeared to increase calcium channel activity.

1.Transfections

HEK293 cells were maintained in DMEM (Gibco #320-1965AJ), 5.5% Defined/Supplemented bovine calf serum (Hyclone #A-2151-L), 100 U/ml penicillin G and 100 μg/ml streptomycin. $Ca^{2+}$-phosphate based transient transfections were performed and analyzed as described above. Cells were co-transfected with either 8 μg pcDNA1$\alpha_{1B-1}$ (described in Example II.C), 5 μg pHBCaCH$\alpha_2$A (see, Example IV.B.), 2 μg pHBCaCH$\beta_{1b}$RBS(A) ($\beta_{1-2}$ expression plasmid; see Examples III.A. and IX.E.), and 2 μg pCMVβ-gal [Clontech, Palo Alto, Calif.] (2:1.8:1 molar ratio of $Ca^{2+}$ channel subunit expression plasmids) or with 3 μg pcDNA1$\alpha_{1B-1}$ or pcDNA1$\alpha_{1B-2}$, 11.25 μg pHBCaCH$\alpha_2$A, 0.75 or 1.0 μg pHBCaCH$\beta_{1b}$RBS(A) or pcDNA1$\beta_{1-3}$ and 2 μg pCMVβ-gal (2:10.9:1 molar ratio of $Ca^{2+}$ channel subunit expression plasmids). Plasmid pCMVβ-gal, a β-galactosidase expression plasmid, was included in the transfections as a marker to permit transfection efficiency estimates by histochemical staining. When less than three subunits were expressed, pCMVPL2, a pCMV promoter-containing vector that lacks a cDNA insert, was substituted to maintain equal moles of pCMV-based DNA in the transfection. pUC18 DNA was used to maintain the total mass of DNA in the transfection at 20 μg/plate.

RNA from the transfected cells was analyzed by Northern blot analysis for calcium channel subunit mRNA expression using random primed $^{32}$P-labeled subunit specific probes. HEK293 cells co-transfected with $\alpha_{1B\text{-}1}$, $\alpha_{2b}$ and $\beta_{1\text{-}2}$ expression plasmids (8, 5 and 2 μg, respectively; molar ratio=2:1.8:1) did not express equivalent levels of each $Ca^{2+}$ channel subunit mRNA. Relatively high levels of $\alpha_{1B\text{-}1}$ and $\beta_{1\text{-}2}$ mRNAs were expressed, but significantly lower levels of $\alpha_{2b}$ mRNA were expressed. Based on autoradiograph exposures required to produce equivalent signals for all three mRNAs, $\alpha_{2b}$ transcript levels were estimated to be 5 to 10 times lower than $\alpha_{1B\text{-}1}$ and $\beta_{1\text{-}2}$ transcript levels. Untransfected HEK293 cells did not express detectable levels of $\alpha_{1B\text{-}1}$, $\alpha_{2b}$, or $\beta_{1\text{-}2}$ mRNAs.

To achieve equivalent $Ca^{2+}$ channel subunit mRNA expression levels, a series of transfections was performed with various amounts of $\alpha_{1B\text{-}1}$, $\alpha_{2b}$ and $\beta_{1\text{-}2}$ expression plasmids. Because the $\alpha_{1B\text{-}1}$ and $\beta_{1\text{-}2}$ mRNAs were expressed at very high levels compared to $\alpha_{2b}$ mRNA, the mass of $\alpha_{1B\text{-}1}$ and $\beta_{1\text{-}2}$ plasmids was lowered and the mass of $\alpha_{2b}$ plasmid was increased in the transfection experiments. Co-transfection with 3, 11.25 and 0.75 μg of $\alpha_{1B\text{-}1}$, $\alpha_{2b}$ and $\beta_{1\text{-}2}$ expression plasmids, respectively (molar ratio=2:10.9:1), approached equivalent expression levels of each $Ca^{2+}$ channel subunit mRNA. The relative molar quantity of $\alpha_{2b}$ expression plasmid to $\alpha_{1B\text{-}1}$ and $\beta_{1\text{-}2}$ expression plasmids was increased 6-fold. The mass of $\alpha_{1B\text{-}1}$ and $\beta_{1\text{-}2}$ plasmids in the transfection was decreased 2.67-fold and the mass of $\alpha_{2b}$ plasmid was increased 2.25-fold. The 6-fold molar increase of $\alpha_{2b}$ relative to $\alpha_{1B\text{-}1}$ and $\beta_{1\text{-}2}$ required to achieve near equal abundance mRNA levels is consistent with the previous 5- to 10-fold lower estimate of relative $\alpha_{2b}$ mRNA abundance. ω-CgTx GVIA binding to cells transfected with various amounts of expression plasmids indicated that the 3, 11.25 and 0.75 μg of $\alpha_{1B\text{-}1}$, $\alpha_{2b}$ and $\beta_{1\text{-}2}$ plasmids, respectively, improved the level of cell surface expression of channel complexes. Further increases in the mass of $\alpha_{2b}$ and $\beta_{1\text{-}2}$ expression plasmids while $\alpha_{1B\text{-}1}$ was held constant, and alterations in the mass of the $\alpha_{1B\text{-}1}$ expression plasmid while $\alpha_{2b}$ and $\beta_{1\text{-}2}$ were held constant, indicated that the cell surface expression of ω-CgTx GVIA binding sites per cell was nearly optimal. All subsequent transfections were performed with 3, 11.25 and 0.75 μg or 1.0 μg of $\alpha_{1B\text{-}1}$ or $\alpha_{1B\text{-}2}$, $\alpha_{12b}$ and $\beta_{1\text{-}2}$ or $\beta_{1\text{-}3}$ expression plasmids, respectively.

2. $^{125}$I-ω-CgTx GVIA Binding to Transfected Cells

Statistical analysis of the $K_d$ and $B_{max}$ values was performed using one-way analysis of variance (ANOVA) followed by the Tukey-Kramer test for multiple pairwise comparisons ($p \leqq 0.05$).

Combinations of human voltage-dependent $Ca^{2+}$ channel subunits, $\alpha_{1B\text{-}1}$, $\alpha_{1B\text{-}2}$, $\alpha_{2b}$, $\beta_{1\text{-}2}$ and $\beta_{1\text{-}3}$, were analyzed for saturation binding of $^{125}$I-ω-CgTx GVIA. About 200,000 cells were used per assay, except for the $\alpha_{1B\text{-}1}$, $\alpha_{1B\text{-}2}$, $\alpha_{1B\text{-}1}\alpha_{2b}$ and $\alpha_{1B\text{-}2}\alpha_{2b}$ combinations which were assayed with $1\times10^6$ cells per tube The transfected cells displayed a single-class of saturable, high-affinity binding sites. The values for the dissociation constants ($K_d$) and binding capacities ($B_{max}$) were determined for the different combinations. The results are summarized as follows:

| Subunit Combination | $K_d$ (pM) | $B_{max}$ (sites/cell) |
|---|---|---|
| $\alpha_{1B\text{-}1}\alpha_{2b}\beta_{1\text{-}2}$ | 54.9 ± 11.1 (n = 4) | 45,324 ± 15,606 |
| $\alpha_{1B\text{-}1}\alpha_{2b}\beta_{1\text{-}3}$ | 53.2 ± 3.6 (n = 3) | 91,004 ± 37,654 |
| $\alpha_{1B\text{-}1}\beta_{1\text{-}2}$ | 17.9 ± 1.9 (n = 3) | 5,756 ± 2,163 |
| $\alpha_{1B\text{-}1}\beta_{1\text{-}3}$ | 17.9 ± 1.6 (n = 3) | 8,729 ± 2,980 |
| $\alpha_{1B\text{-}1}\alpha_{2b}$ | 84.6 ± 15.3 (n = 3) | 2,256 ± 356 |
| $\alpha_{1B\text{-}1}$ | 31.7 ± 4.2 (n = 3) | 757 ± 128 |
| $\alpha_{1B\text{-}2}\alpha_{2b}\beta_{1\text{-}2}$ | 53.0 ± 4.8 (n = 3) | 19,371 ± 3,798 |
| $\alpha_{1B\text{-}2}\alpha_{2b}\beta_{1\text{-}3}$ | 44.3 ± 8.1 (n = 3) | 37,652 ± 8,129 |
| $\alpha_{1B\text{-}2}\beta_{1\text{-}2}$ | 16.4 ± 1.2 (n = 3) | 2,126 ± 412 |
| $\alpha_{1B\text{-}2}\beta_{1\text{-}3}$ | 22.2 ± 5.8 (n = 3) | 2,944 ± 1,168 |
| $\alpha_{1B\text{-}2}\alpha_{2b}$ | N.D.* (n = 3) | N.D. |
| $\alpha_{1B\text{-}2}$ | N.D. | N.D. |

*N.D. = not detectable

Cells transfected with subunit combinations lacking either the $\alpha_{1B\text{-}1}$ or the $\alpha_{1B\text{-}2}$ subunit did not exhibit any detectable $^{125}$I-ω-CgTx GVIA binding (≦600 sites/cell). 125I-ω-CgTx GVIA binding to HEK293 cells transfected with $\alpha_{1B\text{-}2}$ alone or $\alpha_{1B\text{-}2}\alpha_{2b}$ was too low for reliable Scatchard analysis of the data. Comparison of the $K_d$ and $B_{max}$ values revealed several relationships between specific combinations of subunits and the binding affinities and capacities of the transfected cells. In cells transfected with all three subunits, ($\alpha_{1B\text{-}1}\alpha_{2b}\beta_{1\text{-}2}$-, $\alpha_{1B\text{-}1}\alpha_{2b}\beta_{1\text{-}3}$-, $\alpha_{1B\text{-}2}\alpha_{2b}\beta_{1\text{-}2}$-, or $\alpha_{1B\text{-}2}\alpha_{2b}\beta_{1\text{-}3}$-transfectants) the $K_d$ values were indistinguishable ($p>0.05$), ranging from 44.3±8.1 pM to 54.9±11.1 pM. In cells transfected, with two-subunit combinations lacking the $\alpha_{2b}$ subunit ($\alpha_{1B\text{-}1}\beta_{1\text{-}2}$, $\alpha_{1B\text{-}1}\beta_{1\text{-}3}$, $\alpha_{1B\text{-}2}\beta_{1\text{-}3}$ or $\alpha_{1B\text{-}2}\beta_{1\text{-}3}$) the $K_d$ values were significantly lower than the three-subunit combinations ($p<0.01$), ranging from 16.4±1.2 to 22.2±5.8 pM. Cells transfected with only the $\alpha_{1B\text{-}1}$ subunit had a $K_d$ value of 31.7±4.2 pM, a value that was not different from the two-subunit combinations lacking $\alpha_{2b}$ ($p<0.05$). As with the comparison between the four $\alpha_{1B}\alpha_{2b}\beta_1$ versus $\alpha_{1B}\beta_1$ combinations, when the $\alpha_{1B\text{-}1}$ was co-expressed with $\alpha_{2b}$, the $K_d$ increased significantly ($p<0.05$) from 31.7±4.2 to 84.6±5.3 pM. These data demonstrate that co-expression of the $\alpha_{2b}$ subunit with $\alpha_{1B\text{-}1}$, $\alpha_{1B\text{-}1}\beta_{1\text{-}2}$, $\alpha_{1B\text{-}1}\beta_{1\text{-}3}$, $\alpha_{1B\text{-}2}\beta_{1\text{-}2}$ or $\alpha_{1B\text{-}2}\beta_{1\text{-}3}$ subunit combinations results in lower binding affinity of the cell surface receptors for $^{125}$I-ω-CgTx GVIA. The $B_{max}$ values of cells transfected with various subunit combinations also differed considerably. Cells transfected with. the $\alpha_{1B\text{-}1}$ subunit alone expressed a low but detectable number of binding sites (approximately 750 binding sites/cell). When the $\alpha_{1B\text{-}1}$ subunit was co-expressed with the $\alpha_{2b}$ subunit, the binding capacity increased approximately three-fold while co-expression of a $\beta_{1\text{-}2}$ or $\beta_{1\text{-}3}$ subunit with $\alpha_{1B\text{-}1}$ resulted in 8- to 10-fold higher expression of surface binding. Cells transfected with all three subunits expressed the highest number of cell surface receptors. The binding capacities of cells transfected with $\alpha_{1B\text{-}1}\alpha_{2b}\beta_{1\text{-}3}$ or $\alpha_{1B\text{-}2}\alpha_{2b}\beta_{1\text{-}3}$ combinations were approximately two-fold higher than the corresponding combinations containing the $\beta_{1\text{-}2}$ subunit. Likewise, cells transfected with $\alpha_{1B\text{-}1}\alpha_{2b}\beta_{1\text{-}2}$ or $\alpha_{1B\text{-}1}\alpha_{2b}\beta_{1\text{-}3}$ combinations .expressed approximately 2.5-fold more binding sites per cell than the corresponding combinations containing $\alpha_{1B\text{-}2}$. In all cases, co-expression of the $\alpha_{2b}$ subunit with $\alpha_{1B}$ and $\beta_1$ increased the surface receptor density compared to cells transfected with only the corresponding $\alpha_{1B}$ and $\beta_1$ combinations; approximately 8-fold for $\alpha_{1B\text{-}1}\alpha_{2b}\beta_{1\text{-}2}$, 10-fold for $\alpha_{1B\text{-}1}\alpha_{2b}\beta_{1\text{-}3}$, 9-fold for $\alpha_{1B\text{-}2}\alpha_{2b}\beta_{1\text{-}2}$, and 13-fold for $\alpha_{1B\text{-}2}\alpha_{2b}\beta_{1\text{-}3}$. Thus, comparison of the $B_{max}$ values suggests that the toxin-binding subunit, $\alpha_{1B\text{-}1}$ or $\alpha_{1B\text{-}2}$, is more efficiently expressed and assembled on the cell surface when co-expressed with either the $\alpha_{2b}$ or the $\beta_{1-2}$ or $\beta_{1-3}$ subunit, and most efficiently expressed when $\alpha_{2b}$ and $\beta_1$ subunits are present.

3. Electrophysiology

Functional expression of $\alpha_{1B-1}\alpha_{2b}\beta_{1-2}$ and $\alpha_{1B-1}\beta_{1-2}$ subunit combinations was evaluated using the whole-cell recording technique. Transfected cells that had no contacts with surrounding cells and simple morphology were used approximately 48 hours after transfection for recording. The pipette solution was (in mM) 135 CsCl, 10 EGTA, 1 $MgCl_2$, 10 HEPES, and 4 mM Mg-ATP (pH 7.3, adjusted with TEA-OH). The external solution was (in mM) 15 $BaCl_2$, 125 Choline Cl, 1 $MgCl_2$, and 10 HEPES (pH 7.3, adjusted with TEA-OH). ω-CgTx GVIA (Bachem) was prepared in the external solution with 0.1% cytochrome C (Sigma) to serve as a carrier. Control experiments showed that cytochrome C had no effect on the $Ba^{2+}$ current.

The macroscopic electrophysiological properties of $Ba^{2+}$ currents in cells transfected with various amounts of the $\alpha_{2b}$ expression plasmid with the relative amounts of $\alpha_{1B-1}$ and $\beta_{1-2}$ plasmids held constant were examined. The amplitudes and densities of the $Ba^{2+}$ currents (15 mM $BaCl_2$) recorded from whole cells of these transfectants differed dramatically. The average currents from 7 to 11 cells of three types of transfections (no $\alpha_{2b}$; 2:1.8:1 [$\alpha_{1B-1}$:$\alpha_{2b}$:$\beta_{1-2}$] molar ratio; and 2:10.9:1 [$\alpha_{1B-1}$:$\alpha_{2b}$:$\beta_{1-2}$] molar ratio) were determined. The smallest currents (range: 10 to 205 pA) were recorded when $\alpha_{2b}$ was not included in the transfection, and the largest currents (range: 50 to 8300 pA) were recorded with the 2:10.9:1 ratio of $\alpha_{1B-1}\alpha_{2b}\beta_{1-2}$ plasmids, the ratio that resulted in near equivalent mRNA levels for each subunit transcript. When the amount of $\alpha_{2b}$ plasmid was adjusted to yield approximately an equal abundance of subunit mRNAs, the average peak $Ba^{2+}$ current increased from 433 pA to 1,824 pA (4.2-fold) with a corresponding increase in average current density from 26 pA/pF to 127 pA/pF (4.9-fold). This increase is in the presence of a 2.7-fold decrease in the mass of $\alpha_{1B-1}$ and $\beta_{1-2}$ expression plasmids in the transfections. In all transfections, the magnitudes of the $Ba^{2+}$ currents did not follow a normal distribution.

To compare the subunit combinations and determine the effects of $\alpha_{2b}$ the current-voltage properties of cells transfected with $\alpha_{1B-1}\beta_{1-2}$ or with $\alpha_{1B-1}\alpha_{2b}\beta_{1-2}$ in either the 2:1.8:1 ($\alpha_{1B-1}$:$\alpha_{2b}$:$\beta_{1-2}$) molar ratio or the 2:10.9:1 ($\alpha_{1B-1}$:$\alpha_{2b}$:$\beta_{1-2}$) molar ratio transfectants were examined. The extreme examples of no $\alpha_{2b}$ and 11.25 μg $\alpha_{2b}$ (2:10.9:1 molar ratio) showed no significant differences in the current voltage plot at test potentials between 0 mV and +40 mV ($p<0.05$). The slight differences observed at either side of the peak region of the current voltage plot were likely due to normalization. The very small currents observed in the $\alpha_{1B-1}\beta_{1-2}$ transfected cells have a substantially higher component of residual leak relative to the barium current that is activated by the test pulse. When the current voltage plots are normalized, this leak is a much greater component than in the $\alpha_{1B-1}\alpha_{2b}\beta_{1-2}$ transfected cells and as a result, the current-voltage plot appears broader. This is the most likely explanation of the apparent differences in the current voltage plots, especially given the fact that the current-voltage plot for the $\alpha_{1B-1}\beta_{1-2}$ transfected cells diverge on both sides of the peak. Typically, when the voltage-dependence activation is shifted, the entire current-voltage plot is shifted, which was not observed. To qualitatively compare the kinetics of each, the average responses of test pulses from −90 mV to 10 mV were normalized and plotted. No significant differences in activation or inactivation kinetics of whole-cell $Ba^{2+}$ currents were observed with any combination.

G. Expression of DNA Encoding Human Neuronal Calcium Channel $\alpha_{1E-3}\alpha_{2b}\beta_{1-3}$ and $\alpha_{1E-1}\alpha_{2b}\beta_{1-3}$ Subunits in HEK Cells Functional expression of the $\alpha_{1E-1}\alpha_{2b}\beta_{1-3}$ and $\alpha_{1E-3}\alpha_{2b}\beta_{1-3}$, as well as $\alpha_{1E-3}$ was evaluated using the whole cell recording technique.

1. Methods

Recordings were performed on transiently transfected HEK 293 cells, which had no contacts with surrounding cells and which had simple morphology, two days following the transfection. The internal solution used to fill pipettes for recording the barium current from the transfected recombinant calcium channels was (in mM) 135 CsCl, 10 EGTA, 1 $MgCl_2$, 10 HEPES, and 4 mM Mg-ATP (pH 7.4-7.5, adjusted with TEA-OH). The external solution for recording the barium current was (in mM) 15 $BaCl_2$, 150 Choline Cl, 1 $MgCl_2$, and 10 HEPES and 5 TEA-OH (pH 7.3, adjusted with TEA-OH). In experiments in which $Ca^{2+}$ was replaced for $Ba^{2+}$, a Laminar flow chamber was used in order to completely exchange the extracellular solution and prevent any mixing of $Ba^{2+}$ and $Ca^{2+}$. ω-CgTx GVIA was prepared in the external solution with 0.1% cytochrome C to serve as a carrier, the toxin was applied by pressurized puffer pipette. Series resistance was compensated 70-85% and currents were analyzed only if the voltage error from series resistance was less than 5 mV. Leak resistance and capacitance was corrected by subtracting the scaled current observed with the P/−4 protocol as implemented by pClamp (Axon Instruments).

2. Electrophysiology Results

Cells transfected with $\alpha_{1E-1}\alpha_{2b}\beta_{1-3}$ or $\alpha_{1E-3}\alpha_{2b}\beta_{1-3}$ showed strong barium currents with whole cell patch clamp recordings. Cells expressing $\alpha_{1E-3}\alpha_{2b}\beta_{1-3}$ had larger peak currents than those expressing $\alpha_{1E-1}\alpha_{2b}\beta_{1-3}$. In addition, the kinetics of activation and inactivation are clearly substantially faster in the cells expressing $\alpha_{1E}$ calcium channels. HEK 293 cells expressing $\alpha_{1E-3}$ alone have a significant degree of functional calcium channels, with properties similar to those expressing $\alpha_{1E-1}\alpha_{2b}\beta_{1-3}$ but with substantially smaller peak barium currents. Thus, with $\alpha_{1E}$, the $\alpha_2$ and $\beta_1$ subunits are not required for functional expression of $\alpha_{1E}$ mediated calcium channels, but do substantially increase the number of functional calcium channels.

Examination of the current voltage properties of $\alpha_{1E}\alpha_{2b}\beta_{1-3}$ expressing cells indicates that $\alpha_{1E-3}\alpha_{2b}\beta_{1-3}$ is a high-voltage activated calcium channel and the peak current is reached at a potential only slightly less positive than other neuronal calcium channels also expressing $\alpha_{2b}$ and $\beta_1$, and $\alpha_{1B}$ and $\alpha_{1D}$. Current voltage properties of $\alpha_{1E-1}\alpha_{2b}\beta_{1-3}$ and $\alpha_{1E-3}\alpha_{2b}\beta_{1-3}$ are statistically different from those of $\alpha_{1E-1}\alpha_{2b}\beta_{1-3}$. Current voltage curves for $\alpha_{1E-1}\alpha_{2b}\beta_{1-3}$ and $\alpha_{1E-1}\alpha_{2b}\beta_{1-3}$ peak at approximately +5 mV, as does the current voltage curve for $\alpha_{1E-3}$ alone.

The kinetics and voltage dependence of inactivation using both prepulse (200 ms) and steady-state inactivation was examined. $\alpha_{1E}$ mediated calcium channels are rapidly inactivated relative to previously cloned calcium channels and other high voltage-activated calcium channels. $\alpha_{1E-3}\alpha_{2b}\beta_{1-3}$ mediated calcium channels are inactivated rapidly and are thus sensitive to relatively brief (200 ms) prepulses as well as long prepulses (>20s steady state inactivation), but recover rapidly from steady state inactivation. The kinetics of the rapid inactivation has two components, one with a time constant of approximately 25 ms and the other approximately 400 ms.

To determine whether $\alpha_{1E}$ mediated calcium channels have properties of low voltage activated calcium channels, the details of tail currents activated by a test pulse ranging −60 to +90 mV were measured at −60 mV. Tail currents recorded at −60 mV could be well fit by a single exponential of 150 to 300 μs; at least an order of magnitude faster than those typically observed with low voltage-activated calcium channels.

HEK 293 cells expressing $\alpha_{1E-3}\alpha_{2b}\beta_{1-3}$ flux more current with $Ba^{2+}$ as the charge carrier and currents carried by $Ba^{2+}$ and $Ca^{2+}$ have different current-voltage properties. Furthermore, the time course of inactivation is slower and the amount of prepulse inactivation less with $Ca^{2+}$ as the charge carrier.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. An isolated and substantially purified human calcium channel subunit designated $\alpha_{1E\text{-}3}$ comprising the amino acid sequence as set forth in SEQ ID NO:40.

2. An isolated and substantially purified human calcium channel subunit designated $\alpha_{1E\text{-}3}$ encoded by the nucleotide sequence as set forth in SEQ ID NO:39.

* * * * *

SEQUENCE LISTING

```
<160> NUMBER OF SEQ ID NOS: 65

<210> SEQ ID NO 1
<211> LENGTH: 7635
<212> TYPE: DNA
<213> ORGANISM: Human

<400> SEQUENCE: 1

gggcgagcgc ctccgtcccc ggatgtgagc tccggctgcc cgcggtcccg agccagcggc     60

gcgcgggcgg cggcggcggg caccgggcac cgcggcgggc gggcagacgg gcgggcatgg    120

ggggagcgcc gagcggcccc ggcggccggg ccggcatcac cgcggcgtct ctccgctaga    180

ggaggggaca agccagttct cctttgcagc aaaaaattac atgtatatat tattaagata    240

atatatacat tggattttat ttttttaaaa agtttatttt gctccatttt tgaaaaagag    300

agagcttggg tggcgagcgg ttttttttta aaatcaatta tccttatttt ctgttatttg    360

tccccgtccc tccccacccc cctgctgaag cgagaataag ggcagggacc gcggctccta    420

cctcttggtg atccccttcc ccattccgcc cccgccccaa cgcccagcac agtgccctgc    480

acacagtagt cgctcaataa atgttcgtgg atgatgatga tgatgatgat gaaaaaaatg    540

cagcatcaac ggcagcagca agcggaccac gcgaacgagg caaactatgc aagaggcacc    600

agacttcctc tttctggtga aggaccaact tctcagccga atagctccaa gcaaactgtc    660

ctgtcttggc aagctgcaat cgatgctgct agacaggcca aggctgccca aactatgagc    720

acctctgcac ccccacctgt aggatctctc tcccaaagaa aacgtcagca atacgccaag    780

agcaaaaaac agggtaactc gtccaacagc cgacctgccc gcgccctttt ctgtttatca    840

ctcaataacc ccatccgaag agcctgcatt agtatagtgg aatggaaacc atttgacata    900

tttatattat tggctatttt tgccaattgt gtggccttag ctatttacat cccattccct    960

gaagatgatt ctaattcaac aaatcataac ttggaaaaag tagaatatgc cttcctgatt   1020

atttttacag tcgagacatt tttgaagatt atagcgtatg gattattgct acatcctaat   1080

gcttatgtta ggaatggatg gaatttactg gattttgtta tagtaatagt aggattgttt   1140

agtgtaattt tggaacaatt aaccaaagaa acagaaggcg ggaaccactc aagcggcaaa   1200

tctggaggct ttgatgtcaa agccctccgt gcctttcgag tgttgcgacc acttcgacta   1260

gtgtcaggag tgcccagttt acaagttgtc ctgaactcca ttataaaagc catggttccc   1320

ctccttcaca tagccctttt ggtattattt gtaatcataa tctatgctat tataggattg   1380

gaacttttta ttggaaaaat gcacaaaaca tgttttttttg ctgactcaga tatcgtagct   1440

gaagaggacc cagctccatg tgcgttctca gggaatggac gccagtgtac tgccaatggc   1500

acggaatgta ggagtggctg ggttggcccg aacggaggca tcaccaactt tgataacttt   1560

gcctttgcca tgcttactgt gtttcagtgc atcaccatgg agggctggac agacgtgctc   1620

tactggatga atgatgctat gggatttgaa ttgccctggg tgtattttgt cagtctcgtc   1680
```

-continued

```
atctttgggt catttttcgt actaaatctt gtacttggtg tattgagcgg agaattctca   1740
aaggaaagag agaaggcaaa agcacgggga gatttccaga agctccggga gaagcagcag   1800
ctggaggagg atctaaaggg ctacttggat tggatcaccc aagctgagga catcgatccg   1860
gagaatgagg aagaaggagg agaggaaggc aaacgaaata ctagcatgcc caccagcgag   1920
actgagtctg tgaacacaga gaacgtcagc ggtgaaggcg agaaccgagg ctgctgtgga   1980
agtctctgtc aagccatctc aaaatccaaa ctcagccgac gctggcgtcg ctggaaccga   2040
ttcaatcgca gaagatgtag ggccgccgtg aagtctgtca cgttttactg gctggttatc   2100
gtcctggtgt ttctgaacac cttaaccatt tcctctgagc actacaatca gccagattgg   2160
ttgacacaga ttcaagatat tgccaacaaa gtcctcttgg ctctgttcac ctgcgagatg   2220
ctggtaaaaa tgtacagctt gggcctccaa gcatatttcg tctctctttt caaccggttt   2280
gattgcttcg tggtgtgtgg tggaatcact gagacgatct tggtggaact ggaaatcatg   2340
tctcccctgg ggatctctgt gtttcggtgt gtgcgcctct taagaatctt caaagtgacc   2400
aggcactgga cttccctgag caacttagtg gcatccttat taaactccat gaagtccatc   2460
gcttcgctgt tgcttctgct tttctcttc attatcatct tttccttgct tgggatgcag    2520
ctgtttggcg gcaagtttaa ttttgatgaa acgcaaacca agcggagcac ctttgacaat   2580
ttccctcaag cacttctcac agtgttccag atcctgacag gcgaagactg gaatgctgtg   2640
atgtacgatg gcatcatggc ttacgggggc ccatcctctt caggaatgat cgtctgcatc   2700
tacttcatca tcctcttcat ttgtggtaac tatattctac tgaatgtctt cttggccatc   2760
gctgtagaca atttggctga tgctgaaagt ctgaacactg ctcagaaaga agaagcggaa   2820
gaaaaggaga ggaaaaagat tgccagaaaa gagagcctag aaaataaaaa gaacaacaaa   2880
ccagaagtca accagatagc caacagtgac aacaaggtta caattgatga ctatagagaa   2940
gaggatgaag acaaggaccc ctatccgcct tgcgatgtgc cagtagggga agaggaagag   3000
gaagaggagg aggatgaacc tgaggttcct gccggacccc gtcctcgaag gatctcggag   3060
ttgaacatga aggaaaaaat tgcccccatc cctgaaggga gcgctttctt cattcttagc   3120
aagaccaacc cgatccgcgt aggctgccac aagctcatca accaccacat cttcaccaac   3180
ctcatccttg tcttcatcat gctgagcagt gctgccctgg ccgcagagga ccccatccgc   3240
agccactcct tccggaacac gatactgggt tactttgact atgccttcac agccatcttt   3300
actgttgaga tcctgttgaa gatgacaact tttggagctt tcctccacaa aggggccttc   3360
tgcaggaact acttcaattt gctggatatg ctggtggttg gggtgtctct ggtgtcattt   3420
gggattcaat ccagtgccat ctccgttgtg aagattctga gggtcttaag ggtcctgcgt   3480
cccctcaggg ccatcaacag agcaaaagga cttaagcacg tggtccagtg cgtcttcgtg   3540
gccatccgga ccatcggcaa catcatgatc gtcaccaccc tcctgcagtt catgtttgcc   3600
tgtatcgggg tccagttgtt caaggggaag ttctatcgct gtacggatga agccaaaagt   3660
aaccctgaag aatgcagggg acttttcatc ctctacaagg atggggatgt tgacagtcct   3720
gtggtccgtg aacggatctg gcaaaacagt gatttcaact tcgacaacgt cctctctgct   3780
atgatggcgc tcttcacagt ctccacgttt gagggctggc ctgcgttgct gtataaagcc   3840
atcgactcga atggagagaa catcggccca atctacaacc accgcgtgga gatctccatc   3900
ttcttcatca tctacatcat cattgtagct ttcttcatga tgaacatctt tgtgggcttt   3960
gtcatcgtta catttcagga acaaggagaa aaagagtata agaactgtga gctggacaaa   4020
```

-continued aatcagcgtc agtgtgttga atacgccttg aaagcacgtc ccttgcggag atacatcccc 4080
aaaaacccct accagtacaa gttctggtac gtggtgaact cttcgccttt cgaatacatg 4140
atgtttgtcc tcatcatgct caacacactc tgcttggcca tgcagcacta cgagcagtcc 4200
aagatgttca atgatgccat ggacattctg aacatggtct tcaccggggt gttcaccgtc 4260
gagatggttt tgaaagtcat cgcatttaag cctaaggggt attttagtga cgcctggaac 4320
acgtttgact ccctcatcgt aatcggcagc attatagacg tggccctcag cgaagcagac 4380
ccaactgaaa gtgaaaatgt ccctgtccca actgctacac ctgggaactc tgaagagagc 4440
aatagaatct ccatcacctt tttccgtctt ttccgagtga tgcgattggt gaagcttctc 4500
agcagggggg aaggcatccg gacattgctg tggactttta ttaagttctt tcaggcgctc 4560
ccgtatgtgg ccctcctcat agccatgctg ttcttcatct atgcggtcat tggcatgcag 4620
atgtttggga aagttgccat gagagataac aaccagatca ataggaacaa taacttccag 4680
acgtttcccc aggcggtgct gctgctcttc aggtgtgcaa caggtgaggc ctggcaggag 4740
atcatgctgg cctgtctccc agggaagctc tgtgaccctg agtcagatta caaccccggg 4800
gaggagcata catgtgggag caactttgcc attgtctatt tcatcagttt ttacatgctc 4860
tgtgcatttc tgatcatcaa tctgtttgtg gctgtcatca tggataattt cgactatctg 4920
acccgggact ggtctatttt ggggcctcac catttagatg aattcaaaag aatatggtca 4980
gaatatgacc ctgaggcaaa gggaaggata aaacaccttg atgtggtcac tctgcttcga 5040
cgcatccagc ctcccctggg gtttgggaag ttatgtccac acagggtagc gtgcaagaga 5100
ttagttgcca tgaacatgcc tctcaacagt gacgggacag tcatgtttaa tgcaaccctg 5160
tttgctttgg ttcgaacggc tcttaagatc aagaccgaag ggaacctgga gcaagctaat 5220
gaagaacttc gggctgtgat aaagaaaatt tggaagaaaa ccagcatgaa attacttgac 5280
caagttgtcc ctccagctgg tgatgatgag gtaaccgtgg ggaagttcta tgccactttc 5340
ctgatacagg actactttag gaaattcaag aaacggaaag aacaaggact ggtgggaaag 5400
taccctgcga agaacaccac aattgcccta caggcgggat taaggacact gcatgacatt 5460
gggccagaaa tccggcgtgc tatatcgtgt gatttgcaag atgacgagcc tgaggaaaca 5520
aaacgagaag aagaagatga tgtgttcaaa agaaatggtg ccctgcttgg aaaccatgtc 5580
aatcatgtta atagtgatag gagagattcc cttcagcaga ccaataccac ccaccgtccc 5640
ctgcatgtcc aaaggccttc aattccacct gcaagtgata ctgagaaacc gctgtttcct 5700
ccagcaggaa attcggtgtg tcataaccat cataaccata attccatagg aaagcaagtt 5760
cccacctcaa caaatgccaa tctcaataat gccaatatgt ccaaagctgc ccatggaaag 5820
cggcccagca ttgggaacct tgagcatgtg tctgaaaatg ggcatcattc ttcccacaag 5880
catgaccggg agcctcagag aaggtccagt gtgaaaagaa cccgctatta tgaaacttac 5940
attaggtccg actcaggaga tgaacagctc ccaactattt gccgggaaga cccagagata 6000
catggctatt tcagggaccc ccactgcttg ggggagcagg agtatttcag tagtgaggaa 6060
tgctacgagg atgacagctc gcccacctgg agcaggcaaa actatggcta ctacagcaga 6120
tacccaggca gaaacatcga ctctgagagg ccccgaggct accatcatcc ccaaggattc 6180
ttggaggacg atgactcgcc cgtttgctat gattcacgga gatctccaag gagacgccta 6240
ctacctccca ccccagcatc ccaccggaga tcctccttca actttgagtg cctgcgccgg 6300
cagagcagcc aggaagaggt cccgtcgtct cccatcttcc cccatcgcac ggccctgcct 6360
ctgcatctaa tgcagcaaca gatcatggca gttgccggcc tagattcaag taaagcccag 6420

-continued aagtactcac cgagtcactc gacccggtcg tgggccaccc ctccagcaac ccctccctac 6480
cgggactgga caccgtgcta caccccccctg atccaagtgg agcagtcaga ggccctggac 6540
caggtgaacg gcagcctgcc gtccctgcac cgcagctcct ggtacacaga cgagcccgac 6600
atctcctacc ggactttcac accagccagc ctgactgtcc ccagcagctt ccggaacaaa 6660
aacagcgaca agcagaggag tgcggacagc ttggtggagg cagtcctgat atccgaaggc 6720
ttgggacgct atgcaaggga cccaaaattt gtgtcagcaa caaaacacga aatcgctgat 6780
gcctgtgacc tcaccatcga cgagatggag agtgcagcca gcaccctgct taatgggaac 6840
gtgcgtcccc gagccaacgg ggatgtgggc cccctctcac accggcagga ctatgagcta 6900
caggactttg gtcctggcta cagcgacgaa gagccagacc ctgggaggga tgaggaggac 6960
ctggcggatg aaatgatatg catcaccacc ttgtagcccc cagcgagggg cagactggct 7020
ctggcctcag gtggggcgca ggagagccag gggaaaagtg cctcatagtt aggaaagttt 7080
aggcactagt tgggagtaat attcaattaa ttagactttt gtataagaga tgtcatgcct 7140
caagaaagcc ataaacctgg taggaacagg tcccaagcgg ttgagcctgg cagagtacca 7200
tgcgctcggc cccagctgca ggaaacagca ggccccgccc tctcacagag gatgggtgag 7260
gaggccagac ctgccctgcc ccattgtcca gatgggcact gctgtggagt ctgcttctcc 7320
catgtaccag ggcaccaggc ccacccaact gaaggcatgg cggcggggtg caggggaaag 7380
ttaaaggtga tgacgatcat cacacctgtg tcgttacctc agccatcggt ctagcatatc 7440
agtcactggg cccaacatat ccatttttaa accctttccc ccaaatacac tgcgtcctgg 7500
ttcctgttta gctgttctga aatacggtgt gtaagtaagt cagaacccag ctaccagtga 7560
ttattgcgag ggcaatggga cctcataaat aaggttttct gtgatgtgac gccagtttac 7620
ataagagaat atcac 7635

<210> SEQ ID NO 2
<211> LENGTH: 2161
<212> TYPE: PRT
<213> ORGANISM: Human

<400> SEQUENCE: 2

Met Met Met Met Met Met Met Lys Lys Met Gln His Gln Arg Gln Gln
1 5 10 15

Gln Ala Asp His Ala Asn Glu Ala Asn Tyr Ala Arg Gly Thr Arg Leu
20 25 30

Pro Leu Ser Gly Glu Gly Pro Thr Ser Gln Pro Asn Ser Ser Lys Gln
35 40 45

Thr Val Leu Ser Trp Gln Ala Ala Ile Asp Ala Ala Arg Gln Ala Lys
50 55 60

Ala Ala Gln Thr Met Ser Thr Ser Ala Pro Pro Pro Val Gly Ser Leu
65 70 75 80

Ser Gln Arg Lys Arg Gln Gln Tyr Ala Lys Ser Lys Lys Gln Gly Asn
85 90 95

Ser Ser Asn Ser Arg Pro Ala Arg Ala Leu Phe Cys Leu Ser Leu Asn
100 105 110

Asn Pro Ile Arg Arg Ala Cys Ile Ser Ile Val Glu Trp Lys Pro Phe
115 120 125

Asp Ile Phe Ile Leu Leu Ala Ile Phe Ala Asn Cys Val Ala Leu Ala
130 135 140

Ile Tyr Ile Pro Phe Pro Glu Asp Asp Ser Asn Ser Thr Asn His Asn

-continued

```
145                 150                 155                 160

Leu Glu Lys Val Glu Tyr Ala Phe Leu Ile Ile Phe Thr Val Glu Thr
            165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
            245                 250                 255

Leu Gln Val Val Leu Asn Ser Ile Ile Lys Ala Met Val Pro Leu Leu
            260                 265                 270

His Ile Ala Leu Leu Val Leu Phe Val Ile Ile Ile Tyr Ala Ile Ile
        275                 280                 285

Gly Leu Glu Leu Phe Ile Gly Lys Met His Lys Thr Cys Phe Phe Ala
    290                 295                 300

Asp Ser Asp Ile Val Ala Glu Glu Asp Pro Ala Pro Cys Ala Phe Ser
305                 310                 315                 320

Gly Asn Gly Arg Gln Cys Thr Ala Asn Gly Thr Glu Cys Arg Ser Gly
            325                 330                 335

Trp Val Gly Pro Asn Gly Gly Ile Thr Asn Phe Asp Asn Phe Ala Phe
            340                 345                 350

Ala Met Leu Thr Val Phe Gln Cys Ile Thr Met Glu Gly Trp Thr Asp
        355                 360                 365

Val Leu Tyr Trp Met Asn Asp Ala Met Gly Phe Glu Leu Pro Trp Val
    370                 375                 380

Tyr Phe Val Ser Leu Val Ile Phe Gly Ser Phe Phe Val Leu Asn Leu
385                 390                 395                 400

Val Leu Gly Val Leu Ser Gly Glu Phe Ser Lys Glu Arg Glu Lys Ala
            405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
        435                 440                 445

Asp Pro Glu Asn Glu Glu Glu Gly Gly Glu Glu Gly Lys Arg Asn Thr
    450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Cys Gln Ala Ile
            485                 490                 495

Ser Lys Ser Lys Leu Ser Arg Arg Trp Arg Arg Trp Asn Arg Phe Asn
            500                 505                 510

Arg Arg Arg Cys Arg Ala Ala Val Lys Ser Val Thr Phe Tyr Trp Leu
        515                 520                 525

Val Ile Val Leu Val Phe Leu Asn Thr Leu Thr Ile Ser Ser Glu His
    530                 535                 540

Tyr Asn Gln Pro Asp Trp Leu Thr Gln Ile Gln Asp Ile Ala Asn Lys
545                 550                 555                 560

Val Leu Leu Ala Leu Phe Thr Cys Glu Met Leu Val Lys Met Tyr Ser
            565                 570                 575
```

-continued

```
Leu Gly Leu Gln Ala Tyr Phe Val Ser Leu Phe Asn Arg Phe Asp Cys
            580                 585                 590

Phe Val Val Cys Gly Gly Ile Thr Glu Thr Ile Leu Val Glu Leu Glu
        595                 600                 605

Ile Met Ser Pro Leu Gly Ile Ser Val Phe Arg Cys Val Arg Leu Leu
    610                 615                 620

Arg Ile Phe Lys Val Thr Arg His Trp Thr Ser Leu Ser Asn Leu Val
625                 630                 635                 640

Ala Ser Leu Leu Asn Ser Met Lys Ser Ile Ala Ser Leu Leu Leu Leu
                645                 650                 655

Leu Phe Leu Phe Ile Ile Ile Phe Ser Leu Leu Gly Met Gln Leu Phe
            660                 665                 670

Gly Gly Lys Phe Asn Phe Asp Glu Thr Gln Thr Lys Arg Ser Thr Phe
        675                 680                 685

Asp Asn Phe Pro Gln Ala Leu Leu Thr Val Phe Gln Ile Leu Thr Gly
    690                 695                 700

Glu Asp Trp Asn Ala Val Met Tyr Asp Gly Ile Met Ala Tyr Gly Gly
705                 710                 715                 720

Pro Ser Ser Ser Gly Met Ile Val Cys Ile Tyr Phe Ile Ile Leu Phe
                725                 730                 735

Ile Cys Gly Asn Tyr Ile Leu Leu Asn Val Phe Leu Ala Ile Ala Val
            740                 745                 750

Asp Asn Leu Ala Asp Ala Glu Ser Leu Asn Thr Ala Gln Lys Glu Glu
        755                 760                 765

Ala Glu Glu Lys Glu Arg Lys Lys Ile Ala Arg Lys Glu Ser Leu Glu
    770                 775                 780

Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
            820                 825                 830

Glu Glu Asp Glu Pro Glu Val Pro Ala Gly Pro Arg Pro Arg Arg Ile
        835                 840                 845

Ser Glu Leu Asn Met Lys Glu Lys Ile Ala Pro Ile Pro Glu Gly Ser
    850                 855                 860

Ala Phe Phe Ile Leu Ser Lys Thr Asn Pro Ile Arg Val Gly Cys His
865                 870                 875                 880

Lys Leu Ile Asn His His Ile Phe Thr Asn Leu Ile Leu Val Phe Ile
                885                 890                 895

Met Leu Ser Ser Ala Ala Leu Ala Ala Glu Asp Pro Ile Arg Ser His
            900                 905                 910

Ser Phe Arg Asn Thr Ile Leu Gly Tyr Phe Asp Tyr Ala Phe Thr Ala
        915                 920                 925

Ile Phe Thr Val Glu Ile Leu Leu Lys Met Thr Thr Phe Gly Ala Phe
    930                 935                 940

Leu His Lys Gly Ala Phe Cys Arg Asn Tyr Phe Asn Leu Leu Asp Met
945                 950                 955                 960

Leu Val Val Gly Val Ser Leu Val Ser Phe Gly Ile Gln Ser Ser Ala
                965                 970                 975

Ile Ser Val Val Lys Ile Leu Arg Val Leu Arg Val Leu Arg Pro Leu
            980                 985                 990
```

-continued

```
Arg Ala Ile Asn Arg Ala Lys Gly Leu Lys His Val Val Gln Cys Val
        995                 1000                1005

Phe Val Ala Ile Arg Thr Ile Gly Asn Ile Met Ile Val Thr Thr Leu
    1010                1015                1020

Leu Gln Phe Met Phe Ala Cys Ile Gly Val Gln Leu Phe Lys Gly Lys
1025                1030                1035                1040

Phe Tyr Arg Cys Thr Asp Glu Ala Lys Ser Asn Pro Glu Glu Cys Arg
                1045                1050                1055

Gly Leu Phe Ile Leu Tyr Lys Asp Gly Asp Val Asp Ser Pro Val Val
            1060                1065                1070

Arg Glu Arg Ile Trp Gln Asn Ser Asp Phe Asn Phe Asp Asn Val Leu
        1075                1080                1085

Ser Ala Met Met Ala Leu Phe Thr Val Ser Thr Phe Glu Gly Trp Pro
    1090                1095                1100

Ala Leu Leu Tyr Lys Ala Ile Asp Ser Asn Gly Glu Asn Ile Gly Pro
1105                1110                1115                1120

Ile Tyr Asn His Arg Val Glu Ile Ser Ile Phe Phe Ile Ile Tyr Ile
                1125                1130                1135

Ile Ile Val Ala Phe Phe Met Met Asn Ile Phe Val Gly Phe Val Ile
            1140                1145                1150

Val Thr Phe Gln Glu Gln Gly Glu Lys Glu Tyr Lys Asn Cys Glu Leu
        1155                1160                1165

Asp Lys Asn Gln Arg Gln Cys Val Glu Tyr Ala Leu Lys Ala Arg Pro
    1170                1175                1180

Leu Arg Arg Tyr Ile Pro Lys Asn Pro Tyr Gln Tyr Lys Phe Trp Tyr
1185                1190                1195                1200

Val Val Asn Ser Ser Pro Phe Glu Tyr Met Met Phe Val Leu Ile Met
                1205                1210                1215

Leu Asn Thr Leu Cys Leu Ala Met Gln His Tyr Glu Gln Ser Lys Met
            1220                1225                1230

Phe Asn Asp Ala Met Asp Ile Leu Asn Met Val Phe Thr Gly Val Phe
        1235                1240                1245

Thr Val Glu Met Val Leu Lys Val Ile Ala Phe Lys Pro Lys Gly Tyr
    1250                1255                1260

Phe Ser Asp Ala Trp Asn Thr Phe Asp Ser Leu Ile Val Ile Gly Ser
1265                1270                1275                1280

Ile Ile Asp Val Ala Leu Ser Glu Ala Asp Pro Thr Glu Ser Glu Asn
                1285                1290                1295

Val Pro Val Pro Thr Ala Thr Pro Gly Asn Ser Glu Glu Ser Asn Arg
            1300                1305                1310

Ile Ser Ile Thr Phe Phe Arg Leu Phe Arg Val Met Arg Leu Val Lys
        1315                1320                1325

Leu Leu Ser Arg Gly Glu Gly Ile Arg Thr Leu Leu Trp Thr Phe Ile
    1330                1335                1340

Lys Phe Phe Gln Ala Leu Pro Tyr Val Ala Leu Leu Ile Ala Met Leu
1345                1350                1355                1360

Phe Phe Ile Tyr Ala Val Ile Gly Met Gln Met Phe Gly Lys Val Ala
                1365                1370                1375

Met Arg Asp Asn Asn Gln Ile Asn Arg Asn Asn Asn Phe Gln Thr Phe
            1380                1385                1390

Pro Gln Ala Val Leu Leu Leu Phe Arg Cys Ala Thr Gly Glu Ala Trp
        1395                1400                1405

Gln Glu Ile Met Leu Ala Cys Leu Pro Gly Lys Leu Cys Asp Pro Glu
```

-continued 1410 1415 1420

Ser Asp Tyr Asn Pro Gly Glu Glu His Thr Cys Gly Ser Asn Phe Ala
1425 1430 1435 1440

Ile Val Tyr Phe Ile Ser Phe Tyr Met Leu Cys Ala Phe Leu Ile Ile
1445 1450 1455

Asn Leu Phe Val Ala Val Ile Met Asp Asn Phe Asp Tyr Leu Thr Arg
1460 1465 1470

Asp Trp Ser Ile Leu Gly Pro His His Leu Asp Glu Phe Lys Arg Ile
1475 1480 1485

Trp Ser Glu Tyr Asp Pro Glu Ala Lys Gly Arg Ile Lys His Leu Asp
1490 1495 1500

Val Val Thr Leu Leu Arg Arg Ile Gln Pro Pro Leu Gly Phe Gly Lys
1505 1510 1515 1520

Leu Cys Pro His Arg Val Ala Cys Lys Arg Leu Val Ala Met Asn Met
1525 1530 1535

Pro Leu Asn Ser Asp Gly Thr Val Met Phe Asn Ala Thr Leu Phe Ala
1540 1545 1550

Leu Val Arg Thr Ala Leu Lys Ile Lys Thr Glu Gly Asn Leu Glu Gln
1555 1560 1565

Ala Asn Glu Glu Leu Arg Ala Val Ile Lys Lys Ile Trp Lys Lys Thr
1570 1575 1580

Ser Met Lys Leu Leu Asp Gln Val Val Pro Pro Ala Gly Asp Asp Glu
1585 1590 1595 1600

Val Thr Val Gly Lys Phe Tyr Ala Thr Phe Leu Ile Gln Asp Tyr Phe
1605 1610 1615

Arg Lys Phe Lys Lys Arg Lys Glu Gln Gly Leu Val Gly Lys Tyr Pro
1620 1625 1630

Ala Lys Asn Thr Thr Ile Ala Leu Gln Ala Gly Leu Arg Thr Leu His
1635 1640 1645

Asp Ile Gly Pro Glu Ile Arg Arg Ala Ile Ser Cys Asp Leu Gln Asp
1650 1655 1660

Asp Glu Pro Glu Glu Thr Lys Arg Glu Glu Glu Asp Asp Val Phe Lys
1665 1670 1675 1680

Arg Asn Gly Ala Leu Leu Gly Asn His Val Asn His Val Asn Ser Asp
1685 1690 1695

Arg Arg Asp Ser Leu Gln Gln Thr Asn Thr Thr His Arg Pro Leu His
1700 1705 1710

Val Gln Arg Pro Ser Ile Pro Pro Ala Ser Asp Thr Glu Lys Pro Leu
1715 1720 1725

Phe Pro Pro Ala Gly Asn Ser Val Cys His Asn His His Asn His Asn
1730 1735 1740

Ser Ile Gly Lys Gln Val Pro Thr Ser Thr Asn Ala Asn Leu Asn Asn
1745 1750 1755 1760

Ala Asn Met Ser Lys Ala Ala His Gly Lys Arg Pro Ser Ile Gly Asn
1765 1770 1775

Leu Glu His Val Ser Glu Asn Gly His His Ser Ser His Lys His Asp
1780 1785 1790

Arg Glu Pro Gln Arg Arg Ser Ser Val Lys Arg Thr Arg Tyr Tyr Glu
1795 1800 1805

Thr Tyr Ile Arg Ser Asp Ser Gly Asp Glu Gln Leu Pro Thr Ile Cys
1810 1815 1820

Arg Glu Asp Pro Glu Ile His Gly Tyr Phe Arg Asp Pro His Cys Leu
1825 1830 1835 1840

-continued

```
Gly Glu Gln Glu Tyr Phe Ser Ser Glu Glu Cys Tyr Glu Asp Asp Ser
                1845                1850                1855

Ser Pro Thr Trp Ser Arg Gln Asn Tyr Gly Tyr Tyr Ser Arg Tyr Pro
            1860                1865                1870

Gly Arg Asn Ile Asp Ser Glu Arg Pro Arg Gly Tyr His His Pro Gln
        1875                1880                1885

Gly Phe Leu Glu Asp Asp Asp Ser Pro Val Cys Tyr Asp Ser Arg Arg
    1890                1895                1900

Ser Pro Arg Arg Arg Leu Leu Pro Pro Thr Pro Ala Ser His Arg Arg
1905                1910                1915                1920

Ser Ser Phe Asn Phe Glu Cys Leu Arg Arg Gln Ser Ser Gln Glu Glu
                1925                1930                1935

Val Pro Ser Ser Pro Ile Phe Pro His Arg Thr Ala Leu Pro Leu His
            1940                1945                1950

Leu Met Gln Gln Gln Ile Met Ala Val Ala Gly Leu Asp Ser Ser Lys
        1955                1960                1965

Ala Gln Lys Tyr Ser Pro Ser His Ser Thr Arg Ser Trp Ala Thr Pro
    1970                1975                1980

Pro Ala Thr Pro Pro Tyr Arg Asp Trp Thr Pro Cys Tyr Thr Pro Leu
1985                1990                1995                2000

Ile Gln Val Glu Gln Ser Glu Ala Leu Asp Gln Val Asn Gly Ser Leu
                2005                2010                2015

Pro Ser Leu His Arg Ser Ser Trp Tyr Thr Asp Glu Pro Asp Ile Ser
            2020                2025                2030

Tyr Arg Thr Phe Thr Pro Ala Ser Leu Thr Val Pro Ser Ser Phe Arg
        2035                2040                2045

Asn Lys Asn Ser Asp Lys Gln Arg Ser Ala Asp Ser Leu Val Glu Ala
    2050                2055                2060

Val Leu Ile Ser Glu Gly Leu Gly Arg Tyr Ala Arg Asp Pro Lys Phe
2065                2070                2075                2080

Val Ser Ala Thr Lys His Glu Ile Ala Asp Ala Cys Asp Leu Thr Ile
                2085                2090                2095

Asp Glu Met Glu Ser Ala Ala Ser Thr Leu Leu Asn Gly Asn Val Arg
            2100                2105                2110

Pro Arg Ala Asn Gly Asp Val Gly Pro Leu Ser His Arg Gln Asp Tyr
        2115                2120                2125

Glu Leu Gln Asp Phe Gly Pro Gly Tyr Ser Asp Glu Glu Pro Asp Pro
    2130                2135                2140

Gly Arg Asp Glu Glu Asp Leu Ala Asp Glu Met Ile Cys Ile Thr Thr
2145                2150                2155                2160

Leu


<210> SEQ ID NO 3
<211> LENGTH: 104
<212> TYPE: DNA
<213> ORGANISM: Human
<220> FEATURE:
<221> NAME/KEY: misc_feature
<222> LOCATION: (1)...(104)
<223> OTHER INFORMATION: A 104-nucleotide alternative exon of alpha-1D

<400> SEQUENCE: 3

gtaaatgatg cgataggatg ggaatggcca tgggtgtatt ttgttagtct gatcatcctt      60

ggctcatttt tcgtccttaa cctggttctt ggtgtcctta gtgg                      104
```

-continued

<210> SEQ ID NO 4
<211> LENGTH: 34
<212> TYPE: PRT
<213> ORGANISM: Human

<400> SEQUENCE: 4

```
Val Asn Asp Ala Ile Gly Trp Glu Trp Pro Trp Val Tyr Phe Val Ser
 1               5                  10                  15

Leu Ile Ile Leu Gly Ser Phe Phe Val Leu Asn Leu Val Leu Gly Val
            20                  25                  30

Leu Ser
```

<210> SEQ ID NO 5
<211> LENGTH: 6575
<212> TYPE: DNA
<213> ORGANISM: Human

<400> SEQUENCE: 5

```
atggtcaatg agaatacgag gatgtacatt ccagaggaaa accaccaagg ttccaactat     60

gggagcccac gccccgccca tgccaacatg aatgccaatg cggcagcggg gctggcccct    120

gagcacatcc ccaccccggg ggctgccctg tcgtggcagg cggccatcga cgcagcccgg    180

caggctaagc tgatgggcag cgctggcaat gcgaccatct ccacagtcag ctccacgcag    240

cggaagcgcc agcaatatgg gaaacccaag aagcagggca gcaccacggc cacacgcccg    300

ccccgagccc tgctctgcct gaccctgaag aaccccatcc ggagggcctg catcagcatt    360

gtcgaatgga aaccatttga aataattatt ttactgacta tttttgccaa ttgtgtggcc    420

ttagcgatct atattccctt tccagaagat gattccaacg ccaccaattc caacctggaa    480

cgagtggaat atctctttct cataattttt acggtggaag cgtttttaaa agtaatcgcc    540

tatggactcc tctttcaccc caatgcctac ctccgcaacg gctggaacct actagatttt    600

ataattgtgg ttgtggggct ttttagtgca attttagaac aagcaaccaa agcagatggg    660

gcaaacgctc tcggagggaa aggggccgga tttgatgtga aggcgctgag ggccttccgc    720

gtgctgcgcc ccctgcggct ggtgtccgga gtcccaagtc tccaggtggt cctgaattcc    780

atcatcaagg ccatggtccc cctgctgcac atcgccctgc ttgtgctgtt tgtcatcatc    840

atctacgcca tcatcggctt ggagctcttc atggggaaga tgcacaagac ctgctacaac    900

caggagggca tagcagatgt tccagcagaa gatgaccctt ccccttgtgc gctggaaacg    960

ggccacgggc ggcagtgcca gaacggcacg gtgtgcaagc ccggctggga tggtcccaag   1020

cacggcatca ccaactttga caactttgcc ttcgccatgc tcacggtgtt ccagtgcatc   1080

accatggagg gctggacgga cgtgctgtac tgggtcaatg atgccgtagg aagggactgg   1140

ccctggatct attttgttac actaatcatc atagggtcat tttttgtact taacttggtt   1200

ctcggtgtgc ttagcggaga gttttccaaa gagagggaga aggccaaggc ccggggagat   1260

ttccagaagc tgcgggagaa gcagcagcta gaagaggatc tcaaaggcta cctggattgg   1320

atcactcagg ccgaagacat cgatcctgag aatgaggacg aaggcatgga tgaggagaag   1380

ccccgaaaca gaggcactcc ggcgggcatg cttgatcaga agaaagggaa gtttgcttgg   1440

tttagtcact ccacagaaac ccatgtgagc atgcccacca gtgagaccga gtccgtcaac   1500

accgaaaacg tggctggagg tgacatcgag ggagaaaact gcggggccag gctggcccac   1560

cggatctcca agtcaaagtt cagccgctac tggcgccggt ggaatcggtt ctgcagaagg   1620

aagtgccgcg ccgcagtcaa gtctaatgtc ttctactggc tggtgatttt cctggtgttc   1680
```

-continued

```
ctcaacacgc tcaccattgc ctctgagcac tacaaccagc ccaactggct cacagaagtc   1740
caagacacgg caaacaaggc cctgctggcc ctgttcacgg cagagatgct cctgaagatg   1800
tacagcctgg gcctgcaggc ctacttcgtg tccctcttca accgctttga ctgcttcgtc   1860
gtgtgtggcg gcatcctgga gaccatcctg gtggagacca agatcatgtc cccactgggc   1920
atctccgtgc tcagatgcgt ccggctgctg aggattttca agatcacgag gtactggaac   1980
tccttgagca acctggtggc atccttgctg aactctgtgc gctccatcgc ctccctgctc   2040
cttctcctct tcctcttcat catcatcttc tccctcctgg ggatgcagct ctttggagga   2100
aagttcaact ttgatgagat gcagacccgg aggagcacat tcgataactt cccccagtcc   2160
ctcctcactg tgtttcagat cctgaccggg gaggactgga attcggtgat gtatgatggg   2220
atcatggctt atgggggccc ctcttttcca gggatgttag tctgtattta cttcatcatc   2280
ctcttcatct gtggaaacta tatcctactg aatgtgttct tggccattgc tgtggacaac   2340
ctggctgatg ctgagagcct cacatctgcc caaaaggagg aggaagagga gaaggagaga   2400
aagaagctgg ccaggactgc cagcccagag aagaaacaag agttggtgga gaagccggca   2460
gtgggggaat ccaaggagga gaagattgag ctgaaatcca tcacggctga cggagagtct   2520
ccacccgcca ccaagatcaa catggatgac ctccagccca atgaaaatga ggataagagc   2580
ccctacccca acccagaaac tacaggagaa gaggatgagg aggagccaga gatgcctgtc   2640
ggccctcgcc cacgaccact ctctgagctt caccttaagg aaaaggcagt gcccatgcca   2700
gaagccagcg cgtttttcat cttcagctct aacaacaggt ttcgcctcca gtgccaccgc   2760
attgtcaatg acacgatctt caccaacctg atcctcttct tcattctgct cagcagcatt   2820
tccctggctg ctgaggaccc ggtccagcac acctccttca ggaaccatat tctgttttat   2880
tttgatattg tttttaccac cattttcacc attgaaattg ctctgaagat gactgcttat   2940
ggggctttct tgcacaaggg ttctttctgc cggaactact tcaacatcct ggacctgctg   3000
gtggtcagcg tgtccctcat ctcctttggc atccagtcca gtgcaatcaa tgtcgtgaag   3060
atcttgcgag tcctgcgagt actcaggccc ctgagggcca tcaacagggc caaggggcta   3120
aagcatgtgg ttcagtgtgt gtttgtcgcc atccggacca tcgggaacat cgtgattgtc   3180
accaccctgc tgcagttcat gtttgcctgc atcggggtcc agctcttcaa gggaaagctg   3240
tacacctgtt cagacagttc caagcagaca gaggcggaat gcaagggcaa ctacatcacg   3300
tacaaagacg gggaggttga ccaccccatc atccaacccc gcagctggga gaacagcaag   3360
tttgactttg acaatgttct ggcagccatg atggccctct tcaccgtctc caccttcgaa   3420
gggtggccag agctgctgta ccgctccatc gactcccaca cggaagacaa gggccccatc   3480
tacaactacc gtgtggagat ctccatcttc ttcatcatct acatcatcat catcgccttc   3540
ttcatgatga acatcttcgt gggcttcgtc atcgtcacct ttcaggagca gggggagcag   3600
gagtacaaga actgtgagct ggacaagaac cagcgacagt gcgtggaata cgccctcaag   3660
gcccggcccc tgcggaggta catccccaag aaccagcacc agtacaaagt gtggtacgtg   3720
gtcaactcca cctacttcga gtacctgatg ttcgtcctca tcctgctcaa caccatctgc   3780
ctggccatgc agcactacgg ccagagctgc ctgttcaaaa tcgccatgaa catcctcaac   3840
atgctcttca ctggcctctt caccgtggag atgatcctga agctcattgc cttcaaaccc   3900
aagggttact ttagtgatcc ctggaatgtt tttgacttcc tcatcgtaat tggcagcata   3960
attgacgtca ttctcagtga gactaatcca gctgaacata cccaatgctc tccctctatg   4020
```

-continued

```
aacgcagagg aaaactcccg catctccatc accttcttcc gcctgttccg ggtcatgcgt   4080
ctggtgaagc tgctgagccg tggggagggc atccggacgc tgctgtggac cttcatcaag   4140
tccttccagg ccctgcccta tgtggccctc ctgatcgtga tgctgttctt catctacgcg   4200
gtgatcggga tgcaggtgtt tgggaaaatt gccctgaatg ataccacaga gatcaaccgg   4260
aacaacaact ttcagacctt cccccaggcc gtgctgctcc tcttcaggtg tgccaccggg   4320
gaggcctggc aggacatcat gctggcctgc atgccaggca agaagtgtgc cccagagtcc   4380
gagcccagca acagcacgga gggtgaaaca ccctgtggta gcagctttgc tgtcttctac   4440
ttcatcagct tctacatgct ctgtgccttc ctgatcatca acctctttgt agctgtcatc   4500
atggacaact ttgactacct gacaagggac tggtccatcc ttggtcccca ccacctggat   4560
gagtttaaaa gaatctgggc agagtatgac cctgaagcca agggtcgtat caaacacctg   4620
gatgtggtga ccctcctccg gcggattcag ccgccactag gttttgggaa gctgtgccct   4680
caccgcgtgg cttgcaaacg cctggtctcc atgaacatgc ctctgaacag cgacgggaca   4740
gtcatgttca atgccaccct gtttgccctg gtcaggacgg ccctgaggat caaaacagaa   4800
gggaacctag aacaagccaa tgaggagctg cgggcgatca tcaagaagat ctggaagcgg   4860
accagcatga agctgctgga ccaggtggtg ccccctgcag gtgatgatga ggtcaccgtt   4920
ggcaagttct acgccacgtt cctgatccag gagtacttcc ggaagttcaa gaagcgcaaa   4980
gagcagggcc ttgtgggcaa gccctcccag aggaacgcgc tgtctctgca ggctggcttg   5040
cgcacactgc atgacatcgg gcctgagatc cgacgggcca tctctggaga tctcaccgct   5100
gaggaggagc tggacaaggc catgaaggag gctgtgtccg ctgcttctga agatgacatc   5160
ttcaggaggg ccggtggcct gttcggcaac cacgtcagct actaccaaag cgacggccgg   5220
agcgccttcc cccagacctt caccactcag cgcccgctgc acatcaacaa ggcgggcagc   5280
agccagggcg acactgagtc gccatcccac gagaagctgg tggactccac cttcaccccg   5340
agcagctact cgtccaccgg ctccaacgcc aacatcaaca acgccaacaa caccgccctg   5400
ggtcgcctcc ctcgccccgc cggctacccc agcacagtca gcactgtgga gggccacggg   5460
ccccccttgt cccctgccat ccgggtgcag gaggtggcgt ggaagctcag ctccaacagg   5520
tgccactccc gggagagcca ggcagccatg gcgcgtcagg aggagacgtc tcaggatgag   5580
acctatgaag tgaagatgaa ccatgacacg gaggcctgca gtgagcccag cctgctctcc   5640
acagagatgc tctcctacca ggatgacgaa aatcggcaac tgacgctccc agaggaggac   5700
aagagggaca tccggcaatc tccgaagagg ggtttcctcc gctctgcctc actaggtcga   5760
agggcctcct tccacctgga atgtctgaag cgacagaagg accgaggggg agacatctct   5820
cagaagacag tcctgccctt gcatctggtt catcatcagg cattggcagt ggcaggcctg   5880
agccccctcc tccagagaag ccattcccct gcctcattcc ctaggccttt tgccacccca   5940
ccagccacac ctggcagccg aggctggccc ccacagcccg tccccaccct gcggcttgag   6000
ggggtcgagt ccagtgagaa actcaacagc agcttcccat ccatccactg cggctcctgg   6060
gctgagacca cccccggtgg cgggggcagc agcgccgccc ggagagtccg gcccgtctcc   6120
ctcatggtgc ccagccaggc tggggcccca gggaggcagt tccacggcag tgccagcagc   6180
ctggtggaag cggtcttgat ttcagaagga ctggggcagt ttgctcaaga tcccaagttc   6240
atcgaggtca ccacccagga gctggccgac gcctgcgaca tgaccataga ggagatggag   6300
agcgcggccg acaacatcct cagcgggggc gccccacaga gccccaatgg cgccctctta   6360
ccctttgtga actgcaggga cgcggggcag gaccgagccg gggggcgaaga ggacgcgggc   6420
```

-continued

```
tgtgtgcgcg cgcggggtcg accgagtgag gaggagctcc aggacagcag ggtctacgtc   6480

agcagcctgt agtgggcgct gccagatgcg ggcttttttt tatttgtttc aatgttccta   6540

atgggttcgt ttcagaagtg cctcactgtt ctcgt                              6575


<210> SEQ ID NO 6
<211> LENGTH: 2163
<212> TYPE: PRT
<213> ORGANISM: Human

<400> SEQUENCE: 6

Met Val Asn Glu Asn Thr Arg Met Tyr Ile Pro Glu Glu Asn His Gln
 1               5                  10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
    290                 295                 300

Ala Asp Val Pro Ala Glu Asp Asp Pro Ser Pro Cys Ala Leu Glu Thr
305                 310                 315                 320

Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
```

-continued

```
        340                 345                 350

Met Leu Thr Val Phe Gln Cys Ile Thr Met Glu Gly Trp Thr Asp Val
    355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Arg
    450                 455                 460

Gly Thr Pro Ala Gly Met Leu Asp Gln Lys Lys Gly Lys Phe Ala Trp
465                 470                 475                 480

Phe Ser His Ser Thr Glu Thr His Val Ser Met Pro Thr Ser Glu Thr
                485                 490                 495

Glu Ser Val Asn Thr Glu Asn Val Ala Gly Gly Asp Ile Glu Gly Glu
            500                 505                 510

Asn Cys Gly Ala Arg Leu Ala His Arg Ile Ser Lys Ser Lys Phe Ser
        515                 520                 525

Arg Tyr Trp Arg Arg Trp Asn Arg Phe Cys Arg Arg Lys Cys Arg Ala
    530                 535                 540

Ala Val Lys Ser Asn Val Phe Tyr Trp Leu Val Ile Phe Leu Val Phe
545                 550                 555                 560

Leu Asn Thr Leu Thr Ile Ala Ser Glu His Tyr Asn Gln Pro Asn Trp
                565                 570                 575

Leu Thr Glu Val Gln Asp Thr Ala Asn Lys Ala Leu Leu Ala Leu Phe
            580                 585                 590

Thr Ala Glu Met Leu Leu Lys Met Tyr Ser Leu Gly Leu Gln Ala Tyr
        595                 600                 605

Phe Val Ser Leu Phe Asn Arg Phe Asp Cys Phe Val Val Cys Gly Gly
    610                 615                 620

Ile Leu Glu Thr Ile Leu Val Glu Thr Lys Ile Met Ser Pro Leu Gly
625                 630                 635                 640

Ile Ser Val Leu Arg Cys Val Arg Leu Leu Arg Ile Phe Lys Ile Thr
                645                 650                 655

Arg Tyr Trp Asn Ser Leu Ser Asn Leu Val Ala Ser Leu Leu Asn Ser
            660                 665                 670

Val Arg Ser Ile Ala Ser Leu Leu Leu Leu Leu Phe Leu Phe Ile Ile
        675                 680                 685

Ile Phe Ser Leu Leu Gly Met Gln Leu Phe Gly Gly Lys Phe Asn Phe
    690                 695                 700

Asp Glu Met Gln Thr Arg Arg Ser Thr Phe Asp Asn Phe Pro Gln Ser
705                 710                 715                 720

Leu Leu Thr Val Phe Gln Ile Leu Thr Gly Glu Asp Trp Asn Ser Val
                725                 730                 735

Met Tyr Asp Gly Ile Met Ala Tyr Gly Gly Pro Ser Phe Pro Gly Met
            740                 745                 750

Leu Val Cys Ile Tyr Phe Ile Ile Leu Phe Ile Cys Gly Asn Tyr Ile
        755                 760                 765
```

-continued

```
Leu Leu Asn Val Phe Leu Ala Ile Ala Val Asp Asn Leu Ala Asp Ala
    770                 775                 780

Glu Ser Leu Thr Ser Ala Gln Lys Glu Glu Glu Glu Glu Lys Glu Arg
785                 790                 795                 800

Lys Lys Leu Ala Arg Thr Ala Ser Pro Glu Lys Lys Gln Glu Leu Val
                805                 810                 815

Glu Lys Pro Ala Val Gly Glu Ser Lys Glu Glu Lys Ile Glu Leu Lys
            820                 825                 830

Ser Ile Thr Ala Asp Gly Glu Ser Pro Pro Ala Thr Lys Ile Asn Met
        835                 840                 845

Asp Asp Leu Gln Pro Asn Glu Asn Glu Asp Lys Ser Pro Tyr Pro Asn
    850                 855                 860

Pro Glu Thr Thr Gly Glu Glu Asp Glu Glu Glu Pro Glu Met Pro Val
865                 870                 875                 880

Gly Pro Arg Pro Arg Pro Leu Ser Glu Leu His Leu Lys Glu Lys Ala
                885                 890                 895

Val Pro Met Pro Glu Ala Ser Ala Phe Phe Ile Phe Ser Ser Asn Asn
            900                 905                 910

Arg Phe Arg Leu Gln Cys His Arg Ile Val Asn Asp Thr Ile Phe Thr
        915                 920                 925

Asn Leu Ile Leu Phe Phe Ile Leu Leu Ser Ser Ile Ser Leu Ala Ala
    930                 935                 940

Glu Asp Pro Val Gln His Thr Ser Phe Arg Asn His Ile Leu Phe Tyr
945                 950                 955                 960

Phe Asp Ile Val Phe Thr Thr Ile Phe Thr Ile Glu Ile Ala Leu Lys
                965                 970                 975

Met Thr Ala Tyr Gly Ala Phe Leu His Lys Gly Ser Phe Cys Arg Asn
            980                 985                 990

Tyr Phe Asn Ile Leu Asp Leu Leu Val Val Ser Val Ser Leu Ile Ser
        995                 1000                1005

Phe Gly Ile Gln Ser Ser Ala Ile Asn Val Val Lys Ile Leu Arg Val
    1010                1015                1020

Leu Arg Val Leu Arg Pro Leu Arg Ala Ile Asn Arg Ala Lys Gly Leu
1025                1030                1035                1040

Lys His Val Val Gln Cys Val Phe Val Ala Ile Arg Thr Ile Gly Asn
                1045                1050                1055

Ile Val Ile Val Thr Thr Leu Leu Gln Phe Met Phe Ala Cys Ile Gly
            1060                1065                1070

Val Gln Leu Phe Lys Gly Lys Leu Tyr Thr Cys Ser Asp Ser Ser Lys
        1075                1080                1085

Gln Thr Glu Ala Glu Cys Lys Gly Asn Tyr Ile Thr Tyr Lys Asp Gly
    1090                1095                1100

Glu Val Asp His Pro Ile Ile Gln Pro Arg Ser Trp Glu Asn Ser Lys
1105                1110                1115                1120

Phe Asp Phe Asp Asn Val Leu Ala Ala Met Met Ala Leu Phe Thr Val
                1125                1130                1135

Ser Thr Phe Glu Gly Trp Pro Glu Leu Leu Tyr Arg Ser Ile Asp Ser
            1140                1145                1150

His Thr Glu Asp Lys Gly Pro Ile Tyr Asn Tyr Arg Val Glu Ile Ser
        1155                1160                1165

Ile Phe Phe Ile Ile Tyr Ile Ile Ile Ile Ala Phe Phe Met Met Asn
    1170                1175                1180
```

-continued

Ile Phe Val Gly Phe Val Ile Val Thr Phe Gln Glu Gln Gly Glu Gln
1185 1190 1195 1200

Glu Tyr Lys Asn Cys Glu Leu Asp Lys Asn Gln Arg Gln Cys Val Glu
1205 1210 1215

Tyr Ala Leu Lys Ala Arg Pro Leu Arg Arg Tyr Ile Pro Lys Asn Gln
1220 1225 1230

His Gln Tyr Lys Val Trp Tyr Val Val Asn Ser Thr Tyr Phe Glu Tyr
1235 1240 1245

Leu Met Phe Val Leu Ile Leu Leu Asn Thr Ile Cys Leu Ala Met Gln
1250 1255 1260

His Tyr Gly Gln Ser Cys Leu Phe Lys Ile Ala Met Asn Ile Leu Asn
1265 1270 1275 1280

Met Leu Phe Thr Gly Leu Phe Thr Val Glu Met Ile Leu Lys Leu Ile
1285 1290 1295

Ala Phe Lys Pro Lys Gly Tyr Phe Ser Asp Pro Trp Asn Val Phe Asp
1300 1305 1310

Phe Leu Ile Val Ile Gly Ser Ile Ile Asp Val Ile Leu Ser Glu Thr
1315 1320 1325

Asn Pro Ala Glu His Thr Gln Cys Ser Pro Ser Met Asn Ala Glu Glu
1330 1335 1340

Asn Ser Arg Ile Ser Ile Thr Phe Phe Arg Leu Phe Arg Val Met Arg
1345 1350 1355 1360

Leu Val Lys Leu Leu Ser Arg Gly Glu Gly Ile Arg Thr Leu Leu Trp
1365 1370 1375

Thr Phe Ile Lys Ser Phe Gln Ala Leu Pro Tyr Val Ala Leu Leu Ile
1380 1385 1390

Val Met Leu Phe Phe Ile Tyr Ala Val Ile Gly Met Gln Val Phe Gly
1395 1400 1405

Lys Ile Ala Leu Asn Asp Thr Thr Glu Ile Asn Arg Asn Asn Asn Phe
1410 1415 1420

Gln Thr Phe Pro Gln Ala Val Leu Leu Leu Phe Arg Cys Ala Thr Gly
1425 1430 1435 1440

Glu Ala Trp Gln Asp Ile Met Leu Ala Cys Met Pro Gly Lys Lys Cys
1445 1450 1455

Ala Pro Glu Ser Glu Pro Ser Asn Ser Thr Glu Gly Glu Thr Pro Cys
1460 1465 1470

Gly Ser Ser Phe Ala Val Phe Tyr Phe Ile Ser Phe Tyr Met Leu Cys
1475 1480 1485

Ala Phe Leu Ile Ile Asn Leu Phe Val Ala Val Ile Met Asp Asn Phe
1490 1495 1500

Asp Tyr Leu Thr Arg Asp Trp Ser Ile Leu Gly Pro His His Leu Asp
1505 1510 1515 1520

Glu Phe Lys Arg Ile Trp Ala Glu Tyr Asp Pro Glu Ala Lys Gly Arg
1525 1530 1535

Ile Lys His Leu Asp Val Val Thr Leu Leu Arg Arg Ile Gln Pro Pro
1540 1545 1550

Leu Gly Phe Gly Lys Leu Cys Pro His Arg Val Ala Cys Lys Arg Leu
1555 1560 1565

Val Ser Met Asn Met Pro Leu Asn Ser Asp Gly Thr Val Met Phe Asn
1570 1575 1580

Ala Thr Leu Phe Ala Leu Val Arg Thr Ala Leu Arg Ile Lys Thr Glu
1585 1590 1595 1600

Gly Asn Leu Glu Gln Ala Asn Glu Glu Leu Arg Ala Ile Ile Lys Lys

-continued

```
                1605                1610                1615

Ile Trp Lys Arg Thr Ser Met Lys Leu Leu Asp Gln Val Val Pro Pro
            1620                1625                1630

Ala Gly Asp Asp Glu Val Thr Val Gly Lys Phe Tyr Ala Thr Phe Leu
        1635                1640                1645

Ile Gln Glu Tyr Phe Arg Lys Phe Lys Lys Arg Lys Glu Gln Gly Leu
    1650                1655                1660

Val Gly Lys Pro Ser Gln Arg Asn Ala Leu Ser Leu Gln Ala Gly Leu
1665                1670                1675                1680

Arg Thr Leu His Asp Ile Gly Pro Glu Ile Arg Arg Ala Ile Ser Gly
                1685                1690                1695

Asp Leu Thr Ala Glu Glu Glu Leu Asp Lys Ala Met Lys Glu Ala Val
            1700                1705                1710

Ser Ala Ala Ser Glu Asp Asp Ile Phe Arg Arg Ala Gly Gly Leu Phe
        1715                1720                1725

Gly Asn His Val Ser Tyr Tyr Gln Ser Asp Gly Arg Ser Ala Phe Pro
    1730                1735                1740

Gln Thr Phe Thr Thr Gln Arg Pro Leu His Ile Asn Lys Ala Gly Ser
1745                1750                1755                1760

Ser Gln Gly Asp Thr Glu Ser Pro Ser His Glu Lys Leu Val Asp Ser
                1765                1770                1775

Thr Phe Thr Pro Ser Ser Tyr Ser Ser Thr Gly Ser Asn Ala Asn Ile
            1780                1785                1790

Asn Asn Ala Asn Asn Thr Ala Leu Gly Arg Leu Pro Arg Pro Ala Gly
        1795                1800                1805

Tyr Pro Ser Thr Val Ser Thr Val Glu Gly His Gly Pro Pro Leu Ser
    1810                1815                1820

Pro Ala Ile Arg Val Gln Glu Val Ala Trp Lys Leu Ser Ser Asn Arg
1825                1830                1835                1840

Cys His Ser Arg Glu Ser Gln Ala Ala Met Ala Arg Gln Glu Glu Thr
                1845                1850                1855

Ser Gln Asp Glu Thr Tyr Glu Val Lys Met Asn His Asp Thr Glu Ala
            1860                1865                1870

Cys Ser Glu Pro Ser Leu Leu Ser Thr Glu Met Leu Ser Tyr Gln Asp
        1875                1880                1885

Asp Glu Asn Arg Gln Leu Thr Leu Pro Glu Glu Asp Lys Arg Asp Ile
    1890                1895                1900

Arg Gln Ser Pro Lys Arg Gly Phe Leu Arg Ser Ala Ser Leu Gly Arg
1905                1910                1915                1920

Arg Ala Ser Phe His Leu Glu Cys Leu Lys Arg Gln Lys Asp Arg Gly
                1925                1930                1935

Gly Asp Ile Ser Gln Lys Thr Val Leu Pro Leu His Leu Val His His
            1940                1945                1950

Gln Ala Leu Ala Val Ala Gly Leu Ser Pro Leu Leu Gln Arg Ser His
        1955                1960                1965

Ser Pro Ala Ser Phe Pro Arg Pro Phe Ala Thr Pro Pro Ala Thr Pro
    1970                1975                1980

Gly Ser Arg Gly Trp Pro Pro Gln Pro Val Pro Thr Leu Arg Leu Glu
1985                1990                1995                2000

Gly Val Glu Ser Ser Glu Lys Leu Asn Ser Ser Phe Pro Ser Ile His
                2005                2010                2015

Cys Gly Ser Trp Ala Glu Thr Thr Pro Gly Gly Gly Gly Ser Ser Ala
            2020                2025                2030
```

-continued

```
Ala Arg Arg Val Arg Pro Val Ser Leu Met Val Pro Ser Gln Ala Gly
        2035                2040                2045

Ala Pro Gly Arg Gln Phe His Gly Ser Ala Ser Ser Leu Val Glu Ala
    2050                2055                2060

Val Leu Ile Ser Glu Gly Leu Gly Gln Phe Ala Gln Asp Pro Lys Phe
2065                2070                2075                2080

Ile Glu Val Thr Thr Gln Glu Leu Ala Asp Ala Cys Asp Met Thr Ile
                2085                2090                2095

Glu Glu Met Glu Ser Ala Ala Asp Asn Ile Leu Ser Gly Gly Ala Pro
            2100                2105                2110

Gln Ser Pro Asn Gly Ala Leu Leu Pro Phe Val Asn Cys Arg Asp Ala
        2115                2120                2125

Gly Gln Asp Arg Ala Gly Gly Glu Glu Asp Ala Gly Cys Val Arg Ala
    2130                2135                2140

Arg Gly Arg Pro Ser Glu Glu Glu Leu Gln Asp Ser Arg Val Tyr Val
2145                2150                2155                2160

Ser Ser Leu


<210> SEQ ID NO 7
<211> LENGTH: 133
<212> TYPE: DNA
<213> ORGANISM: Human

<400> SEQUENCE: 7

agaccacggc ttcctcgaat cttgcgcgaa gccgccggcc atcggaggag ggattaatcc      60

agacccgccg gggggtgttt tcacatttct tcctcttcgt ggctgctcct cctattaaaa     120

ccatttttgg tcc                                                         133


<210> SEQ ID NO 8
<211> LENGTH: 89
<212> TYPE: DNA
<213> ORGANISM: Human

<400> SEQUENCE: 8

cgctgagggc cttccgcgtg ctgcgccccc tgcggctggt gtccggagtc ccaagtctcc      60

aggtggtcct gaattccatc atcaaggcc                                         89


<210> SEQ ID NO 9
<211> LENGTH: 84
<212> TYPE: DNA
<213> ORGANISM: Human
<220> FEATURE:
<221> NAME/KEY: misc_feature
<222> LOCATION: (1)...(84)
<223> OTHER INFORMATION: An alternative exon of alpha-1C

<400> SEQUENCE: 9

cactatttct gtgatgcatg gaatacattt gacgccttga ttgttgtggg tagcattgtt      60

gatatagcaa tcaccgaggt aaac                                              84


<210> SEQ ID NO 10
<211> LENGTH: 28
<212> TYPE: PRT
<213> ORGANISM: Human

<400> SEQUENCE: 10

His Tyr Phe Cys Asp Ala Trp Asn Thr Phe Asp Ala Leu Ile Val Val
 1               5                  10                  15
```

-continued

```
Gly Ser Ile Val Asp Ile Ala Ile Thr Glu Val Asn
            20                  25


<210> SEQ ID NO 11
<211> LENGTH: 7362
<212> TYPE: DNA
<213> ORGANISM: Human

<400> SEQUENCE: 11

gcggcggcgg ctgcggcggt ggggccgggc gaggtccgtg cggtcccggc ggctccgtgg      60

ctgctccgct ctgagcgcct gcgcgccccg cgccctccct gccggggccg ctgggccggg     120

gatgcacgcg gggcccggga gccatggtcc gcttcgggga cgagctgggc ggccgctatg     180

gaggccccgg cggcggagag cgggcccggg gcggcggggc cggcggggcg gggggcccgg     240

gtcccggggg gctgcagccc ggccagcggg tcctctacaa gcaatcgatc gcgcagcgcg     300

cgcggaccat ggcgctgtac aaccccatcc cggtcaagca gaactgcttc accgtcaacc     360

gctcgctctt cgtcttcagc gaggacaacg tcgtccgcaa atacgcgaag cgcatcaccg     420

agtggcctcc attcgagaat atgatcctgg ccaccatcat cgccaactgc atcgtgctgg     480

ccctggagca gcacctccct gatggggaca aaacgcccat gtccgagcgg ctggacgaca     540

cggagcccta tttcatcggg atcttttgct tcgaggcagg gatcaaaatc atcgctctgg     600

gctttgtctt ccacaagggc tcttacctgc ggaacggctg gaacgtcatg gacttcgtgg     660

tcgtcctcac agggatcctt gccacggctg gaactgactt cgacctgcga acactgaggg     720

ctgtgcgtgt gctgaggccc ctgaagctgg tgtctgggat tccaagtttg caggtggtgc     780

tcaagtccat catgaaggcc atggttccac tcctgcagat tgggctgctt ctcttctttg     840

ccatcctcat gtttgccatc attggcctgg agttctacat gggcaagttc cacaaggcct     900

gtttccccaa cagcacagat gcggagcccg tgggtgactt cccctgtggc aaggaggccc     960

cagcccggct gtgcgagggc gacactgagt gccgggagta ctggccagga cccaactttg    1020

gcatcaccaa ctttgacaat atcctgtttg ccatcttgac ggtgttccag tgcatcacca    1080

tggagggctg gactgacatc ctctataata caaacgatgc ggccggcaac acctggaact    1140

ggctctactt catccctctc atcatcatcg gctccttctt catgctcaac ctggtgctgg    1200

gcgtgctctc gggggagttt gccaaggagc gagagagggt ggagaaccgc cgcgccttcc    1260

tgaagctgcg ccggcagcag cagatcgagc gagagctcaa cgggtacctg gagtggatct    1320

tcaaggcgga ggaagtcatg ctggccgagg aggacaggaa tgcagaggag aagtcccctt    1380

tggacgtgct gaagagagcg gccaccaaga agagcagaaa tgacctgatc cacgcagagg    1440

agggagagga ccggtttgca gatctctgtg ctgttggatc cccccttcgcc cgcgccagcc    1500

tcaagagcgg gaagacagag agctcgtcat acttccggag gaaggagaag atgttccggt    1560

tttttatccg gcgcatggtg aaggctcaga gcttctactg ggtggtgctg tgcgtggtgg    1620

ccctgaacac actgtgtgtg gccatggtgc attacaacca gccgcggcgg cttaccacga    1680

ccctgtattt tgcagagttt gttttcctgg gtctcttcct cacagagatg tccctgaaga    1740

tgtatggcct ggggcccaga agctacttcc ggtcctcctt caactgcttc gactttgggg    1800

tcatcgtggg gagcgtcttt gaagtggtct gggcggccat caagccggga agctcctttg    1860

ggatcagtgt gctgcgggcc ctccgcctgc tgaggatctt caaagtcacg aagtactgga    1920

gctccctgcg gaacctggtg gtgtccctgc tgaactccat gaagtccatc atcagcctgc    1980

tcttcttgct cttcctgttc attgtggtct tcgccctgct ggggatgcag ctgtttgggg    2040
```

-continued

```
gacagttcaa cttccaggat gagactccca caaccaactt cgacaccttc cctgccgcca   2100
tcctcactgt cttccagatc ctgacgggag aggactggaa tgcagtgatg tatcacggga   2160
tcgaatcgca aggcggcgtc agcaaaggca tgttctcgtc cttttacttc attgtcctga   2220
cactgttcgg aaactacact ctgctgaatg tctttctggc catcgctgtg gacaacctgg   2280
ccaacgccca agagctgacc aaggatgaag aggagatgga agaagcagcc aatcagaagc   2340
ttgctctgca aaaggccaaa gaagtggctg aagtcagccc catgtctgcc gcgaacatct   2400
ccatcgccgc caggcagcag aactcggcca aggcgcgctc ggtgtgggag cagcgggcca   2460
gccagctacg gctgcagaac ctgcgggcca gctgcgaggc gctgtacagc gagatggacc   2520
ccgaggagcg gctgcgcttc gccactacgc gccacctgcg gcccgacatg aagacgcacc   2580
tggaccggcc gctggtggtg gagctgggcc gcgacggcgc gcgggggccc gtgggaggca   2640
aagcccgacc tgaggctgcg gaggcccccg agggcgtcga ccctccgcgc aggcaccacc   2700
ggcaccgcga caaggacaag acccccgcgg cgggggacca ggaccgagca gaggccccga   2760
aggcggagag cggggagccc ggtgcccggg aggagcggcc gcggccgcac cgcagccaca   2820
gcaaggaggc cgcggggccc ccggaggcgc ggagcgagcg cggccgaggc ccaggccccg   2880
agggcggccg gcggcaccac cggcgcggct ccccggagga ggcggccgag cgggagcccc   2940
gacgccaccg cgcgcaccgg caccaggatc cgagcaagga gtgcgccggc gccaagggcg   3000
agcggcgcgc gcggcaccgc ggcggccccc gagcggggcc ccgggaggcg gagagcgggg   3060
aggagccggc gcggcggcac cggcccggcc acaaggcgca gcctgctcac gaggctgtgg   3120
agaaggagac cacggagaag gaggccacgg agaaggaggc tgagatagtg gaagccgaca   3180
aggaaaagga gctccggaac caccagcccc gggagccaca ctgtgacctg gagaccagtg   3240
ggactgtgac tgtgggtccc atgcacacac tgcccagcac ctgtctccag aaggtggagg   3300
aacagccaga ggatgcagac aatcagcgga acgtcactcg catgggcagt cagcccccag   3360
acccgaacac tattgtacat atcccagtga tgctgacggg ccctcttggg gaagccacgg   3420
tcgttcccag tggtaacgtg gacctggaaa gccaagcaga ggggaagaag gaggtggaag   3480
cggatgacgt gatgaggagc ggcccccggc ctatcgtccc atacagctcc atgttctgtt   3540
taagccccac caacctgctc cgccgcttct gccactacat cgtgaccatg aggtacttcg   3600
aggtggtcat tctcgtggtc atcgccttga gcagcatcgc cctggctgct gaggacccag   3660
tgcgcacaga ctcgcccagg aacaacgctc tgaaatacct ggattacatt ttcactggtg   3720
tctttacctt tgagatggtg ataaagatga tcgacttggg actgctgctt caccctggag   3780
cctatttccg ggacttgtgg aacattctgg acttcattgt ggtcagtggc gccctggtgg   3840
cgtttgcttt ctcaggatcc aaagggaaag acatcaatac catcaagtct ctgagagtcc   3900
ttcgtgtcct gcggcccctc aagaccatca aacggctgcc caagctcaag gctgtgtttg   3960
actgtgtggt gaactccctg aagaatgtcc tcaacatctt gattgtctac atgctcttca   4020
tgttcatatt tgccgtcatt gcggtgcagc tcttcaaagg gaagtttttc tactgcacag   4080
atgaatccaa ggagctggag agggactgca ggggtcagta tttggattat gagaaggagg   4140
aagtggaagc tcagcccagg cagtggaaga aatacgactt tcactacgac aatgtgctct   4200
gggctctgct gacgctgttc acagtgtcca cgggagaagg ctggcccatg gtgctgaaac   4260
actccgtgga tgccacctat gaggagcagg gtccaagccc tgggtaccgc atggagctgt   4320
ccatcttcta cgtggtctac tttgtggtct ttcccttctt cttcgtcaac atctttgtgg   4380
```

-continued ctttgatcat catcaccttc caggagcagg gggacaaggt gatgtctgaa tgcagcctgg 4440
agaagaacga gagggcttgc attgacttcg ccatcagcgc caaacccctg acacggtaca 4500
tgccccaaaa ccggcagtcg ttccagtata agacgtggac atttgtggtc tccccgccct 4560
ttgaatactt catcatggcc atgatagccc tcaacactgt ggtgctgatg atgaagttct 4620
atgatgcacc ctatgagtac gagctgatgc tgaaatgcct gaacatcgtg ttcacatcca 4680
tgttctccat ggaatgcgtg ctgaagatca tcgcctttgg ggtgctgaac tatttcagag 4740
atgcctggaa tgtctttgac tttgtcactg tgttgggaag tattactgat attttagtaa 4800
cagagattgc ggaaacgaac aatttcatca acctcagctt cctccgcctc tttcgagctg 4860
cgcggctgat caagctgctc cgccagggct acaccatccg catcctgctg tggacctttg 4920
tccagtcctt caaggccctg ccctacgtgt gtctgctcat tgccatgctg ttcttcatct 4980
acgccatcat cggcatgcag gtgtttggga atattgccct ggatgatgac accagcatca 5040
accgccacaa caacttccgg acgtttttgc aagccctgat gctgctgttc aggagcgcca 5100
cgggggaggc ctggcacgag atcatgctgt cctgcctgag caaccaggcc tgtgatgagc 5160
aggccaatgc caccgagtgt ggaagtgact ttgcctactt ctacttcgtc tccttcatct 5220
tcctgtgctc ctttctgatg ttgaacctct ttgtggctgt gatcatggac aattttgagt 5280
acctcacgcg ggactcttcc atcctaggtc ctcaccactt ggatgagttc atccgggtct 5340
gggctgaata cgacccggct gcgtgtgggc gcatcagtta caatgacatg tttgagatgc 5400
tgaaacacat gtccccgcct ctggggctgg ggaagaaatg ccctgctcga gttgcttaca 5460
agcgcctggt tcgcatgaac atgcccatct ccaacgagga catgactgtt cacttcacgt 5520
ccacgctgat ggccctcatc cggacggcac tggagatcaa gctggcccca gctgggacaa 5580
agcagcatca gtgtgacgcg gagttgagga aggagatttc cgttgtgtgg gccaatctgc 5640
cccagaagac tttggacttg ctggtaccac cccataagcc tgatgagatg acagtgggga 5700
aggtttatgc agctctgatg atatttgact tctacaagca gaacaaaacc accagagacc 5760
agatgcagca ggctcctgga ggcctctccc agatgggtcc tgtgtccctg ttccaccctc 5820
tgaaggccac cctggagcag acacagccgg ctgtgctccg aggagcccgg gttttccttc 5880
gacagaagag ttccacctcc ctcagcaatg gcggggccat acaaaaccaa gagagtggca 5940
tcaaagagtc tgtctcctgg ggcactcaaa ggacccagga tgcaccccat gaggccaggc 6000
cacccctgga gcgtggccac tccacagaga tccctgtggg gcggtcagga gcactggctg 6060
tggacgttca gatgcagagc ataacccgga ggggccctga tggggagccc cagcctgggc 6120
tggagagcca gggtcgagcg gcctccatgc cccgccttgc ggccgagact cagcccgtca 6180
cagatgccag ccccatgaag cgctccatct ccacgctggc ccagcggccc cgtgggactc 6240
atctttgcag caccaccccg gaccgcccac cccctagcca ggcgtcgtcg caccaccacc 6300
accaccgctg ccaccgccgc agggacagga agcagaggtc cctggagaag gggcccagcc 6360
tgtctgccga tatggatggc gcaccaagca gtgctgtggg gccggggctg cccccgggag 6420
aggggcctac aggctgccgg cgggaacgag agcgccggca ggagcggggc cggtcccagg 6480
agcggaggca gccctcatcc tcctcctcgg agaagcagcg cttctactcc tgcgaccgct 6540
ttgggggccg tgagcccccg aagcccaagc cctccctcag cagccaccca acgtcgccaa 6600
cagctggcca ggagccggga ccccacccac agggcagtgg ttccgtgaat gggagcccct 6660
tgctgtcaac atctggtgct agcacccccg gccgcggtgg gcggaggcag ctcccccaga 6720
cgcccctgac tccccgcccc agcatcacct acaagacggc caactcctca cccatccact 6780

-continued tcgccggggc tcagaccagc ctccctgcct tctccccagg ccggctcagc cgtgggcttt 6840
ccgaacacaa cgccctgctg cagagagacc ccctcagcca gcccctggcc cctggctctc 6900
gaattggctc tgacccttac ctggggcagc gtctggacag tgaggcctct gtccacgccc 6960
tgcctgagga cacgctcact ttcgaggagg ctgtggccac caactcgggc cgctcctcca 7020
ggacttccta cgtgtcctcc ctgacctccc agtctcaccc tctccgccgc gtgcccaacg 7080
gttaccactg caccctggga ctcagctcgg gtggccgagc acggcacagc taccaccacc 7140
ctgaccaaga ccactggtgc tagctgcacc gtgaccgctc agacgcctgc atgcagcagg 7200
cgtgtgttcc agtggatgag ttttatcatc cacacggggc agtcggccct cgggggaggc 7260
cttgcccacc ttggtgaggc tcctgtggcc cctccctccc cctcctcccc tcttttactc 7320
tagacgacga ataaagccct gttgcttgag tgtacgtacc gc 7362

<210> SEQ ID NO 12
<211> LENGTH: 2339
<212> TYPE: PRT
<213> ORGANISM: Human

<400> SEQUENCE: 12

Met Val Arg Phe Gly Asp Glu Leu Gly Gly Arg Tyr Gly Gly Pro Gly
1 5 10 15

Gly Gly Glu Arg Ala Arg Gly Gly Gly Ala Gly Gly Ala Gly Gly Pro
20 25 30

Gly Pro Gly Gly Leu Gln Pro Gly Gln Arg Val Leu Tyr Lys Gln Ser
35 40 45

Ile Ala Gln Arg Ala Arg Thr Met Ala Leu Tyr Asn Pro Ile Pro Val
50 55 60

Lys Gln Asn Cys Phe Thr Val Asn Arg Ser Leu Phe Val Phe Ser Glu
65 70 75 80

Asp Asn Val Val Arg Lys Tyr Ala Lys Arg Ile Thr Glu Trp Pro Pro
85 90 95

Phe Glu Asn Met Ile Leu Ala Thr Ile Ile Ala Asn Cys Ile Val Leu
100 105 110

Ala Leu Glu Gln His Leu Pro Asp Gly Asp Lys Thr Pro Met Ser Glu
115 120 125

Arg Leu Asp Asp Thr Glu Pro Tyr Phe Ile Gly Ile Phe Cys Phe Glu
130 135 140

Ala Gly Ile Lys Ile Ile Ala Leu Gly Phe Val Phe His Lys Gly Ser
145 150 155 160

Tyr Leu Arg Asn Gly Trp Asn Val Met Asp Phe Val Val Val Leu Thr
165 170 175

Gly Ile Leu Ala Thr Ala Gly Thr Asp Phe Asp Leu Arg Thr Leu Arg
180 185 190

Ala Val Arg Val Leu Arg Pro Leu Lys Leu Val Ser Gly Ile Pro Ser
195 200 205

Leu Gln Val Val Leu Lys Ser Ile Met Lys Ala Met Val Pro Leu Leu
210 215 220

Gln Ile Gly Leu Leu Leu Phe Phe Ala Ile Leu Met Phe Ala Ile Ile
225 230 235 240

Gly Leu Glu Phe Tyr Met Gly Lys Phe His Lys Ala Cys Phe Pro Asn
245 250 255

Ser Thr Asp Ala Glu Pro Val Gly Asp Phe Pro Cys Gly Lys Glu Ala
260 265 270

-continued

```
Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685
```

-continued

```
Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
        995                 1000                1005

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
                1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
        1075                1080                1085

Gly Glu Ala Thr Val Val Pro Ser Gly Asn Val Asp Leu Glu Ser Gln
    1090                1095                1100

Ala Glu Gly Lys Lys Glu Val Glu Ala Asp Asp Val Met Arg Ser Gly
```

-continued 1105 1110 1115 1120

Pro Arg Pro Ile Val Pro Tyr Ser Ser Met Phe Cys Leu Ser Pro Thr
1125 1130 1135

Asn Leu Leu Arg Arg Phe Cys His Tyr Ile Val Thr Met Arg Tyr Phe
1140 1145 1150

Glu Val Val Ile Leu Val Val Ile Ala Leu Ser Ser Ile Ala Leu Ala
1155 1160 1165

Ala Glu Asp Pro Val Arg Thr Asp Ser Pro Arg Asn Asn Ala Leu Lys
1170 1175 1180

Tyr Leu Asp Tyr Ile Phe Thr Gly Val Phe Thr Phe Glu Met Val Ile
1185 1190 1195 1200

Lys Met Ile Asp Leu Gly Leu Leu Leu His Pro Gly Ala Tyr Phe Arg
1205 1210 1215

Asp Leu Trp Asn Ile Leu Asp Phe Ile Val Val Ser Gly Ala Leu Val
1220 1225 1230

Ala Phe Ala Phe Ser Gly Ser Lys Gly Lys Asp Ile Asn Thr Ile Lys
1235 1240 1245

Ser Leu Arg Val Leu Arg Val Leu Arg Pro Leu Lys Thr Ile Lys Arg
1250 1255 1260

Leu Pro Lys Leu Lys Ala Val Phe Asp Cys Val Val Asn Ser Leu Lys
1265 1270 1275 1280

Asn Val Leu Asn Ile Leu Ile Val Tyr Met Leu Phe Met Phe Ile Phe
1285 1290 1295

Ala Val Ile Ala Val Gln Leu Phe Lys Gly Lys Phe Phe Tyr Cys Thr
1300 1305 1310

Asp Glu Ser Lys Glu Leu Glu Arg Asp Cys Arg Gly Gln Tyr Leu Asp
1315 1320 1325

Tyr Glu Lys Glu Glu Val Glu Ala Gln Pro Arg Gln Trp Lys Lys Tyr
1330 1335 1340

Asp Phe His Tyr Asp Asn Val Leu Trp Ala Leu Leu Thr Leu Phe Thr
1345 1350 1355 1360

Val Ser Thr Gly Glu Gly Trp Pro Met Val Leu Lys His Ser Val Asp
1365 1370 1375

Ala Thr Tyr Glu Glu Gln Gly Pro Ser Pro Gly Tyr Arg Met Glu Leu
1380 1385 1390

Ser Ile Phe Tyr Val Val Tyr Phe Val Val Phe Pro Phe Phe Phe Val
1395 1400 1405

Asn Ile Phe Val Ala Leu Ile Ile Ile Thr Phe Gln Glu Gln Gly Asp
1410 1415 1420

Lys Val Met Ser Glu Cys Ser Leu Glu Lys Asn Glu Arg Ala Cys Ile
1425 1430 1435 1440

Asp Phe Ala Ile Ser Ala Lys Pro Leu Thr Arg Tyr Met Pro Gln Asn
1445 1450 1455

Arg Gln Ser Phe Gln Tyr Lys Thr Trp Thr Phe Val Val Ser Pro Pro
1460 1465 1470

Phe Glu Tyr Phe Ile Met Ala Met Ile Ala Leu Asn Thr Val Val Leu
1475 1480 1485

Met Met Lys Phe Tyr Asp Ala Pro Tyr Glu Tyr Glu Leu Met Leu Lys
1490 1495 1500

Cys Leu Asn Ile Val Phe Thr Ser Met Phe Ser Met Glu Cys Val Leu
1505 1510 1515 1520

Lys Ile Ile Ala Phe Gly Val Leu Asn Tyr Phe Arg Asp Ala Trp Asn
1525 1530 1535

-continued

```
Val Phe Asp Phe Val Thr Val Leu Gly Ser Ile Thr Asp Ile Leu Val
            1540                1545                1550

Thr Glu Ile Ala Glu Thr Asn Asn Phe Ile Asn Leu Ser Phe Leu Arg
        1555                1560                1565

Leu Phe Arg Ala Ala Arg Leu Ile Lys Leu Leu Arg Gln Gly Tyr Thr
    1570                1575                1580

Ile Arg Ile Leu Leu Trp Thr Phe Val Gln Ser Phe Lys Ala Leu Pro
1585                1590                1595                1600

Tyr Val Cys Leu Leu Ile Ala Met Leu Phe Phe Ile Tyr Ala Ile Ile
                1605                1610                1615

Gly Met Gln Val Phe Gly Asn Ile Ala Leu Asp Asp Asp Thr Ser Ile
            1620                1625                1630

Asn Arg His Asn Asn Phe Arg Thr Phe Leu Gln Ala Leu Met Leu Leu
        1635                1640                1645

Phe Arg Ser Ala Thr Gly Glu Ala Trp His Glu Ile Met Leu Ser Cys
    1650                1655                1660

Leu Ser Asn Gln Ala Cys Asp Glu Gln Ala Asn Ala Thr Glu Cys Gly
1665                1670                1675                1680

Ser Asp Phe Ala Tyr Phe Tyr Phe Val Ser Phe Ile Phe Leu Cys Ser
                1685                1690                1695

Phe Leu Met Leu Asn Leu Phe Val Ala Val Ile Met Asp Asn Phe Glu
            1700                1705                1710

Tyr Leu Thr Arg Asp Ser Ser Ile Leu Gly Pro His His Leu Asp Glu
        1715                1720                1725

Phe Ile Arg Val Trp Ala Glu Tyr Asp Pro Ala Ala Cys Gly Arg Ile
    1730                1735                1740

Ser Tyr Asn Asp Met Phe Glu Met Leu Lys His Met Ser Pro Pro Leu
1745                1750                1755                1760

Gly Leu Gly Lys Lys Cys Pro Ala Arg Val Ala Tyr Lys Arg Leu Val
                1765                1770                1775

Arg Met Asn Met Pro Ile Ser Asn Glu Asp Met Thr Val His Phe Thr
            1780                1785                1790

Ser Thr Leu Met Ala Leu Ile Arg Thr Ala Leu Glu Ile Lys Leu Ala
        1795                1800                1805

Pro Ala Gly Thr Lys Gln His Gln Cys Asp Ala Glu Leu Arg Lys Glu
    1810                1815                1820

Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
            1860                1865                1870

Gln Met Gln Gln Ala Pro Gly Gly Leu Ser Gln Met Gly Pro Val Ser
        1875                1880                1885

Leu Phe His Pro Leu Lys Ala Thr Leu Glu Gln Thr Gln Pro Ala Val
    1890                1895                1900

Leu Arg Gly Ala Arg Val Phe Leu Arg Gln Lys Ser Ser Thr Ser Leu
1905                1910                1915                1920

Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
            1940                1945                1950
```

-continued

Pro Pro Leu Glu Arg Gly His Ser Thr Glu Ile Pro Val Gly Arg Ser
1955 1960 1965

Gly Ala Leu Ala Val Asp Val Gln Met Gln Ser Ile Thr Arg Arg Gly
1970 1975 1980

Pro Asp Gly Glu Pro Gln Pro Gly Leu Glu Ser Gln Gly Arg Ala Ala
1985 1990 1995 2000

Ser Met Pro Arg Leu Ala Ala Glu Thr Gln Pro Val Thr Asp Ala Ser
2005 2010 2015

Pro Met Lys Arg Ser Ile Ser Thr Leu Ala Gln Arg Pro Arg Gly Thr
2020 2025 2030

His Leu Cys Ser Thr Thr Pro Asp Arg Pro Pro Pro Ser Gln Ala Ser
2035 2040 2045

Ser His His His His His Arg Cys His Arg Arg Arg Asp Arg Lys Gln
2050 2055 2060

Arg Ser Leu Glu Lys Gly Pro Ser Leu Ser Ala Asp Met Asp Gly Ala
2065 2070 2075 2080

Pro Ser Ser Ala Val Gly Pro Gly Leu Pro Pro Gly Glu Gly Pro Thr
2085 2090 2095

Gly Cys Arg Arg Glu Arg Glu Arg Arg Gln Glu Arg Gly Arg Ser Gln
2100 2105 2110

Glu Arg Arg Gln Pro Ser Ser Ser Ser Ser Glu Lys Gln Arg Phe Tyr
2115 2120 2125

Ser Cys Asp Arg Phe Gly Gly Arg Glu Pro Pro Lys Pro Lys Pro Ser
2130 2135 2140

Leu Ser Ser His Pro Thr Ser Pro Thr Ala Gly Gln Glu Pro Gly Pro
2145 2150 2155 2160

His Pro Gln Gly Ser Gly Ser Val Asn Gly Ser Pro Leu Leu Ser Thr
2165 2170 2175

Ser Gly Ala Ser Thr Pro Gly Arg Gly Gly Arg Arg Gln Leu Pro Gln
2180 2185 2190

Thr Pro Leu Thr Pro Arg Pro Ser Ile Thr Tyr Lys Thr Ala Asn Ser
2195 2200 2205

Ser Pro Ile His Phe Ala Gly Ala Gln Thr Ser Leu Pro Ala Phe Ser
2210 2215 2220

Pro Gly Arg Leu Ser Arg Gly Leu Ser Glu His Asn Ala Leu Leu Gln
2225 2230 2235 2240

Arg Asp Pro Leu Ser Gln Pro Leu Ala Pro Gly Ser Arg Ile Gly Ser
2245 2250 2255

Asp Pro Tyr Leu Gly Gln Arg Leu Asp Ser Glu Ala Ser Val His Ala
2260 2265 2270

Leu Pro Glu Asp Thr Leu Thr Phe Glu Glu Ala Val Ala Thr Asn Ser
2275 2280 2285

Gly Arg Ser Ser Arg Thr Ser Tyr Val Ser Ser Leu Thr Ser Gln Ser
2290 2295 2300

His Pro Leu Arg Arg Val Pro Asn Gly Tyr His Cys Thr Leu Gly Leu
2305 2310 2315 2320

Ser Ser Gly Gly Arg Ala Arg His Ser Tyr His His Pro Asp Gln Asp
2325 2330 2335

His Trp Cys

<210> SEQ ID NO 13
<211> LENGTH: 7175
<212> TYPE: DNA
<213> ORGANISM: Human

-continued

<400> SEQUENCE: 13

```
gcggcggcgg ctgcggcggt ggggccgggc gaggtccgtg cggtcccggc ggctccgtgg      60
ctgctccgct ctgagcgcct gcgcgccccg cgccctccct gccggggccg ctgggccggg     120
gatgcacgcg gggcccggga gccatggtcc gcttcgggga cgagctgggc ggccgctatg     180
gaggccccgg cggcggagag cgggcccggg gcggcggggc cggcggggcg gggggcccgg     240
gtcccggggg gctgcagccc ggccagcggg tcctctacaa gcaatcgatc gcgcagcgcg     300
cgcggaccat ggcgctgtac aaccccatcc cggtcaagca gaactgcttc accgtcaacc     360
gctcgctctt cgtcttcagc gaggacaacg tcgtccgcaa atacgcgaag cgcatcaccg     420
agtggcctcc attcgagaat atgatcctgg ccaccatcat cgccaactgc atcgtgctgg     480
ccctggagca gcacctccct gatggggaca aaacgcccat gtccgagcgg ctggacgaca     540
cggagcccta tttcatcggg atcttttgct tcgaggcagg gatcaaaatc atcgctctgg     600
gctttgtctt ccacaagggc tcttacctgc ggaacggctg gaacgtcatg gacttcgtgg     660
tcgtcctcac agggatcctt gccacggctg gaactgactt cgacctgcga acactgaggg     720
ctgtgcgtgt gctgaggccc ctgaagctgg tgtctgggat tccaagtttg caggtggtgc     780
tcaagtccat catgaaggcc atggttccac tcctgcagat tgggctgctt ctcttctttg     840
ccatcctcat gtttgccatc attggcctgg agttctacat gggcaagttc cacaaggcct     900
gtttccccaa cagcacagat gcggagcccg tgggtgactt cccctgtggc aaggaggccc     960
cagcccggct gtgcgagggc gacactgagt gccgggagta ctggccagga cccaactttg    1020
gcatcaccaa ctttgacaat atcctgtttg ccatcttgac ggtgttccag tgcatcacca    1080
tggagggctg gactgacatc ctctataata caaacgatgc ggccggcaac acctggaact    1140
ggctctactt catccctctc atcatcatcg gctccttctt catgctcaac ctggtgctgg    1200
gcgtgctctc gggggagttt gccaaggagc gagagagggt ggagaaccgc cgcgccttcc    1260
tgaagctgcg ccggcagcag cagatcgagc gagagctcaa cgggtacctg gagtggatct    1320
tcaaggcgga ggaagtcatg ctggccgagg aggacaggaa tgcagaggag aagtcccctt    1380
tggacgtgct gaagagagcg gccaccaaga agagcagaaa tgacctgatc cacgcagagg    1440
agggagagga ccggtttgca gatctctgtg ctgttggatc cccccttcgcc cgcgccagcc    1500
tcaagagcgg gaagacagag agctcgtcat acttccggag gaaggagaag atgttccggt    1560
tttttatccg gcgcatggtg aaggctcaga gcttctactg ggtggtgctg tgcgtggtgg    1620
ccctgaacac actgtgtgtg gccatggtgc attacaacca gccgcggcgg cttaccacga    1680
ccctgtattt tgcagagttt gttttcctgg gtctcttcct cacagagatg tccctgaaga    1740
tgtatggcct ggggcccaga agctacttcc ggtcctcctt caactgcttc gactttgggg    1800
tcatcgtggg gagcgtcttt gaagtggtct gggcggccat caagccggga agctcctttg    1860
ggatcagtgt gctgcgggcc ctccgcctgc tgaggatctt caaagtcacg aagtactgga    1920
gctccctgcg gaacctggtg gtgtccctgc tgaactccat gaagtccatc atcagcctgc    1980
tcttcttgct cttcctgttc attgtggtct tcgccctgct ggggatgcag ctgtttgggg    2040
gacagttcaa cttccaggat gagactccca caaccaactt cgacaccttc cctgccgcca    2100
tcctcactgt cttccagatc ctgacgggag aggactggaa tgcagtgatg tatcacggga    2160
tcgaatcgca aggcggcgtc agcaaaggca tgttctcgtc cttttacttc attgtcctga    2220
cactgttcgg aaactacact ctgctgaatg tctttctggc catcgctgtg gacaacctgg    2280
```

-continued

```
ccaacgccca agagctgacc aaggatgaag aggagatgga agaagcagcc aatcagaagc   2340
ttgctctgca aaaggccaaa gaagtggctg aagtcagccc catgtctgcc gcgaacatct   2400
ccatcgccgc caggcagcag aactcggcca aggcgcgctc ggtgtgggag cagcgggcca   2460
gccagctacg gctgcagaac ctgcgggcca gctgcgaggc gctgtacagc gagatggacc   2520
ccgaggagcg gctgcgcttc gccactacgc gccacctgcg gcccgacatg aagacgcacc   2580
tggaccggcc gctggtggtg gagctgggcc gcgacggcgc gcgggggccc gtgggaggca   2640
aagcccgacc tgaggctgcg gaggcccccg agggcgtcga ccctccgcgc aggcaccacc   2700
ggcaccgcga caaggacaag acccccgcgg cgggggacca ggaccgagca gaggccccga   2760
aggcggagag cggggagccc ggtgcccggg aggagcggcc gcggccgcac cgcagccaca   2820
gcaaggaggc cgcggggccc ccggaggcgc ggagcgagcg cggccgaggc ccaggccccg   2880
agggcggccg gcggcaccac cggcgcggct ccccggagga ggcggccgag cgggagcccc   2940
gacgccaccg cgcgcaccgg caccaggatc cgagcaagga gtgcgccggc gccaagggcg   3000
agcggcgcgc gcggcaccgc ggcggccccc gagcggggcc ccgggaggcg gagagcgggg   3060
aggagccggc gcggcggcac cggcccggc acaaggcgca gcctgctcac gaggctgtgg   3120
agaaggagac cacggagaag gaggccacgg agaaggaggc tgagatagtg gaagccgaca   3180
aggaaaagga gctccggaac caccagcccc gggagccaca ctgtgacctg gagaccagtg   3240
ggactgtgac tgtgggtccc atgcacacac tgcccagcac ctgtctccag aaggtggagg   3300
aacagccaga ggatgcagac aatcagcgga acgtcactcg catgggcagt cagcccccag   3360
acccgaacac tattgtacat atcccagtga tgctgacggg ccctcttggg gaagccacgg   3420
tcgttcccag tggtaacgtg gacctggaaa gccaagcaga ggggaagaag gaggtggaag   3480
cggatgacgt gatgaggagc ggcccccggc ctatcgtccc atacagctcc atgttctgtt   3540
taagccccac caacctgctc cgccgcttct gccactacat cgtgaccatg aggtacttcg   3600
aggtggtcat tctcgtggtc atcgccttga gcagcatcgc cctggctgct gaggacccag   3660
tgcgcacaga ctcgcccagg aacaacgctc tgaaatacct ggattacatt ttcactggtg   3720
tctttacctt tgagatggtg ataaagatga tcgacttggg actgctgctt caccctggag   3780
cctatttccg ggacttgtgg aacattctgg acttcattgt ggtcagtggc gccctggtgg   3840
cgtttgcttt ctcaggatcc aaagggaaag acatcaatac catcaagtct ctgagagtcc   3900
ttcgtgtcct gcggcccctc aagaccatca aacggctgcc caagctcaag gctgtgtttg   3960
actgtgtggt gaactccctg aagaatgtcc tcaacatctt gattgtctac atgctcttca   4020
tgttcatatt tgccgtcatt gcggtgcagc tcttcaaagg gaagtttttc tactgcacag   4080
atgaatccaa ggagctggag agggactgca ggggtcagta tttggattat gagaaggagg   4140
aagtggaagc tcagcccagg cagtggaaga aatacgactt tcactacgac aatgtgctct   4200
gggctctgct gacgctgttc acagtgtcca cgggagaagg ctggcccatg gtgctgaaac   4260
actccgtgga tgccacctat gaggagcagg gtccaagccc tgggtaccgc atggagctgt   4320
ccatcttcta cgtggtctac tttgtggtct ttcccttctt cttcgtcaac atctttgtgg   4380
ctttgatcat catcaccttc caggagcagg gggacaaggt gatgtctgaa tgcagcctgg   4440
agaagaacga gagggcttgc attgacttcg ccatcagcgc caaacccctg acacggtaca   4500
tgccccaaaa ccggcagtcg ttccagtata agacgtggac atttgtggtc tccccgccct   4560
ttgaatactt catcatggcc atgatagccc tcaacactgt ggtgctgatg atgaagttct   4620
atgatgcacc ctatgagtac gagctgatgc tgaaatgcct gaacatcgtg ttcacatcca   4680
```

-continued

```
tgttctccat ggaatgcgtg ctgaagatca tcgcctttgg ggtgctgaac tatttcagag   4740
atgcctggaa tgtctttgac tttgtcactg tgttgggaag tattactgat attttagtaa   4800
cagagattgc ggaaacgaac aatttcatca acctcagctt cctccgcctc tttcgagctg   4860
cgcggctgat caagctgctc cgccagggct acaccatccg catcctgctg tggacctttg   4920
tccagtcctt caaggccctg ccctacgtgt gtctgctcat tgccatgctg ttcttcatct   4980
acgccatcat cggcatgcag gtgtttggga atattgccct ggatgatgac accagcatca   5040
accgccacaa caacttccgg acgtttttgc aagccctgat gctgctgttc aggagcgcca   5100
cgggggaggc ctggcacgag atcatgctgt cctgcctgag caaccaggcc tgtgatgagc   5160
aggccaatgc caccgagtgt ggaagtgact ttgcctactt ctacttcgtc tccttcatct   5220
tcctgtgctc ctttctgatg ttgaacctct ttgtggctgt gatcatggac aattttgagt   5280
acctcacgcg ggactcttcc atcctaggtc ctcaccactt ggatgagttc atccgggtct   5340
gggctgaata cgacccggct gcgtgtgggc gcatcagtta caatgacatg tttgagatgc   5400
tgaaacacat gtccccgcct ctggggctgg ggaagaaatg ccctgctcga gttgcttaca   5460
agcgcctggt tcgcatgaac atgcccatct ccaacgagga catgactgtt cacttcacgt   5520
ccacgctgat ggccctcatc cggacggcac tggagatcaa gctggcccca gctgggacaa   5580
agcagcatca gtgtgacgcg gagttgagga aggagatttc cgttgtgtgg gccaatctgc   5640
cccagaagac tttggacttg ctggtaccac cccataagcc tgatgagatg acagtgggga   5700
aggtttatgc agctctgatg atatttgact tctacaagca gaacaaaacc accagagacc   5760
agatgcagca ggctcctgga ggcctctccc agatgggtcc tgtgtccctg ttccaccctc   5820
tgaaggccac cctggagcag acacagccgg ctgtgctccg aggagcccgg gttttccttc   5880
gacagaagag ttccacctcc ctcagcaatg gcggggccat acaaaaccaa gagagtggca   5940
tcaaagagtc tgtctcctgg ggcactcaaa ggacccagga tgcaccccat gaggccaggc   6000
cacccctgga gcgtggccac tccacagaga tccctgtggg gcggtcagga gcactggctg   6060
tggacgttca gatgcagagc ataacccgga ggggccctga tggggagccc cagcctgggc   6120
tggagagcca gggtcgagcg gcctccatgc cccgccttgc ggccgagact cagcccgtca   6180
cagatgccag ccccatgaag cgctccatct ccacgctggc ccagcggccc cgtgggactc   6240
atctttgcag caccaccccg gaccgcccac cccctagcca ggcgtcgtcg caccaccacc   6300
accaccgctg ccaccgccgc agggacagga agcagaggtc cctggagaag gggcccagcc   6360
tgtctgccga tatggatggc gcaccaagca gtgctgtggg gccggggctg cccccgggag   6420
aggggcctac aggctgccgg cgggaacgag agcgccggca ggagcggggc cggtcccagg   6480
agcggaggca gccctcatcc tcctcctcgg agaagcagcg cttctactcc tgcgaccgct   6540
ttgggggccg tgagcccccg aagcccaagc cctccctcag cagccaccca acgtcgccaa   6600
cagctggcca ggagccggga ccccacccac aggccggctc agccgtgggc tttccgaaca   6660
caacgccctg ctgcagagag accccctcag ccagcccctg gcccctggct ctcgaattgg   6720
ctctgaccct tacctggggc agcgtctgga cagtgaggcc tctgtccacg ccctgcctga   6780
ggacacgctc actttcgagg aggctgtggc caccaactcg ggccgctcct ccaggacttc   6840
ctacgtgtcc tccctgacct cccagtctca ccctctccgc cgcgtgccca acggttacca   6900
ctgcaccctg ggactcagct cgggtggccg agcacggcac agctaccacc accctgacca   6960
agaccactgg tgctagctgc accgtgaccg ctcagacgcc tgcatgcagc aggcgtgtgt   7020
```

-continued

```
tccagtggat gagttttatc atccacacgg ggcagtcggc cctcggggga ggccttgccc   7080

accttggtga ggctcctgtg gcccctccct ccccctcctc ccctctttta ctctagacga   7140

cgaataaagc cctgttgctt gagtgtacgt accgc                               7175


<210> SEQ ID NO 14
<211> LENGTH: 2237
<212> TYPE: PRT
<213> ORGANISM: Human

<400> SEQUENCE: 14

Met Val Arg Phe Gly Asp Glu Leu Gly Gly Arg Tyr Gly Gly Pro Gly
 1               5                  10                  15

Gly Gly Glu Arg Ala Arg Gly Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Asn Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350
```

-continued

```
Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765
```

-continued

```
Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
        995                 1000                1005

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
                1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
        1075                1080                1085

Gly Glu Ala Thr Val Val Pro Ser Gly Asn Val Asp Leu Glu Ser Gln
    1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
        1155                1160                1165

Ala Glu Asp Pro Val Arg Thr Asp Ser Pro Arg Asn Asn Ala Leu Lys
    1170                1175                1180

Tyr Leu Asp Tyr Ile Phe Thr Gly Val Phe Thr Phe Glu Met Val Ile
```

-continued

```
1185                1190                1195                1200

Lys Met Ile Asp Leu Gly Leu Leu Leu His Pro Gly Ala Tyr Phe Arg
                1205                1210                1215

Asp Leu Trp Asn Ile Leu Asp Phe Ile Val Val Ser Gly Ala Leu Val
            1220                1225                1230

Ala Phe Ala Phe Ser Gly Ser Lys Gly Lys Asp Ile Asn Thr Ile Lys
        1235                1240                1245

Ser Leu Arg Val Leu Arg Val Leu Arg Pro Leu Lys Thr Ile Lys Arg
    1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
            1300                1305                1310

Asp Glu Ser Lys Glu Leu Glu Arg Asp Cys Arg Gly Gln Tyr Leu Asp
        1315                1320                1325

Tyr Glu Lys Glu Glu Val Glu Ala Gln Pro Arg Gln Trp Lys Lys Tyr
    1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
                1365                1370                1375

Ala Thr Tyr Glu Glu Gln Gly Pro Ser Pro Gly Tyr Arg Met Glu Leu
            1380                1385                1390

Ser Ile Phe Tyr Val Val Tyr Phe Val Val Phe Pro Phe Phe Phe Val
        1395                1400                1405

Asn Ile Phe Val Ala Leu Ile Ile Ile Thr Phe Gln Glu Gln Gly Asp
    1410                1415                1420

Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
                1445                1450                1455

Arg Gln Ser Phe Gln Tyr Lys Thr Trp Thr Phe Val Val Ser Pro Pro
            1460                1465                1470

Phe Glu Tyr Phe Ile Met Ala Met Ile Ala Leu Asn Thr Val Val Leu
        1475                1480                1485

Met Met Lys Phe Tyr Asp Ala Pro Tyr Glu Tyr Glu Leu Met Leu Lys
    1490                1495                1500

Cys Leu Asn Ile Val Phe Thr Ser Met Phe Ser Met Glu Cys Val Leu
1505                1510                1515                1520

Lys Ile Ile Ala Phe Gly Val Leu Asn Tyr Phe Arg Asp Ala Trp Asn
                1525                1530                1535

Val Phe Asp Phe Val Thr Val Leu Gly Ser Ile Thr Asp Ile Leu Val
            1540                1545                1550

Thr Glu Ile Ala Glu Thr Asn Asn Phe Ile Asn Leu Ser Phe Leu Arg
        1555                1560                1565

Leu Phe Arg Ala Ala Arg Leu Ile Lys Leu Leu Arg Gln Gly Tyr Thr
    1570                1575                1580

Ile Arg Ile Leu Leu Trp Thr Phe Val Gln Ser Phe Lys Ala Leu Pro
1585                1590                1595                1600

Tyr Val Cys Leu Leu Ile Ala Met Leu Phe Phe Ile Tyr Ala Ile Ile
                1605                1610                1615
```

-continued

```
Gly Met Gln Val Phe Gly Asn Ile Ala Leu Asp Asp Asp Thr Ser Ile
            1620                1625                1630

Asn Arg His Asn Asn Phe Arg Thr Phe Leu Gln Ala Leu Met Leu Leu
        1635                1640                1645

Phe Arg Ser Ala Thr Gly Glu Ala Trp His Glu Ile Met Leu Ser Cys
    1650                1655                1660

Leu Ser Asn Gln Ala Cys Asp Glu Gln Ala Asn Ala Thr Glu Cys Gly
1665                1670                1675                1680

Ser Asp Phe Ala Tyr Phe Tyr Phe Val Ser Phe Ile Phe Leu Cys Ser
                1685                1690                1695

Phe Leu Met Leu Asn Leu Phe Val Ala Val Ile Met Asp Asn Phe Glu
            1700                1705                1710

Tyr Leu Thr Arg Asp Ser Ser Ile Leu Gly Pro His His Leu Asp Glu
        1715                1720                1725

Phe Ile Arg Val Trp Ala Glu Tyr Asp Pro Ala Ala Cys Gly Arg Ile
    1730                1735                1740

Ser Tyr Asn Asp Met Phe Glu Met Leu Lys His Met Ser Pro Pro Leu
1745                1750                1755                1760

Gly Leu Gly Lys Lys Cys Pro Ala Arg Val Ala Tyr Lys Arg Leu Val
                1765                1770                1775

Arg Met Asn Met Pro Ile Ser Asn Glu Asp Met Thr Val His Phe Thr
            1780                1785                1790

Ser Thr Leu Met Ala Leu Ile Arg Thr Ala Leu Glu Ile Lys Leu Ala
        1795                1800                1805

Pro Ala Gly Thr Lys Gln His Gln Cys Asp Ala Glu Leu Arg Lys Glu
    1810                1815                1820

Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
            1860                1865                1870

Gln Met Gln Gln Ala Pro Gly Gly Leu Ser Gln Met Gly Pro Val Ser
        1875                1880                1885

Leu Phe His Pro Leu Lys Ala Thr Leu Glu Gln Thr Gln Pro Ala Val
    1890                1895                1900

Leu Arg Gly Ala Arg Val Phe Leu Arg Gln Lys Ser Ser Thr Ser Leu
1905                1910                1915                1920

Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
            1940                1945                1950

Pro Pro Leu Glu Arg Gly His Ser Thr Glu Ile Pro Val Gly Arg Ser
        1955                1960                1965

Gly Ala Leu Ala Val Asp Val Gln Met Gln Ser Ile Thr Arg Arg Gly
    1970                1975                1980

Pro Asp Gly Glu Pro Gln Pro Gly Leu Glu Ser Gln Gly Arg Ala Ala
1985                1990                1995                2000

Ser Met Pro Arg Leu Ala Ala Glu Thr Gln Pro Val Thr Asp Ala Ser
                2005                2010                2015

Pro Met Lys Arg Ser Ile Ser Thr Leu Ala Gln Arg Pro Arg Gly Thr
            2020                2025                2030
```

-continued

```
His Leu Cys Ser Thr Thr Pro Asp Arg Pro Pro Pro Ser Gln Ala Ser
        2035                2040                2045

Ser His His His His His Arg Cys His Arg Arg Arg Asp Arg Lys Gln
    2050                2055                2060

Arg Ser Leu Glu Lys Gly Pro Ser Leu Ser Ala Asp Met Asp Gly Ala
2065                2070                2075                2080

Pro Ser Ser Ala Val Gly Pro Gly Leu Pro Pro Gly Glu Gly Pro Thr
                2085                2090                2095

Gly Cys Arg Arg Glu Arg Glu Arg Arg Gln Glu Arg Gly Arg Ser Gln
            2100                2105                2110

Glu Arg Arg Gln Pro Ser Ser Ser Ser Ser Glu Lys Gln Arg Phe Tyr
        2115                2120                2125

Ser Cys Asp Arg Phe Gly Gly Arg Glu Pro Pro Lys Pro Lys Pro Ser
    2130                2135                2140

Leu Ser Ser His Pro Thr Ser Pro Thr Ala Gly Gln Glu Pro Gly Pro
2145                2150                2155                2160

His Pro Gln Ala Gly Ser Ala Val Gly Phe Pro Asn Thr Thr Pro Cys
                2165                2170                2175

Cys Arg Glu Thr Pro Ser Ala Ser Pro Trp Pro Leu Ala Leu Glu Leu
            2180                2185                2190

Ala Leu Thr Leu Thr Trp Gly Ser Val Trp Thr Val Arg Pro Leu Ser
        2195                2200                2205

Thr Pro Cys Leu Arg Thr Arg Ser Leu Ser Arg Arg Leu Trp Pro Pro
    2210                2215                2220

Thr Arg Ala Ala Pro Pro Gly Leu Pro Thr Cys Pro Pro
2225                2230                2235
```

<210> SEQ ID NO 15
<211> LENGTH: 1546
<212> TYPE: DNA
<213> ORGANISM: Human

<400> SEQUENCE: 15

```
atggtccaga agaccagcat gtcccggggc ccttacccac cctcccagga gatccccatg     60

gaggtcttcg accccagccc gcagggcaaa tacagcaaga ggaaagggcg attcaaacgg    120

tcagatggga gcacgtcctc ggataccaca tccaacagct ttgtccgcca gggctcagcg    180

gagtcctaca ccagccgtcc atcagactct gatgtatctc tggaggagga ccgggaagcc    240

ttaaggaagg aagcagagcg ccaggcatta gcgcagctcg agaaggccaa gaccaagcca    300

gtggcatttg ctgtgcggac aaatgttggc tacaatccgt ctccagggga tgaggtgcct    360

gtgcagggag tggccatcac cttcgagccc aaagacttcc tgcacatcaa ggagaaatac    420

aataatgact ggtggatcgg gcggctggtg aaggagggct gtgaggttgg cttcattccc    480

agccccgtca aactggacag ccttcgcctg ctgcaggaac agaagctgcg ccagaaccgc    540

ctcggctcca gcaaatcagg cgataactcc agttccagtc tgggagatgt ggtgactggc    600

acccgccgcc ccacaccccc tgccagtgcc aaacagaagc agaagtcgac agagcatgtg    660

ccccccctatg acgtggtgcc ttccatgagg cccatcatcc tggtgggacc gtcgctcaag    720

ggctacgagg ttacagacat gatgcagaaa gctttatttg acttcttgaa gcatcggttt    780

gatggcagga tctccatcac tcgtgtgacg gcagatattt ccctggctaa gcgctcagtt    840

ctcaacaacc ccagcaaaca catcatcatt gagcgctcca acacacgctc cagcctggct    900

gaggtgcaga gtgaaatcga gcgaatcttc gagctggccc ggacccttca gttggtcgct    960
```

-continued

```
ctggatgctg acaccatcaa tcacccagcc cagctgtcca agacctcgct ggcccccatc   1020

attgtttaca tcaagatcac ctctcccaag gtacttcaaa ggctcatcaa gtcccgagga   1080

aagtctcagt ccaaacacct caatgtccaa atagcggcct cggaaaagct ggcacagtgc   1140

ccccctgaaa tgtttgacat catcctggat gagaaccaat tggaggatgc ctgcgagcat   1200

ctggcggagt acttggaagc ctattggaag gccacacacc cgcccagcag cacgccaccc   1260

aatccgctgc tgaaccgcac catggctacc gcagccctgg ctgccagccc tgcccctgtc   1320

tccaacctcc aggtacaggt gctcacctcg ctcaggagaa acctcggctt ctggggcggg   1380

ctggagtcct cacagcgggg cagtgtggtg ccccaggagc aggaacatgc catgtagtgg   1440

gcgccctgcc cgtcttccct cctgctctgg ggtcggaact ggagtgcagg gaacatggag   1500

gaggaaggga agagctttat tttgtaaaaa aataagatga gcggca                  1546
```

<210> SEQ ID NO 16
<211> LENGTH: 478
<212> TYPE: PRT
<213> ORGANISM: Human

<400> SEQUENCE: 16

```
Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
        35                  40                  45

Thr Thr Ser Asn Ser Phe Val Arg Gln Gly Ser Ala Glu Ser Tyr Thr
    50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Ala Lys Gln Lys Gln Lys Ser Thr Glu His Val Pro Pro Tyr Asp
    210                 215                 220

Val Val Pro Ser Met Arg Pro Ile Ile Leu Val Gly Pro Ser Leu Lys
225                 230                 235                 240

Gly Tyr Glu Val Thr Asp Met Met Gln Lys Ala Leu Phe Asp Phe Leu
                245                 250                 255

Lys His Arg Phe Asp Gly Arg Ile Ser Ile Thr Arg Val Thr Ala Asp
            260                 265                 270
```

-continued

```
Ile Ser Leu Ala Lys Arg Ser Val Leu Asn Asn Pro Ser Lys His Ile
        275                 280                 285

Ile Ile Glu Arg Ser Asn Thr Arg Ser Ser Leu Ala Glu Val Gln Ser
    290                 295                 300

Glu Ile Glu Arg Ile Phe Glu Leu Ala Arg Thr Leu Gln Leu Val Ala
305                 310                 315                 320

Leu Asp Ala Asp Thr Ile Asn His Pro Ala Gln Leu Ser Lys Thr Ser
                325                 330                 335

Leu Ala Pro Ile Ile Val Tyr Ile Lys Ile Thr Ser Pro Lys Val Leu
            340                 345                 350

Gln Arg Leu Ile Lys Ser Arg Gly Lys Ser Gln Ser Lys His Leu Asn
        355                 360                 365

Val Gln Ile Ala Ala Ser Glu Lys Leu Ala Gln Cys Pro Pro Glu Met
    370                 375                 380

Phe Asp Ile Ile Leu Asp Glu Asn Gln Leu Glu Asp Ala Cys Glu His
385                 390                 395                 400

Leu Ala Glu Tyr Leu Glu Ala Tyr Trp Lys Ala Thr His Pro Pro Ser
                405                 410                 415

Ser Thr Pro Pro Asn Pro Leu Leu Asn Arg Thr Met Ala Thr Ala Ala
            420                 425                 430

Leu Ala Ala Ser Pro Ala Pro Val Ser Asn Leu Gln Val Gln Val Leu
        435                 440                 445

Thr Ser Leu Arg Arg Asn Leu Gly Phe Trp Gly Gly Leu Glu Ser Ser
    450                 455                 460

Gln Arg Gly Ser Val Val Pro Gln Glu Gln Glu His Ala Met
465                 470                 475
```

<210> SEQ ID NO 17
<211> LENGTH: 1851
<212> TYPE: DNA
<213> ORGANISM: Human
<220> FEATURE:
<221> NAME/KEY: misc_feature
<222> LOCATION: (1)...(1797)
<223> OTHER INFORMATION: Beta 1-3

<400> SEQUENCE: 17

```
atggtccaga agaccagcat gtcccggggc ccttacccac cctcccagga gatccccatg      60

ggagtcttcg accccagccc gcagggcaaa tacagcaaga ggaaagggcg attcaaacgg     120

tcagatggga gcacgtcctc ggataccaca tccaacagct ttgtccgcca gggctcagcg     180

gagtcctaca ccagccgtcc atcagactct gatgtatctc tggaggagga ccgggaagcc     240

ttaaggaagg aagcagagcg ccaggcatta gcgcagctcg agaaggccaa gaccaagcca     300

gtggcatttg ctgtgcggac aaatgttggc tacaatccgt ctccagggga tgaggtgcct     360

gtgcagggag tggccatcac cttcgagccc aaagacttcc tgcacatcaa ggagaaatac     420

aataatgact ggtggatcgg gcggctggtg aaggagggct gtgaggttgg cttcattccc     480

agccccgtca aactggacag ccttcgcctg ctgcaggaac agaagctgcg ccagaaccgc     540

ctcggctcca gcaaatcagg cgataactcc agttccagtc tgggagatgt ggtgactggc     600

acccgccgcc ccacaccccc tgccagtgcc aaacagaagc agaagtcgac agagcatgtg     660

ccccccctatg acgtggtgcc ttccatgagg cccatcatcc tggtgggacc gtcgctcaag     720

ggctacgagg ttacagacat gatgcagaaa gctttatttg acttcttgaa gcatcggttt     780

gatggcagga tctccatcac tcgtgtgacg gcagatattt ccctggctaa gcgctcagtt     840
```

-continued

```
ctcaacaacc ccagcaaaca catcatcatt gagcgctcca acacacgctc cagcctggct    900

gaggtgcaga gtgaaatcga gcgaatcttc gagctggccc ggacccttca gttggtcgct    960

ctggatgctg acaccatcaa tcacccagcc cagctgtcca agacctcgct ggcccccatc   1020

attgtttaca tcaagatcac ctctcccaag gtacttcaaa ggctcatcaa gtcccgagga   1080

aagtctcagt ccaaacacct caatgtccaa atagcggcct cggaaaagct ggcacagtgc   1140

ccccctgaaa tgtttgacat catcctggat gagaaccaat tggaggatgc ctgcgagcat   1200

ctggcggagt acttggaagc ctattggaag gccacacacc cgcccagcag cacgccaccc   1260

aatccgctgc tgaaccgcac catggctacc gcagccctgg ctgccagccc tgcccctgtc   1320

tccaacctcc agggacccta ccttgcttcc ggggaccagc cactggaacg ggccaccggg   1380

gagcacgcca gcatgcacga gtacccaggg gagctgggcc agcccccagg cctttacccc   1440

agcagccacc caccaggccg ggcaggcacg ctacgggcac tgtcccgcca agacactttt   1500

gatgccgaca cccccggcag ccgaaactct gcctacacgg agctgggaga ctcatgtgtg   1560

gacatggaga ctgacccctc agaggggcca gggcttggag accctgcagg gggcggcacg   1620

cccccagccc gacagggatc ctgggaggac gaggaagaag actatgagga agagctgacc   1680

gacaaccgga accggggccg gaataaggcc cgctactgcg ctgagggtgg gggtccagtt   1740

ttggggcgca acaagaatga gctggagggc tggggacgag gcgtctacat tcgctgagag   1800

gcaggggcca cacggcggga ggaagggctc tgagcccagg ggaggggagg g            1851
```

<210> SEQ ID NO 18
<211> LENGTH: 598
<212> TYPE: PRT
<213> ORGANISM: Human

<400> SEQUENCE: 18

```
Met Val Gln Lys Thr Ser Met Ser Arg Gly Pro Tyr Pro Pro Ser Gln
 1               5                  10                  15

Glu Ile Pro Met Gly Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
        35                  40                  45

Thr Thr Ser Asn Ser Phe Val Arg Gln Gly Ser Ala Glu Ser Tyr Thr
    50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
```

-continued

```
        195                 200                 205

Ser Ala Lys Gln Lys Gln Lys Ser Thr Glu His Val Pro Pro Tyr Asp
    210                 215                 220

Val Val Pro Ser Met Arg Pro Ile Ile Leu Val Gly Pro Ser Leu Lys
225                 230                 235                 240

Gly Tyr Glu Val Thr Asp Met Met Gln Lys Ala Leu Phe Asp Phe Leu
                245                 250                 255

Lys His Arg Phe Asp Gly Arg Ile Ser Ile Thr Arg Val Thr Ala Asp
            260                 265                 270

Ile Ser Leu Ala Lys Arg Ser Val Leu Asn Asn Pro Ser Lys His Ile
        275                 280                 285

Ile Ile Glu Arg Ser Asn Thr Arg Ser Ser Leu Ala Glu Val Gln Ser
    290                 295                 300

Glu Ile Glu Arg Ile Phe Glu Leu Ala Arg Thr Leu Gln Leu Val Ala
305                 310                 315                 320

Leu Asp Ala Asp Thr Ile Asn His Pro Ala Gln Leu Ser Lys Thr Ser
                325                 330                 335

Leu Ala Pro Ile Ile Val Tyr Ile Lys Ile Thr Ser Pro Lys Val Leu
            340                 345                 350

Gln Arg Leu Ile Lys Ser Arg Gly Lys Ser Gln Ser Lys His Leu Asn
        355                 360                 365

Val Gln Ile Ala Ala Ser Glu Lys Leu Ala Gln Cys Pro Pro Glu Met
    370                 375                 380

Phe Asp Ile Ile Leu Asp Glu Asn Gln Leu Glu Asp Ala Cys Glu His
385                 390                 395                 400

Leu Ala Glu Tyr Leu Glu Ala Tyr Trp Lys Ala Thr His Pro Pro Ser
                405                 410                 415

Ser Thr Pro Pro Asn Pro Leu Leu Asn Arg Thr Met Ala Thr Ala Ala
            420                 425                 430

Leu Ala Ala Ser Pro Ala Pro Val Ser Asn Leu Gln Gly Pro Tyr Leu
        435                 440                 445

Ala Ser Gly Asp Gln Pro Leu Glu Arg Ala Thr Gly Glu His Ala Ser
    450                 455                 460

Met His Glu Tyr Pro Gly Glu Leu Gly Gln Pro Pro Gly Leu Tyr Pro
465                 470                 475                 480

Ser Ser His Pro Pro Gly Arg Ala Gly Thr Leu Arg Ala Leu Ser Arg
                485                 490                 495

Gln Asp Thr Phe Asp Ala Asp Thr Pro Gly Ser Arg Asn Ser Ala Tyr
            500                 505                 510

Thr Glu Leu Gly Asp Ser Cys Val Asp Met Glu Thr Asp Pro Ser Glu
        515                 520                 525

Gly Pro Gly Leu Gly Asp Pro Ala Gly Gly Gly Thr Pro Pro Ala Arg
    530                 535                 540

Gln Gly Ser Trp Glu Asp Glu Glu Glu Asp Tyr Glu Glu Glu Leu Thr
545                 550                 555                 560

Asp Asn Arg Asn Arg Gly Arg Asn Lys Ala Arg Tyr Cys Ala Glu Gly
                565                 570                 575

Gly Gly Pro Val Leu Gly Arg Asn Lys Asn Glu Leu Glu Gly Trp Gly
            580                 585                 590

Arg Gly Val Tyr Ile Arg
        595
```

<210> SEQ ID NO 19

-continued

<211> LENGTH: 3600
<212> TYPE: DNA
<213> ORGANISM: Human
<220> FEATURE:
<221> NAME/KEY: misc_feature
<222> LOCATION: (35)...(3310)
<223> OTHER INFORMATION: Alpha-2

<400> SEQUENCE: 19

```
gcgggggagg gggcattgat cttcgatcgc gaagatggct gctggctgcc tgctggcctt     60
gactctgaca cttttccaat ctttgctcat cggcccctcg tcggaggagc cgttcccttc    120
ggccgtcact atcaaatcat gggtggataa gatgcaagaa gaccttgtca cactggcaaa    180
aacagcaagt ggagtcaatc agcttgttga tatttatgag aaatatcaag atttgtatac    240
tgtggaacca aataatgcac gccagctggt agaaattgca gccagggata ttgagaaact    300
tctgagcaac agatctaaag ccctggtgag cctggcattg gaagcggaga aagttcaagc    360
agctcaccag tggagagaag attttgcaag caatgaagtt gtctactaca atgcaaagga    420
tgatctcgat cctgagaaaa atgacagtga gccaggcagc cagaggataa aacctgtttt    480
cattgaagat gctaattttg gacgacaaat atcttatcag cacgcagcag tccatattcc    540
tactgacatc tatgagggct caacaattgt gttaaatgaa ctcaactgga caagtgcctt    600
agatgaagtt ttcaaaaaga atcgcgagga agacccttca ttattgtggc aggtttttgg    660
cagtgccact ggcctagctc gatattatcc agcttcacca tgggttgata atagtagaac    720
tccaaataag attgaccttt atgatgtacg cagaagacca tggtacatcc aaggagctgc    780
atctcctaaa gacatgctta ttctggtgga tgtgagtgga agtgttagtg gattgacact    840
taaactgatc cgaacatctg tctccgaaat gttagaaacc ctctcagatg atgatttcgt    900
gaatgtagct tcatttaaca gcaatgctca ggatgtaagc tgttttcagc accttgtcca    960
agcaaatgta agaaataaaa aagtgttgaa agacgcggtg aataatatca cagccaaagg   1020
aattacagat tataagaagg gctttagttt tgcttttgaa cagctgctta attataatgt   1080
ttccagagca aactgcaata agattattat gctattcacg gatggaggag aagagagagc   1140
ccaggagata tttaacaaat acaataaaga taaaaaagta cgtgtattca ggttttcagt   1200
tggtcaacac aattatgaga gaggacctat tcagtggatg gcctgtgaaa acaaaggtta   1260
ttattatgaa attccttcca ttggtgcaat aagaatcaat actcaggaat atttggatgt   1320
tttgggaaga ccaatggttt tagcaggaga caaagctaag caagtccaat ggacaaatgt   1380
gtacctggat gcattggaac tgggacttgt cattactgga actcttccgg tcttcaacat   1440
aaccggccaa tttgaaaata agacaaactt aaagaaccag ctgattcttg gtgtgatggg   1500
agtagatgtg tctttggaag atattaaaag actgacacca cgttttacac tgtgccccaa   1560
tgggtattac tttgcaatcg atcctaatgg ttatgtttta ttacatccaa atcttcagcc   1620
aaagaacccc aaatctcagg agccagtaac attggatttc cttgatgcag agttagagaa   1680
tgatattaaa gtggagattc gaaataagat gattgatggg gaaagtggag aaaaaacatt   1740
cagaactctg gttaaatctc aagatgagag atatattgac aaaggaaaca ggacatacac   1800
atggacacct gtcaatggca cagattacag tttggccttg gtattaccaa cctacagttt   1860
ttactatata aaagccaaac tagaagagac aataactcag gccagatcaa aaaagggcaa   1920
aatgaaggat tcggaaaccc tgaagccaga taattttgaa gaatctggct atacattcat   1980
agcaccaaga gattactgca atgacctgaa aatatcggat aataacactg aatttctttt   2040
aaatttcaac gagtttattg atagaaaaac tccaaacaac ccatcatgta acgcggattt   2100
```

-continued

```
gattaataga gtcttgcttg atgcaggctt tacaaatgaa cttgtccaaa attactggag   2160

taagcagaaa aatatcaagg gagtgaaagc acgatttgtt gtgactgatg gtgggattac   2220

cagagtttat cccaaagagg ctggagaaaa ttggcaagaa aacccagaga catatgagga   2280

cagcttctat aaaaggagcc tagataatga taactatgtt ttcactgctc cctactttaa   2340

caaaagtgga cctggtgcct atgaatcggg cattatggta agcaaagctg tagaaatata   2400

tattcaaggg aaacttctta aacctgcagt tgttggaatt aaaattgatg taaattcctg   2460

gatagagaat ttcaccaaaa cctcaatcag agatccgtgt gctggtccag tttgtgactg   2520

caaaagaaac agtgacgtaa tggattgtgt gattctggat gatggtgggt ttcttctgat   2580

ggcaaatcat gatgattata ctaatcagat tggaagattt tttggagaga ttgatcccag   2640

cttgatgaga cacctggtta atatatcagt ttatgctttt aacaaatctt atgattatca   2700

gtcagtatgt gagcccggtg ctgcaccaaa acaaggagca ggacatcgct cagcatatgt   2760

gccatcagta gcagacatat tacaaattgg ctggtgggcc actgctgctg cctggtctat   2820

tctacagcag tttctcttga gtttgacctt tccacgactc cttgaggcag ttgagatgga   2880

ggatgatgac ttcacggcct ccctgtccaa gcagagctgc attactgaac aaacccagta   2940

tttcttcgat aacgacagta aatcattcag tggtgtatta gactgtggaa actgttccag   3000

aatctttcat ggagaaaagc ttatgaacac caacttaata ttcataatgg ttgagagcaa   3060

agggacatgt ccatgtgaca cacgactgct catacaagcg gagcagactt ctgacggtcc   3120

aaatccttgt gacatggtta agcaacctag ataccgaaaa gggcctgatg tctgctttga   3180

taacaatgtc ttggaggatt atactgactg tggtggtgtt tctggattaa atccctccct   3240

gtggtatatc attggaatcc agtttctact actttggctg gtatctggca gcacacaccg   3300

gctgttatga ccttctaaaa accaaatctg catagttaaa ctccagaccc tgccaaaaca   3360

tgagccctgc cctcaattac agtaacgtag ggtcagctat aaaatcagac aaacattagc   3420

tgggcctgtt ccatggcata acactaaggc gcagactcct aaggcaccca ctggctgcat   3480

gtcagggtgt cagatcctta aacgtgtgtg aatgctgcat catctatgtg taacatcaaa   3540

gcaaaatcct atacgtgtcc tctattggaa aatttgggcg tttgttgttg cattgttggt   3600
```

```
<210> SEQ ID NO 20
<211> LENGTH: 1091
<212> TYPE: PRT
<213> ORGANISM: Human

<400> SEQUENCE: 20

Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110
```

-continued

```
Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525
```

-continued

```
Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
    770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
            900                 905                 910

Ala Asp Ile Leu Gln Ile Gly Trp Trp Ala Thr Ala Ala Ala Trp Ser
        915                 920                 925

Ile Leu Gln Gln Phe Leu Leu Ser Leu Thr Phe Pro Arg Leu Leu Glu
    930                 935                 940

Ala Val Glu Met Glu Asp Asp Asp Phe Thr Ala Ser Leu Ser Lys Gln
```

-continued

```
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser Gly Leu Asn Pro Ser Leu Trp Tyr Ile
            1060                1065                1070

Ile Gly Ile Gln Phe Leu Leu Leu Trp Leu Val Ser Gly Ser Thr His
        1075                1080                1085

Arg Leu Leu
    1090


<210> SEQ ID NO 21
<211> LENGTH: 323
<212> TYPE: DNA
<213> ORGANISM: Human

<400> SEQUENCE: 21

ccccctgcca gtggccaaac agaagcagaa gtcgggtaat gaaatgacta acttagcctt      60

tgaactagac cccctagagt tagaggagga agaggctgag cttggtgagc agagtggctc     120

tgccaagact agtgttagca gtgtcaccac cccgccaccc catggcaaac gcatcccctt     180

ctttaagaag acagagcatg tgcccccta tgacgtggtg ccttccatga ggcccatcat      240

cctggtggga ccgtcgctca agggctacga ggttacagac atgatgcaga aagctttatt     300

tgacttcttg aagcatcggt ttg                                             323


<210> SEQ ID NO 22
<211> LENGTH: 57
<212> TYPE: DNA
<213> ORGANISM: Human

<400> SEQUENCE: 22

cctattggtg taggtatacc aacaattaat ttaagaaaaa ggagacccaa tatccag         57


<210> SEQ ID NO 23
<211> LENGTH: 180
<212> TYPE: DNA
<213> ORGANISM: Human

<400> SEQUENCE: 23

tggtcctttg cctgcgcctg tgccgccttc atcctcctct ttctcggcgg tctcgccctc      60

ctgctgttct ccctgcctcg aatgccccgg aacccatggg agtcctgcat ggatgctgag     120

cccgagcact aaccctcctg cggccctagc gaccctcagg cttcttccca ggaagcgggg     180


<210> SEQ ID NO 24
<211> LENGTH: 43
<212> TYPE: PRT
<213> ORGANISM: Human
```

-continued

<400> SEQUENCE: 24

```
Trp Ser Phe Ala Cys Ala Cys Ala Ala Phe Ile Leu Leu Phe Leu Gly
 1               5                  10                  15

Gly Leu Ala Leu Leu Leu Phe Ser Leu Pro Arg Met Pro Arg Asn Pro
            20                  25                  30

Trp Glu Ser Cys Met Asp Ala Glu Pro Glu His
        35                  40
```

<210> SEQ ID NO 25
<211> LENGTH: 22
<212> TYPE: DNA
<213> ORGANISM: Human
<220> FEATURE:
<221> NAME/KEY: misc_feature
<222> LOCATION: (1)...(22)
<223> OTHER INFORMATION: oligonucleotide

<400> SEQUENCE: 25
aattcggtac gtacactcga gc 22

<210> SEQ ID NO 26
<211> LENGTH: 18
<212> TYPE: DNA
<213> ORGANISM: Human
<220> FEATURE:
<221> NAME/KEY: misc_feature
<222> LOCATION: (1)...(18)
<223> OTHER INFORMATION: oligonucleotide

<400> SEQUENCE: 26
gctcgagtgt acgtaccg 18

<210> SEQ ID NO 27
<211> LENGTH: 20
<212> TYPE: DNA
<213> ORGANISM: Human
<220> FEATURE:
<221> NAME/KEY: misc_feature
<222> LOCATION: (1)...(20)
<223> OTHER INFORMATION: oligonucleotide

<400> SEQUENCE: 27
ccatggtacc ttcgttgacg 20

<210> SEQ ID NO 28
<211> LENGTH: 24
<212> TYPE: DNA
<213> ORGANISM: Human
<220> FEATURE:
<221> NAME/KEY: misc_feature
<222> LOCATION: (1)...(24)
<223> OTHER INFORMATION: oligonucleotide

<400> SEQUENCE: 28
aattcgtcaa cgaaggtacc atgg 24

<210> SEQ ID NO 29
<211> LENGTH: 2153
<212> TYPE: DNA
<213> ORGANISM: Human
<220> FEATURE:
<221> NAME/KEY: misc_feature
<222> LOCATION: (53)...(1504)
<223> OTHER INFORMATION: Beta-3-1

<400> SEQUENCE: 29

-continued

```
ccgcctcgga cccccctgtcc cgggggaggg ggagagcccg ctaccctggt ctatgtcttt      60
ttctgactcc agtgcaacct tcctgctgaa cgagggttca gccgactcct acaccagccg     120
cccatctctg gactcagacg tctccctgga ggaggaccgg gagagtgccc ggcgtgaagt     180
agagagccag gctcagcagc agctcgaaag ggccaagcac aaacctgtgg catttgcggt     240
gaggaccaat gtcagctact gtggcgtact ggatgaggag tgcccagtcc agggctctgg     300
agtcaacttt gaggccaaag attttctgca cattaaagag aagtacagca atgactggtg     360
gatcgggcgg ctagtgaaag agggcgggga catcgccttc atccccagcc cccagcgcct     420
ggagagcatc cggctcaaac aggagcagaa ggccaggaga tctgggaacc cttccagcct     480
gagtgacatt ggcaaccgac gctcccctcc gccatctcta gccaagcaga agcaaaagca     540
ggcggaacat gttcccccgt atgacgtggt gccctccatg cggcctgtgg tgctggtggg     600
accctctctg aaaggttatg aggtcacaga catgatgcag aaggctctct tcgacttcct     660
caaacacaga tttgatggca ggatctccat cacccgagtc acagccgacc tctccctggc     720
aaagcgatct gtgctcaaca atccgggcaa gaggaccatc attgagcgct cctctgcccg     780
ctccagcatt gcggaagtgc agagtgagat cgagcgcata tttgagctgg ccaaatccct     840
gcagctagta gtgttggacg ctgacaccat caaccaccca gcacagctgg ccaagacctc     900
gctggccccc atcatcgtct ttgtcaaagt gtcctcacca aaggtactcc agcgtctcat     960
tcgctcccgg gggaagtcac agatgaagca cctgaccgta cagatgatgg catatgataa    1020
gctggttcag tgcccaccgg agtcatttga tgtgattctg gatgagaacc agctggagga    1080
tgcctgtgag cacctggctg agtacctgga ggtttactgg cgggccacgc accacccagc    1140
ccctggcccc ggacttctgg gtcctcccag tgccatcccc ggacttcaga accagcagct    1200
gctgggggag cgtggcgagg agcactcccc ccttgagcgg gacagcttga tgccctctga    1260
tgaggccagc gagagctccc gccaagcctg gacaggatct tcacagcgta gctcccgcca    1320
cctggaggag gactatgcag atgcctacca ggacctgtac cagcctcacc gccaacacac    1380
ctcggggctg cctagtgcta acgggcatga cccccaagac cggcttctag cccaggactc    1440
agaacacaac cacagtgacc ggaactggca gcgcaaccgg ccttggccca aggatagcta    1500
ctgacagcct cctgctgccc taccctggca ggcacaggcg cagctggctg gggggcccac    1560
tccaggcagg gtggcgttag actggcatca ggctggcact aggctcagcc cccaaaaccc    1620
cctgcccagc cccagcttca gggctgcctg tggtcccaag gttctgggag aaacagggga    1680
ccccctcacc tcctgggcag tgacccctac taggctccca ttccaggtac tagctgtgtg    1740
ttctgcaccc ctggcacctt cctctcctcc cacacaggaa gctgccccac tgggcagtgc    1800
cctcaggcca ggatcccctt agcagggtcc ttcccaccag actcagggaa gggatgcccc    1860
attaaagtga caaaagggtg ggtgtgggca ccatggcatg aggaagaaac aaggtccctg    1920
agcaggcaca agtcctgaca gtcaagggac tgctttggca tccagggcct ccagtcacct    1980
cactgccata cattagaaat gagacaattc aaagcccccc cagggtggca cacccatctg    2040
ttgctggggt gtggcagcca catccaagac tggagcagca ggctggccac gcttgggcca    2100
gagagagctc acagctgaag ctcttggagg gaagggctct cctcacccaa tcg           2153
```

<210> SEQ ID NO 30
<211> LENGTH: 483
<212> TYPE: PRT
<213> ORGANISM: Human

<400> SEQUENCE: 30

-continued

```
Met Ser Phe Ser Asp Ser Ser Ala Thr Phe Leu Leu Asn Glu Gly Ser
 1               5                  10                  15

Ala Asp Ser Tyr Thr Ser Arg Pro Ser Leu Asp Ser Asp Val Ser Leu
            20                  25                  30

Glu Glu Asp Arg Glu Ser Ala Arg Arg Glu Val Glu Ser Gln Ala Gln
        35                  40                  45

Gln Gln Leu Glu Arg Ala Lys His Lys Pro Val Ala Phe Ala Val Arg
    50                  55                  60

Thr Asn Val Ser Tyr Cys Gly Val Leu Asp Glu Glu Cys Pro Val Gln
65                  70                  75                  80

Gly Ser Gly Val Asn Phe Glu Ala Lys Asp Phe Leu His Ile Lys Glu
                85                  90                  95

Lys Tyr Ser Asn Asp Trp Trp Ile Gly Arg Leu Val Lys Glu Gly Gly
            100                 105                 110

Asp Ile Ala Phe Ile Pro Ser Pro Gln Arg Leu Glu Ser Ile Arg Leu
        115                 120                 125

Lys Gln Glu Gln Lys Ala Arg Arg Ser Gly Asn Pro Ser Ser Leu Ser
    130                 135                 140

Asp Ile Gly Asn Arg Arg Ser Pro Pro Pro Ser Leu Ala Lys Gln Lys
145                 150                 155                 160

Gln Lys Gln Ala Glu His Val Pro Pro Tyr Asp Val Val Pro Ser Met
                165                 170                 175

Arg Pro Val Val Leu Val Gly Pro Ser Leu Lys Gly Tyr Glu Val Thr
            180                 185                 190

Asp Met Met Gln Lys Ala Leu Phe Asp Phe Leu Lys His Arg Phe Asp
        195                 200                 205

Gly Arg Ile Ser Ile Thr Arg Val Thr Ala Asp Leu Ser Leu Ala Lys
    210                 215                 220

Arg Ser Val Leu Asn Asn Pro Gly Lys Arg Thr Ile Ile Glu Arg Ser
225                 230                 235                 240

Ser Ala Arg Ser Ser Ile Ala Glu Val Gln Ser Glu Ile Glu Arg Ile
                245                 250                 255

Phe Glu Leu Ala Lys Ser Leu Gln Leu Val Val Leu Asp Ala Asp Thr
            260                 265                 270

Ile Asn His Pro Ala Gln Leu Ala Lys Thr Ser Leu Ala Pro Ile Ile
        275                 280                 285

Val Phe Val Lys Val Ser Ser Pro Lys Val Leu Gln Arg Leu Ile Arg
    290                 295                 300

Ser Arg Gly Lys Ser Gln Met Lys His Leu Thr Val Gln Met Met Ala
305                 310                 315                 320

Tyr Asp Lys Leu Val Gln Cys Pro Pro Glu Ser Phe Asp Val Ile Leu
                325                 330                 335

Asp Glu Asn Gln Leu Glu Asp Ala Cys Glu His Leu Ala Glu Tyr Leu
            340                 345                 350

Glu Val Tyr Trp Arg Ala Thr His His Pro Ala Pro Gly Pro Gly Leu
        355                 360                 365

Leu Gly Pro Pro Ser Ala Ile Pro Gly Leu Gln Asn Gln Gln Leu Leu
    370                 375                 380

Gly Glu Arg Gly Glu Glu His Ser Pro Leu Glu Arg Asp Ser Leu Met
385                 390                 395                 400

Pro Ser Asp Glu Ala Ser Glu Ser Ser Arg Gln Ala Trp Thr Gly Ser
                405                 410                 415
```

-continued

```
Ser Gln Arg Ser Ser Arg His Leu Glu Glu Asp Tyr Ala Asp Ala Tyr
            420                 425                 430

Gln Asp Leu Tyr Gln Pro His Arg Gln His Thr Ser Gly Leu Pro Ser
        435                 440                 445

Ala Asn Gly His Asp Pro Gln Asp Arg Leu Leu Ala Gln Asp Ser Glu
    450                 455                 460

His Asn His Ser Asp Arg Asn Trp Gln Arg Asn Arg Pro Trp Pro Lys
465                 470                 475                 480

Asp Ser Tyr


<210> SEQ ID NO 31
<211> LENGTH: 2144
<212> TYPE: DNA
<213> ORGANISM: Human
<220> FEATURE:
<221> NAME/KEY: misc_feature
<222> LOCATION: (51)...(1492)
<223> OTHER INFORMATION: A Beta3 subunit of human calcium channel

<400> SEQUENCE: 31

cgcccccggc gccgctcgtt cccccgaccc ggactccccc atgtatgacg actcctacgt     60

gcccgggttt gaggactcgg aggcggtttc agccgactcc tacaccagcc gcccatctct    120

ggactcagac gtctccctgg aggaggaccg ggagagtgcc cggcgtgaag tagagagcca    180

ggctcagcag cagctcgaaa gggccaagca caaacctgtg gcatttgcgg tgaggaccaa    240

tgtcagctac tgtggcgtac tggatgagga gtgcccagtc cagggctctg gagtcaactt    300

tgaggccaaa gattttctgc acattaaaga gaagtacagc aatgactggt ggatcgggcg    360

gctagtgaaa gagggcgggg acatcgcctt catccccagc ccccagcgcc tggagagcat    420

ccggctcaaa caggagcaga aggccaggag atctgggaac ccttccagcc tgagtgacat    480

tggcaaccga cgctcccctc cgccatctct agccaagcag aagcaaaagc aggcggaaca    540

tgttcccccg tatgacgtgg tgccctccat gcggcctgtg gtgctggtgg gaccctctct    600

gaaaggttat gaggtcacag acatgatgca gaaggctctc ttcgacttcc tcaaacacag    660

atttgatggc aggatctcca tcacccgagt cacagccgac ctctccctgg caaagcgatc    720

tgtgctcaac aatccgggca agaggaccat cattgagcgc tcctctgccc gctccagcat    780

tgcggaagtg cagagtgaga tcgagcgcat atttgagctg gccaaatccc tgcagctagt    840

agtgttggac gctgacacca tcaaccaccc agcacagctg gccaagacct cgctggcccc    900

catcatcgtc tttgtcaaag tgtcctcacc aaaggtactc cagcgtctca ttcgctcccg    960

ggggaagtca cagatgaagc acctgaccgt acagatgatg gcatatgata agctggttca   1020

gtgcccaccg gagtcatttg atgtgattct ggatgagaac cagctggagg atgcctgtga   1080

gcacctggct gagtacctgg aggtttactg gcgggccacg caccacccag cccctggccc   1140

cggacttctg ggtcctccca gtgccatccc cggacttcag aaccagcagc tgctgggggga   1200

gcgtggcgag gagcactccc cccttgagcg ggacagcttg atgccctctg atgaggccag   1260

cgagagctcc cgccaagcct ggacaggatc ttcacagcgt agctcccgcc acctggagga   1320

ggactatgca gatgcctacc aggacctgta ccagcctcac cgccaacaca cctcggggct   1380

gcctagtgct aacgggcatg acccccaaga ccggcttcta gcccaggact cagaacacaa   1440

ccacagtgac cggaactggc agcgcaaccg gccttggccc aaggatagct actgacagcc   1500

tcctgctgcc ctaccctggc aggcacaggc gcagctggct ggggggccca ctccaggcag   1560

ggtggcgtta gactggcatc aggctggcac taggctcagc ccccaaaacc ccctgcccag   1620
```

```
ccccagcttc agggctgcct gtggtcccaa ggttctggga gaaacagggg accccctcac   1680

ctcctgggca gtgaccccta ctaggctccc attccaggta ctagctgtgt gttctgcacc   1740

cctggcacct tcctctcctc ccacacagga agctgcccca ctgggcagtg ccctcaggcc   1800

aggatcccct tagcagggtc cttcccacca gactcaggga agggatgccc cattaaagtg   1860

acaaaagggt gggtgtgggc accatggcat gaggaagaaa caaggtccct gagcaggcac   1920

aagtcctgac agtcaaggga ctgctttggc atccagggcc tccagtcacc tcactgccat   1980

acattagaaa tgagacaatt caaagccccc ccagggtggc acacccatct gttgctgggg   2040

tgtggcagcc acatccaaga ctggagcagc aggctggcca cgcttgggcc agagagagct   2100

cacagctgaa gctcttggag ggaagggctc tcctcaccca atcg                    2144
```

```
<210> SEQ ID NO 32
<211> LENGTH: 28
<212> TYPE: DNA
<213> ORGANISM: Human
<220> FEATURE:
<221> NAME/KEY: misc_feature
<222> LOCATION: (1)...(28)
<223> OTHER INFORMATION: oligonucleotide

<400> SEQUENCE: 32

ctcagtacca tctctgatac cagcccca                                        28
```

```
<210> SEQ ID NO 33
<211> LENGTH: 7808
<212> TYPE: DNA
<213> ORGANISM: Human
<220> FEATURE:
<221> NAME/KEY: misc_feature
<222> LOCATION: (237)...(7769)
<223> OTHER INFORMATION: Alpha-1A-1

<400> SEQUENCE: 33

gatgtcccga gctgctatcc ccggctcggc ccgggcagcc gccttctgag cccccgaccc     60

gaggcgccga gccgccgccg cccgatgggc tgggccgtgg agcgtctccg cagtcgtagc    120

tccagccgcc gcgctcccag ccccggcagc ctcagcatca gcggcggcgg cggcggcggc    180

ggcgtcttcc gcatcgttcg ccgcagcgta acccggagcc ctttgctctt tgcagaatgg    240

cccgcttcgg agacgagatg ccggcccgct acgggggagg aggctccggg gcagccgccg    300

gggtggtcgt gggcagcgga ggcgggcgag gagccggggg cagccggcag ggcgggcagc    360

ccggggcgca aaggatgtac aagcagtcaa tggcgcagag agcgcggacc atggcactct    420

acaaccccat ccccgtccga cagaactgcc tcacggttaa ccggtctctc ttcctcttca    480

gcgaagacaa cgtggtgaga aaatacgcca aaaagatcac cgaatggcct ccctttgaat    540

atatgatttt agccaccatc atagcgaatt gcatcgtcct cgcactggag cagcatctgc    600

ctgatgatga caagaccccg atgtctgaac ggctggatga cacagaacca tacttcattg    660

gaatttttg tttcgaggct ggaattaaaa tcattgccct tgggtttgcc ttccacaaag    720

gctcctactt gaggaatggc tggaatgtca tggactttgt ggtggtgcta acgggcatct    780

tggcgacagt tgggacggag tttgacctac ggacgctgag ggcagttcga gtgctgcggc    840

cgctcaagct ggtgtctgga atcccaagtt tacaagtcgt cctgaagtcg atcatgaagg    900

cgatgatccc tttgctgcag atcggcctcc tcctattttt tgcaatcctt atttttgcaa    960

tcatagggtt agaattttat atgggaaaat ttcataccac ctgctttgaa gaggggacag   1020
```

-continued

```
atgacattca gggtgagtct ccggctccat gtgggacaga agagcccgcc cgcacctgcc   1080
ccaatgggac caaatgtcag ccctactggg aagggcccaa caacgggatc actcagttcg   1140
acaacatcct gtttgcagtg ctgactgttt tccagtgcat aaccatggaa gggtggactg   1200
atctcctcta caatagcaac gatgcctcag ggaacacttg gaactggttg tacttcatcc   1260
ccctcatcat catcggctcc ttttttatgc tgaaccttgt gctgggtgtg ctgtcagggg   1320
agtttgccaa agaaagggaa cgggtggaga accggcgggc ttttctgaag ctgaggcggc   1380
aacaacagat tgaacgtgag ctcaatgggt acatggaatg gatctcaaaa gcagaagagg   1440
tgatcctcgc cgaggatgaa actgacgggg agcagaggca tccctttgat ggagctctgc   1500
ggagaaccac cataaagaaa agcaagacag atttgctcaa ccccgaagag gctgaggatc   1560
agctggctga tatagcctct gtgggttctc ccttcgcccg agccagcatt aaaagtgcca   1620
agctggagaa ctcgaccttt tttcacaaaa aggagaggag gatgcgtttc tacatccgcc   1680
gcatggtcaa aactcaggcc ttctactgga ctgtactcag tttggtagct ctcaacacgc   1740
tgtgtgttgc tattgttcac tacaaccagc ccgagtggct ctccgacttc ctttactatg   1800
cagaattcat tttcttagga ctctttatgt ccgaaatgtt tataaaaatg tacgggcttg   1860
ggacgcggcc ttacttccac tcttccttca actgctttga ctgtggggtt atcattggga   1920
gcatcttcga ggtcatctgg gctgtcataa aacctggcac atcctttgga atcagcgtgt   1980
tacgagccct caggttattg cgtattttca aagtcacaaa gtactgggca tctctcagaa   2040
acctggtcgt ctctctcctc aactccatga agtccatcat cagcctgttg tttctccttt   2100
tcctgttcat tgtcgtcttc gcccttttgg gaatgcaact cttcggcggc cagtttaatt   2160
tcgatgaagg gactcctccc accaacttcg atacttttcc agcagcaata atgacggtgt   2220
ttcagatcct gacgggcgaa gactggaacg aggtcatgta cgacgggatc aagtctcagg   2280
ggggcgtgca gggcggcatg gtgttctcca tctatttcat tgtactgacg ctctttggga   2340
actacaccct cctgaatgtg ttcttggcca tcgctgtgga caatctggcc aacgcccagg   2400
agctcaccaa ggtggaggcg gacgagcaag aggaagaaga agcagcgaac cagaaacttg   2460
ccctacagaa agccaaggag gtggcagaag tgagtcctct gtccgcggcc aacatgtcta   2520
tagctgtgaa agagcaacag aagaatcaaa agccagccaa gtccgtgtgg gagcagcgga   2580
ccagtgagat gcgaaagcag aacttgctgg ccagccggga ggccctgtat aacgaaatgg   2640
acccggacga gcgctggaag gctgcctaca cgcggcacct gcggccagac atgaagacgc   2700
acttggaccg gccgctggtg gtggacccgc aggagaaccg caacaacaac accaacaaga   2760
gccgggcggc cgagcccacc gtggaccagc gcctcggcca gcagcgcgcc gaggacttcc   2820
tcaggaaaca ggcccgctac cacgatcggg cccgggaccc cagcggctcg gcgggcctgg   2880
acgcacggag gccctgggcg ggaagccagg aggccgagct gagccgggag ggaccctacg   2940
gccgcgagtc ggaccaccac gcccgggagg gcagcctgga gcaacccggg ttctgggagg   3000
gcgaggccga gcgaggcaag gccggggacc cccaccggag gcacgtgcac cggcaggggg   3060
gcagcaggga gagccgcagc gggtccccgc gcacgggcgc ggacggggag catcgacgtc   3120
atcgcgcgca ccgcaggccc ggggaggagg gtccggagga caaggcggag cggagggcgc   3180
ggcaccgcga gggcagccgg ccggcccggg gcggcgaggg cgagggcgag ggccccgacg   3240
ggggcgagcg caggagaagg caccggcatg gcgctccagc cacgtacgag ggggacgcgc   3300
ggagggagga caaggagcgg aggcatcgga ggaggaaaga gaaccagggc tccggggtcc   3360
ctgtgtcggg ccccaacctg tcaaccaccc ggccaatcca gcaggacctg ggccgccaag   3420
```

-continued

```
acccacccct ggcagaggat attgacaaca tgaagaacaa caagctggcc accgcggagt   3480
cggccgctcc ccacggcagc cttggccacg ccggcctgcc ccagagccca gccaagatgg   3540
gaaacagcac cgaccccggc cccatgctgg ccatccctgc catggccacc aacccccaga   3600
acgccgccag ccgccggacg cccaacaacc cggggaaccc atccaatccc ggcccccccca   3660
agacccccga gaatagcctt atcgtcacca accccagcgg cacccagacc aattcagcta   3720
agactgccag gaaacccgac cacaccacag tggacatccc cccagcctgc ccaccccccc   3780
tcaaccacac cgtcgtacaa gtgaacaaaa acgccaaccc agacccactg ccaaaaaaag   3840
aggaagagaa gaaggaggag gaggaagacg accgtgggga agacggccct aagccaatgc   3900
ctccctatag ctccatgttc atcctgtcca cgaccaaccc ccttcgccgc ctgtgccatt   3960
acatcctgaa cctgcgctac tttgagatgt gcatcctcat ggtcattgcc atgagcagca   4020
tcgccctggc cgccgaggac cctgtgcagc ccaacgcacc tcggaacaac gtgctgcgat   4080
actttgacta cgtttttaca ggcgtcttca cctttgagat ggtgatcaag atgattgacc   4140
tggggctcgt cctgcatcag ggtgcctact tccgtgacct ctggaatatt ctcgacttca   4200
tagtggtcag tggggccctg gtagcctttg ccttcactgg caatagcaaa ggaaaagaca   4260
tcaacacgat taaatccctc cgagtcctcc gggtgctacg acctcttaaa accatcaagc   4320
ggctgccaaa gctcaaggct gtgtttgact gtgtggtgaa ctcacttaaa aacgtcttca   4380
acatcctcat cgtctacatg ctattcatgt tcatcttcgc cgtggtggct gtgcagctct   4440
tcaaggggaa attcttccac tgcactgacg agtccaaaga gtttgagaaa gattgtcgag   4500
gcaaatacct cctctacgag aagaatgagg tgaaggcgcg agaccgggag tggaagaagt   4560
atgaattcca ttacgacaat gtgctgtggg ctctgctgac cctcttcacc gtgtccacgg   4620
gagaaggctg gccacaggtc ctcaagcatt cggtggacgc caccttttgag aaccagggcc   4680
ccagccccgg gtaccgcatg gagatgtcca ttttctacgt cgtctacttt gtggtgttcc   4740
ccttcttctt tgtcaatatc tttgtggcct tgatcatcat caccttccag gagcaagggg   4800
acaagatgat ggaggaatac agcctggaga aaaatgagag ggcctgcatt gatttcgcca   4860
tcagcgccaa gccgctgacc cgacacatgc cgcagaacaa gcagagcttc cagtaccgca   4920
tgtggcagtt cgtggtgtct ccgcctttcg agtacacgat catggccatg atcgccctca   4980
acaccatcgt gcttatgatg aagttctatg gggcttctgt tgcttatgaa aatgccctgc   5040
gggtgttcaa catcgtcttc acctccctct tctctctgga atgtgtgctg aaagtcatgg   5100
cttttgggat tctgaattat ttccgcgatg cctggaacat cttcgacttt gtgactgttc   5160
tgggcagcat caccgatatc ctcgtgactg agtttgggaa tccgaataac ttcatcaacc   5220
tgagctttct ccgcctcttc cgagctgccc ggctcatcaa acttctccgt cagggttaca   5280
ccatccgcat tcttctctgg acctttgtgc agtccttcaa ggccctgcct tatgtctgtc   5340
tgctgatcgc catgctcttc ttcatctatg ccatcattgg gatgcaggtg tttggtaaca   5400
ttggcatcga cgtggaggac gaggacagtg atgaagatga gttccaaatc actgagcaca   5460
ataacttccg gaccttcttc caggccctca tgcttctctt ccggagtgcc accggggaag   5520
cttggcacaa catcatgctt tcctgcctca gcgggaaacc gtgtgataag aactctggca   5580
tcctgactcg agagtgtggc aatgaatttg cttattttta ctttgtttcc ttcatcttcc   5640
tctgctcgtt tctgatgctg aatctctttg tcgccgtcat catggacaac tttgagtacc   5700
tcacccgaga ctcctccatc ctgggccccc accacctgga tgagtacgtg cgtgtctggg   5760
```

-continued

```
ccgagtatga ccccgcagct tggggccgca tgccttacct ggacatgtat cagatgctga   5820

gacacatgtc tccgcccctg ggtctgggga agaagtgtcc ggccagagtg gcttacaagc   5880

ggcttctgcg gatggacctg cccgtcgcag atgacaacac cgtccacttc aattccaccc   5940

tcatggctct gatccgcaca gccctggaca tcaagattgc caagggagga gccgacaaac   6000

agcagatgga cgctgagctg cggaaggaga tgatggcgat ttggcccaat ctgtcccaga   6060

agacgctaga cctgctggtc acacctcaca agtccacgga cctcaccgtg gggaagatct   6120

acgcagccat gatgatcatg gagtactacc ggcagagcaa ggccaagaag ctgcaggcca   6180

tgcgcgagga gcaggaccgg acacccctca tgttccagcg catggagccc ccgtccccaa   6240

cgcaggaagg gggacctggc cagaacgccc tcccctccac ccagctggac ccaggaggag   6300

ccctgatggc tcacgaaagc ggcctcaagg agagcccgtc ctgggtgacc cagcgtgccc   6360

aggagatgtt ccagaagacg ggcacatgga gtccggaaca aggcccccct accgacatgc   6420

ccaacagcca gcctaactct cagtccgtgg agatgcgaga gatgggcaga gatggctact   6480

ccgacagcga gcactacctc cccatggaag gccagggccg ggctgcctcc atgccccgcc   6540

tccctgcaga gaaccagagg agaaggggcc ggccacgtgg gaataacctc agtaccatct   6600

cagacaccag ccccatgaag cgttcagcct ccgtgctggg ccccaaggcc cgacgcctgg   6660

acgattactc gctggagcgg gtcccgcccg aggagaacca gcggcaccac cagcggcgcc   6720

gcgaccgcag ccaccgcgcc tctgagcgct ccctgggccg ctacaccgat gtggacacag   6780

gcttggggac agacctgagc atgaccaccc aatccgggga cctgccgtcg aaggagcggg   6840

accaggagcg gggccggccc aaggatcgga agcatcgaca gcaccaccac caccaccacc   6900

accaccacca tcccccgccc cccgacaagg accgctatgc ccaggaacgg ccggaccacg   6960

gccgggcacg ggctcgggac cagcgctggt cccgctcgcc cagcgagggc cgagagcaca   7020

tggcgcaccg gcagggcagt agttccgtaa gtggaagccc agccccctca acatctggta   7080

ccagcactcc gcggcggggc cgccgccagc tcccccagac cccctccacc ccccggccac   7140

acgtgtccta ttcccctgtg atccgtaagg ccggcggctc ggggcccccg cagcagcagc   7200

agcagcagca gcagcagcag caggcggtgg ccaggccggg ccgggcggcc accagcggcc   7260

ctcggaggta cccaggcccc acggccgagc ctctggccgg agatcggccg cccacggggg   7320

gccacagcag cggccgctcg cccaggatgg agaggcgggt cccaggcccg gcccggagcg   7380

agtcccccag ggcctgtcga cacggcgggg cccggtggcc ggcatctggc ccgcacgtgt   7440

ccgaggggcc cccgggtccc cggcaccatg gctactaccg gggctccgac tacgacgagg   7500

ccgatggccc gggcagcggg ggcggcgagg aggccatggc cggggcctac gacgcgccac   7560

cccccgtacg acacgcgtcc tcgggcgcca ccgggcgctc gcccaggact ccccgggcct   7620

cgggcccggc ctgcgcctcg ccttctcggc acggccggcg actccccaac ggctactacc   7680

cggcgcacgg actggccagg ccccgcgggc cgggctccag gaagggcctg cacgaaccct   7740

acagcgagag tgacgatgat tggtgctaag cccgggcgag gtggcgcccg cccggccccc   7800

cacgcacc                                                            7808
```

```
<210> SEQ ID NO 34
<211> LENGTH: 2510
<212> TYPE: PRT
<213> ORGANISM: Human

<400> SEQUENCE: 34

Met Ala Arg Phe Gly Asp Glu Met Pro Ala Arg Tyr Gly Gly Gly Gly
```

-continued

```
1               5                   10                  15

Ser Gly Ala Ala Ala Gly Val Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
        355                 360                 365

Arg Val Glu Asn Arg Arg Ala Phe Leu Lys Leu Arg Arg Gln Gln Gln
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
            420                 425                 430
```

-continued

```
Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
    770                 775                 780

Met Arg Lys Gln Asn Leu Leu Ala Ser Arg Glu Ala Leu Tyr Asn Glu
785                 790                 795                 800

Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845
```

-continued

```
Val Asp Gln Arg Leu Gly Gln Gln Arg Ala Glu Asp Phe Leu Arg Lys
    850                 855                 860

Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
            900                 905                 910

Ser Leu Glu Gln Pro Gly Phe Trp Glu Gly Glu Ala Glu Arg Gly Lys
        915                 920                 925

Ala Gly Asp Pro His Arg Arg His Val His Arg Gln Gly Gly Ser Arg
    930                 935                 940

Glu Ser Arg Ser Gly Ser Pro Arg Thr Gly Ala Asp Gly Glu His Arg
945                 950                 955                 960

Arg His Arg Ala His Arg Arg Pro Gly Glu Glu Gly Pro Glu Asp Lys
                965                 970                 975

Ala Glu Arg Arg Ala Arg His Arg Glu Gly Ser Arg Pro Ala Arg Gly
            980                 985                 990

Gly Glu Gly Glu Gly Glu Gly Pro Asp Gly Gly Glu Arg Arg Arg Arg
        995                 1000                1005

His Arg His Gly Ala Pro Ala Thr Tyr Glu Gly Asp Ala Arg Arg Glu
    1010                1015                1020

Asp Lys Glu Arg Arg His Arg Arg Arg Lys Glu Asn Gln Gly Ser Gly
1025                1030                1035                1040

Val Pro Val Ser Gly Pro Asn Leu Ser Thr Thr Arg Pro Ile Gln Gln
                1045                1050                1055

Asp Leu Gly Arg Gln Asp Pro Pro Leu Ala Glu Asp Ile Asp Asn Met
            1060                1065                1070

Lys Asn Asn Lys Leu Ala Thr Ala Glu Ser Ala Ala Pro His Gly Ser
        1075                1080                1085

Leu Gly His Ala Gly Leu Pro Gln Ser Pro Ala Lys Met Gly Asn Ser
    1090                1095                1100

Thr Asp Pro Gly Pro Met Leu Ala Ile Pro Ala Met Ala Thr Asn Pro
1105                1110                1115                1120

Gln Asn Ala Ala Ser Arg Arg Thr Pro Asn Asn Pro Gly Asn Pro Ser
                1125                1130                1135

Asn Pro Gly Pro Pro Lys Thr Pro Glu Asn Ser Leu Ile Val Thr Asn
            1140                1145                1150

Pro Ser Gly Thr Gln Thr Asn Ser Ala Lys Thr Ala Arg Lys Pro Asp
        1155                1160                1165

His Thr Thr Val Asp Ile Pro Pro Ala Cys Pro Pro Pro Leu Asn His
    1170                1175                1180

Thr Val Val Gln Val Asn Lys Asn Ala Asn Pro Asp Pro Leu Pro Lys
1185                1190                1195                1200

Lys Glu Glu Glu Lys Lys Glu Glu Glu Glu Asp Asp Arg Gly Glu Asp
                1205                1210                1215

Gly Pro Lys Pro Met Pro Pro Tyr Ser Ser Met Phe Ile Leu Ser Thr
            1220                1225                1230

Thr Asn Pro Leu Arg Arg Leu Cys His Tyr Ile Leu Asn Leu Arg Tyr
        1235                1240                1245

Phe Glu Met Cys Ile Leu Met Val Ile Ala Met Ser Ser Ile Ala Leu
    1250                1255                1260

Ala Ala Glu Asp Pro Val Gln Pro Asn Ala Pro Arg Asn Asn Val Leu
```

-continued 1265 1270 1275 1280

Arg Tyr Phe Asp Tyr Val Phe Thr Gly Val Phe Thr Phe Glu Met Val
1285 1290 1295

Ile Lys Met Ile Asp Leu Gly Leu Val Leu His Gln Gly Ala Tyr Phe
1300 1305 1310

Arg Asp Leu Trp Asn Ile Leu Asp Phe Ile Val Val Ser Gly Ala Leu
1315 1320 1325

Val Ala Phe Ala Phe Thr Gly Asn Ser Lys Gly Lys Asp Ile Asn Thr
1330 1335 1340

Ile Lys Ser Leu Arg Val Leu Arg Val Leu Arg Pro Leu Lys Thr Ile
1345 1350 1355 1360

Lys Arg Leu Pro Lys Leu Lys Ala Val Phe Asp Cys Val Val Asn Ser
1365 1370 1375

Leu Lys Asn Val Phe Asn Ile Leu Ile Val Tyr Met Leu Phe Met Phe
1380 1385 1390

Ile Phe Ala Val Val Ala Val Gln Leu Phe Lys Gly Lys Phe Phe His
1395 1400 1405

Cys Thr Asp Glu Ser Lys Glu Phe Glu Lys Asp Cys Arg Gly Lys Tyr
1410 1415 1420

Leu Leu Tyr Glu Lys Asn Glu Val Lys Ala Arg Asp Arg Glu Trp Lys
1425 1430 1435 1440

Lys Tyr Glu Phe His Tyr Asp Asn Val Leu Trp Ala Leu Leu Thr Leu
1445 1450 1455

Phe Thr Val Ser Thr Gly Glu Gly Trp Pro Gln Val Leu Lys His Ser
1460 1465 1470

Val Asp Ala Thr Phe Glu Asn Gln Gly Pro Ser Pro Gly Tyr Arg Met
1475 1480 1485

Glu Met Ser Ile Phe Tyr Val Val Tyr Phe Val Val Phe Pro Phe Phe
1490 1495 1500

Phe Val Asn Ile Phe Val Ala Leu Ile Ile Ile Thr Phe Gln Glu Gln
1505 1510 1515 1520

Gly Asp Lys Met Met Glu Glu Tyr Ser Leu Glu Lys Asn Glu Arg Ala
1525 1530 1535

Cys Ile Asp Phe Ala Ile Ser Ala Lys Pro Leu Thr Arg His Met Pro
1540 1545 1550

Gln Asn Lys Gln Ser Phe Gln Tyr Arg Met Trp Gln Phe Val Val Ser
1555 1560 1565

Pro Pro Phe Glu Tyr Thr Ile Met Ala Met Ile Ala Leu Asn Thr Ile
1570 1575 1580

Val Leu Met Met Lys Phe Tyr Gly Ala Ser Val Ala Tyr Glu Asn Ala
1585 1590 1595 1600

Leu Arg Val Phe Asn Ile Val Phe Thr Ser Leu Phe Ser Leu Glu Cys
1605 1610 1615

Val Leu Lys Val Met Ala Phe Gly Ile Leu Asn Tyr Phe Arg Asp Ala
1620 1625 1630

Trp Asn Ile Phe Asp Phe Val Thr Val Leu Gly Ser Ile Thr Asp Ile
1635 1640 1645

Leu Val Thr Glu Phe Gly Asn Pro Asn Asn Phe Ile Asn Leu Ser Phe
1650 1655 1660

Leu Arg Leu Phe Arg Ala Ala Arg Leu Ile Lys Leu Leu Arg Gln Gly
1665 1670 1675 1680

Tyr Thr Ile Arg Ile Leu Leu Trp Thr Phe Val Gln Ser Phe Lys Ala
1685 1690 1695

-continued

Leu Pro Tyr Val Cys Leu Leu Ile Ala Met Leu Phe Phe Ile Tyr Ala
1700 1705 1710

Ile Ile Gly Met Gln Val Phe Gly Asn Ile Gly Ile Asp Val Glu Asp
1715 1720 1725

Glu Asp Ser Asp Glu Asp Glu Phe Gln Ile Thr Glu His Asn Asn Phe
1730 1735 1740

Arg Thr Phe Phe Gln Ala Leu Met Leu Leu Phe Arg Ser Ala Thr Gly
1745 1750 1755 1760

Glu Ala Trp His Asn Ile Met Leu Ser Cys Leu Ser Gly Lys Pro Cys
1765 1770 1775

Asp Lys Asn Ser Gly Ile Leu Thr Arg Glu Cys Gly Asn Glu Phe Ala
1780 1785 1790

Tyr Phe Tyr Phe Val Ser Phe Ile Phe Leu Cys Ser Phe Leu Met Leu
1795 1800 1805

Asn Leu Phe Val Ala Val Ile Met Asp Asn Phe Glu Tyr Leu Thr Arg
1810 1815 1820

Asp Ser Ser Ile Leu Gly Pro His His Leu Asp Glu Tyr Val Arg Val
1825 1830 1835 1840

Trp Ala Glu Tyr Asp Pro Ala Ala Trp Gly Arg Met Pro Tyr Leu Asp
1845 1850 1855

Met Tyr Gln Met Leu Arg His Met Ser Pro Pro Leu Gly Leu Gly Lys
1860 1865 1870

Lys Cys Pro Ala Arg Val Ala Tyr Lys Arg Leu Leu Arg Met Asp Leu
1875 1880 1885

Pro Val Ala Asp Asp Asn Thr Val His Phe Asn Ser Thr Leu Met Ala
1890 1895 1900

Leu Ile Arg Thr Ala Leu Asp Ile Lys Ile Ala Lys Gly Gly Ala Asp
1905 1910 1915 1920

Lys Gln Gln Met Asp Ala Glu Leu Arg Lys Glu Met Met Ala Ile Trp
1925 1930 1935

Pro Asn Leu Ser Gln Lys Thr Leu Asp Leu Leu Val Thr Pro His Lys
1940 1945 1950

Ser Thr Asp Leu Thr Val Gly Lys Ile Tyr Ala Ala Met Met Ile Met
1955 1960 1965

Glu Tyr Tyr Arg Gln Ser Lys Ala Lys Lys Leu Gln Ala Met Arg Glu
1970 1975 1980

Glu Gln Asp Arg Thr Pro Leu Met Phe Gln Arg Met Glu Pro Pro Ser
1985 1990 1995 2000

Pro Thr Gln Glu Gly Gly Pro Gly Gln Asn Ala Leu Pro Ser Thr Gln
2005 2010 2015

Leu Asp Pro Gly Gly Ala Leu Met Ala His Glu Ser Gly Leu Lys Glu
2020 2025 2030

Ser Pro Ser Trp Val Thr Gln Arg Ala Gln Glu Met Phe Gln Lys Thr
2035 2040 2045

Gly Thr Trp Ser Pro Glu Gln Gly Pro Pro Thr Asp Met Pro Asn Ser
2050 2055 2060

Gln Pro Asn Ser Gln Ser Val Glu Met Arg Glu Met Gly Arg Asp Gly
2065 2070 2075 2080

Tyr Ser Asp Ser Glu His Tyr Leu Pro Met Glu Gly Gln Gly Arg Ala
2085 2090 2095

Ala Ser Met Pro Arg Leu Pro Ala Glu Asn Gln Arg Arg Arg Gly Arg
2100 2105 2110

-continued

```
Pro Arg Gly Asn Asn Leu Ser Thr Ile Ser Asp Thr Ser Pro Met Lys
        2115                2120                2125

Arg Ser Ala Ser Val Leu Gly Pro Lys Ala Arg Arg Leu Asp Asp Tyr
    2130                2135                2140

Ser Leu Glu Arg Val Pro Pro Glu Glu Asn Gln Arg His His Gln Arg
2145                2150                2155                2160

Arg Arg Asp Arg Ser His Arg Ala Ser Glu Arg Ser Leu Gly Arg Tyr
                2165                2170                2175

Thr Asp Val Asp Thr Gly Leu Gly Thr Asp Leu Ser Met Thr Thr Gln
            2180                2185                2190

Ser Gly Asp Leu Pro Ser Lys Glu Arg Asp Gln Glu Arg Gly Arg Pro
        2195                2200                2205

Lys Asp Arg Lys His Arg Gln His His His His His His His His His
    2210                2215                2220

His Pro Pro Pro Pro Asp Lys Asp Arg Tyr Ala Gln Glu Arg Pro Asp
2225                2230                2235                2240

His Gly Arg Ala Arg Ala Arg Asp Gln Arg Trp Ser Arg Ser Pro Ser
                2245                2250                2255

Glu Gly Arg Glu His Met Ala His Arg Gln Gly Ser Ser Ser Val Ser
            2260                2265                2270

Gly Ser Pro Ala Pro Ser Thr Ser Gly Thr Ser Thr Pro Arg Arg Gly
        2275                2280                2285

Arg Arg Gln Leu Pro Gln Thr Pro Ser Thr Pro Arg Pro His Val Ser
    2290                2295                2300

Tyr Ser Pro Val Ile Arg Lys Ala Gly Gly Ser Gly Pro Pro Gln Gln
2305                2310                2315                2320

Gln Gln Gln Gln Gln Gln Gln Gln Gln Ala Val Ala Arg Pro Gly Arg
                2325                2330                2335

Ala Ala Thr Ser Gly Pro Arg Arg Tyr Pro Gly Pro Thr Ala Glu Pro
            2340                2345                2350

Leu Ala Gly Asp Arg Pro Pro Thr Gly Gly His Ser Ser Gly Arg Ser
        2355                2360                2365

Pro Arg Met Glu Arg Arg Val Pro Gly Pro Ala Arg Ser Glu Ser Pro
    2370                2375                2380

Arg Ala Cys Arg His Gly Gly Ala Arg Trp Pro Ala Ser Gly Pro His
2385                2390                2395                2400

Val Ser Glu Gly Pro Pro Gly Pro Arg His His Gly Tyr Tyr Arg Gly
                2405                2410                2415

Ser Asp Tyr Asp Glu Ala Asp Gly Pro Gly Ser Gly Gly Gly Glu Glu
            2420                2425                2430

Ala Met Ala Gly Ala Tyr Asp Ala Pro Pro Pro Val Arg His Ala Ser
        2435                2440                2445

Ser Gly Ala Thr Gly Arg Ser Pro Arg Thr Pro Arg Ala Ser Gly Pro
    2450                2455                2460

Ala Cys Ala Ser Pro Ser Arg His Gly Arg Arg Leu Pro Asn Gly Tyr
2465                2470                2475                2480

Tyr Pro Ala His Gly Leu Ala Arg Pro Arg Gly Pro Gly Ser Arg Lys
                2485                2490                2495

Gly Leu His Glu Pro Tyr Ser Glu Ser Asp Asp Asp Trp Cys
            2500                2505                2510
```

<210> SEQ ID NO 35
<211> LENGTH: 7791
<212> TYPE: DNA

-continued

<213> ORGANISM: Human
<220> FEATURE:
<221> NAME/KEY: misc_feature
<222> LOCATION: (237)...(7037)
<223> OTHER INFORMATION: Alpha-1A-2

<400> SEQUENCE: 35
gatgtcccga gctgctatcc ccggctcggc ccgggcagcc gccttctgag cccccgaccc 60
gaggcgccga gccgccgccg cccgatgggc tgggccgtgg agcgtctccg cagtcgtagc 120
tccagccgcc gcgctcccag ccccggcagc ctcagcatca gcggcggcgg cggcggcggc 180
ggcgtcttcc gcatcgttcg ccgcagcgta acccggagcc ctttgctctt tgcagaatgg 240
cccgcttcgg agacgagatg ccggcccgct acgggggagg aggctccggg gcagccgccg 300
gggtggtcgt gggcagcgga ggcgggcgag gagccggggg cagccggcag ggcgggcagc 360
ccggggcgca aaggatgtac aagcagtcaa tggcgcagag agcgcggacc atggcactct 420
acaaccccat ccccgtccga cagaactgcc tcacggttaa ccggtctctc ttcctcttca 480
gcgaagacaa cgtggtgaga aaatacgcca aaaagatcac cgaatggcct ccctttgaat 540
atatgatttt agccaccatc atagcgaatt gcatcgtcct cgcactggag cagcatctgc 600
ctgatgatga caagaccccg atgtctgaac ggctggatga cacagaacca tacttcattg 660 gaatttttttg tttcgaggct ggaattaaaa tcattgccct tgggtttgcc ttccacaaag 720
gctcctactt gaggaatggc tggaatgtca tggactttgt ggtggtgcta acgggcatct 780
tggcgacagt tgggacggag tttgacctac ggacgctgag ggcagttcga gtgctgcggc 840
cgctcaagct ggtgtctgga atcccaagtt tacaagtcgt cctgaagtcg atcatgaagg 900
cgatgatccc tttgctgcag atcggcctcc tcctattttt tgcaatcctt atttttgcaa 960
tcatagggtt agaattttat atgggaaaat ttcataccac ctgctttgaa gaggggacag 1020
atgacattca gggtgagtct ccggctccat gtgggacaga agagcccgcc cgcacctgcc 1080
ccaatgggac caaatgtcag ccctactggg aagggcccaa caacgggatc actcagttcg 1140
acaacatcct gtttgcagtg ctgactgttt tccagtgcat aaccatggaa gggtggactg 1200
atctcctcta caatagcaac gatgcctcag ggaacacttg gaactggttg tacttcatcc 1260
ccctcatcat catcggctcc ttttttatgc tgaaccttgt gctgggtgtg ctgtcagggg 1320
agtttgccaa agaaagggaa cgggtggaga accggcgggc ttttctgaag ctgaggcggc 1380
aacaacagat tgaacgtgag ctcaatgggt acatggaatg gatctcaaaa gcagaagagg 1440
tgatcctcgc cgaggatgaa actgacgggg agcagaggca tccctttgat ggagctctgc 1500
ggagaaccac cataaagaaa agcaagacag atttgctcaa ccccgaagag gctgaggatc 1560
agctggctga tatagcctct gtgggttctc ccttcgcccg agccagcatt aaaagtgcca 1620
agctggagaa ctcgaccttt tttcacaaaa aggagaggag gatgcgtttc tacatccgcc 1680
gcatggtcaa aactcaggcc ttctactgga ctgtactcag tttggtagct ctcaacacgc 1740
tgtgtgttgc tattgttcac tacaaccagc ccgagtggct ctccgacttc ctttactatg 1800
cagaattcat tttcttagga ctctttatgt ccgaaatgtt tataaaaatg tacgggcttg 1860
ggacgcggcc ttacttccac tcttccttca actgctttga ctgtggggtt atcattggga 1920
gcatcttcga ggtcatctgg gctgtcataa aacctggcac atcctttgga atcagcgtgt 1980
tacgagccct caggttattg cgtattttca aagtcacaaa gtactgggca tctctcagaa 2040
acctggtcgt ctctctcctc aactccatga agtccatcat cagcctgttg tttctccttt 2100
tcctgttcat tgtcgtcttc gcccttttgg gaatgcaact cttcggcggc cagtttaatt 2160

-continued

```
tcgatgaagg gactcctccc accaacttcg atacttttcc agcagcaata atgacggtgt   2220
ttcagatcct gacgggcgaa gactggaacg aggtcatgta cgacgggatc aagtctcagg   2280
ggggcgtgca gggcggcatg gtgttctcca tctatttcat tgtactgacg ctctttggga   2340
actacaccct cctgaatgtg ttcttggcca tcgctgtgga caatctggcc aacgcccagg   2400
agctcaccaa ggtggaggcg gacgagcaag aggaagaaga agcagcgaac cagaaacttg   2460
ccctacagaa agccaaggag gtggcagaag tgagtcctct gtccgcggcc aacatgtcta   2520
tagctgtgaa agagcaacag aagaatcaaa agccagccaa gtccgtgtgg gagcagcgga   2580
ccagtgagat gcgaaagcag aacttgctgg ccagccggga ggccctgtat aacgaaatgg   2640
acccggacga gcgctggaag gctgcctaca cgcggcacct gcggccagac atgaagacgc   2700
acttggaccg gccgctggtg gtggacccgc aggagaaccg caacaacaac accaacaaga   2760
gccgggcggc cgagcccacc gtggaccagc gcctcggcca gcagcgcgcc gaggacttcc   2820
tcaggaaaca ggcccgctac cacgatcggg cccgggaccc cagcggctcg gcgggcctgg   2880
acgcacggag gccctgggcg ggaagccagg aggccgagct gagccgggag ggaccctacg   2940
gccgcgagtc ggaccaccac gcccgggagg gcagcctgga gcaacccggg ttctgggagg   3000
gcgaggccga gcgaggcaag gccggggacc cccaccggag gcacgtgcac cggcaggggg   3060
gcagcaggga gagccgcagc gggtccccgc gcacgggcgc ggacggggag catcgacgtc   3120
atcgcgcgca ccgcaggccc ggggaggagg gtccggagga caaggcggag cggagggcgc   3180
ggcaccgcga gggcagccgg ccggcccggg gcggcgaggg cgagggcgag ggccccgacg   3240
ggggcgagcg caggagaagg caccggcatg gcgctccagc cacgtacgag gggacgcgc    3300
ggagggagga caaggagcgg aggcatcgga ggaggaaaga gaaccagggc tccggggtcc   3360
ctgtgtcggg ccccaacctg tcaaccaccc ggccaatcca gcaggacctg ggccgccaag   3420
acccacccct ggcagaggat attgacaaca tgaagaacaa caagctggcc accgcggagt   3480
cggccgctcc ccacggcagc cttggccacg ccggcctgcc ccagagccca gccaagatgg   3540
gaaacagcac cgaccccggc cccatgctgg ccatccctgc catggccacc aacccccaga   3600
acgccgccag ccgccggacg cccaacaacc cggggaaccc atccaatccc ggcccccccca   3660
agacccccga gaatagcctt atcgtcacca accccagcgg cacccagacc aattcagcta   3720
agactgccag gaaacccgac cacaccacag tggacatccc cccagcctgc ccaccccccc   3780
tcaaccacac cgtcgtacaa gtgaacaaaa acgccaaccc agacccactg ccaaaaaaag   3840
aggaagagaa gaaggaggag gaggaagacg accgtgggga agacggccct aagccaatgc   3900
ctccctatag ctccatgttc atcctgtcca cgaccaaccc ccttcgccgc ctgtgccatt   3960
acatcctgaa cctgcgctac tttgagatgt gcatcctcat ggtcattgcc atgagcagca   4020
tcgccctggc cgccgaggac cctgtgcagc ccaacgcacc tcggaacaac gtgctgcgat   4080
actttgacta cgtttttaca ggcgtcttca cctttgagat ggtgatcaag atgattgacc   4140
tggggctcgt cctgcatcag ggtgcctact tccgtgacct ctggaatatt ctcgacttca   4200
tagtggtcag tggggccctg gtagcctttg ccttcactgg caatagcaaa ggaaaagaca   4260
tcaacacgat taaatccctc cgagtcctcc gggtgctacg acctcttaaa accatcaagc   4320
ggctgccaaa gctcaaggct gtgtttgact gtgtggtgaa ctcacttaaa aacgtcttca   4380
acatcctcat cgtctacatg ctattcatgt tcatcttcgc cgtggtggct gtgcagctct   4440
tcaaggggaa attcttccac tgcactgacg agtccaaaga gtttgagaaa gattgtcgag   4500
```

-continued

```
gcaaatacct cctctacgag aagaatgagg tgaaggcgcg agaccgggag tggaagaagt   4560
atgaattcca ttacgacaat gtgctgtggg ctctgctgac cctcttcacc gtgtccacgg   4620
gagaaggctg gccacaggtc ctcaagcatt cggtggacgc cacctttgag aaccagggcc   4680
ccagccccgg gtaccgcatg gagatgtcca ttttctacgt cgtctacttt gtggtgttcc   4740
ccttcttctt tgtcaatatc tttgtggcct tgatcatcat caccttccag gagcaagggg   4800
acaagatgat ggaggaatac agcctggaga aaaatgagag ggcctgcatt gatttcgcca   4860
tcagcgccaa gccgctgacc cgacacatgc cgcagaacaa gcagagcttc cagtaccgca   4920
tgtggcagtt cgtggtgtct ccgcctttcg agtacacgat catggccatg atcgccctca   4980
acaccatcgt gcttatgatg aagttctatg gggcttctgt tgcttatgaa aatgccctgc   5040
gggtgttcaa catcgtcttc acctccctct tctctctgga atgtgtgctg aaagtcatgg   5100
cttttgggat tctgaattat ttccgcgatg cctggaacat cttcgacttt gtgactgttc   5160
tgggcagcat caccgatatc ctcgtgactg agtttgggaa tccgaataac ttcatcaacc   5220
tgagctttct ccgcctcttc cgagctgccc ggctcatcaa acttctccgt cagggttaca   5280
ccatccgcat tcttctctgg acctttgtgc agtccttcaa ggccctgcct tatgtctgtc   5340
tgctgatcgc catgctcttc ttcatctatg ccatcattgg gatgcaggtg tttggtaaca   5400
ttggcatcga cgtggaggac gaggacagtg atgaagatga gttccaaatc actgagcaca   5460
ataacttccg gaccttcttc caggccctca tgcttctctt ccggagtgcc accggggaag   5520
cttggcacaa catcatgctt tcctgcctca gcgggaaacc gtgtgataag aactctggca   5580
tcctgactcg agagtgtggc aatgaatttg cttattttta ctttgtttcc ttcatcttcc   5640
tctgctcgtt tctgatgctg aatctctttg tcgccgtcat catggacaac tttgagtacc   5700
tcacccgaga ctcctccatc ctgggccccc accacctgga tgagtacgtg cgtgtctggg   5760
ccgagtatga ccccgcagct tggggccgca tgccttacct ggacatgtat cagatgctga   5820
gacacatgtc tccgcccctg ggtctgggga agaagtgtcc ggccagagtg gcttacaagc   5880
ggcttctgcg gatggacctg cccgtcgcag atgacaacac cgtccacttc aattccaccc   5940
tcatggctct gatccgcaca gccctggaca tcaagattgc caagggagga gccgacaaac   6000
agcagatgga cgctgagctg cggaaggaga tgatggcgat ttggcccaat ctgtcccaga   6060
agacgctaga cctgctggtc acacctcaca agtccacgga cctcaccgtg gggaagatct   6120
acgcagccat gatgatcatg gagtactacc ggcagagcaa ggccaagaag ctgcaggcca   6180
tgcgcgagga gcaggaccgg acacccctca tgttccagcg catggagccc ccgtccccaa   6240
cgcaggaagg gggacctggc cagaacgccc tcccctccac ccagctggac ccaggaggag   6300
ccctgatggc tcacgaaagc ggcctcaagg agagcccgtc ctgggtgacc cagcgtgccc   6360
aggagatgtt ccagaagacg ggcacatgga gtccggaaca aggcccccct accgacatgc   6420
ccaacagcca gcctaactct cagtccgtgg agatgcgaga gatgggcaga gatggctact   6480
ccgacagcga gcactacctc cccatggaag gccagggccg ggctgcctcc atgccccgcc   6540
tccctgcaga gaaccagagg agaaggggcc ggccacgtgg gaataacctc agtaccatct   6600
cagacaccag ccccatgaag cgttcagcct ccgtgctggg ccccaaggcc cgacgcctgg   6660
acgattactc gctggagcgg gtcccgcccg aggagaacca gcggcaccac cagcggcgcc   6720
gcgaccgcag ccaccgcgcc tctgagcgct ccctgggccg ctacaccgat gtggacacag   6780
gcttggggac agacctgagc atgaccaccc aatccgggga cctgccgtcg aaggagcggg   6840
accaggagcg gggccggccc aaggatcgga agcatcgaca gcaccaccac caccaccacc   6900
```

```
accaccacca tcccccgccc cccgacaagg accgctatgc ccaggaacgg ccggaccacg   6960

gccgggcacg ggctcgggac cagcgctggt cccgctcgcc cagcgagggc cgagagcaca   7020

tggcgcaccg gcagtagttc cgtaagtgga agcccagccc cctcaacatc tggtaccagc   7080

actccgcggc ggggccgccg ccagctcccc cagacccccct ccacccccccg gccacacgtg   7140

tcctattccc ctgtgatccg taaggccggc ggctcggggc ccccgcagca gcagcagcag   7200

cagcaggcgg tggccaggcc gggccgggcg gccaccagcg gccctcggag gtacccaggc   7260

cccacggccg agcctctggc cggagatcgg ccgcccacgg ggggccacag cagcggccgc   7320

tcgcccagga tggagaggcg ggtcccaggc ccggcccgga gcgagtcccc cagggcctgt   7380

cgacacggcg gggcccggtg gccggcatct ggcccgcacg tgtccgaggg gcccccgggt   7440

ccccggcacc atggctacta ccggggctcc gactacgacg aggccgatgg cccgggcagc   7500

gggggcggcg aggaggccat ggccggggcc tacgacgcgc caccccccgt acgacacgcg   7560

tcctcgggcg ccaccgggcg ctcgcccagg actccccggg cctcgggccc ggcctgcgcc   7620

tcgccttctc ggcacggccg gcgactcccc aacggctact acccggcgca cggactggcc   7680

aggccccgcg ggccgggctc caggaagggc ctgcacgaac cctacagcga gagtgacgat   7740

gattggtgct aagcccgggc gaggtggcgc ccgcccggcc ccccacgcac c            7791

<210> SEQ ID NO 36
<211> LENGTH: 2266
<212> TYPE: PRT
<213> ORGANISM: Human

<400> SEQUENCE: 36

Met Ala Arg Phe Gly Asp Glu Met Pro Ala Arg Tyr Gly Gly Gly Gly
1               5                   10                  15

Ser Gly Ala Ala Ala Gly Val Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
```

-continued

```
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
        355                 360                 365

Arg Val Glu Asn Arg Arg Ala Phe Leu Lys Leu Arg Arg Gln Gln Gln
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
            420                 425                 430

Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640
```

-continued

```
Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
    770                 775                 780

Met Arg Lys Gln Asn Leu Leu Ala Ser Arg Glu Ala Leu Tyr Asn Glu
785                 790                 795                 800

Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845

Val Asp Gln Arg Leu Gly Gln Gln Arg Ala Glu Asp Phe Leu Arg Lys
    850                 855                 860

Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
            900                 905                 910

Ser Leu Glu Gln Pro Gly Phe Trp Glu Gly Glu Ala Glu Arg Gly Lys
        915                 920                 925

Ala Gly Asp Pro His Arg Arg His Val His Arg Gln Gly Gly Ser Arg
    930                 935                 940

Glu Ser Arg Ser Gly Ser Pro Arg Thr Gly Ala Asp Gly Glu His Arg
945                 950                 955                 960

Arg His Arg Ala His Arg Arg Pro Gly Glu Glu Gly Pro Glu Asp Lys
                965                 970                 975

Ala Glu Arg Arg Ala Arg His Arg Glu Gly Ser Arg Pro Ala Arg Gly
            980                 985                 990

Gly Glu Gly Glu Gly Glu Gly Pro Asp Gly Gly Glu Arg Arg Arg Arg
        995                 1000                1005

His Arg His Gly Ala Pro Ala Thr Tyr Glu Gly Asp Ala Arg Arg Glu
    1010                1015                1020

Asp Lys Glu Arg Arg His Arg Arg Arg Lys Glu Asn Gln Gly Ser Gly
1025                1030                1035                1040

Val Pro Val Ser Gly Pro Asn Leu Ser Thr Thr Arg Pro Ile Gln Gln
                1045                1050                1055
```

-continued

```
Asp Leu Gly Arg Gln Asp Pro Pro Leu Ala Glu Asp Ile Asp Asn Met
            1060                1065                1070

Lys Asn Asn Lys Leu Ala Thr Ala Glu Ser Ala Ala Pro His Gly Ser
        1075                1080                1085

Leu Gly His Ala Gly Leu Pro Gln Ser Pro Ala Lys Met Gly Asn Ser
    1090                1095                1100

Thr Asp Pro Gly Pro Met Leu Ala Ile Pro Ala Met Ala Thr Asn Pro
1105                1110                1115                1120

Gln Asn Ala Ala Ser Arg Arg Thr Pro Asn Asn Pro Gly Asn Pro Ser
                1125                1130                1135

Asn Pro Gly Pro Pro Lys Thr Pro Glu Asn Ser Leu Ile Val Thr Asn
            1140                1145                1150

Pro Ser Gly Thr Gln Thr Asn Ser Ala Lys Thr Ala Arg Lys Pro Asp
        1155                1160                1165

His Thr Thr Val Asp Ile Pro Pro Ala Cys Pro Pro Pro Leu Asn His
    1170                1175                1180

Thr Val Val Gln Val Asn Lys Asn Ala Asn Pro Asp Pro Leu Pro Lys
1185                1190                1195                1200

Lys Glu Glu Glu Lys Lys Glu Glu Glu Glu Asp Asp Arg Gly Glu Asp
                1205                1210                1215

Gly Pro Lys Pro Met Pro Pro Tyr Ser Ser Met Phe Ile Leu Ser Thr
            1220                1225                1230

Thr Asn Pro Leu Arg Arg Leu Cys His Tyr Ile Leu Asn Leu Arg Tyr
        1235                1240                1245

Phe Glu Met Cys Ile Leu Met Val Ile Ala Met Ser Ser Ile Ala Leu
    1250                1255                1260

Ala Ala Glu Asp Pro Val Gln Pro Asn Ala Pro Arg Asn Asn Val Leu
1265                1270                1275                1280

Arg Tyr Phe Asp Tyr Val Phe Thr Gly Val Phe Thr Phe Glu Met Val
                1285                1290                1295

Ile Lys Met Ile Asp Leu Gly Leu Val Leu His Gln Gly Ala Tyr Phe
            1300                1305                1310

Arg Asp Leu Trp Asn Ile Leu Asp Phe Ile Val Val Ser Gly Ala Leu
        1315                1320                1325

Val Ala Phe Ala Phe Thr Gly Asn Ser Lys Gly Lys Asp Ile Asn Thr
    1330                1335                1340

Ile Lys Ser Leu Arg Val Leu Arg Val Leu Arg Pro Leu Lys Thr Ile
1345                1350                1355                1360

Lys Arg Leu Pro Lys Leu Lys Ala Val Phe Asp Cys Val Val Asn Ser
                1365                1370                1375

Leu Lys Asn Val Phe Asn Ile Leu Ile Val Tyr Met Leu Phe Met Phe
            1380                1385                1390

Ile Phe Ala Val Val Ala Val Gln Leu Phe Lys Gly Lys Phe Phe His
        1395                1400                1405

Cys Thr Asp Glu Ser Lys Glu Phe Glu Lys Asp Cys Arg Gly Lys Tyr
    1410                1415                1420

Leu Leu Tyr Glu Lys Asn Glu Val Lys Ala Arg Asp Arg Glu Trp Lys
1425                1430                1435                1440

Lys Tyr Glu Phe His Tyr Asp Asn Val Leu Trp Ala Leu Leu Thr Leu
                1445                1450                1455

Phe Thr Val Ser Thr Gly Glu Gly Trp Pro Gln Val Leu Lys His Ser
            1460                1465                1470

Val Asp Ala Thr Phe Glu Asn Gln Gly Pro Ser Pro Gly Tyr Arg Met
```

-continued

```
        1475                1480                1485

Glu Met Ser Ile Phe Tyr Val Val Tyr Phe Val Val Phe Pro Phe Phe
    1490                1495                1500

Phe Val Asn Ile Phe Val Ala Leu Ile Ile Ile Thr Phe Gln Glu Gln
1505                1510                1515                1520

Gly Asp Lys Met Met Glu Glu Tyr Ser Leu Glu Lys Asn Glu Arg Ala
                1525                1530                1535

Cys Ile Asp Phe Ala Ile Ser Ala Lys Pro Leu Thr Arg His Met Pro
            1540                1545                1550

Gln Asn Lys Gln Ser Phe Gln Tyr Arg Met Trp Gln Phe Val Val Ser
        1555                1560                1565

Pro Pro Phe Glu Tyr Thr Ile Met Ala Met Ile Ala Leu Asn Thr Ile
    1570                1575                1580

Val Leu Met Met Lys Phe Tyr Gly Ala Ser Val Ala Tyr Glu Asn Ala
1585                1590                1595                1600

Leu Arg Val Phe Asn Ile Val Phe Thr Ser Leu Phe Ser Leu Glu Cys
                1605                1610                1615

Val Leu Lys Val Met Ala Phe Gly Ile Leu Asn Tyr Phe Arg Asp Ala
            1620                1625                1630

Trp Asn Ile Phe Asp Phe Val Thr Val Leu Gly Ser Ile Thr Asp Ile
        1635                1640                1645

Leu Val Thr Glu Phe Gly Asn Pro Asn Asn Phe Ile Asn Leu Ser Phe
    1650                1655                1660

Leu Arg Leu Phe Arg Ala Ala Arg Leu Ile Lys Leu Leu Arg Gln Gly
1665                1670                1675                1680

Tyr Thr Ile Arg Ile Leu Leu Trp Thr Phe Val Gln Ser Phe Lys Ala
                1685                1690                1695

Leu Pro Tyr Val Cys Leu Leu Ile Ala Met Leu Phe Phe Ile Tyr Ala
            1700                1705                1710

Ile Ile Gly Met Gln Val Phe Gly Asn Ile Gly Ile Asp Val Glu Asp
        1715                1720                1725

Glu Asp Ser Asp Glu Asp Glu Phe Gln Ile Thr Glu His Asn Asn Phe
    1730                1735                1740

Arg Thr Phe Phe Gln Ala Leu Met Leu Leu Phe Arg Ser Ala Thr Gly
1745                1750                1755                1760

Glu Ala Trp His Asn Ile Met Leu Ser Cys Leu Ser Gly Lys Pro Cys
                1765                1770                1775

Asp Lys Asn Ser Gly Ile Leu Thr Arg Glu Cys Gly Asn Glu Phe Ala
            1780                1785                1790

Tyr Phe Tyr Phe Val Ser Phe Ile Phe Leu Cys Ser Phe Leu Met Leu
        1795                1800                1805

Asn Leu Phe Val Ala Val Ile Met Asp Asn Phe Glu Tyr Leu Thr Arg
    1810                1815                1820

Asp Ser Ser Ile Leu Gly Pro His His Leu Asp Glu Tyr Val Arg Val
1825                1830                1835                1840

Trp Ala Glu Tyr Asp Pro Ala Ala Trp Gly Arg Met Pro Tyr Leu Asp
                1845                1850                1855

Met Tyr Gln Met Leu Arg His Met Ser Pro Pro Leu Gly Leu Gly Lys
            1860                1865                1870

Lys Cys Pro Ala Arg Val Ala Tyr Lys Arg Leu Leu Arg Met Asp Leu
        1875                1880                1885

Pro Val Ala Asp Asp Asn Thr Val His Phe Asn Ser Thr Leu Met Ala
    1890                1895                1900
```

-continued

```
Leu Ile Arg Thr Ala Leu Asp Ile Lys Ile Ala Lys Gly Gly Ala Asp
1905                1910                1915                1920

Lys Gln Gln Met Asp Ala Glu Leu Arg Lys Glu Met Met Ala Ile Trp
                1925                1930                1935

Pro Asn Leu Ser Gln Lys Thr Leu Asp Leu Leu Val Thr Pro His Lys
            1940                1945                1950

Ser Thr Asp Leu Thr Val Gly Lys Ile Tyr Ala Ala Met Met Ile Met
        1955                1960                1965

Glu Tyr Tyr Arg Gln Ser Lys Ala Lys Lys Leu Gln Ala Met Arg Glu
    1970                1975                1980

Glu Gln Asp Arg Thr Pro Leu Met Phe Gln Arg Met Glu Pro Pro Ser
1985                1990                1995                2000

Pro Thr Gln Glu Gly Gly Pro Gly Gln Asn Ala Leu Pro Ser Thr Gln
                2005                2010                2015

Leu Asp Pro Gly Gly Ala Leu Met Ala His Glu Ser Gly Leu Lys Glu
            2020                2025                2030

Ser Pro Ser Trp Val Thr Gln Arg Ala Gln Glu Met Phe Gln Lys Thr
        2035                2040                2045

Gly Thr Trp Ser Pro Glu Gln Gly Pro Pro Thr Asp Met Pro Asn Ser
    2050                2055                2060

Gln Pro Asn Ser Gln Ser Val Glu Met Arg Glu Met Gly Arg Asp Gly
2065                2070                2075                2080

Tyr Ser Asp Ser Glu His Tyr Leu Pro Met Glu Gly Gln Gly Arg Ala
                2085                2090                2095

Ala Ser Met Pro Arg Leu Pro Ala Glu Asn Gln Arg Arg Arg Gly Arg
            2100                2105                2110

Pro Arg Gly Asn Asn Leu Ser Thr Ile Ser Asp Thr Ser Pro Met Lys
        2115                2120                2125

Arg Ser Ala Ser Val Leu Gly Pro Lys Ala Arg Arg Leu Asp Asp Tyr
    2130                2135                2140

Ser Leu Glu Arg Val Pro Pro Glu Glu Asn Gln Arg His His Gln Arg
2145                2150                2155                2160

Arg Arg Asp Arg Ser His Arg Ala Ser Glu Arg Ser Leu Gly Arg Tyr
                2165                2170                2175

Thr Asp Val Asp Thr Gly Leu Gly Thr Asp Leu Ser Met Thr Thr Gln
            2180                2185                2190

Ser Gly Asp Leu Pro Ser Lys Glu Arg Asp Gln Glu Arg Gly Arg Pro
        2195                2200                2205

Lys Asp Arg Lys His Arg Gln His His His His His His His His His
    2210                2215                2220

His Pro Pro Pro Pro Asp Lys Asp Arg Tyr Ala Gln Glu Arg Pro Asp
2225                2230                2235                2240

His Gly Arg Ala Arg Ala Arg Asp Gln Arg Trp Ser Arg Ser Pro Ser
                2245                2250                2255

Glu Gly Arg Glu His Met Ala His Arg Gln
            2260                2265
```

<210> SEQ ID NO 37
<211> LENGTH: 7032
<212> TYPE: DNA
<213> ORGANISM: Human
<220> FEATURE:
<221> NAME/KEY: misc_feature
<222> LOCATION: (166)...(6921)
<223> OTHER INFORMATION: Alpha-1E-1

-continued

<400> SEQUENCE: 37

```
gctgctgctg cctctccgaa gagctcgcgg agctccccag aggcggtggt ccccgtgctt     60
gtctggatgc ggctctgagt ctccgtgtgt ctttctgctt gttgctgtgt gcgggtgttc    120
ggccgcgatc acctttgtgt gtcttctgtc tgtttaaacc tcaggatggc tcgcttcggg    180
gaggcggtgg tcgccaggcc agggtccggc gatggagact cggaccagag caggaaccgg    240
caaggaaccc ccgtgccggc ctcggggcag gcggccgcct acaagcagac gaaagcacag    300
agggcgcgga ctatggcttt gtacaacccc attcccgtcc ggcagaactg tttcaccgtc    360
aacagatccc tgttcatctt cggagaagat aacattgtca ggaaatatgc caagaagctc    420
atcgattggc cgccatttga gtacatgatc ctggccacca tcattgccaa ctgcatcgtc    480
ctggccctgg agcagcatct tcctgaggat gacaagaccc ccatgtcccg aagactggag    540
aagacagaac cttatttcat tggatctttt tgctttgaag ctgggatcaa aattgtggcc    600
ctggggttca tcttccataa gggctcttac ctccgcaatg gctggaatgt catggacttc    660
atcgtggtcc tcagtggcat cctggccact gcaggaaccc acttcaatac tcacgtggac    720
ctgaggaccc tccgggctgt gcgtgtcctg cggcctttga agctcgtgtc agggatacct    780
agcctgcaga ttgtgttgaa gtccatcatg aaggccatgg tacctcttct gcagattggc    840
cttctgctct tctttgccat cctgatgttt gctatcattg gtttggagtt ctacagtggc    900
aagttacatc gagcgtgctt catgaacaat tcaggtattc tagaaggatt tgaccccccct    960
cacccatgtg gtgtgcaggg ctgcccagct ggttatgaat gcaaggactg gatcggcccc   1020
aatgatggga tcacccagtt tgataacatc ctttttgctg tgctgactgt cttccagtgc   1080
atcaccatgg aagggtggac cactgtgctg tacaatacca atgatgcctt aggagccacc   1140
tggaattggc tgtacttcat ccccctcatc atcattggat ccttctttgt tctcaaccta   1200
gtcctgggag tgctttccgg ggaatttgcc aaagagagag agagagtgga gaaccgaagg   1260
gctttcatga agctgcggcg ccagcagcag attgagcgtg agctgaatgg ctaccgtgcc   1320
tggatagaca aagcagagga agtcatgctc gctgaagaaa ataaaaatgc tggaacatcc   1380
gccttagaag tgcttcgaag ggcaaccatc aagaggagcc ggacagaggc catgactcga   1440
gactccagtg atgagcactg tgttgatatc tcctctgtgg gcacacctct ggcccgagcc   1500
agtatcaaaa gtgcaaaggt agacggggtc tcttatttcc ggcacaagga aaggcttctg   1560
cgcatctcca ttcgccacat ggttaaatcc caggtgtttt actggattgt gctgagcctt   1620
gtggcactca acactgcctg tgtggccatt gtccatcaca accagcccca gtggctcacc   1680
cacctcctct actatgcaga atttctgttt ctgggactct tcctcttgga gatgtccctg   1740
aagatgtatg gcatggggcc tcgcctttat tttcactctt cattcaactg ctttgatttt   1800
ggggtcacag tgggcagtat ctttgaagtg gtctgggcaa tcttcagacc tggtacgtct   1860
tttggaatca gtgtcttgcg agccctccgg cttctaagaa tatttaaaat aaccaagtat   1920
tgggcttccc tacggaattt ggtggtctcc ttgatgagct caatgaagtc tatcatcagt   1980
ttgcttttcc tcctcttcct cttcatcgtt gtctttgctc tcctaggaat gcagttattt   2040
ggaggcaggt ttaactttaa tgatgggact ccttcggcaa attttgatac cttccctgca   2100
gccatcatga ctgtgttcca gatcctgacg ggtgaggact ggaatgaggt gatgtacaat   2160
gggatccgct cccagggtgg ggtcagctca ggcatgtggt ctgccatcta cttcattgtg   2220
ctcaccttgt ttggcaacta cacgctactg aatgtgttct tggctatcgc tgtggataat   2280
```

-continued

```
ctcgccaacg cccaggaact gaccaaggat gaacaggagg aagaagaggc cttcaaccag   2340
aaacatgcac tgcagaaggc caaggaggtc agcccgatgt ctgcacccaa catgccttcg   2400
atcgagaggg agcggaggcg ccggcaccac atgtccgtgt gggagcagcg taccagccag   2460
ctgaggaagc acatgcagat gtccagccag gaggccctca acagagagga ggcgccgacc   2520
atgaacccgc tcaacccccct caacccgctc agctccctca acccgctcaa tgcccacccc   2580
agcctttatc ggcgacccag ggccattgag ggcctggccc tgggcctggc cctggagaag   2640
ttcgaggagg agcgcatcag ccgtgggggg tccctcaagg gggatggagg ggaccgatcc   2700
agtgccctgg acaaccagag gacccctttg tccctgggcc agcgggagcc accatggctg   2760
gccaggccct gtcatggaaa ctgtgacccg actcagcagg aggcaggggg aggagaggct   2820
gtggtgacct ttgaggaccg ggccaggcac aggcagagcc aacggcgcag ccggcatcgc   2880
cgcgtcagga cagaaggcaa ggagtcctct tcagcctccc ggagcaggtc tgccagccag   2940
gaacgcagtc tggatgaagc catgcccact gaaggggaga aggaccatga gctcaggggc   3000
aaccatggtg ccaaggagcc aacgatccaa gaagagagag cccaggattt aaggaggacc   3060
aacagtctga tggtgtccag aggctccggg ctggcaggag gccttgatga ggctgacacc   3120
cccctagtcc tgccccatcc tgagctggaa gtggggaagc acgtggtgct gacggagcag   3180
gagccagaag gcagcagtga gcaggccctg ctggggaatg tgcagctaga catgggccgg   3240
gtcatcagcc agagcgagcc tgacctctcc tgcatcacgg ccaacacgga caaggccacc   3300
accgagagca ccagcgtcac cgtcgccatc cccgacgtgg acccccttggt ggactcaacc   3360
gtggtgcaca ttagcaacaa gacggatggg gaagccagtc ccttgaagga ggcagagatc   3420
agagaggatg aggaggaggt ggagaagaag aagcagaaga aggagaagcg tgagacaggc   3480
aaagccatgg tgccccacag ctcaatgttc atcttcagca ccaccaaccc gatccggagg   3540
gcctgccact acatcgtgaa cctgcgctac tttgagatgt gcatcctcct ggtgattgca   3600
gccagcagca tcgccctggc ggcagaggac cccgtcctga ccaactcgga gcgcaacaaa   3660
gtcctgaggt attttgacta tgtgttcacg ggcgtgttca cctttgagat ggttataaag   3720
atgatagacc aaggcttgat cctgcaggat gggtcctact tccgagactt gtggaacatc   3780
ctggactttg tggtggtcgt tggcgcattg gtggcctttg ctctggcgaa cgctttggga   3840
accaacaaag gacgggacat caagaccatc aagtctctgc gggtgctccg agttctaagg   3900
ccactgaaaa ccatcaagcg cttgcccaag ctcaaggccg tcttcgactg cgtagtgacc   3960
tccttgaaga atgtcttcaa catactcatt gtgtacaagc tcttcatgtt catctttgct   4020
gtcatcgcag ttcagctctt caagggaaag ttcttttatt gcacggacag ttccaaggac   4080
acagagaagg agtgcatagg caactatgta gatcacgaga aaaacaagat ggaggtgaag   4140
ggccgggaat ggaagcgcca tgaattccac tacgacaaca ttatctgggc cctgctgacc   4200
ctcttcaccg tctccacagg ggaaggatgg cctcaagttc tgcagcactc tgtagatgtg   4260
acagaggaag accgaggccc aagccgcagc aaccgcatgg agatgtctat cttttatgta   4320
gtctactttg tggtcttccc cttcttcttt gtcaatatct ttgtggctct catcatcatc   4380
accttccagg agcaagggga taagatgatg gaggagtgca gcctggagaa gaatgagagg   4440
gcgtgcatcg acttcgccat cagcgccaaa cctctcaccc gctacatgcc gcagaacaga   4500
cacaccttcc agtaccgcgt gtggcacttt gtggtgtctc cgtcctttga gtacaccatt   4560
atggccatga tcgccttgaa tactgttgtg ctgatgatga agtattattc tgctccctgt   4620
acctatgagc tggccctgaa gtacctgaat atcgccttca ccatggtgtt ttccctggaa   4680
```

-continued

```
tgtgtcctga aggtcatcgc ttttggcttt ttgaactatt tccgagacac ctggaatatc   4740
tttgacttca tcaccgtgat tggcagtatc acagaaatta tcctgacaga cagcaagctg   4800
gtgaacacca gtggcttcaa tatgagcttt ctgaagctct tccgagctgc ccgcctcata   4860
aagctcctgc gtcagggcta taccatacgc attttgctgt ggacctttgt gcagtccttt   4920
aaggccctcc cttatgtctg ccttttaatt gccatgcttt tcttcattta tgccatcatt   4980
gggatgcagg tatttggaaa cataaaatta gacgaggaga gtcacatcaa ccggcacaac   5040
aacttccgga gtttctttgg gtccctaatg ctactcttca ggagtgccac aggtgaggcc   5100
tggcaggaga ttatgctgtc atgccttggg gagaagggct gtgagcctga caccaccgca   5160
ccatcagggc agaacgagaa tgaacgctgc ggcaccgatc tggcctacgt gtactttgtc   5220
tccttcatct tcttctgctc cttcttgatg ctcaacctgt ttgtggccgt catcatggac   5280
aactttgagt acctgactcg ggactcctcc atcctggggc ctcaccactt ggacgagttt   5340
gtccgcgtct gggcagaata tgaccgagca gcatgtggcc gcatccatta cactgagatg   5400
tatgaaatgc tgactctcat gtcacctccg ctaggcctcg gcaagagatg tccctccaaa   5460
gtggcatata agaggttggt cctgatgaac atgccagtag ctgaggacat gacggtccac   5520
ttcacctcca cacttatggc tctgatccgg acagctctgg acattaaaat tgccaaaggt   5580
ggtgcagaca ggcagcagct agactcagag ctacaaaagg agaccctagc catctggcct   5640
cacctatccc agaagatgct ggatctgctt gtgcccatgc ccaaagcctc tgacctgact   5700
gtgggcaaaa tctatgcagc aatgatgatc atggactact ataagcagag taaggtgaag   5760
aagcagaggc agcagctgga ggaacagaaa aatgccccca tgttccagcg catggagcct   5820
tcatctctgc ctcaggagat cattgctaat gccaaagccc tgccttacct ccagcaggac   5880
cccgtttcag gcctgagtgg ccggagtgga tacccttcga tgagtccact ctctccccag   5940
gatatattcc agttggcttg tatggacccc gccgatgacg gacagttcca agaacggcag   6000
tctctggtgg tgacagaccc tagctccatg agacgttcat tttccactat tcgggataag   6060
cgttcaaatt cctcgtggtt ggaggaattc tccatggagc gaagcagtga aaatacctac   6120
aagtcccgtc gccggagtta ccactcctcc ttgcggctgt cagcccaccg cctgaactct   6180
gattcaggcc acaagtctga cactcacccc tcagggggca gggagcggcg acgatcaaaa   6240
gagcgaaagc atcttctctc tcctgatgtc tcccgctgca attcagaaga gcgagggacc   6300
caggctgact gggagtcccc agagcgccgt caatccaggt cacccagtga gggcaggtca   6360
cagacgccca acagacaggg cacaggttcc ctaagtgaga gctccatccc ctctgtctct   6420
gacaccagca ccccaagaag aagtcgtcgg cagctcccac ccgtcccgcc aaagccccgg   6480
cccctccttt cctacagctc cctgattcga cacgcgggca gcatctctcc acctgctgat   6540
ggaagcgagg agggctcccc gctgacctcc caagctctgg agagcaacaa tgcttggctg   6600
accgagtctt ccaactctcc gcacccccag cagaggcaac atgcctcccc acagcgctac   6660
atctccgagc cctacttggc cctgcacgaa gactcccacg cctcagactg tgttgaggag   6720
gagacgctca ctttcgaagc agccgtggct actagcctgg gccgttccaa caccatcggc   6780
tcagccccac ccctgcggca tagctggcag atgcccaacg ggcactatcg gcggcggagg   6840
cgcgggggc ctgggccagg catgatgtgt ggggctgtca acaacctgct aagtgacacg   6900
gaagaagatg acaaatgcta gaggctgctc ccccctccga tgcatgctct tctctcacat   6960
ggagaaaacc aagacagaat tgggaagcca gtgcggcccc gcggggagga agagggaaaa   7020
```

-continued ggaagatgga ag 7032

<210> SEQ ID NO 38
<211> LENGTH: 2251
<212> TYPE: PRT
<213> ORGANISM: Human

<400> SEQUENCE: 38

Met Ala Arg Phe Gly Glu Ala Val Val Ala Arg Pro Gly Ser Gly Asp
1 5 10 15

Gly Asp Ser Asp Gln Ser Arg Asn Arg Gln Gly Thr Pro Val Pro Ala
20 25 30

Ser Gly Gln Ala Ala Ala Tyr Lys Gln Thr Lys Ala Gln Arg Ala Arg
35 40 45

Thr Met Ala Leu Tyr Asn Pro Ile Pro Val Arg Gln Asn Cys Phe Thr
50 55 60

Val Asn Arg Ser Leu Phe Ile Phe Gly Glu Asp Asn Ile Val Arg Lys
65 70 75 80

Tyr Ala Lys Lys Leu Ile Asp Trp Pro Pro Phe Glu Tyr Met Ile Leu
85 90 95

Ala Thr Ile Ile Ala Asn Cys Ile Val Leu Ala Leu Glu Gln His Leu
100 105 110

Pro Glu Asp Asp Lys Thr Pro Met Ser Arg Arg Leu Glu Lys Thr Glu
115 120 125

Pro Tyr Phe Ile Gly Ile Phe Cys Phe Glu Ala Gly Ile Lys Ile Val
130 135 140

Ala Leu Gly Phe Ile Phe His Lys Gly Ser Tyr Leu Arg Asn Gly Trp
145 150 155 160

Asn Val Met Asp Phe Ile Val Val Leu Ser Gly Ile Leu Ala Thr Ala
165 170 175

Gly Thr His Phe Asn Thr His Val Asp Leu Arg Thr Leu Arg Ala Val
180 185 190

Arg Val Leu Arg Pro Leu Lys Leu Val Ser Gly Ile Pro Ser Leu Gln
195 200 205

Ile Val Leu Lys Ser Ile Met Lys Ala Met Val Pro Leu Leu Gln Ile
210 215 220

Gly Leu Leu Leu Phe Phe Ala Ile Leu Met Phe Ala Ile Ile Gly Leu
225 230 235 240

Glu Phe Tyr Ser Gly Lys Leu His Arg Ala Cys Phe Met Asn Asn Ser
245 250 255

Gly Ile Leu Glu Gly Phe Asp Pro Pro His Pro Cys Gly Val Gln Gly
260 265 270

Cys Pro Ala Gly Tyr Glu Cys Lys Asp Trp Ile Gly Pro Asn Asp Gly
275 280 285

Ile Thr Gln Phe Asp Asn Ile Leu Phe Ala Val Leu Thr Val Phe Gln
290 295 300

Cys Ile Thr Met Glu Gly Trp Thr Thr Val Leu Tyr Asn Thr Asn Asp
305 310 315 320

Ala Leu Gly Ala Thr Trp Asn Trp Leu Tyr Phe Ile Pro Leu Ile Ile
325 330 335

Ile Gly Ser Phe Phe Val Leu Asn Leu Val Leu Gly Val Leu Ser Gly
340 345 350

Glu Phe Ala Lys Glu Arg Glu Arg Val Glu Asn Arg Arg Ala Phe Met
355 360 365

-continued

```
Lys Leu Arg Arg Gln Gln Gln Ile Glu Arg Glu Leu Asn Gly Tyr Arg
    370                 375                 380

Ala Trp Ile Asp Lys Ala Glu Glu Val Met Leu Ala Glu Glu Asn Lys
385                 390                 395                 400

Asn Ala Gly Thr Ser Ala Leu Glu Val Leu Arg Arg Ala Thr Ile Lys
                405                 410                 415

Arg Ser Arg Thr Glu Ala Met Thr Arg Asp Ser Ser Asp Glu His Cys
            420                 425                 430

Val Asp Ile Ser Ser Val Gly Thr Pro Leu Ala Arg Ala Ser Ile Lys
        435                 440                 445

Ser Ala Lys Val Asp Gly Val Ser Tyr Phe Arg His Lys Glu Arg Leu
    450                 455                 460

Leu Arg Ile Ser Ile Arg His Met Val Lys Ser Gln Val Phe Tyr Trp
465                 470                 475                 480

Ile Val Leu Ser Leu Val Ala Leu Asn Thr Ala Cys Val Ala Ile Val
                485                 490                 495

His His Asn Gln Pro Gln Trp Leu Thr His Leu Leu Tyr Tyr Ala Glu
            500                 505                 510

Phe Leu Phe Leu Gly Leu Phe Leu Leu Glu Met Ser Leu Lys Met Tyr
        515                 520                 525

Gly Met Gly Pro Arg Leu Tyr Phe His Ser Ser Phe Asn Cys Phe Asp
    530                 535                 540

Phe Gly Val Thr Val Gly Ser Ile Phe Glu Val Val Trp Ala Ile Phe
545                 550                 555                 560

Arg Pro Gly Thr Ser Phe Gly Ile Ser Val Leu Arg Ala Leu Arg Leu
                565                 570                 575

Leu Arg Ile Phe Lys Ile Thr Lys Tyr Trp Ala Ser Leu Arg Asn Leu
            580                 585                 590

Val Val Ser Leu Met Ser Ser Met Lys Ser Ile Ile Ser Leu Leu Phe
        595                 600                 605

Leu Leu Phe Leu Phe Ile Val Val Phe Ala Leu Leu Gly Met Gln Leu
    610                 615                 620

Phe Gly Gly Arg Phe Asn Phe Asn Asp Gly Thr Pro Ser Ala Asn Phe
625                 630                 635                 640

Asp Thr Phe Pro Ala Ala Ile Met Thr Val Phe Gln Ile Leu Thr Gly
                645                 650                 655

Glu Asp Trp Asn Glu Val Met Tyr Asn Gly Ile Arg Ser Gln Gly Gly
            660                 665                 670

Val Ser Ser Gly Met Trp Ser Ala Ile Tyr Phe Ile Val Leu Thr Leu
        675                 680                 685

Phe Gly Asn Tyr Thr Leu Leu Asn Val Phe Leu Ala Ile Ala Val Asp
    690                 695                 700

Asn Leu Ala Asn Ala Gln Glu Leu Thr Lys Asp Glu Gln Glu Glu Glu
705                 710                 715                 720

Glu Ala Phe Asn Gln Lys His Ala Leu Gln Lys Ala Lys Glu Val Ser
                725                 730                 735

Pro Met Ser Ala Pro Asn Met Pro Ser Ile Glu Arg Glu Arg Arg Arg
            740                 745                 750

Arg His His Met Ser Val Trp Glu Gln Arg Thr Ser Gln Leu Arg Lys
        755                 760                 765

His Met Gln Met Ser Ser Gln Glu Ala Leu Asn Arg Glu Glu Ala Pro
    770                 775                 780

Thr Met Asn Pro Leu Asn Pro Leu Asn Pro Leu Ser Ser Leu Asn Pro
```

-continued

```
785                 790                 795                 800

Leu Asn Ala His Pro Ser Leu Tyr Arg Arg Pro Arg Ala Ile Glu Gly
                805                 810                 815

Leu Ala Leu Gly Leu Ala Leu Glu Lys Phe Glu Glu Glu Arg Ile Ser
            820                 825                 830

Arg Gly Gly Ser Leu Lys Gly Asp Gly Gly Asp Arg Ser Ser Ala Leu
        835                 840                 845

Asp Asn Gln Arg Thr Pro Leu Ser Leu Gly Gln Arg Glu Pro Pro Trp
    850                 855                 860

Leu Ala Arg Pro Cys His Gly Asn Cys Asp Pro Thr Gln Gln Glu Ala
865                 870                 875                 880

Gly Gly Gly Glu Ala Val Val Thr Phe Glu Asp Arg Ala Arg His Arg
                885                 890                 895

Gln Ser Gln Arg Arg Ser Arg His Arg Arg Val Arg Thr Glu Gly Lys
            900                 905                 910

Glu Ser Ser Ser Ala Ser Arg Ser Arg Ser Ala Ser Gln Glu Arg Ser
        915                 920                 925

Leu Asp Glu Ala Met Pro Thr Glu Gly Glu Lys Asp His Glu Leu Arg
    930                 935                 940

Gly Asn His Gly Ala Lys Glu Pro Thr Ile Gln Glu Glu Arg Ala Gln
945                 950                 955                 960

Asp Leu Arg Arg Thr Asn Ser Leu Met Val Ser Arg Gly Ser Gly Leu
                965                 970                 975

Ala Gly Gly Leu Asp Glu Ala Asp Thr Pro Leu Val Leu Pro His Pro
            980                 985                 990

Glu Leu Glu Val Gly Lys His Val Val Leu Thr Glu Gln Glu Pro Glu
        995                 1000                1005

Gly Ser Ser Glu Gln Ala Leu Leu Gly Asn Val Gln Leu Asp Met Gly
    1010                1015                1020

Arg Val Ile Ser Gln Ser Glu Pro Asp Leu Ser Cys Ile Thr Ala Asn
1025                1030                1035                1040

Thr Asp Lys Ala Thr Thr Glu Ser Thr Ser Val Thr Val Ala Ile Pro
                1045                1050                1055

Asp Val Asp Pro Leu Val Asp Ser Thr Val Val His Ile Ser Asn Lys
            1060                1065                1070

Thr Asp Gly Glu Ala Ser Pro Leu Lys Glu Ala Glu Ile Arg Glu Asp
        1075                1080                1085

Glu Glu Glu Val Glu Lys Lys Lys Gln Lys Lys Glu Lys Arg Glu Thr
    1090                1095                1100

Gly Lys Ala Met Val Pro His Ser Ser Met Phe Ile Phe Ser Thr Thr
1105                1110                1115                1120

Asn Pro Ile Arg Arg Ala Cys His Tyr Ile Val Asn Leu Arg Tyr Phe
                1125                1130                1135

Glu Met Cys Ile Leu Leu Val Ile Ala Ala Ser Ser Ile Ala Leu Ala
            1140                1145                1150

Ala Glu Asp Pro Val Leu Thr Asn Ser Glu Arg Asn Lys Val Leu Arg
        1155                1160                1165

Tyr Phe Asp Tyr Val Phe Thr Gly Val Phe Thr Phe Glu Met Val Ile
    1170                1175                1180

Lys Met Ile Asp Gln Gly Leu Ile Leu Gln Asp Gly Ser Tyr Phe Arg
1185                1190                1195                1200

Asp Leu Trp Asn Ile Leu Asp Phe Val Val Val Val Gly Ala Leu Val
                1205                1210                1215
```

-continued

```
Ala Phe Ala Leu Ala Asn Ala Leu Gly Thr Asn Lys Gly Arg Asp Ile
            1220                1225                1230

Lys Thr Ile Lys Ser Leu Arg Val Leu Arg Val Leu Arg Pro Leu Lys
        1235                1240                1245

Thr Ile Lys Arg Leu Pro Lys Leu Lys Ala Val Phe Asp Cys Val Val
    1250                1255                1260

Thr Ser Leu Lys Asn Val Phe Asn Ile Leu Ile Val Tyr Lys Leu Phe
1265                1270                1275                1280

Met Phe Ile Phe Ala Val Ile Ala Val Gln Leu Phe Lys Gly Lys Phe
                1285                1290                1295

Phe Tyr Cys Thr Asp Ser Ser Lys Asp Thr Glu Lys Glu Cys Ile Gly
            1300                1305                1310

Asn Tyr Val Asp His Glu Lys Asn Lys Met Glu Val Lys Gly Arg Glu
        1315                1320                1325

Trp Lys Arg His Glu Phe His Tyr Asp Asn Ile Ile Trp Ala Leu Leu
    1330                1335                1340

Thr Leu Phe Thr Val Ser Thr Gly Glu Gly Trp Pro Gln Val Leu Gln
1345                1350                1355                1360

His Ser Val Asp Val Thr Glu Glu Asp Arg Gly Pro Ser Arg Ser Asn
                1365                1370                1375

Arg Met Glu Met Ser Ile Phe Tyr Val Val Tyr Phe Val Val Phe Pro
            1380                1385                1390

Phe Phe Phe Val Asn Ile Phe Val Ala Leu Ile Ile Ile Thr Phe Gln
        1395                1400                1405

Glu Gln Gly Asp Lys Met Met Glu Glu Cys Ser Leu Glu Lys Asn Glu
    1410                1415                1420

Arg Ala Cys Ile Asp Phe Ala Ile Ser Ala Lys Pro Leu Thr Arg Tyr
1425                1430                1435                1440

Met Pro Gln Asn Arg His Thr Phe Gln Tyr Arg Val Trp His Phe Val
                1445                1450                1455

Val Ser Pro Ser Phe Glu Tyr Thr Ile Met Ala Met Ile Ala Leu Asn
            1460                1465                1470

Thr Val Val Leu Met Met Lys Tyr Tyr Ser Ala Pro Cys Thr Tyr Glu
        1475                1480                1485

Leu Ala Leu Lys Tyr Leu Asn Ile Ala Phe Thr Met Val Phe Ser Leu
    1490                1495                1500

Glu Cys Val Leu Lys Val Ile Ala Phe Gly Phe Leu Asn Tyr Phe Arg
1505                1510                1515                1520

Asp Thr Trp Asn Ile Phe Asp Phe Ile Thr Val Ile Gly Ser Ile Thr
                1525                1530                1535

Glu Ile Ile Leu Thr Asp Ser Lys Leu Val Asn Thr Ser Gly Phe Asn
            1540                1545                1550

Met Ser Phe Leu Lys Leu Phe Arg Ala Ala Arg Leu Ile Lys Leu Leu
        1555                1560                1565

Arg Gln Gly Tyr Thr Ile Arg Ile Leu Leu Trp Thr Phe Val Gln Ser
    1570                1575                1580

Phe Lys Ala Leu Pro Tyr Val Cys Leu Leu Ile Ala Met Leu Phe Phe
1585                1590                1595                1600

Ile Tyr Ala Ile Ile Gly Met Gln Val Phe Gly Asn Ile Lys Leu Asp
                1605                1610                1615

Glu Glu Ser His Ile Asn Arg His Asn Asn Phe Arg Ser Phe Phe Gly
            1620                1625                1630
```

-continued

```
Ser Leu Met Leu Leu Phe Arg Ser Ala Thr Gly Glu Ala Trp Gln Glu
        1635                1640                1645

Ile Met Leu Ser Cys Leu Gly Glu Lys Gly Cys Glu Pro Asp Thr Thr
    1650                1655                1660

Ala Pro Ser Gly Gln Asn Glu Asn Glu Arg Cys Gly Thr Asp Leu Ala
1665                1670                1675                1680

Tyr Val Tyr Phe Val Ser Phe Ile Phe Phe Cys Ser Phe Leu Met Leu
                1685                1690                1695

Asn Leu Phe Val Ala Val Ile Met Asp Asn Phe Glu Tyr Leu Thr Arg
            1700                1705                1710

Asp Ser Ser Ile Leu Gly Pro His His Leu Asp Glu Phe Val Arg Val
        1715                1720                1725

Trp Ala Glu Tyr Asp Arg Ala Ala Cys Gly Arg Ile His Tyr Thr Glu
    1730                1735                1740

Met Tyr Glu Met Leu Thr Leu Met Ser Pro Pro Leu Gly Leu Gly Lys
1745                1750                1755                1760

Arg Cys Pro Ser Lys Val Ala Tyr Lys Arg Leu Val Leu Met Asn Met
                1765                1770                1775

Pro Val Ala Glu Asp Met Thr Val His Phe Thr Ser Thr Leu Met Ala
            1780                1785                1790

Leu Ile Arg Thr Ala Leu Asp Ile Lys Ile Ala Lys Gly Gly Ala Asp
        1795                1800                1805

Arg Gln Gln Leu Asp Ser Glu Leu Gln Lys Glu Thr Leu Ala Ile Trp
    1810                1815                1820

Pro His Leu Ser Gln Lys Met Leu Asp Leu Leu Val Pro Met Pro Lys
1825                1830                1835                1840

Ala Ser Asp Leu Thr Val Gly Lys Ile Tyr Ala Ala Met Met Ile Met
                1845                1850                1855

Asp Tyr Tyr Lys Gln Ser Lys Val Lys Lys Gln Arg Gln Gln Leu Glu
            1860                1865                1870

Glu Gln Lys Asn Ala Pro Met Phe Gln Arg Met Glu Pro Ser Ser Leu
        1875                1880                1885

Pro Gln Glu Ile Ile Ala Asn Ala Lys Ala Leu Pro Tyr Leu Gln Gln
    1890                1895                1900

Asp Pro Val Ser Gly Leu Ser Gly Arg Ser Gly Tyr Pro Ser Met Ser
1905                1910                1915                1920

Pro Leu Ser Pro Gln Asp Ile Phe Gln Leu Ala Cys Met Asp Pro Ala
                1925                1930                1935

Asp Asp Gly Gln Phe Gln Glu Arg Gln Ser Leu Val Val Thr Asp Pro
            1940                1945                1950

Ser Ser Met Arg Arg Ser Phe Ser Thr Ile Arg Asp Lys Arg Ser Asn
        1955                1960                1965

Ser Ser Trp Leu Glu Glu Phe Ser Met Glu Arg Ser Ser Glu Asn Thr
    1970                1975                1980

Tyr Lys Ser Arg Arg Arg Ser Tyr His Ser Ser Leu Arg Leu Ser Ala
1985                1990                1995                2000

His Arg Leu Asn Ser Asp Ser Gly His Lys Ser Asp Thr His Pro Ser
                2005                2010                2015

Gly Gly Arg Glu Arg Arg Arg Ser Lys Glu Arg Lys His Leu Leu Ser
            2020                2025                2030

Pro Asp Val Ser Arg Cys Asn Ser Glu Glu Arg Gly Thr Gln Ala Asp
        2035                2040                2045

Trp Glu Ser Pro Glu Arg Arg Gln Ser Arg Ser Pro Ser Glu Gly Arg
```

-continued

```
    2050                2055                2060

Ser Gln Thr Pro Asn Arg Gln Gly Thr Gly Ser Leu Ser Glu Ser Ser
2065                2070                2075                2080

Ile Pro Ser Val Ser Asp Thr Ser Thr Pro Arg Arg Ser Arg Arg Gln
                2085                2090                2095

Leu Pro Pro Val Pro Pro Lys Pro Arg Pro Leu Leu Ser Tyr Ser Ser
            2100                2105                2110

Leu Ile Arg His Ala Gly Ser Ile Ser Pro Pro Ala Asp Gly Ser Glu
        2115                2120                2125

Glu Gly Ser Pro Leu Thr Ser Gln Ala Leu Glu Ser Asn Asn Ala Trp
    2130                2135                2140

Leu Thr Glu Ser Ser Asn Ser Pro His Pro Gln Gln Arg Gln His Ala
2145                2150                2155                2160

Ser Pro Gln Arg Tyr Ile Ser Glu Pro Tyr Leu Ala Leu His Glu Asp
                2165                2170                2175

Ser His Ala Ser Asp Cys Val Glu Glu Glu Thr Leu Thr Phe Glu Ala
            2180                2185                2190

Ala Val Ala Thr Ser Leu Gly Arg Ser Asn Thr Ile Gly Ser Ala Pro
        2195                2200                2205

Pro Leu Arg His Ser Trp Gln Met Pro Asn Gly His Tyr Arg Arg Arg
    2210                2215                2220

Arg Arg Gly Gly Pro Gly Pro Gly Met Met Cys Gly Ala Val Asn Asn
2225                2230                2235                2240

Leu Leu Ser Asp Thr Glu Glu Asp Asp Lys Cys
                2245                2250

<210> SEQ ID NO 39
<211> LENGTH: 7089
<212> TYPE: DNA
<213> ORGANISM: Human
<220> FEATURE:
<221> NAME/KEY: misc_feature
<222> LOCATION: (166)...(6978)
<223> OTHER INFORMATION: Alpha-1E-3

<400> SEQUENCE: 39

gctgctgctg cctctccgaa gagctcgcgg agctccccag aggcggtggt ccccgtgctt     60

gtctggatgc ggctctgagt ctccgtgtgt ctttctgctt gttgctgtgt gcgggtgttc    120

ggccgcgatc acctttgtgt gtcttctgtc tgtttaaacc tcaggatggc tcgcttcggg    180

gaggcggtgg tcgccaggcc agggtccggc gatggagact cggaccagag caggaaccgg    240

caaggaaccc ccgtgccggc ctcggggcag gcggccgcct acaagcagac gaaagcacag    300

agggcgcgga ctatggcttt gtacaacccc attcccgtcc ggcagaactg tttcaccgtc    360

aacagatccc tgttcatctt cggagaagat aacattgtca ggaaatatgc caagaagctc    420

atcgattggc cgccatttga gtacatgatc ctggccacca tcattgccaa ctgcatcgtc    480

ctggccctgg agcagcatct tcctgaggat gacaagaccc ccatgtcccg aagactggag    540

aagacagaac cttatttcat tgggatcttt tgctttgaag ctgggatcaa aattgtggcc    600

ctggggttca tcttccataa gggctcttac ctccgcaatg gctggaatgt catggacttc    660

atcgtggtcc tcagtggcat cctggccact gcaggaaccc acttcaatac tcacgtggac    720

ctgaggaccc tccgggctgt gcgtgtcctg cggcctttga agctcgtgtc agggatacct    780

agcctgcaga ttgtgttgaa gtccatcatg aaggccatgg tacctcttct gcagattggc    840

cttctgctct tctttgccat cctgatgttt gctatcattg gtttggagtt ctacagtggc    900
```

-continued

```
aagttacatc gagcgtgctt catgaacaat tcaggtattc tagaaggatt tgacccccct    960
cacccatgtg gtgtgcaggg ctgcccagct ggttatgaat gcaaggactg gatcggcccc   1020
aatgatggga tcacccagtt tgataacatc ctttttgctg tgctgactgt cttccagtgc   1080
atcaccatgg aagggtggac cactgtgctg tacaatacca atgatgcctt aggagccacc   1140
tggaattggc tgtacttcat ccccctcatc atcattggat ccttctttgt tctcaaccta   1200
gtcctgggag tgctttccgg ggaatttgcc aaagagagag agagagtgga gaaccgaagg   1260
gctttcatga agctgcggcg ccagcagcag attgagcgtg agctgaatgg ctaccgtgcc   1320
tggatagaca aagcagagga agtcatgctc gctgaagaaa ataaaaatgc tggaacatcc   1380
gccttagaag tgcttcgaag ggcaaccatc aagaggagcc ggacagaggc catgactcga   1440
gactccagtg atgagcactg tgttgatatc tcctctgtgg gcacacctct ggcccgagcc   1500
agtatcaaaa gtgcaaaggt agacggggtc tcttatttcc ggcacaagga aaggcttctg   1560
cgcatctcca ttcgccacat ggttaaatcc caggtgtttt actggattgt gctgagcctt   1620
gtggcactca acactgcctg tgtggccatt gtccatcaca accagcccca gtggctcacc   1680
cacctcctct actatgcaga atttctgttt ctgggactct tcctcttgga gatgtccctg   1740
aagatgtatg gcatggggcc tcgcctttat tttcactctt cattcaactg ctttgatttt   1800
ggggtcacag tgggcagtat ctttgaagtg gtctgggcaa tcttcagacc tggtacgtct   1860
tttggaatca gtgtcttgcg agccctccgg cttctaagaa tatttaaaat aaccaagtat   1920
tgggcttccc tacggaattt ggtggtctcc ttgatgagct caatgaagtc tatcatcagt   1980
ttgcttttcc tcctcttcct cttcatcgtt gtctttgctc tcctaggaat gcagttattt   2040
ggaggcaggt ttaactttaa tgatgggact ccttcggcaa attttgatac cttccctgca   2100
gccatcatga ctgtgttcca gatcctgacg ggtgaggact ggaatgaggt gatgtacaat   2160
gggatccgct cccagggtgg ggtcagctca ggcatgtggt ctgccatcta cttcattgtg   2220
ctcaccttgt ttggcaacta cacgctactg aatgtgttct tggctatcgc tgtggataat   2280
ctcgccaacg cccaggaact gaccaaggat gaacaggagg aagaagaggc cttcaaccag   2340
aaacatgcac tgcagaaggc caaggaggtc agcccgatgt ctgcacccaa catgccttcg   2400
atcgaaagag acagaaggag aagacaccac atgtcgatgt gggagccacg cagcagccac   2460
ctgagggagc ggaggcgccg gcaccacatg tccgtgtggg agcagcgtac cagccagctg   2520
aggaagcaca tgcagatgtc cagccaggag gccctcaaca gagaggaggc gccgaccatg   2580
aacccgctca acccccctcaa cccgctcagc tccctcaacc cgctcaatgc ccaccccagc   2640
ctttatcggc gacccagggc cattgagggc ctggccctgg gcctggccct ggagaagttc   2700
gaggaggagc gcatcagccg tggggggtcc ctcaaggggg atggagggga ccgatccagt   2760
gccctggaca accagaggac ccctttgtcc ctgggccagc gggagccacc atggctggcc   2820
aggccctgtc atggaaactg tgacccgact cagcaggagg caggggggagg agaggctgtg   2880
gtgacctttg aggaccgggc caggcacagg cagagccaac ggcgcagccg gcatcgccgc   2940
gtcaggacag aaggcaagga gtcctcttca gcctcccgga gcaggtctgc cagccaggaa   3000
cgcagtctgg atgaagccat gcccactgaa ggggagaagg accatgagct caggggcaac   3060
catggtgcca aggagccaac gatccaagaa gagagagccc aggatttaag gaggaccaac   3120
agtctgatgg tgtccagagg ctccgggctg gcaggaggcc ttgatgaggc tgacaccccc   3180
ctagtcctgc cccatcctga gctggaagtg gggaagcacg tggtgctgac ggagcaggag   3240
```

-continued

```
ccagaaggca gcagtgagca ggccctgctg gggaatgtgc agctagacat gggccgggtc   3300
atcagccaga gcgagcctga cctctcctgc atcacggcca acacggacaa ggccaccacc   3360
gagagcacca gcgtcaccgt cgccatcccc gacgtggacc ccttggtgga ctcaaccgtg   3420
gtgcacatta gcaacaagac ggatggggaa gccagtccct tgaaggaggc agagatcaga   3480
gaggatgagg aggaggtgga gaagaagaag cagaagaagg agaagcgtga gacaggcaaa   3540
gccatggtgc cccacagctc aatgttcatc ttcagcacca ccaacccgat ccggagggcc   3600
tgccactaca tcgtgaacct gcgctacttt gagatgtgca tcctcctggt gattgcagcc   3660
agcagcatcg ccctggcggc agaggacccc gtcctgacca actcggagcg caacaaagtc   3720
ctgaggtatt ttgactatgt gttcacgggc gtgttcacct ttgagatggt tataaagatg   3780
atagaccaag gcttgatcct gcaggatggg tcctacttcc gagacttgtg gaacatcctg   3840
gactttgtgg tggtcgttgg cgcattggtg gcctttgctc tggcgaacgc tttgggaacc   3900
aacaaaggac gggacatcaa gaccatcaag tctctgcggg tgctccgagt tctaaggcca   3960
ctgaaaacca tcaagcgctt gcccaagctc aaggccgtct tcgactgcgt agtgacctcc   4020
ttgaagaatg tcttcaacat actcattgtg tacaagctct tcatgttcat ctttgctgtc   4080
atcgcagttc agctcttcaa gggaaagttc ttttattgca cggacagttc caaggacaca   4140
gagaaggagt gcataggcaa ctatgtagat cacgagaaaa acaagatgga ggtgaagggc   4200
cgggaatgga agcgccatga attccactac gacaacatta tctgggccct gctgaccctc   4260
ttcaccgtct ccacagggga aggatggcct caagttctgc agcactctgt agatgtgaca   4320
gaggaagacc gaggcccaag ccgcagcaac cgcatggaga tgtctatctt ttatgtagtc   4380
tactttgtgg tcttcccctt cttctttgtc aatatctttg tggctctcat catcatcacc   4440
ttccaggagc aaggggataa gatgatggag gagtgcagcc tggagaagaa tgagagggcg   4500
tgcatcgact tcgccatcag cgccaaacct ctcacccgct acatgccgca gaacagacac   4560
accttccagt accgcgtgtg gcactttgtg gtgtctccgt cctttgagta caccattatg   4620
gccatgatcg ccttgaatac tgttgtgctg atgatgaagt attattctgc tccctgtacc   4680
tatgagctgg ccctgaagta cctgaatatc gccttcacca tggtgttttc cctggaatgt   4740
gtcctgaagg tcatcgcttt tggctttttg aactatttcc gagacacctg gaatatcttt   4800
gacttcatca ccgtgattgg cagtatcaca gaaattatcc tgacagacag caagctggtg   4860
aacaccagtg gcttcaatat gagctttctg aagctcttcc gagctgcccg cctcataaag   4920
ctcctgcgtc agggctatac catacgcatt ttgctgtgga cctttgtgca gtcctttaag   4980
gccctccctt atgtctgcct tttaattgcc atgcttttct tcatttatgc catcattggg   5040
atgcaggtat ttggaaacat aaaattagac gaggagagtc acatcaaccg gcacaacaac   5100
ttccggagtt tctttgggtc cctaatgcta ctcttcagga gtgccacagg tgaggcctgg   5160
caggagatta tgctgtcatg ccttggggag aagggctgtg agcctgacac caccgcacca   5220
tcagggcaga acgagaatga acgctgcggc accgatctgg cctacgtgta ctttgtctcc   5280
ttcatcttct tctgctcctt cttgatgctc aacctgtttg tggccgtcat catggacaac   5340
tttgagtacc tgactcggga ctcctccatc ctggggcctc accacttgga cgagtttgtc   5400
cgcgtctggg cagaatatga ccgagcagca tgtggccgca tccattacac tgagatgtat   5460
gaaatgctga ctctcatgtc acctccgcta ggcctcggca agagatgtcc ctccaaagtg   5520
gcatataaga ggttggtcct gatgaacatg ccagtagctg aggacatgac ggtccacttc   5580
acctccacac ttatggctct gatccggaca gctctggaca ttaaaattgc caaaggtggt   5640
```

-continued

```
gcagacaggc agcagctaga ctcagagcta caaaaggaga ccctagccat ctggcctcac   5700

ctatcccaga agatgctgga tctgcttgtg cccatgccca aagcctctga cctgactgtg   5760

ggcaaaatct atgcagcaat gatgatcatg gactactata agcagagtaa ggtgaagaag   5820

cagaggcagc agctggagga acagaaaaat gcccccatgt tccagcgcat ggagccttca   5880

tctctgcctc aggagatcat tgctaatgcc aaagccctgc cttacctcca gcaggacccc   5940

gtttcaggcc tgagtggccg gagtggatac ccttcgatga gtccactctc tccccaggat   6000

atattccagt tggcttgtat ggaccccgcc gatgacggac agttccaaga acggcagtct   6060

ctggtggtga cagaccctag ctccatgaga cgttcatttt ccactattcg ggataagcgt   6120

tcaaattcct cgtggttgga ggaattctcc atggagcgaa gcagtgaaaa tacctacaag   6180

tcccgtcgcc ggagttacca ctcctccttg cggctgtcag cccaccgcct gaactctgat   6240

tcaggccaca agtctgacac tcacccctca gggggcaggg agcggcgacg atcaaaagag   6300

cgaaagcatc ttctctctcc tgatgtctcc cgctgcaatt cagaagagcg agggacccag   6360

gctgactggg agtccccaga gcgccgtcaa tccaggtcac ccagtgaggg caggtcacag   6420

acgcccaaca gacagggcac aggttcccta agtgagagct ccatcccctc tgtctctgac   6480

accagcaccc caagaagaag tcgtcggcag ctcccacccg tcccgccaaa gccccggccc   6540

ctcctttcct acagctccct gattcgacac gcgggcagca tctctccacc tgctgatgga   6600

agcgaggagg gctccccgct gacctcccaa gctctggaga gcaacaatgc ttggctgacc   6660

gagtcttcca actctccgca cccccagcag aggcaacatg cctccccaca gcgctacatc   6720

tccgagccct acttggccct gcacgaagac tcccacgcct cagactgtgt tgaggaggag   6780

acgctcactt tcgaagcagc cgtggctact agcctgggcc gttccaacac catcggctca   6840

gccccacccc tgcggcatag ctggcagatg cccaacgggc actatcggcg gcggaggcgc   6900

ggggggcctg ggccaggcat gatgtgtggg gctgtcaaca acctgctaag tgacacggaa   6960

gaagatgaca aatgctagag gctgctcccc cctccgatgc atgctcttct ctcacatgga   7020

gaaaaccaag acagaattgg gaagccagtg cggccccgcg gggaggaaga gggaaaagga   7080

agatggaag                                                           7089
```

<210> SEQ ID NO 40
<211> LENGTH: 2270
<212> TYPE: PRT
<213> ORGANISM: Human

<400> SEQUENCE: 40

```
Met Ala Arg Phe Gly Glu Ala Val Val Ala Arg Pro Gly Ser Gly Asp
 1               5                  10                  15

Gly Asp Ser Asp Gln Ser Arg Asn Arg Gln Gly Thr Pro Val Pro Ala
            20                  25                  30

Ser Gly Gln Ala Ala Ala Tyr Lys Gln Thr Lys Ala Gln Arg Ala Arg
        35                  40                  45

Thr Met Ala Leu Tyr Asn Pro Ile Pro Val Arg Gln Asn Cys Phe Thr
    50                  55                  60

Val Asn Arg Ser Leu Phe Ile Phe Gly Glu Asp Asn Ile Val Arg Lys
65                  70                  75                  80

Tyr Ala Lys Lys Leu Ile Asp Trp Pro Pro Phe Glu Tyr Met Ile Leu
                85                  90                  95

Ala Thr Ile Ile Ala Asn Cys Ile Val Leu Ala Leu Glu Gln His Leu
            100                 105                 110
```

-continued

```
Pro Glu Asp Asp Lys Thr Pro Met Ser Arg Arg Leu Glu Lys Thr Glu
        115                 120                 125

Pro Tyr Phe Ile Gly Ile Phe Cys Phe Glu Ala Gly Ile Lys Ile Val
    130                 135                 140

Ala Leu Gly Phe Ile Phe His Lys Gly Ser Tyr Leu Arg Asn Gly Trp
145                 150                 155                 160

Asn Val Met Asp Phe Ile Val Val Leu Ser Gly Ile Leu Ala Thr Ala
                165                 170                 175

Gly Thr His Phe Asn Thr His Val Asp Leu Arg Thr Leu Arg Ala Val
            180                 185                 190

Arg Val Leu Arg Pro Leu Lys Leu Val Ser Gly Ile Pro Ser Leu Gln
        195                 200                 205

Ile Val Leu Lys Ser Ile Met Lys Ala Met Val Pro Leu Leu Gln Ile
    210                 215                 220

Gly Leu Leu Leu Phe Phe Ala Ile Leu Met Phe Ala Ile Ile Gly Leu
225                 230                 235                 240

Glu Phe Tyr Ser Gly Lys Leu His Arg Ala Cys Phe Met Asn Asn Ser
                245                 250                 255

Gly Ile Leu Glu Gly Phe Asp Pro Pro His Pro Cys Gly Val Gln Gly
            260                 265                 270

Cys Pro Ala Gly Tyr Glu Cys Lys Asp Trp Ile Gly Pro Asn Asp Gly
        275                 280                 285

Ile Thr Gln Phe Asp Asn Ile Leu Phe Ala Val Leu Thr Val Phe Gln
    290                 295                 300

Cys Ile Thr Met Glu Gly Trp Thr Thr Val Leu Tyr Asn Thr Asn Asp
305                 310                 315                 320

Ala Leu Gly Ala Thr Trp Asn Trp Leu Tyr Phe Ile Pro Leu Ile Ile
                325                 330                 335

Ile Gly Ser Phe Phe Val Leu Asn Leu Val Leu Gly Val Leu Ser Gly
            340                 345                 350

Glu Phe Ala Lys Glu Arg Glu Arg Val Glu Asn Arg Arg Ala Phe Met
        355                 360                 365

Lys Leu Arg Arg Gln Gln Gln Ile Glu Arg Glu Leu Asn Gly Tyr Arg
    370                 375                 380

Ala Trp Ile Asp Lys Ala Glu Glu Val Met Leu Ala Glu Glu Asn Lys
385                 390                 395                 400

Asn Ala Gly Thr Ser Ala Leu Glu Val Leu Arg Arg Ala Thr Ile Lys
                405                 410                 415

Arg Ser Arg Thr Glu Ala Met Thr Arg Asp Ser Ser Asp Glu His Cys
            420                 425                 430

Val Asp Ile Ser Ser Val Gly Thr Pro Leu Ala Arg Ala Ser Ile Lys
        435                 440                 445

Ser Ala Lys Val Asp Gly Val Ser Tyr Phe Arg His Lys Glu Arg Leu
    450                 455                 460

Leu Arg Ile Ser Ile Arg His Met Val Lys Ser Gln Val Phe Tyr Trp
465                 470                 475                 480

Ile Val Leu Ser Leu Val Ala Leu Asn Thr Ala Cys Val Ala Ile Val
                485                 490                 495

His His Asn Gln Pro Gln Trp Leu Thr His Leu Leu Tyr Tyr Ala Glu
            500                 505                 510

Phe Leu Phe Leu Gly Leu Phe Leu Leu Glu Met Ser Leu Lys Met Tyr
        515                 520                 525
```

-continued

```
Gly Met Gly Pro Arg Leu Tyr Phe His Ser Ser Phe Asn Cys Phe Asp
    530                 535                 540

Phe Gly Val Thr Val Gly Ser Ile Phe Glu Val Val Trp Ala Ile Phe
545                 550                 555                 560

Arg Pro Gly Thr Ser Phe Gly Ile Ser Val Leu Arg Ala Leu Arg Leu
                565                 570                 575

Leu Arg Ile Phe Lys Ile Thr Lys Tyr Trp Ala Ser Leu Arg Asn Leu
            580                 585                 590

Val Val Ser Leu Met Ser Ser Met Lys Ser Ile Ile Ser Leu Leu Phe
        595                 600                 605

Leu Leu Phe Leu Phe Ile Val Val Phe Ala Leu Leu Gly Met Gln Leu
    610                 615                 620

Phe Gly Gly Arg Phe Asn Phe Asn Asp Gly Thr Pro Ser Ala Asn Phe
625                 630                 635                 640

Asp Thr Phe Pro Ala Ala Ile Met Thr Val Phe Gln Ile Leu Thr Gly
                645                 650                 655

Glu Asp Trp Asn Glu Val Met Tyr Asn Gly Ile Arg Ser Gln Gly Gly
            660                 665                 670

Val Ser Ser Gly Met Trp Ser Ala Ile Tyr Phe Ile Val Leu Thr Leu
        675                 680                 685

Phe Gly Asn Tyr Thr Leu Leu Asn Val Phe Leu Ala Ile Ala Val Asp
    690                 695                 700

Asn Leu Ala Asn Ala Gln Glu Leu Thr Lys Asp Glu Gln Glu Glu Glu
705                 710                 715                 720

Glu Ala Phe Asn Gln Lys His Ala Leu Gln Lys Ala Lys Glu Val Ser
                725                 730                 735

Pro Met Ser Ala Pro Asn Met Pro Ser Ile Glu Arg Asp Arg Arg Arg
            740                 745                 750

Arg His His Met Ser Met Trp Glu Pro Arg Ser Ser His Leu Arg Glu
        755                 760                 765

Arg Arg Arg Arg His His Met Ser Val Trp Glu Gln Arg Thr Ser Gln
    770                 775                 780

Leu Arg Lys His Met Gln Met Ser Ser Gln Glu Ala Leu Asn Arg Glu
785                 790                 795                 800

Glu Ala Pro Thr Met Asn Pro Leu Asn Pro Leu Asn Pro Leu Ser Ser
                805                 810                 815

Leu Asn Pro Leu Asn Ala His Pro Ser Leu Tyr Arg Arg Pro Arg Ala
            820                 825                 830

Ile Glu Gly Leu Ala Leu Gly Leu Ala Leu Glu Lys Phe Glu Glu Glu
        835                 840                 845

Arg Ile Ser Arg Gly Gly Ser Leu Lys Gly Asp Gly Gly Asp Arg Ser
    850                 855                 860

Ser Ala Leu Asp Asn Gln Arg Thr Pro Leu Ser Leu Gly Gln Arg Glu
865                 870                 875                 880

Pro Pro Trp Leu Ala Arg Pro Cys His Gly Asn Cys Asp Pro Thr Gln
                885                 890                 895

Gln Glu Ala Gly Gly Gly Glu Ala Val Val Thr Phe Glu Asp Arg Ala
            900                 905                 910

Arg His Arg Gln Ser Gln Arg Arg Ser Arg His Arg Arg Val Arg Thr
        915                 920                 925

Glu Gly Lys Glu Ser Ser Ser Ala Ser Arg Ser Arg Ser Ala Ser Gln
    930                 935                 940

Glu Arg Ser Leu Asp Glu Ala Met Pro Thr Glu Gly Glu Lys Asp His
```

-continued 945 950 955 960

Glu Leu Arg Gly Asn His Gly Ala Lys Glu Pro Thr Ile Gln Glu Glu
965 970 975

Arg Ala Gln Asp Leu Arg Arg Thr Asn Ser Leu Met Val Ser Arg Gly
980 985 990

Ser Gly Leu Ala Gly Gly Leu Asp Glu Ala Asp Thr Pro Leu Val Leu
995 1000 1005

Pro His Pro Glu Leu Glu Val Gly Lys His Val Val Leu Thr Glu Gln
1010 1015 1020

Glu Pro Glu Gly Ser Ser Glu Gln Ala Leu Leu Gly Asn Val Gln Leu
1025 1030 1035 1040

Asp Met Gly Arg Val Ile Ser Gln Ser Glu Pro Asp Leu Ser Cys Ile
1045 1050 1055

Thr Ala Asn Thr Asp Lys Ala Thr Thr Glu Ser Thr Ser Val Thr Val
1060 1065 1070

Ala Ile Pro Asp Val Asp Pro Leu Val Asp Ser Thr Val Val His Ile
1075 1080 1085

Ser Asn Lys Thr Asp Gly Glu Ala Ser Pro Leu Lys Glu Ala Glu Ile
1090 1095 1100

Arg Glu Asp Glu Glu Glu Val Glu Lys Lys Lys Gln Lys Lys Glu Lys
1105 1110 1115 1120

Arg Glu Thr Gly Lys Ala Met Val Pro His Ser Ser Met Phe Ile Phe
1125 1130 1135

Ser Thr Thr Asn Pro Ile Arg Arg Ala Cys His Tyr Ile Val Asn Leu
1140 1145 1150

Arg Tyr Phe Glu Met Cys Ile Leu Leu Val Ile Ala Ala Ser Ser Ile
1155 1160 1165

Ala Leu Ala Ala Glu Asp Pro Val Leu Thr Asn Ser Glu Arg Asn Lys
1170 1175 1180

Val Leu Arg Tyr Phe Asp Tyr Val Phe Thr Gly Val Phe Thr Phe Glu
1185 1190 1195 1200

Met Val Ile Lys Met Ile Asp Gln Gly Leu Ile Leu Gln Asp Gly Ser
1205 1210 1215

Tyr Phe Arg Asp Leu Trp Asn Ile Leu Asp Phe Val Val Val Val Gly
1220 1225 1230

Ala Leu Val Ala Phe Ala Leu Ala Asn Ala Leu Gly Thr Asn Lys Gly
1235 1240 1245

Arg Asp Ile Lys Thr Ile Lys Ser Leu Arg Val Leu Arg Val Leu Arg
1250 1255 1260

Pro Leu Lys Thr Ile Lys Arg Leu Pro Lys Leu Lys Ala Val Phe Asp
1265 1270 1275 1280

Cys Val Val Thr Ser Leu Lys Asn Val Phe Asn Ile Leu Ile Val Tyr
1285 1290 1295

Lys Leu Phe Met Phe Ile Phe Ala Val Ile Ala Val Gln Leu Phe Lys
1300 1305 1310

Gly Lys Phe Phe Tyr Cys Thr Asp Ser Ser Lys Asp Thr Glu Lys Glu
1315 1320 1325

Cys Ile Gly Asn Tyr Val Asp His Glu Lys Asn Lys Met Glu Val Lys
1330 1335 1340

Gly Arg Glu Trp Lys Arg His Glu Phe His Tyr Asp Asn Ile Ile Trp
1345 1350 1355 1360

Ala Leu Leu Thr Leu Phe Thr Val Ser Thr Gly Glu Gly Trp Pro Gln
1365 1370 1375

-continued

```
Val Leu Gln His Ser Val Asp Val Thr Glu Glu Asp Arg Gly Pro Ser
            1380                1385                1390

Arg Ser Asn Arg Met Glu Met Ser Ile Phe Tyr Val Val Tyr Phe Val
        1395                1400                1405

Val Phe Pro Phe Phe Phe Val Asn Ile Phe Val Ala Leu Ile Ile Ile
    1410                1415                1420

Thr Phe Gln Glu Gln Gly Asp Lys Met Met Glu Glu Cys Ser Leu Glu
1425                1430                1435                1440

Lys Asn Glu Arg Ala Cys Ile Asp Phe Ala Ile Ser Ala Lys Pro Leu
                1445                1450                1455

Thr Arg Tyr Met Pro Gln Asn Arg His Thr Phe Gln Tyr Arg Val Trp
            1460                1465                1470

His Phe Val Val Ser Pro Ser Phe Glu Tyr Thr Ile Met Ala Met Ile
        1475                1480                1485

Ala Leu Asn Thr Val Val Leu Met Met Lys Tyr Tyr Ser Ala Pro Cys
    1490                1495                1500

Thr Tyr Glu Leu Ala Leu Lys Tyr Leu Asn Ile Ala Phe Thr Met Val
1505                1510                1515                1520

Phe Ser Leu Glu Cys Val Leu Lys Val Ile Ala Phe Gly Phe Leu Asn
                1525                1530                1535

Tyr Phe Arg Asp Thr Trp Asn Ile Phe Asp Phe Ile Thr Val Ile Gly
            1540                1545                1550

Ser Ile Thr Glu Ile Ile Leu Thr Asp Ser Lys Leu Val Asn Thr Ser
        1555                1560                1565

Gly Phe Asn Met Ser Phe Leu Lys Leu Phe Arg Ala Ala Arg Leu Ile
    1570                1575                1580

Lys Leu Leu Arg Gln Gly Tyr Thr Ile Arg Ile Leu Leu Trp Thr Phe
1585                1590                1595                1600

Val Gln Ser Phe Lys Ala Leu Pro Tyr Val Cys Leu Leu Ile Ala Met
                1605                1610                1615

Leu Phe Phe Ile Tyr Ala Ile Ile Gly Met Gln Val Phe Gly Asn Ile
            1620                1625                1630

Lys Leu Asp Glu Glu Ser His Ile Asn Arg His Asn Asn Phe Arg Ser
        1635                1640                1645

Phe Phe Gly Ser Leu Met Leu Leu Phe Arg Ser Ala Thr Gly Glu Ala
    1650                1655                1660

Trp Gln Glu Ile Met Leu Ser Cys Leu Gly Glu Lys Gly Cys Glu Pro
1665                1670                1675                1680

Asp Thr Thr Ala Pro Ser Gly Gln Asn Glu Asn Glu Arg Cys Gly Thr
                1685                1690                1695

Asp Leu Ala Tyr Val Tyr Phe Val Ser Phe Ile Phe Phe Cys Ser Phe
            1700                1705                1710

Leu Met Leu Asn Leu Phe Val Ala Val Ile Met Asp Asn Phe Glu Tyr
        1715                1720                1725

Leu Thr Arg Asp Ser Ser Ile Leu Gly Pro His His Leu Asp Glu Phe
    1730                1735                1740

Val Arg Val Trp Ala Glu Tyr Asp Arg Ala Ala Cys Gly Arg Ile His
1745                1750                1755                1760

Tyr Thr Glu Met Tyr Glu Met Leu Thr Leu Met Ser Pro Pro Leu Gly
                1765                1770                1775

Leu Gly Lys Arg Cys Pro Ser Lys Val Ala Tyr Lys Arg Leu Val Leu
            1780                1785                1790
```

-continued

Met Asn Met Pro Val Ala Glu Asp Met Thr Val His Phe Thr Ser Thr
1795 1800 1805

Leu Met Ala Leu Ile Arg Thr Ala Leu Asp Ile Lys Ile Ala Lys Gly
1810 1815 1820

Gly Ala Asp Arg Gln Gln Leu Asp Ser Glu Leu Gln Lys Glu Thr Leu
1825 1830 1835 1840

Ala Ile Trp Pro His Leu Ser Gln Lys Met Leu Asp Leu Leu Val Pro
1845 1850 1855

Met Pro Lys Ala Ser Asp Leu Thr Val Gly Lys Ile Tyr Ala Ala Met
1860 1865 1870

Met Ile Met Asp Tyr Tyr Lys Gln Ser Lys Val Lys Lys Gln Arg Gln
1875 1880 1885

Gln Leu Glu Glu Gln Lys Asn Ala Pro Met Phe Gln Arg Met Glu Pro
1890 1895 1900

Ser Ser Leu Pro Gln Glu Ile Ile Ala Asn Ala Lys Ala Leu Pro Tyr
1905 1910 1915 1920

Leu Gln Gln Asp Pro Val Ser Gly Leu Ser Gly Arg Ser Gly Tyr Pro
1925 1930 1935

Ser Met Ser Pro Leu Ser Pro Gln Asp Ile Phe Gln Leu Ala Cys Met
1940 1945 1950

Asp Pro Ala Asp Asp Gly Gln Phe Gln Glu Arg Gln Ser Leu Val Val
1955 1960 1965

Thr Asp Pro Ser Ser Met Arg Arg Ser Phe Ser Thr Ile Arg Asp Lys
1970 1975 1980

Arg Ser Asn Ser Ser Trp Leu Glu Glu Phe Ser Met Glu Arg Ser Ser
1985 1990 1995 2000

Glu Asn Thr Tyr Lys Ser Arg Arg Arg Ser Tyr His Ser Ser Leu Arg
2005 2010 2015

Leu Ser Ala His Arg Leu Asn Ser Asp Ser Gly His Lys Ser Asp Thr
2020 2025 2030

His Pro Ser Gly Gly Arg Glu Arg Arg Arg Ser Lys Glu Arg Lys His
2035 2040 2045

Leu Leu Ser Pro Asp Val Ser Arg Cys Asn Ser Glu Glu Arg Gly Thr
2050 2055 2060

Gln Ala Asp Trp Glu Ser Pro Glu Arg Arg Gln Ser Arg Ser Pro Ser
2065 2070 2075 2080

Glu Gly Arg Ser Gln Thr Pro Asn Arg Gln Gly Thr Gly Ser Leu Ser
2085 2090 2095

Glu Ser Ser Ile Pro Ser Val Ser Asp Thr Ser Thr Pro Arg Arg Ser
2100 2105 2110

Arg Arg Gln Leu Pro Pro Val Pro Pro Lys Pro Arg Pro Leu Leu Ser
2115 2120 2125

Tyr Ser Ser Leu Ile Arg His Ala Gly Ser Ile Ser Pro Pro Ala Asp
2130 2135 2140

Gly Ser Glu Glu Gly Ser Pro Leu Thr Ser Gln Ala Leu Glu Ser Asn
2145 2150 2155 2160

Asn Ala Trp Leu Thr Glu Ser Ser Asn Ser Pro His Pro Gln Gln Arg
2165 2170 2175

Gln His Ala Ser Pro Gln Arg Tyr Ile Ser Glu Pro Tyr Leu Ala Leu
2180 2185 2190

His Glu Asp Ser His Ala Ser Asp Cys Val Glu Glu Glu Thr Leu Thr
2195 2200 2205

Phe Glu Ala Ala Val Ala Thr Ser Leu Gly Arg Ser Asn Thr Ile Gly

-continued

```
2210                2215                2220

Ser Ala Pro Pro Leu Arg His Ser Trp Gln Met Pro Asn Gly His Tyr
2225                2230                2235                2240

Arg Arg Arg Arg Arg Gly Gly Pro Gly Pro Gly Met Met Cys Gly Ala
                2245                2250                2255

Val Asn Asn Leu Leu Ser Asp Thr Glu Glu Asp Asp Lys Cys
            2260                2265                2270


<210> SEQ ID NO 41
<211> LENGTH: 2634
<212> TYPE: DNA
<213> ORGANISM: Human
<220> FEATURE:
<221> NAME/KEY: misc_feature
<222> LOCATION: (1)...(1983)
<223> OTHER INFORMATION: Beta-2d

<400> SEQUENCE: 41

atggtccaaa gggacatgtc caagtctcct cccacaccgg cggcggcggt ggcgcaggag     60

atccagatgg aactgctaga gaacgtggct cccgcggggg cgctcggagc cgccgcacag    120

tcatatggaa aaggagccag aaggaaaaac agatttaaag gatctgatgg aagcacgtca    180

tctgatacta cctcaaatag ttttgttcgc cagggttcgg cagactccta cactagccgt    240

ccatccgatt ccgatgtatc tctggaggag gaccgggagg cagtgcgcag agaagcggag    300

cggcaggccc aggcacagtt ggaaaaagca aagacaaagc ccgttgcatt tgcggttcgg    360

acaaatgtca gctacagtgc ggcccatgaa gatgatgttc cagtgcctgg catggccatc    420

tcattcgaag caaaagattt tctgcatgtt aaggaaaaat ttaacaatga ctggtggata    480

gggcgattgg taaaagaagg ctgtgaaatc ggattcattc caagcccagt caaactagaa    540

aacatgaggc tgcagcatga acagagagcc aagcaaggga aattctactc cagtaaatca    600

ggaggaaatt catcatccag tttgggtgac atagtaccta gttccagaaa atcaacacct    660

ccatcatctg ctatagacat agatgctact ggcttagatg cagaagaaaa tgatattcca    720

gcaaaccacc gctcccctaa acccagtgca aacagtgtaa cgtcacccca ctccaaagag    780

aaaagaatgc ccttctttaa gaagacagag cacactcctc cgtatgatgt ggtaccttcc    840

atgcgaccag tggtcctagt gggcccttct ctgaagggct acgaggtcac agatatgatg    900

caaaaagcgc tgtttgattt tttaaaacac agatttgaag ggcggatatc catcacaagg    960

gtcaccgctg acatctcgct tgccaaacgc tcggtattaa acaatcccag taagcacgca   1020

ataatagaaa gatccaacac aaggtcaagc ttagcggaag ttcagagtga aatcgaaagg   1080

atttttgaac ttgcaagaac attgcagttg gtggtccttg acgcggatac aattaatcat   1140

ccagctcaac tcagtaaaac ctccttggcc cctattatag tatatgtaaa gatttcttct   1200

cctaaggttt tacaaaggtt aataaaatct cgagggaaat ctcaagctaa acacctcaac   1260

gtccagatgg tagcagctga taaactggct cagtgtcctc cagagctgtt cgatgtgatc   1320

ttggatgaga accagcttga ggatgcctgt gagcaccttg ccgactatct ggaggcctac   1380

tggaaggcca cccatcctcc cagcagtagc ctccccaacc ctctccttag ccgtacatta   1440

gccacttcaa gtctgcctct tagccccacc ctagcctcta attcacaggg ttctcaaggt   1500

gatcagagga ctgatcgctc cgctcctatc cgttctgctt cccaagctga agaagaacct   1560

agtgtggaac cagtcaagaa atcccagcac cgctcttcct cctcagcccc acaccacaac   1620

catcgcagtg ggacaagtcg cggcctctcc aggcaagaga catttgactc ggaaacccag   1680
```

-continued

```
gagagtcgag actctgccta cgtagagcca aaggaagatt attcccatga ccacgtggac   1740

cactatgcct cacaccgtga ccacaaccac agagacgaga cccacgggag cagtgaccac   1800

agacacaggg agtcccggca ccgttcccgg gacgtggatc gagagcagga ccacaacgag   1860

tgcaacaagc agcgcagccg tcataaatcc aaggatcgct actgtgaaaa ggatggagaa   1920

gtgatatcaa aaaaacggaa tgaggctggg gagtggaaca gggatgttta catcccccaa   1980

tgagttttgc ccttttgtgt tttttttttt tttttttga agtcttgtat aactaacagc   2040

atccccaaaa caaaaagtct ttggggtcta cactgcaatc atatgtgatc tgtcttgtaa   2100

tattttgtat tattgctgtt gcttgaatag caatagcatg gatagagtat tgagatactt   2160

tttcttttgt aagtgctaca taaattggcc tggtatggct gcagtcctcc ggttgcatac   2220

tggactcttc aaaaactgtt ttgggtagct gccacttgaa caaaatctgt tgccacccag   2280

gtgatgttag tgttttaaga aatgtagttg atgtatccaa caagccagaa tcagcacaga   2340

taaaaagtgg aatttcttgt ttctccagat ttttaatacg ttaatacgca ggcatctgat   2400

ttgcatattc attcatggac cactgtttct tgcttgtacc tctggctgac taaatttggg   2460

gacagattca gtcttgcctt acacaaaggg gatcataaag ttagaatcta ttttctatgt   2520

actagtactg tgtactgtat agacagtttg taaatgttat ttctgcaaac aaacacctcc   2580

ttattatata taatatatat atatatatca gtttgatcac actattttag agtc         2634


<210> SEQ ID NO 42
<211> LENGTH: 660
<212> TYPE: PRT
<213> ORGANISM: Human

<400> SEQUENCE: 42

Met Val Gln Arg Asp Met Ser Lys Ser Pro Pro Thr Pro Ala Ala Ala
 1               5                  10                  15

Val Ala Gln Glu Ile Gln Met Glu Leu Leu Glu Asn Val Ala Pro Ala
            20                  25                  30

Gly Ala Leu Gly Ala Ala Ala Gln Ser Tyr Gly Lys Gly Ala Arg Arg
        35                  40                  45

Lys Asn Arg Phe Lys Gly Ser Asp Gly Ser Thr Ser Ser Asp Thr Thr
    50                  55                  60

Ser Asn Ser Phe Val Arg Gln Gly Ser Ala Asp Ser Tyr Thr Ser Arg
65                  70                  75                  80

Pro Ser Asp Ser Asp Val Ser Leu Glu Glu Asp Arg Glu Ala Val Arg
                85                  90                  95

Arg Glu Ala Glu Arg Gln Ala Gln Ala Gln Leu Glu Lys Ala Lys Thr
            100                 105                 110

Lys Pro Val Ala Phe Ala Val Arg Thr Asn Val Ser Tyr Ser Ala Ala
        115                 120                 125

His Glu Asp Asp Val Pro Val Pro Gly Met Ala Ile Ser Phe Glu Ala
    130                 135                 140

Lys Asp Phe Leu His Val Lys Glu Lys Phe Asn Asn Asp Trp Trp Ile
145                 150                 155                 160

Gly Arg Leu Val Lys Glu Gly Cys Glu Ile Gly Phe Ile Pro Ser Pro
                165                 170                 175

Val Lys Leu Glu Asn Met Arg Leu Gln His Glu Gln Arg Ala Lys Gln
            180                 185                 190

Gly Lys Phe Tyr Ser Ser Lys Ser Gly Gly Asn Ser Ser Ser Ser Leu
        195                 200                 205
```

-continued

```
Gly Asp Ile Val Pro Ser Ser Arg Lys Ser Thr Pro Pro Ser Ser Ala
    210                 215                 220

Ile Asp Ile Asp Ala Thr Gly Leu Asp Ala Glu Glu Asn Asp Ile Pro
225                 230                 235                 240

Ala Asn His Arg Ser Pro Lys Pro Ser Ala Asn Ser Val Thr Ser Pro
                245                 250                 255

His Ser Lys Glu Lys Arg Met Pro Phe Phe Lys Lys Thr Glu His Thr
            260                 265                 270

Pro Pro Tyr Asp Val Val Pro Ser Met Arg Pro Val Val Leu Val Gly
        275                 280                 285

Pro Ser Leu Lys Gly Tyr Glu Val Thr Asp Met Met Gln Lys Ala Leu
    290                 295                 300

Phe Asp Phe Leu Lys His Arg Phe Glu Gly Arg Ile Ser Ile Thr Arg
305                 310                 315                 320

Val Thr Ala Asp Ile Ser Leu Ala Lys Arg Ser Val Leu Asn Asn Pro
                325                 330                 335

Ser Lys His Ala Ile Ile Glu Arg Ser Asn Thr Arg Ser Ser Leu Ala
            340                 345                 350

Glu Val Gln Ser Glu Ile Glu Arg Ile Phe Glu Leu Ala Arg Thr Leu
        355                 360                 365

Gln Leu Val Val Leu Asp Ala Asp Thr Ile Asn His Pro Ala Gln Leu
    370                 375                 380

Ser Lys Thr Ser Leu Ala Pro Ile Ile Val Tyr Val Lys Ile Ser Ser
385                 390                 395                 400

Pro Lys Val Leu Gln Arg Leu Ile Lys Ser Arg Gly Lys Ser Gln Ala
                405                 410                 415

Lys His Leu Asn Val Gln Met Val Ala Ala Asp Lys Leu Ala Gln Cys
            420                 425                 430

Pro Pro Glu Leu Phe Asp Val Ile Leu Asp Glu Asn Gln Leu Glu Asp
        435                 440                 445

Ala Cys Glu His Leu Ala Asp Tyr Leu Glu Ala Tyr Trp Lys Ala Thr
    450                 455                 460

His Pro Pro Ser Ser Ser Leu Pro Asn Pro Leu Leu Ser Arg Thr Leu
465                 470                 475                 480

Ala Thr Ser Ser Leu Pro Leu Ser Pro Thr Leu Ala Ser Asn Ser Gln
                485                 490                 495

Gly Ser Gln Gly Asp Gln Arg Thr Asp Arg Ser Ala Pro Ile Arg Ser
            500                 505                 510

Ala Ser Gln Ala Glu Glu Glu Pro Ser Val Glu Pro Val Lys Lys Ser
        515                 520                 525

Gln His Arg Ser Ser Ser Ser Ala Pro His His Asn His Arg Ser Gly
    530                 535                 540

Thr Ser Arg Gly Leu Ser Arg Gln Glu Thr Phe Asp Ser Glu Thr Gln
545                 550                 555                 560

Glu Ser Arg Asp Ser Ala Tyr Val Glu Pro Lys Glu Asp Tyr Ser His
                565                 570                 575

Asp His Val Asp His Tyr Ala Ser His Arg Asp His Asn His Arg Asp
            580                 585                 590

Glu Thr His Gly Ser Ser Asp His Arg His Arg Glu Ser Arg His Arg
        595                 600                 605

Ser Arg Asp Val Asp Arg Glu Gln Asp His Asn Glu Cys Asn Lys Gln
    610                 615                 620

Arg Ser Arg His Lys Ser Lys Asp Arg Tyr Cys Glu Lys Asp Gly Glu
```

-continued

```
625                 630                 635                 640

Val Ile Ser Lys Lys Arg Asn Glu Ala Gly Glu Trp Asn Arg Asp Val
                645                 650                 655

Tyr Ile Pro Gln
            660


<210> SEQ ID NO 43
<211> LENGTH: 1823
<212> TYPE: DNA
<213> ORGANISM: Human
<220> FEATURE:
<221> NAME/KEY: misc_feature
<222> LOCATION: (69)...(1631)
<223> OTHER INFORMATION: Beta-4

<400> SEQUENCE: 43

agcccagcct cgggggccag ccccctccgc ccaccgcaca cgggctggcc atgcggcggc     60

tctgaacgat gtcctcctcc tcctacgcca agaacgggac cgcggacggg ccgcactccc    120

ccacctcgca ggtggcccga ggcaccacaa cccggaggag caggttgaaa agatccgatg    180

gcagcaccac ttcgaccagc ttcatcctca gacagggttc agcggattcc tacacaagca    240

ggccgtctga ctccgatgtc tctttggaag aggaccggga agcaattcga caggagagag    300

aacagcaagc agctatccag cttgagagag caaagtccaa acctgtagca tttgccgtga    360

agacaaatgt gagctactgc ggcgccctgg acgaggatgt gcctgttcca agcacagcta    420

tctcctttga tgctaaagac tttctacata ttaaagagaa atataacaat gattggtgga    480

taggaaggct ggtgaaagag ggctgtgaaa ttggcttcat tccaagtcca ctcagattgg    540

agaacatacg gatccagcaa gaacaaaaaa gaggacgttt tcacggaggg aaatcaagtg    600

gaaattcttc ttcaagtctt ggagaaatgg tatctgggac attccgagca actcccacat    660

caacagcaaa acagaagcaa aaagtgacgg agcacattcc tccttacgat gttgtaccgt    720

caatgcgtcc ggtggtgtta gtggggccgt cactgaaagg ttacgaggta acagacatga    780

tgcagaaagc cctctttgat ttcctgaagc acaggtttga tgggaggatt tcaataacga    840

gagtgacagc tgacatttct cttgctaaga ggtctgtcct aaataatccc agcaagagag    900

caataattga acgttcgaac acccggtcca gcttagcgga agtacaaagt gaaattgaaa    960

gaatctttga gttggcaaga tctttgcaac tggttgttct tgatgcagac accatcaatc   1020

acccagcaca acttataaag acttccttag caccaattat tgttcatgta aaagtctcat   1080

ctccaaaggt tttacagcgg ttgattaaat ctagaggaaa gtcacaaagt aaacacttga   1140

atgttcaact ggtggcagct gataaacttg cacaatgccc cccagaaatg tttgatgtta   1200

tattggatga aaatcagctt gaggatgcat gtgaacatct aggggagtac ctggaggcgt   1260

actggcgtgc cacccacaca accagtagca cacccatgac cccgctgctg ggaaggaatt   1320

tgggctccac ggcactctca ccatatccca cagcaatttc tgggttacag agtcagcgaa   1380

tgaggcacag caaccactcc acagagaact ctccaattga aagacgaagt ctaatgacct   1440

ctgatgaaaa ttatcacaat gaaagggctc ggaagagtag gaaccgcttg tcttccagtt   1500

ctcagcatag ccgagatcat taccctcttg tggaagaaga ttaccctgac tcataccagg   1560

acacttacaa accccatagg aaccgaggat cacctggggg atatagccat gactcccgac   1620

ataggctttg agtctaatga aacaaaaaat attcatctgt tgacaatttg ccatagcagt   1680

gctaggataa accaatcatc ttaacttggc taacatagca cagtatttac tgtgctaatg   1740

ggctgctgtc attttatgct aagtaagggg caaaaaaaaa aattacatta tgcccttgag   1800
```

-continued tctagatgga tattagatgc ccg 1823

<210> SEQ ID NO 44
<211> LENGTH: 520
<212> TYPE: PRT
<213> ORGANISM: Human

<400> SEQUENCE: 44

```
Met Ser Ser Ser Ser Tyr Ala Lys Asn Gly Thr Ala Asp Gly Pro His
 1               5                  10                  15

Ser Pro Thr Ser Gln Val Ala Arg Gly Thr Thr Thr Arg Arg Ser Arg
            20                  25                  30

Leu Lys Arg Ser Asp Gly Ser Thr Thr Ser Thr Ser Phe Ile Leu Arg
        35                  40                  45

Gln Gly Ser Ala Asp Ser Tyr Thr Ser Arg Pro Ser Asp Ser Asp Val
    50                  55                  60

Ser Leu Glu Glu Asp Arg Glu Ala Ile Arg Gln Glu Arg Glu Gln Gln
65                  70                  75                  80

Ala Ala Ile Gln Leu Glu Arg Ala Lys Ser Lys Pro Val Ala Phe Ala
                85                  90                  95

Val Lys Thr Asn Val Ser Tyr Cys Gly Ala Leu Asp Glu Asp Val Pro
            100                 105                 110

Val Pro Ser Thr Ala Ile Ser Phe Asp Ala Lys Asp Phe Leu His Ile
        115                 120                 125

Lys Glu Lys Tyr Asn Asn Asp Trp Trp Ile Gly Arg Leu Val Lys Glu
    130                 135                 140

Gly Cys Glu Ile Gly Phe Ile Pro Ser Pro Leu Arg Leu Glu Asn Ile
145                 150                 155                 160

Arg Ile Gln Gln Glu Gln Lys Arg Gly Arg Phe His Gly Gly Lys Ser
                165                 170                 175

Ser Gly Asn Ser Ser Ser Ser Leu Gly Glu Met Val Ser Gly Thr Phe
            180                 185                 190

Arg Ala Thr Pro Thr Ser Thr Ala Lys Gln Lys Gln Lys Val Thr Glu
        195                 200                 205

His Ile Pro Pro Tyr Asp Val Val Pro Ser Met Arg Pro Val Val Leu
    210                 215                 220

Val Gly Pro Ser Leu Lys Gly Tyr Glu Val Thr Asp Met Met Gln Lys
225                 230                 235                 240

Ala Leu Phe Asp Ser Leu Lys His Arg Phe Asp Gly Arg Ile Ser Ile
                245                 250                 255

Thr Arg Val Thr Ala Asp Ile Ser Leu Ala Lys Arg Ser Val Leu Asn
            260                 265                 270

Asn Pro Ser Lys Arg Ala Ile Ile Glu Arg Ser Asn Thr Arg Ser Ser
        275                 280                 285

Leu Ala Glu Val Gln Ser Glu Ile Glu Arg Ile Phe Glu Leu Ala Arg
    290                 295                 300

Ser Leu Gln Leu Val Val Leu Asp Ala Asp Thr Ile Asn His Pro Ala
305                 310                 315                 320

Gln Leu Ile Lys Thr Ser Leu Ala Pro Ile Ile Val His Val Lys Val
                325                 330                 335

Ser Ser Pro Lys Val Leu Gln Arg Leu Ile Lys Ser Arg Gly Lys Ser
            340                 345                 350

Gln Ser Lys His Leu Asn Val Gln Leu Val Ala Ala Asp Lys Leu Ala
        355                 360                 365
```

-continued

```
Gln Cys Pro Pro Glu Met Phe Asp Val Ile Leu Asp Glu Asn Gln Leu
    370                 375                 380

Glu Asp Ala Cys Glu His Leu Gly Glu Tyr Leu Glu Ala Tyr Trp Arg
385                 390                 395                 400

Ala Thr His Thr Thr Ser Ser Thr Pro Met Thr Pro Leu Leu Gly Arg
                405                 410                 415

Asn Leu Gly Ser Thr Ala Leu Ser Pro Tyr Pro Thr Ala Ile Ser Gly
            420                 425                 430

Leu Gln Ser Gln Arg Met Arg His Ser Asn His Ser Thr Glu Asn Ser
        435                 440                 445

Pro Ile Glu Arg Arg Ser Leu Met Thr Ser Asp Glu Asn Tyr His Asn
    450                 455                 460

Glu Arg Ala Arg Lys Ser Arg Asn Arg Leu Ser Ser Ser Ser Gln His
465                 470                 475                 480

Ser Arg Asp His Tyr Pro Leu Val Glu Glu Asp Tyr Pro Asp Ser Tyr
                485                 490                 495

Gln Asp Thr Tyr Lys Pro His Arg Asn Arg Gly Ser Pro Gly Gly Tyr
            500                 505                 510

Ser His Asp Ser Arg His Arg Leu
        515                 520


<210> SEQ ID NO 45
<211> LENGTH: 520
<212> TYPE: PRT
<213> ORGANISM: Human

<400> SEQUENCE: 45

Met Ser Ser Ser Ser Tyr Ala Lys Asn Gly Thr Ala Asp Gly Pro His
 1               5                  10                  15

Ser Pro Thr Ser Gln Val Ala Arg Gly Thr Thr Thr Arg Arg Ser Arg
            20                  25                  30

Leu Lys Arg Ser Asp Gly Ser Thr Thr Ser Thr Ser Phe Ile Leu Arg
        35                  40                  45

Gln Gly Ser Ala Asp Ser Tyr Thr Ser Arg Pro Ser Asp Ser Asp Val
    50                  55                  60

Ser Leu Glu Glu Asp Arg Glu Ala Ile Arg Gln Glu Arg Glu Gln Gln
65                  70                  75                  80

Ala Ala Ile Gln Leu Glu Arg Ala Lys Ser Lys Pro Val Ala Phe Ala
                85                  90                  95

Val Lys Thr Asn Val Ser Tyr Cys Gly Ala Leu Asp Glu Asp Val Pro
            100                 105                 110

Val Pro Ser Thr Ala Ile Ser Phe Asp Ala Lys Asp Phe Leu His Ile
        115                 120                 125

Lys Glu Lys Tyr Asn Asn Asp Trp Trp Ile Gly Arg Leu Val Lys Glu
    130                 135                 140

Gly Cys Glu Ile Gly Phe Ile Pro Ser Pro Leu Arg Leu Glu Asn Ile
145                 150                 155                 160

Arg Ile Gln Gln Glu Gln Lys Arg Gly Arg Phe His Gly Gly Lys Ser
                165                 170                 175

Ser Gly Asn Ser Ser Ser Ser Leu Gly Glu Met Val Ser Gly Thr Phe
            180                 185                 190

Arg Ala Thr Pro Thr Ser Thr Ala Lys Gln Lys Gln Lys Val Thr Glu
        195                 200                 205

His Ile Pro Pro Tyr Asp Val Val Pro Ser Met Arg Pro Val Val Leu
```

-continued

```
    210                 215                 220

Val Gly Pro Ser Leu Lys Gly Tyr Glu Val Thr Asp Met Met Gln Lys
225                 230                 235                 240

Ala Leu Phe Asp Ser Leu Lys His Arg Phe Asp Gly Arg Ile Ser Ile
                245                 250                 255

Thr Arg Val Thr Ala Asp Ile Ser Leu Ala Lys Arg Ser Val Leu Asn
            260                 265                 270

Asn Pro Ser Lys Arg Ala Ile Ile Glu Arg Ser Asn Thr Arg Ser Ser
        275                 280                 285

Leu Ala Glu Val Gln Ser Glu Ile Glu Arg Ile Phe Glu Leu Ala Arg
    290                 295                 300

Ser Leu Gln Leu Val Val Leu Asp Ala Asp Thr Ile Asn His Pro Ala
305                 310                 315                 320

Gln Leu Ile Lys Thr Ser Leu Ala Pro Ile Ile Val His Val Lys Val
                325                 330                 335

Ser Ser Pro Lys Val Leu Gln Arg Leu Ile Lys Ser Arg Gly Lys Ser
            340                 345                 350

Gln Ser Lys His Leu Asn Val Gln Leu Val Ala Ala Asp Lys Leu Ala
        355                 360                 365

Gln Cys Pro Pro Glu Met Phe Asp Val Ile Leu Asp Glu Asn Gln Leu
    370                 375                 380

Glu Asp Ala Cys Glu His Leu Gly Glu Tyr Leu Glu Ala Tyr Trp Arg
385                 390                 395                 400

Ala Thr His Thr Thr Ser Ser Thr Pro Met Thr Pro Leu Leu Gly Arg
                405                 410                 415

Asn Leu Gly Ser Thr Ala Leu Ser Pro Tyr Pro Thr Ala Ile Ser Gly
            420                 425                 430

Leu Gln Ser Gln Arg Met Arg His Ser Asn His Ser Thr Glu Asn Ser
        435                 440                 445

Pro Ile Glu Arg Arg Ser Leu Met Thr Ser Asp Glu Asn Tyr His Asn
    450                 455                 460

Glu Arg Ala Arg Lys Ser Arg Asn Arg Leu Ser Ser Ser Ser Gln His
465                 470                 475                 480

Ser Arg Asp His Tyr Pro Leu Val Glu Glu Asp Tyr Pro Asp Ser Tyr
                485                 490                 495

Gln Asp Thr Tyr Lys Pro His Arg Asn Arg Gly Ser Pro Gly Gly Tyr
            500                 505                 510

Ser His Asp Ser Arg His Arg Leu
        515                 520
```

<210> SEQ ID NO 46
<211> LENGTH: 3636
<212> TYPE: DNA
<213> ORGANISM: Human
<220> FEATURE:
<221> NAME/KEY: misc_feature
<222> LOCATION: (35)...(3346)
<223> OTHER INFORMATION: Alpha-2a

<400> SEQUENCE: 46

```
gcgggggagg gggcattgat cttcgatcgc gaagatggct gctggctgcc tgctggcctt      60

gactctgaca cttttccaat ctttgctcat cggcccctcg tcggaggagc cgttcccttc     120

ggccgtcact atcaaatcat gggtggataa gatgcaagaa gaccttgtca cactggcaaa     180

aacagcaagt ggagtcaatc agcttgttga tatttatgag aaatatcaag atttgtatac     240
```

-continued

```
tgtggaacca aataatgcac gccagctggt agaaattgca gccagggata ttgagaaact    300
tctgagcaac agatctaaag ccctggtgag cctggcattg gaagcggaga aagttcaagc    360
agctcaccag tggagagaag attttgcaag caatgaagtt gtctactaca atgcaaagga    420
tgatctcgat cctgagaaaa atgacagtga gccaggcagc cagaggataa aacctgtttt    480
cattgaagat gctaattttg gacgacaaat atcttatcag cacgcagcag tccatattcc    540
tactgacatc tatgagggct caacaattgt gttaaatgaa ctcaactgga caagtgcctt    600
agatgaagtt ttcaaaaaga atcgcgagga agacccttca ttattgtggc aggtttttgg    660
cagtgccact ggcctagctc gatattatcc agcttcacca tgggttgata atagtagaac    720
tccaaataag attgaccttt atgatgtacg cagaagacca tggtacatcc aaggagctgc    780
atctcctaaa gacatgctta ttctggtgga tgtgagtgga agtgttagtg gattgacact    840
taaactgatc cgaacatctg tctccgaaat gttagaaacc ctctcagatg atgatttcgt    900
gaatgtagct tcatttaaca gcaatgctca ggatgtaagc tgttttcagc accttgtcca    960
agcaaatgta agaaataaaa aagtgttgaa agacgcggtg aataatatca cagccaaagg   1020
aattacagat tataagaagg gctttagttt tgcttttgaa cagctgctta attataatgt   1080
ttccagagca aactgcaata agattattat gctattcacg gatggaggag aagagagagc   1140
ccaggagata tttaacaaat acaataaaga taaaaaagta cgtgtattca ggttttcagt   1200
tggtcaacac aattatgaga gaggacctat tcagtggatg gcctgtgaaa acaaaggtta   1260
ttattatgaa attccttcca ttggtgcaat aagaatcaat actcaggaat atttggatgt   1320
tttgggaaga ccaatggttt tagcaggaga caaagctaag caagtccaat ggacaaatgt   1380
gtacctggat gcattggaac tgggacttgt cattactgga actcttccgg tcttcaacat   1440
aaccggccaa tttgaaaata agacaaactt aaagaaccag ctgattcttg gtgtgatggg   1500
agtagatgtg tctttggaag atattaaaag actgacacca cgttttacac tgtgccccaa   1560
tgggtattac tttgcaatcg atcctaatgg ttatgtttta ttacatccaa atcttcagcc   1620
aaagcctatt ggtgtaggta taccaacaat taatttaaga aaaaggagac ccaatatcca   1680
gaaccccaaa tctcaggagc cagtaacatt ggatttcctt gatgcagagt tagagaatga   1740
tattaaagtg gagattcgaa ataagatgat tgatgggggaa agtggagaaa aaacattcag   1800
aactctggtt aaatctcaag atgagagata tattgacaaa ggaaacagga catacacatg   1860
gacacctgtc aatggcacag attacagttt ggccttggta ttaccaacct acagttttta   1920
ctatataaaa gccaaactag aagagacaat aactcaggcc agatattcgg aaaccctgaa   1980
gccagataat tttgaagaat ctggctatac attcatagca ccaagagatt actgcaatga   2040
cctgaaaata tcggataata acactgaatt tctttttaaat ttcaacgagt ttattgatag   2100
aaaaactcca aacaacccat catgtaacgc ggatttgatt aatagagtct tgcttgatgc   2160
aggctttaca aatgaacttg tccaaaatta ctggagtaag cagaaaaata tcaagggagt   2220
gaaagcacga tttgttgtga ctgatggtgg gattaccaga gtttatccca aagaggctgg   2280
agaaaattgg caagaaaacc cagagacata tgaggacagc ttctataaaa ggagcctaga   2340
taatgataac tatgttttca ctgctcccta ctttaacaaa agtggacctg gtgcctatga   2400
atcgggcatt atggtaagca aagctgtaga aatatatatt caagggaaac ttcttaaacc   2460
tgcagttgtt ggaattaaaa ttgatgtaaa ttcctggata gagaatttca ccaaaacctc   2520
aatcagagat ccgtgtgctg gtccagtttg tgactgcaaa agaaacagtg acgtaatgga   2580
ttgtgtgatt ctggatgatg gtgggtttct tctgatggca aatcatgatg attatactaa   2640
```

```
tcagattgga agatttttg gagagattga tcccagcttg atgagacacc tggttaatat   2700

atcagtttat gcttttaaca aatcttatga ttatcagtca gtatgtgagc ccggtgctgc   2760

accaaaacaa ggagcaggac atcgctcagc atatgtgcca tcagtagcag acatattaca   2820

aattggctgg tgggccactg ctgctgcctg gtctattcta cagcagtttc tcttgagttt   2880

gacctttcca cgactccttg aggcagttga gatggaggat gatgacttca cggcctccct   2940

gtccaagcag agctgcatta ctgaacaaac ccagtatttc ttcgataacg acagtaaatc   3000

attcagtggt gtattagact gtggaaactg ttccagaatc tttcatggag aaaagcttat   3060

gaacaccaac ttaatattca taatggttga gagcaaaggg acatgtccat gtgacacacg   3120

actgctcata caagcggagc agacttctga cggtccaaat ccttgtgaca tggttaagca   3180

acctagatac cgaaaagggc ctgatgtctg ctttgataac aatgtcttgg aggattatac   3240

tgactgtggt ggtgtttctg gattaaatcc ctccctgtgg tatatcattg gaatccagtt   3300

tctactactt tggctggtat ctggcagcac acaccggctg ttatgacctt ctaaaaacca   3360

aatctgcata gttaaactcc agaccctgcc aaaacatgag ccctgccctc aattacagta   3420

acgtagggtc agctataaaa tcagacaaac attagctggg cctgttccat ggcataacac   3480

taaggcgcag actcctaagg cacccactgg ctgcatgtca gggtgtcaga tccttaaacg   3540

tgtgtgaatg ctgcatcatc tatgtgtaac atcaaagcaa aatcctatac gtgtcctcta   3600

ttggaaaatt tgggcgtttg ttgttgcatt gttggt                             3636
```

<210> SEQ ID NO 47
<211> LENGTH: 1103
<212> TYPE: PRT
<213> ORGANISM: Human

<400> SEQUENCE: 47

```
Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190
```

-continued

```
Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Pro Ile Gly Val Gly Ile Pro Thr Ile Asn Leu Arg Lys Arg
    530                 535                 540

Arg Pro Asn Ile Gln Asn Pro Lys Ser Gln Glu Pro Val Thr Leu Asp
545                 550                 555                 560

Phe Leu Asp Ala Glu Leu Glu Asn Asp Ile Lys Val Glu Ile Arg Asn
                565                 570                 575

Lys Met Ile Asp Gly Glu Ser Gly Glu Lys Thr Phe Arg Thr Leu Val
            580                 585                 590

Lys Ser Gln Asp Glu Arg Tyr Ile Asp Lys Gly Asn Arg Thr Tyr Thr
        595                 600                 605

Trp Thr Pro Val Asn Gly Thr Asp Tyr Ser Leu Ala Leu Val Leu Pro
```

-continued

```
    610                 615                 620

Thr Tyr Ser Phe Tyr Tyr Ile Lys Ala Lys Leu Glu Glu Thr Ile Thr
625                 630                 635                 640

Gln Ala Arg Tyr Ser Glu Thr Leu Lys Pro Asp Asn Phe Glu Glu Ser
                645                 650                 655

Gly Tyr Thr Phe Ile Ala Pro Arg Asp Tyr Cys Asn Asp Leu Lys Ile
            660                 665                 670

Ser Asp Asn Asn Thr Glu Phe Leu Leu Asn Phe Asn Glu Phe Ile Asp
        675                 680                 685

Arg Lys Thr Pro Asn Asn Pro Ser Cys Asn Ala Asp Leu Ile Asn Arg
    690                 695                 700

Val Leu Leu Asp Ala Gly Phe Thr Asn Glu Leu Val Gln Asn Tyr Trp
705                 710                 715                 720

Ser Lys Gln Lys Asn Ile Lys Gly Val Lys Ala Arg Phe Val Val Thr
                725                 730                 735

Asp Gly Gly Ile Thr Arg Val Tyr Pro Lys Glu Ala Gly Glu Asn Trp
            740                 745                 750

Gln Glu Asn Pro Glu Thr Tyr Glu Asp Ser Phe Tyr Lys Arg Ser Leu
        755                 760                 765

Asp Asn Asp Asn Tyr Val Phe Thr Ala Pro Tyr Phe Asn Lys Ser Gly
    770                 775                 780

Pro Gly Ala Tyr Glu Ser Gly Ile Met Val Ser Lys Ala Val Glu Ile
785                 790                 795                 800

Tyr Ile Gln Gly Lys Leu Leu Lys Pro Ala Val Val Gly Ile Lys Ile
                805                 810                 815

Asp Val Asn Ser Trp Ile Glu Asn Phe Thr Lys Thr Ser Ile Arg Asp
            820                 825                 830

Pro Cys Ala Gly Pro Val Cys Asp Cys Lys Arg Asn Ser Asp Val Met
        835                 840                 845

Asp Cys Val Ile Leu Asp Asp Gly Gly Phe Leu Leu Met Ala Asn His
    850                 855                 860

Asp Asp Tyr Thr Asn Gln Ile Gly Arg Phe Phe Gly Glu Ile Asp Pro
865                 870                 875                 880

Ser Leu Met Arg His Leu Val Asn Ile Ser Val Tyr Ala Phe Asn Lys
                885                 890                 895

Ser Tyr Asp Tyr Gln Ser Val Cys Glu Pro Gly Ala Ala Pro Lys Gln
            900                 905                 910

Gly Ala Gly His Arg Ser Ala Tyr Val Pro Ser Val Ala Asp Ile Leu
        915                 920                 925

Gln Ile Gly Trp Trp Ala Thr Ala Ala Ala Trp Ser Ile Leu Gln Gln
    930                 935                 940

Phe Leu Leu Ser Leu Thr Phe Pro Arg Leu Leu Glu Ala Val Glu Met
945                 950                 955                 960

Glu Asp Asp Asp Phe Thr Ala Ser Leu Ser Lys Gln Ser Cys Ile Thr
                965                 970                 975

Glu Gln Thr Gln Tyr Phe Phe Asp Asn Asp Ser Lys Ser Phe Ser Gly
            980                 985                 990

Val Leu Asp Cys Gly Asn Cys Ser Arg Ile Phe His Gly Glu Lys Leu
        995                 1000                1005

Met Asn Thr Asn Leu Ile Phe Ile Met Val Glu Ser Lys Gly Thr Cys
    1010                1015                1020

Pro Cys Asp Thr Arg Leu Leu Ile Gln Ala Glu Gln Thr Ser Asp Gly
1025                1030                1035                1040
```

-continued

```
Pro Asn Pro Cys Asp Met Val Lys Gln Pro Arg Tyr Arg Lys Gly Pro
                1045                1050                1055

Asp Val Cys Phe Asp Asn Asn Val Leu Glu Asp Tyr Thr Asp Cys Gly
            1060                1065                1070

Gly Val Ser Gly Leu Asn Pro Ser Leu Trp Tyr Ile Ile Gly Ile Gln
        1075                1080                1085

Phe Leu Leu Leu Trp Leu Val Ser Gly Ser Thr His Arg Leu Leu
    1090                1095                1100


<210> SEQ ID NO 48
<211> LENGTH: 3585
<212> TYPE: DNA
<213> ORGANISM: Human
<220> FEATURE:
<221> NAME/KEY: misc_feature
<222> LOCATION: (35)...(3295)
<223> OTHER INFORMATION: Alpha-2c

<400> SEQUENCE: 48

gcgggggagg gggcattgat cttcgatcgc gaagatggct gctggctgcc tgctggcctt     60

gactctgaca cttttccaat ctttgctcat cggcccctcg tcggaggagc cgttcccttc    120

ggccgtcact atcaaatcat gggtggataa gatgcaagaa gaccttgtca cactggcaaa    180

aacagcaagt ggagtcaatc agcttgttga tatttatgag aaatatcaag atttgtatac    240

tgtggaacca aataatgcac gccagctggt agaaattgca gccagggata ttgagaaact    300

tctgagcaac agatctaaag ccctggtgag cctggcattg gaagcggaga aagttcaagc    360

agctcaccag tggagagaag attttgcaag caatgaagtt gtctactaca atgcaaagga    420

tgatctcgat cctgagaaaa atgacagtga gccaggcagc cagaggataa aacctgtttt    480

cattgaagat gctaattttg gacgacaaat atcttatcag cacgcagcag tccatattcc    540

tactgacatc tatgagggct caacaattgt gttaaatgaa ctcaactgga caagtgcctt    600

agatgaagtt ttcaaaaaga atcgcgagga agacccttca ttattgtggc aggtttttgg    660

cagtgccact ggcctagctc gatattatcc agcttcacca tgggttgata atagtagaac    720

tccaaataag attgaccttt atgatgtacg cagaagacca tggtacatcc aaggagctgc    780

atctcctaaa gacatgctta ttctggtgga tgtgagtgga agtgttagtg gattgacact    840

taaactgatc cgaacatctg tctccgaaat gttagaaacc ctctcagatg atgatttcgt    900

gaatgtagct tcatttaaca gcaatgctca ggatgtaagc tgttttcagc accttgtcca    960

agcaaatgta agaaataaaa aagtgttgaa agacgcggtg aataatatca cagccaaagg   1020

aattacagat tataagaagg gctttagttt tgcttttgaa cagctgctta attataatgt   1080

ttccagagca aactgcaata agattattat gctattcacg gatggaggag aagagagagc   1140

ccaggagata tttaacaaat acaataaaga taaaaaagta cgtgtattca ggttttcagt   1200

tggtcaacac aattatgaga gaggacctat tcagtggatg gcctgtgaaa acaaaggtta   1260

ttattatgaa attccttcca ttggtgcaat aagaatcaat actcaggaat atttggatgt   1320

tttgggaaga ccaatggttt tagcaggaga caaagctaag caagtccaat ggacaaatgt   1380

gtacctggat gcattggaac tgggacttgt cattactgga actcttccgg tcttcaacat   1440

aaccggccaa tttgaaaata agacaaactt aaagaaccag ctgattcttg gtgtgatggg   1500

agtagatgtg tctttggaag atattaaaag actgacacca cgttttacac tgtgccccaa   1560

tgggtattac tttgcaatcg atcctaatgg ttatgtttta ttacatccaa atcttcagcc   1620
```

```
aaaggagcca gtaacattgg atttccttga tgcagagtta gagaatgata ttaaagtgga   1680

gattcgaaat aagatgattg atggggaaag tggagaaaaa acattcagaa ctctggttaa   1740

atctcaagat gagagatata ttgacaaagg aaacaggaca tacacatgga cacctgtcaa   1800

tggcacagat tacagtttgg ccttggtatt accaacctac agtttttact atataaaagc   1860

caaactagaa gagacaataa ctcaggccag atcaaaaaag ggcaaaatga aggattcgga   1920

aaccctgaag ccagataatt ttgaagaatc tggctataca ttcatagcac caagagatta   1980

ctgcaatgac ctgaaaatat cggataataa cactgaattt cttttaaatt tcaacgagtt   2040

tattgataga aaaactccaa acaacccatc atgtaacgcg gatttgatta atagagtctt   2100

gcttgatgca ggctttacaa atgaacttgt ccaaaattac tggagtaagc agaaaaatat   2160

caagggagtg aaagcacgat ttgttgtgac tgatggtggg attaccagag tttatcccaa   2220

agaggctgga gaaaattggc aagaaaaccc agagacatat gaggacagct tctataaaag   2280

gagcctagat aatgataact atgttttcac tgctccctac tttaacaaaa gtggacctgg   2340

tgcctatgaa tcgggcatta tggtaagcaa agctgtagaa atatatattc aagggaaact   2400

tcttaaacct gcagttgttg gaattaaaat tgatgtaaat tcctggatag agaatttcac   2460

caaaacctca atcagagatc cgtgtgctgg tccagtttgt gactgcaaaa gaaacagtga   2520

cgtaatggat tgtgtgattc tggatgatgg tgggtttctt ctgatggcaa atcatgatga   2580

ttatactaat cagattggaa gattttttgg agagattgat cccagcttga tgagacacct   2640

ggttaatata tcagtttatg cttttaacaa atcttatgat tatcagtcag tatgtgagcc   2700

cggtgctgca ccaaaacaag gagcaggaca tcgctcagca tatgtgccat cagtagcaga   2760

catattacaa attggctggt gggccactgc tgctgcctgg tctattctac agcagtttct   2820

cttgagtttg acctttccac gactccttga ggcagttgag atggaggatg atgacttcac   2880

ggcctccctg tccaagcaga gctgcattac tgaacaaacc cagtatttct tcgataacga   2940

cagtaaatca ttcagtggtg tattagactg tggaaactgt tccagaatct ttcatggaga   3000

aaagcttatg aacaccaact taatattcat aatggttgag agcaaaggga catgtccatg   3060

tgacacacga ctgctcatac aagcggagca gacttctgac ggtccaaatc cttgtgacat   3120

ggttaagcaa cctagatacc gaaaagggcc tgatgtctgc tttgataaca atgtcttgga   3180

ggattatact gactgtggtg gtgtttctgg attaaatccc tccctgtggt atatcattgg   3240

aatccagttt ctactacttt ggctggtatc tggcagcaca caccggctgt tatgaccttc   3300

taaaaaccaa atctgcatag ttaaactcca gaccctgcca aaacatgagc cctgccctca   3360

attacagtaa cgtagggtca gctataaaat cagacaaaca ttagctgggc ctgttccatg   3420

gcataacact aaggcgcaga ctcctaaggc acccactggc tgcatgtcag ggtgtcagat   3480

ccttaaacgt gtgtgaatgc tgcatcatct atgtgtaaca tcaaagcaaa atcctatacg   3540

tgtcctctat tggaaaattt gggcgtttgt tgttgcattg ttggt                  3585
```

<210> SEQ ID NO 49
<211> LENGTH: 1086
<212> TYPE: PRT
<213> ORGANISM: Human

<400> SEQUENCE: 49

```
Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
            20                  25                  30
```

-continued

```
Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445
```

-continued

```
Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Glu Pro Val Thr Leu Asp Phe Leu Asp Ala Glu Leu Glu Asn
    530                 535                 540

Asp Ile Lys Val Glu Ile Arg Asn Lys Met Ile Asp Gly Glu Ser Gly
545                 550                 555                 560

Glu Lys Thr Phe Arg Thr Leu Val Lys Ser Gln Asp Glu Arg Tyr Ile
                565                 570                 575

Asp Lys Gly Asn Arg Thr Tyr Thr Trp Thr Pro Val Asn Gly Thr Asp
            580                 585                 590

Tyr Ser Leu Ala Leu Val Leu Pro Thr Tyr Ser Phe Tyr Tyr Ile Lys
        595                 600                 605

Ala Lys Leu Glu Glu Thr Ile Thr Gln Ala Arg Ser Lys Lys Gly Lys
    610                 615                 620

Met Lys Asp Ser Glu Thr Leu Lys Pro Asp Asn Phe Glu Glu Ser Gly
625                 630                 635                 640

Tyr Thr Phe Ile Ala Pro Arg Asp Tyr Cys Asn Asp Leu Lys Ile Ser
                645                 650                 655

Asp Asn Asn Thr Glu Phe Leu Leu Asn Phe Asn Glu Phe Ile Asp Arg
            660                 665                 670

Lys Thr Pro Asn Asn Pro Ser Cys Asn Ala Asp Leu Ile Asn Arg Val
        675                 680                 685

Leu Leu Asp Ala Gly Phe Thr Asn Glu Leu Val Gln Asn Tyr Trp Ser
    690                 695                 700

Lys Gln Lys Asn Ile Lys Gly Val Lys Ala Arg Phe Val Val Thr Asp
705                 710                 715                 720

Gly Gly Ile Thr Arg Val Tyr Pro Lys Glu Ala Gly Glu Asn Trp Gln
                725                 730                 735

Glu Asn Pro Glu Thr Tyr Glu Asp Ser Phe Tyr Lys Arg Ser Leu Asp
            740                 745                 750

Asn Asp Asn Tyr Val Phe Thr Ala Pro Tyr Phe Asn Lys Ser Gly Pro
        755                 760                 765

Gly Ala Tyr Glu Ser Gly Ile Met Val Ser Lys Ala Val Glu Ile Tyr
    770                 775                 780

Ile Gln Gly Lys Leu Leu Lys Pro Ala Val Val Gly Ile Lys Ile Asp
785                 790                 795                 800

Val Asn Ser Trp Ile Glu Asn Phe Thr Lys Thr Ser Ile Arg Asp Pro
                805                 810                 815

Cys Ala Gly Pro Val Cys Asp Cys Lys Arg Asn Ser Asp Val Met Asp
            820                 825                 830

Cys Val Ile Leu Asp Asp Gly Gly Phe Leu Leu Met Ala Asn His Asp
        835                 840                 845

Asp Tyr Thr Asn Gln Ile Gly Arg Phe Phe Gly Glu Ile Asp Pro Ser
    850                 855                 860

Leu Met Arg His Leu Val Asn Ile Ser Val Tyr Ala Phe Asn Lys Ser
```

-continued 865 870 875 880

Tyr Asp Tyr Gln Ser Val Cys Glu Pro Gly Ala Ala Pro Lys Gln Gly
885 890 895

Ala Gly His Arg Ser Ala Tyr Val Pro Ser Val Ala Asp Ile Leu Gln
900 905 910

Ile Gly Trp Trp Ala Thr Ala Ala Ala Trp Ser Ile Leu Gln Gln Phe
915 920 925

Leu Leu Ser Leu Thr Phe Pro Arg Leu Leu Glu Ala Val Glu Met Glu
930 935 940

Asp Asp Asp Phe Thr Ala Ser Leu Ser Lys Gln Ser Cys Ile Thr Glu
945 950 955 960

Gln Thr Gln Tyr Phe Phe Asp Asn Asp Ser Lys Ser Phe Ser Gly Val
965 970 975

Leu Asp Cys Gly Asn Cys Ser Arg Ile Phe His Gly Glu Lys Leu Met
980 985 990

Asn Thr Asn Leu Ile Phe Ile Met Val Glu Ser Lys Gly Thr Cys Pro
995 1000 1005

Cys Asp Thr Arg Leu Leu Ile Gln Ala Glu Gln Thr Ser Asp Gly Pro
1010 1015 1020

Asn Pro Cys Asp Met Val Lys Gln Pro Arg Tyr Arg Lys Gly Pro Asp
1025 1030 1035 1040

Val Cys Phe Asp Asn Asn Val Leu Glu Asp Tyr Thr Asp Cys Gly Gly
1045 1050 1055

Val Ser Gly Leu Asn Pro Ser Leu Trp Tyr Ile Ile Gly Ile Gln Phe
1060 1065 1070

Leu Leu Leu Trp Leu Val Ser Gly Ser Thr His Arg Leu Leu
1075 1080 1085

<210> SEQ ID NO 50
<211> LENGTH: 3564
<212> TYPE: DNA
<213> ORGANISM: Human
<220> FEATURE:
<221> NAME/KEY: misc_feature
<222> LOCATION: (35)...(3374)
<223> OTHER INFORMATION: Alpha-2d

<400> SEQUENCE: 50
gcgggggagg gggcattgat cttcgatcgc gaagatggct gctggctgcc tgctggcctt 60
gactctgaca cttttccaat ctttgctcat cggcccctcg tcggaggagc cgttcccttc 120
ggccgtcact atcaaatcat gggtggataa gatgcaagaa gaccttgtca cactggcaaa 180
aacagcaagt ggagtcaatc agcttgttga tatttatgag aaatatcaag atttgtatac 240
tgtggaacca aataatgcac gccagctggt agaaattgca gccagggata ttgagaaact 300
tctgagcaac agatctaaag ccctggtgag cctggcattg gaagcggaga aagttcaagc 360
agctcaccag tggagagaag attttgcaag caatgaagtt gtctactaca atgcaaagga 420
tgatctcgat cctgagaaaa atgacagtga gccaggcagc cagaggataa aacctgtttt 480
cattgaagat gctaattttg gacgacaaat atcttatcag cacgcagcag tccatattcc 540
tactgacatc tatgagggct caacaattgt gttaaatgaa ctcaactgga caagtgcctt 600
agatgaagtt ttcaaaaaga atcgcgagga agacccttca ttattgtggc aggtttttgg 660
cagtgccact ggcctagctc gatattatcc agcttcacca tgggttgata atagtagaac 720
tccaaataag attgaccttt atgatgtacg cagaagacca tggtacatcc aaggagctgc 780

-continued

```
atctcctaaa gacatgctta ttctggtgga tgtgagtgga agtgttagtg gattgacact    840
taaactgatc cgaacatctg tctccgaaat gttagaaacc ctctcagatg atgatttcgt    900
gaatgtagct tcatttaaca gcaatgctca ggatgtaagc tgttttcagc accttgtcca    960
agcaaatgta agaaataaaa aagtgttgaa agacgcggtg aataatatca cagccaaagg   1020
aattacagat tataagaagg gctttagttt tgcttttgaa cagctgctta attataatgt   1080
ttccagagca aactgcaata agattattat gctattcacg gatggaggag aagagagagc   1140
ccaggagata tttaacaaat acaataaaga taaaaaagta cgtgtattca ggttttcagt   1200
tggtcaacac aattatgaga gaggacctat tcagtggatg gcctgtgaaa acaaaggtta   1260
ttattatgaa attccttcca ttggtgcaat aagaatcaat actcaggaat atttggatgt   1320
tttgggaaga ccaatggttt tagcaggaga caaagctaag caagtccaat ggacaaatgt   1380
gtacctggat gcattggaac tgggacttgt cattactgga actcttccgg tcttcaacat   1440
aaccggccaa tttgaaaata agacaaactt aaagaaccag ctgattcttg gtgtgatggg   1500
agtagatgtg tctttggaag atattaaaag actgacacca cgttttacac tgtgccccaa   1560
tgggtattac tttgcaatcg atcctaatgg ttatgtttta ttacatccaa atcttcagcc   1620
aaaggagcca gtaacattgg atttccttga tgcagagtta gagaatgata ttaaagtgga   1680
gattcgaaat aagatgattg atggggaaag tggagaaaaa acattcagaa ctctggttaa   1740
atctcaagat gagagatata ttgacaaagg aaacaggaca tacacatgga cacctgtcaa   1800
tggcacagat tacagtttgg ccttggtatt accaacctac agtttttact atataaaagc   1860
caaactagaa gagacaataa ctcaggccag atattcggaa accctgaagc cagataattt   1920
tgaagaatct ggctatacat tcatagcacc aagagattac tgcaatgacc tgaaaatatc   1980
ggataataac actgaatttc ttttaaattt caacgagttt attgatagaa aaactccaaa   2040
caacccatca tgtaacgcgg atttgattaa tagagtcttg cttgatgcag gctttacaaa   2100
tgaacttgtc caaaattact ggagtaagca gaaaaatatc aagggagtga aagcacgatt   2160
tgttgtgact gatggtggga ttaccagagt ttatcccaaa gaggctggag aaaattggca   2220
agaaaaccca gagacatatg aggacagctt ctataaaagg agcctagata atgataacta   2280
tgttttcact gctccctact ttaacaaaag tggacctggt gcctatgaat cgggcattat   2340
ggtaagcaaa gctgtagaaa tatatattca agggaaactt cttaaacctg cagttgttgg   2400
aattaaaatt gatgtaaatt cctggataga gaatttcacc aaaacctcaa tcagagatcc   2460
gtgtgctggt ccagtttgtg actgcaaaag aaacagtgac gtaatggatt gtgtgattct   2520
ggatgatggt gggtttcttc tgatggcaaa tcatgatgat tatactaatc agattggaag   2580
attttttgga gagattgatc ccagcttgat gagacacctg gttaatatat cagtttatgc   2640
ttttaacaaa tcttatgatt atcagtcagt atgtgagccc ggtgctgcac caaaacaagg   2700
agcaggacat cgctcagcat atgtgccatc agtagcagac atattacaaa ttggctggtg   2760
ggccactgct gctgcctggt ctattctaca gcagtttctc ttgagtttga cctttccacg   2820
actccttgag gcagttgaga tggaggatga tgacttcacg gcctccctgt ccaagcagag   2880
ctgcattact gaacaaaccc agtatttctt cgataacgac agtaaatcat tcagtggtgt   2940
attagactgt ggaaactgtt ccagaatctt tcatggagaa aagcttatga acaccaactt   3000
aatattcata atggttgaga gcaaagggac atgtccatgt gacacacgac tgctcataca   3060
agcggagcag acttctgacg gtccaaatcc ttgtgacatg gttaagcaac ctagataccg   3120
aaaagggcct gatgtctgct ttgataacaa tgtcttggag gattatactg actgtggtgg   3180
```

-continued

```
tgtttctgga ttaaatccct ccctgtggta tatcattgga atccagtttc tactactttg   3240

gctggtatct ggcagcacac accggctgtt atgaccttct aaaaaccaaa tctgcatagt   3300

taaactccag accctgccaa aacatgagcc ctgccctcaa ttacagtaac gtagggtcag   3360

ctataaaatc agacaaacat tagctgggcc tgttccatgg cataacacta aggcgcagac   3420

tcctaaggca cccactggct gcatgtcagg gtgtcagatc cttaaacgtg tgtgaatgct   3480

gcatcatcta tgtgtaacat caaagcaaaa tcctatacgt gtcctctatt ggaaaatttg   3540

ggcgtttgtt gttgcattgt tggt                                          3564


<210> SEQ ID NO 51
<211> LENGTH: 1079
<212> TYPE: PRT
<213> ORGANISM: Human

<400> SEQUENCE: 51

Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300
```

-continued

```
Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Glu Pro Val Thr Leu Asp Phe Leu Asp Ala Glu Leu Glu Asn
    530                 535                 540

Asp Ile Lys Val Glu Ile Arg Asn Lys Met Ile Asp Gly Glu Ser Gly
545                 550                 555                 560

Glu Lys Thr Phe Arg Thr Leu Val Lys Ser Gln Asp Glu Arg Tyr Ile
                565                 570                 575

Asp Lys Gly Asn Arg Thr Tyr Thr Trp Thr Pro Val Asn Gly Thr Asp
            580                 585                 590

Tyr Ser Leu Ala Leu Val Leu Pro Thr Tyr Ser Phe Tyr Tyr Ile Lys
        595                 600                 605

Ala Lys Leu Glu Glu Thr Ile Thr Gln Ala Arg Tyr Ser Glu Thr Leu
    610                 615                 620

Lys Pro Asp Asn Phe Glu Glu Ser Gly Tyr Thr Phe Ile Ala Pro Arg
625                 630                 635                 640

Asp Tyr Cys Asn Asp Leu Lys Ile Ser Asp Asn Asn Thr Glu Phe Leu
                645                 650                 655

Leu Asn Phe Asn Glu Phe Ile Asp Arg Lys Thr Pro Asn Asn Pro Ser
            660                 665                 670

Cys Asn Ala Asp Leu Ile Asn Arg Val Leu Leu Asp Ala Gly Phe Thr
        675                 680                 685

Asn Glu Leu Val Gln Asn Tyr Trp Ser Lys Gln Lys Asn Ile Lys Gly
    690                 695                 700

Val Lys Ala Arg Phe Val Val Thr Asp Gly Gly Ile Thr Arg Val Tyr
705                 710                 715                 720
```

-continued

```
Pro Lys Glu Ala Gly Glu Asn Trp Gln Glu Asn Pro Glu Thr Tyr Glu
                725                 730                 735

Asp Ser Phe Tyr Lys Arg Ser Leu Asp Asn Asp Asn Tyr Val Phe Thr
            740                 745                 750

Ala Pro Tyr Phe Asn Lys Ser Gly Pro Gly Ala Tyr Glu Ser Gly Ile
        755                 760                 765

Met Val Ser Lys Ala Val Glu Ile Tyr Ile Gln Gly Lys Leu Leu Lys
    770                 775                 780

Pro Ala Val Val Gly Ile Lys Ile Asp Val Asn Ser Trp Ile Glu Asn
785                 790                 795                 800

Phe Thr Lys Thr Ser Ile Arg Asp Pro Cys Ala Gly Pro Val Cys Asp
                805                 810                 815

Cys Lys Arg Asn Ser Asp Val Met Asp Cys Val Ile Leu Asp Asp Gly
            820                 825                 830

Gly Phe Leu Leu Met Ala Asn His Asp Asp Tyr Thr Asn Gln Ile Gly
        835                 840                 845

Arg Phe Phe Gly Glu Ile Asp Pro Ser Leu Met Arg His Leu Val Asn
    850                 855                 860

Ile Ser Val Tyr Ala Phe Asn Lys Ser Tyr Asp Tyr Gln Ser Val Cys
865                 870                 875                 880

Glu Pro Gly Ala Ala Pro Lys Gln Gly Ala Gly His Arg Ser Ala Tyr
                885                 890                 895

Val Pro Ser Val Ala Asp Ile Leu Gln Ile Gly Trp Trp Ala Thr Ala
            900                 905                 910

Ala Ala Trp Ser Ile Leu Gln Gln Phe Leu Leu Ser Leu Thr Phe Pro
        915                 920                 925

Arg Leu Leu Glu Ala Val Glu Met Glu Asp Asp Asp Phe Thr Ala Ser
    930                 935                 940

Leu Ser Lys Gln Ser Cys Ile Thr Glu Gln Thr Gln Tyr Phe Phe Asp
945                 950                 955                 960

Asn Asp Ser Lys Ser Phe Ser Gly Val Leu Asp Cys Gly Asn Cys Ser
                965                 970                 975

Arg Ile Phe His Gly Glu Lys Leu Met Asn Thr Asn Leu Ile Phe Ile
            980                 985                 990

Met Val Glu Ser Lys Gly Thr Cys Pro Cys Asp Thr Arg Leu Leu Ile
        995                 1000                1005

Gln Ala Glu Gln Thr Ser Asp Gly Pro Asn Pro Cys Asp Met Val Lys
    1010                1015                1020

Gln Pro Arg Tyr Arg Lys Gly Pro Asp Val Cys Phe Asp Asn Asn Val
1025                1030                1035                1040

Leu Glu Asp Tyr Thr Asp Cys Gly Gly Val Ser Gly Leu Asn Pro Ser
                1045                1050                1055

Leu Trp Tyr Ile Ile Gly Ile Gln Phe Leu Leu Leu Trp Leu Val Ser
            1060                1065                1070

Gly Ser Thr His Arg Leu Leu
        1075
```

<210> SEQ ID NO 52
<211> LENGTH: 3579
<212> TYPE: DNA
<213> ORGANISM: Human
<220> FEATURE:
<221> NAME/KEY: misc_feature
<222> LOCATION: (35)...(3289)
<223> OTHER INFORMATION: Alpha-2e -continued

<400> SEQUENCE: 52

```
gcgggggagg gggcattgat cttcgatcgc gaagatggct gctggctgcc tgctggcctt     60
gactctgaca cttttccaat ctttgctcat cggcccctcg tcggaggagc cgttcccttc    120
ggccgtcact atcaaatcat gggtggataa gatgcaagaa gaccttgtca cactggcaaa    180
aacagcaagt ggagtcaatc agcttgttga tatttatgag aaatatcaag atttgtatac    240
tgtggaacca aataatgcac gccagctggt agaaattgca gccagggata ttgagaaact    300
tctgagcaac agatctaaag ccctggtgag cctggcattg gaagcggaga aagttcaagc    360
agctcaccag tggagagaag attttgcaag caatgaagtt gtctactaca atgcaaagga    420
tgatctcgat cctgagaaaa atgacagtga gccaggcagc cagaggataa aacctgtttt    480
cattgaagat gctaattttg gacgacaaat atcttatcag cacgcagcag tccatattcc    540
tactgacatc tatgagggct caacaattgt gttaaatgaa ctcaactgga caagtgcctt    600
agatgaagtt ttcaaaaaga atcgcgagga agacccttca ttattgtggc aggtttttgg    660
cagtgccact ggcctagctc gatattatcc agcttcacca tgggttgata atagtagaac    720
tccaaataag attgaccttt atgatgtacg cagaagacca tggtacatcc aaggagctgc    780
atctcctaaa gacatgctta ttctggtgga tgtgagtgga agtgttagtg gattgacact    840
taaactgatc cgaacatctg tctccgaaat gttagaaacc ctctcagatg atgatttcgt    900
gaatgtagct tcatttaaca gcaatgctca ggatgtaagc tgttttcagc accttgtcca    960
agcaaatgta agaaataaaa aagtgttgaa agacgcggtg aataatatca cagccaaagg   1020
aattacagat tataagaagg gctttagttt tgcttttgaa cagctgctta attataatgt   1080
ttccagagca aactgcaata agattattat gctattcacg gatggaggag aagagagagc   1140
ccaggagata tttaacaaat acaataaaga taaaaaagta cgtgtattca ggttttcagt   1200
tggtcaacac aattatgaga gaggacctat tcagtggatg gcctgtgaaa acaaaggtta   1260
ttattatgaa attccttcca ttggtgcaat aagaatcaat actcaggaat atttggatgt   1320
tttgggaaga ccaatggttt tagcaggaga caaagctaag caagtccaat ggacaaatgt   1380
gtacctggat gcattggaac tgggacttgt cattactgga actcttccgg tcttcaacat   1440
aaccggccaa tttgaaaata agacaaactt aaagaaccag ctgattcttg gtgtgatggg   1500
agtagatgtg tctttggaag atattaaaag actgacacca cgttttacac tgtgccccaa   1560
tgggtattac tttgcaatcg atcctaatgg ttatgtttta ttacatccaa atcttcagcc   1620
aaagaacccc aaatctcagg agccagtaac attggatttc cttgatgcag agttagagaa   1680
tgatattaaa gtggagattc gaaataagat gattgatggg gaaagtggag aaaaaacatt   1740
cagaactctg gttaaatctc aagatgagag atatattgac aaaggaaaca ggacatacac   1800
atggacacct gtcaatggca cagattacag tttggccttg gtattaccaa cctacagttt   1860
ttactatata aaagccaaac tagaagagac aataactcag gccagatatt cggaaaccct   1920
gaagccagat aattttgaag aatctggcta tacattcata gcaccaagag attactgcaa   1980
tgacctgaaa atatcggata ataacactga atttctttta aatttcaacg agtttattga   2040
tagaaaaact ccaaacaacc catcatgtaa cgcggatttg attaatagag tcttgcttga   2100
tgcaggcttt acaaatgaac ttgtccaaaa ttactggagt aagcagaaaa atatcaaggg   2160
agtgaaagca cgatttgttg tgactgatgg tgggattacc agagtttatc ccaaagaggc   2220
tggagaaaat tggcaagaaa acccagagac atatgaggac agcttctata aaaggagcct   2280
agataatgat aactatgttt tcactgctcc ctactttaac aaaagtggac ctggtgccta   2340
```

-continued

```
tgaatcgggc attatggtaa gcaaagctgt agaaatatat attcaaggga aacttcttaa   2400

acctgcagtt gttggaatta aaattgatgt aaattcctgg atagagaatt tcaccaaaac   2460

ctcaatcaga gatccgtgtg ctggtccagt ttgtgactgc aaaagaaaca gtgacgtaat   2520

ggattgtgtg attctggatg atggtgggtt tcttctgatg gcaaatcatg atgattatac   2580

taatcagatt ggaagatttt ttggagagat tgatcccagc ttgatgagac acctggttaa   2640

tatatcagtt tatgctttta acaaatctta tgattatcag tcagtatgtg agcccggtgc   2700

tgcaccaaaa caaggagcag gacatcgctc agcatatgtg ccatcagtag cagacatatt   2760

acaaattggc tggtgggcca ctgctgctgc ctggtctatt ctacagcagt ttctcttgag   2820

tttgaccttt ccacgactcc ttgaggcagt tgagatggag gatgatgact tcacggcctc   2880

cctgtccaag cagagctgca ttactgaaca aacccagtat ttcttcgata acgacagtaa   2940

atcattcagt ggtgtattag actgtggaaa ctgttccaga atctttcatg gagaaaagct   3000

tatgaacacc aacttaatat tcataatggt tgagagcaaa gggacatgtc catgtgacac   3060

acgactgctc atacaagcgg agcagacttc tgacggtcca aatccttgtg acatggttaa   3120

gcaacctaga taccgaaaag ggcctgatgt ctgctttgat aacaatgtct tggaggatta   3180

tactgactgt ggtggtgttt ctggattaaa tccctccctg tggtatatca ttggaatcca   3240

gtttctacta ctttggctgg tatctggcag cacacaccgg ctgttatgac cttctaaaaa   3300

ccaaatctgc atagttaaac tccagaccct gccaaaacat gagccctgcc ctcaattaca   3360

gtaacgtagg gtcagctata aaatcagaca aacattagct gggcctgttc catggcataa   3420

cactaaggcg cagactccta aggcacccac tggctgcatg tcagggtgtc agatccttaa   3480

acgtgtgtga atgctgcatc atctatgtgt aacatcaaag caaaatccta tacgtgtcct   3540

ctattggaaa atttgggcgt ttgttgttgc attgttggt                          3579
```

<210> SEQ ID NO 53
<211> LENGTH: 1084
<212> TYPE: PRT
<213> ORGANISM: Human

<400> SEQUENCE: 53

```
Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
```

-continued

```
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575
```

-continued

```
Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
    610                 615                 620

Tyr Ser Glu Thr Leu Lys Pro Asp Asn Phe Glu Glu Ser Gly Tyr Thr
625                 630                 635                 640

Phe Ile Ala Pro Arg Asp Tyr Cys Asn Asp Leu Lys Ile Ser Asp Asn
                645                 650                 655

Asn Thr Glu Phe Leu Leu Asn Phe Asn Glu Phe Ile Asp Arg Lys Thr
            660                 665                 670

Pro Asn Asn Pro Ser Cys Asn Ala Asp Leu Ile Asn Arg Val Leu Leu
        675                 680                 685

Asp Ala Gly Phe Thr Asn Glu Leu Val Gln Asn Tyr Trp Ser Lys Gln
    690                 695                 700

Lys Asn Ile Lys Gly Val Lys Ala Arg Phe Val Val Thr Asp Gly Gly
705                 710                 715                 720

Ile Thr Arg Val Tyr Pro Lys Glu Ala Gly Glu Asn Trp Gln Glu Asn
                725                 730                 735

Pro Glu Thr Tyr Glu Asp Ser Phe Tyr Lys Arg Ser Leu Asp Asn Asp
            740                 745                 750

Asn Tyr Val Phe Thr Ala Pro Tyr Phe Asn Lys Ser Gly Pro Gly Ala
        755                 760                 765

Tyr Glu Ser Gly Ile Met Val Ser Lys Ala Val Glu Ile Tyr Ile Gln
    770                 775                 780

Gly Lys Leu Leu Lys Pro Ala Val Val Gly Ile Lys Ile Asp Val Asn
785                 790                 795                 800

Ser Trp Ile Glu Asn Phe Thr Lys Thr Ser Ile Arg Asp Pro Cys Ala
                805                 810                 815

Gly Pro Val Cys Asp Cys Lys Arg Asn Ser Asp Val Met Asp Cys Val
            820                 825                 830

Ile Leu Asp Asp Gly Gly Phe Leu Leu Met Ala Asn His Asp Asp Tyr
        835                 840                 845

Thr Asn Gln Ile Gly Arg Phe Phe Gly Glu Ile Asp Pro Ser Leu Met
    850                 855                 860

Arg His Leu Val Asn Ile Ser Val Tyr Ala Phe Asn Lys Ser Tyr Asp
865                 870                 875                 880

Tyr Gln Ser Val Cys Glu Pro Gly Ala Ala Pro Lys Gln Gly Ala Gly
                885                 890                 895

His Arg Ser Ala Tyr Val Pro Ser Val Ala Asp Ile Leu Gln Ile Gly
            900                 905                 910

Trp Trp Ala Thr Ala Ala Ala Trp Ser Ile Leu Gln Gln Phe Leu Leu
        915                 920                 925

Ser Leu Thr Phe Pro Arg Leu Leu Glu Ala Val Glu Met Glu Asp Asp
    930                 935                 940

Asp Phe Thr Ala Ser Leu Ser Lys Gln Ser Cys Ile Thr Glu Gln Thr
945                 950                 955                 960

Gln Tyr Phe Phe Asp Asn Asp Ser Lys Ser Phe Ser Gly Val Leu Asp
                965                 970                 975

Cys Gly Asn Cys Ser Arg Ile Phe His Gly Glu Lys Leu Met Asn Thr
            980                 985                 990
```

-continued

```
Asn Leu Ile Phe Ile Met Val Glu Ser Lys Gly Thr Cys Pro Cys Asp
        995                 1000                1005

Thr Arg Leu Leu Ile Gln Ala Glu Gln Thr Ser Asp Gly Pro Asn Pro
    1010                1015                1020

Cys Asp Met Val Lys Gln Pro Arg Tyr Arg Lys Gly Pro Asp Val Cys
1025                1030                1035                1040

Phe Asp Asn Asn Val Leu Glu Asp Tyr Thr Asp Cys Gly Gly Val Ser
                1045                1050                1055

Gly Leu Asn Pro Ser Leu Trp Tyr Ile Ile Gly Ile Gln Phe Leu Leu
            1060                1065                1070

Leu Trp Leu Val Ser Gly Ser Thr His Arg Leu Leu
        1075                1080


<210> SEQ ID NO 54
<211> LENGTH: 1681
<212> TYPE: DNA
<213> ORGANISM: Human
<220> FEATURE:
<221> NAME/KEY: misc_feature
<222> LOCATION: (1)...(1437)
<223> OTHER INFORMATION: Beta-1-1

<400> SEQUENCE: 54

atggtccaga agaccagcat gtcccggggc ccttacccac cctcccagga gatccccatg      60

gaggtcttcg accccagccc gcagggcaaa tacagcaaga ggaaagggcg attcaaacgg     120

tcagatggga gcacgtcctc ggataccaca tccaacagct ttgtccgcca gggctcagcg     180

gagtcctaca ccagccgtcc atcagactct gatgtatctc tggaggagga ccgggaagcc     240

ttaaggaagg aagcagagcg ccaggcatta gcgcagctcg agaaggccaa gaccaagcca     300

gtggcatttg ctgtgcggac aaatgttggc tacaatccgt ctccagggga tgaggtgcct     360

gtgcagggag tggccatcac cttcgagccc aaagacttcc tgcacatcaa ggagaaatac     420

aataatgact ggtggatcgg gcggctggtg aaggagggct gtgaggttgg cttcattccc     480

agccccgtca aactggacag ccttcgcctg ctgcaggaac agaagctgcg ccagaaccgc     540

ctcggctcca gcaaatcagg cgataactcc agttccagtc tgggagatgt ggtgactggc     600

acccgccgcc ccacaccccc tgccagtggt aatgaaatga ctaacttagc ctttgaacta     660

gacccccctag agttagagga ggaagaggct gagcttggtg agcagagtgg ctctgccaag     720

actagtgtta gcagtgtcac caccccgcca ccccatggca aacgcatccc cttctttaag     780

aagacagagc atgtgccccc ctatgacgtg gtgccttcca tgaggcccat catcctggtg     840

ggaccgtcgc tcaagggcta cgaggttaca gacatgatgc agaaagcttt atttgacttc     900

ttgaagcatc ggtttgatgg caggatctcc atcactcgtg tgacggcaga tatttccctg     960

gctaagcgct cagttctcaa caaccccagc aaacacatca tcattgagcg ctccaacaca    1020

cgctccagcc tggctgaggt gcagagtgaa atcgagcgaa tcttcgagct ggcccggacc    1080

cttcagttgg tcgctctgga tgctgacacc atcaatcacc cagcccagct gtccaagacc    1140

tcgctggccc ccatcattgt ttacatcaag atcacctctc ccaaggtact tcaaaggctc    1200

atcaagtccc gaggaaagtc tcagtccaaa cacctcaatg tccaaatagc ggcctcggaa    1260

aagctggcac agtgcccccc tgaaatgttt gacatcatcc tggatgagaa ccaattggag    1320

gatgcctgcg agcatctggc ggagtacttg gaagcctatt ggaaggccac acacccgccc    1380

agcagcacgc cacccaatcc gctgctgaac cgcaccatgg ctaccgcagc cctggctgcc    1440

agccctgccc ctgtctccaa cctccaggta caggtgctca cctcgctcag gagaaacctc    1500
```

-continued

```
ggcttctggg gcgggctgga gtcctcacag cggggcagtg tggtgcccca ggagcaggaa   1560

catgccatgt agtgggcgcc ctgcccgtct tccctcctgc tctggggtcg gaactggagt   1620

gcagggaaca tggaggagga agggaagagc tttattttgt aaaaaaataa gatgagcggc   1680

a                                                                   1681


<210> SEQ ID NO 55
<211> LENGTH: 479
<212> TYPE: PRT
<213> ORGANISM: Human

<400> SEQUENCE: 55

Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
        35                  40                  45

Thr Thr Ser Asn Ser Phe Val Arg Gln Gly Ser Ala Glu Ser Tyr Thr
    50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Gly Asn Glu Met Thr Asn Leu Ala Phe Glu Leu Asp Pro Leu Glu
    210                 215                 220

Leu Glu Glu Glu Glu Ala Glu Leu Gly Glu Gln Ser Gly Ser Ala Lys
225                 230                 235                 240

Thr Ser Val Ser Ser Val Thr Thr Pro Pro Pro His Gly Lys Arg Ile
                245                 250                 255

Pro Phe Phe Lys Lys Thr Glu His Val Pro Pro Tyr Asp Val Val Pro
            260                 265                 270

Ser Met Arg Pro Ile Ile Leu Val Gly Pro Ser Leu Lys Gly Tyr Glu
        275                 280                 285

Val Thr Asp Met Met Gln Lys Ala Leu Phe Asp Phe Leu Lys His Arg
    290                 295                 300

Phe Asp Gly Arg Ile Ser Ile Thr Arg Val Thr Ala Asp Ile Ser Leu
305                 310                 315                 320

Ala Lys Arg Ser Val Leu Asn Asn Pro Ser Lys His Ile Ile Ile Glu
                325                 330                 335
```

-continued

```
Arg Ser Asn Thr Arg Ser Ser Leu Ala Glu Val Gln Ser Glu Ile Glu
            340                 345                 350

Arg Ile Phe Glu Leu Ala Arg Thr Leu Gln Leu Val Ala Leu Asp Ala
        355                 360                 365

Asp Thr Ile Asn His Pro Ala Gln Leu Ser Lys Thr Ser Leu Ala Pro
    370                 375                 380

Ile Ile Val Tyr Ile Lys Ile Thr Ser Pro Lys Val Leu Gln Arg Leu
385                 390                 395                 400

Ile Lys Ser Arg Gly Lys Ser Gln Ser Lys His Leu Asn Val Gln Ile
                405                 410                 415

Ala Ala Ser Glu Lys Leu Ala Gln Cys Pro Pro Glu Met Phe Asp Ile
            420                 425                 430

Ile Leu Asp Glu Asn Gln Leu Glu Asp Ala Cys Glu His Leu Ala Glu
        435                 440                 445

Tyr Leu Glu Ala Tyr Trp Lys Ala Thr His Pro Pro Ser Ser Thr Pro
    450                 455                 460

Pro Asn Pro Leu Leu Asn Arg Thr Met Ala Thr Ala Ala Leu Ala
465                 470                 475


<210> SEQ ID NO 56
<211> LENGTH: 1526
<212> TYPE: DNA
<213> ORGANISM: Human
<220> FEATURE:
<221> NAME/KEY: misc_feature
<222> LOCATION: (1)...(651)
<223> OTHER INFORMATION: Beta-1-4

<400> SEQUENCE: 56

atggtccaga agaccagcat gtcccggggc ccttacccac cctcccagga gatccccatg      60

gaggtcttcg accccagccc gcagggcaaa tacagcaaga ggaaagggcg attcaaacgg     120

tcagatggga gcacgtcctc ggataccaca tccaacagct ttgtccgcca gggctcagcg     180

gagtcctaca ccagccgtcc atcagactct gatgtatctc tggaggagga ccgggaagcc     240

ttaaggaagg aagcagagcg ccaggcatta gcgcagctcg agaaggccaa gaccaagcca     300

gtggcatttg ctgtgcggac aaatgttggc tacaatccgt ctccagggga tgaggtgcct     360

gtgcagggag tggccatcac cttcgagccc aaagacttcc tgcacatcaa ggagaaatac     420

aataatgact ggtggatcgg gcggctggtg aaggagggct gtgaggttgg cttcattccc     480

agccccgtca aactggacag ccttcgcctg ctgcaggaac agaagctgcg ccagaaccgc     540

ctcggctcca gcaaatcagg cgataactcc agttccagtc tgggagatgt ggtgactggc     600

acccgccgcc ccacaccccc tgccagtgac agagcatgtg ccccccctatg acgtggtgcc     660

ttccatgagg cccatcatcc tggtgggacc gtcgctcaag ggctacgagg ttacagacat     720

gatgcagaaa gctttatttg acttcttgaa gcatcggttt gatggcagga tctccatcac     780

tcgtgtgacg gcagatattt ccctggctaa gcgctcagtt ctcaacaacc ccagcaaaca     840

catcatcatt gagcgctcca acacacgctc cagcctggct gaggtgcaga gtgaaatcga     900

gcgaatcttc gagctggccc ggacccttca gttggtcgct ctggatgctg acaccatcaa     960

tcacccagcc cagctgtcca agacctcgct ggcccccatc attgtttaca tcaagatcac    1020

ctctcccaag gtacttcaaa ggctcatcaa gtcccgagga aagtctcagt ccaaacacct    1080

caatgtccaa atagcggcct cggaaaagct ggcacagtgc ccccctgaaa tgtttgacat    1140

catcctggat gagaaccaat tggaggatgc ctgcgagcat ctggcggagt acttggaagc    1200
```

-continued

```
ctattggaag gccacacacc cgcccagcag cacgccaccc aatccgctgc tgaaccgcac   1260

catggctacc gcagccctgg ctgccagccc tgcccctgtc tccaacctcc aggtacaggt   1320

gctcacctcg ctcaggagaa acctcggctt ctggggcggg ctggagtcct cacagcgggg   1380

cagtgtggtg ccccaggagc aggaacatgc catgtagtgg gcgccctgcc cgtcttccct   1440

cctgctctgg ggtcggaact ggagtgcagg gaacatggag gaggaaggga agagctttat   1500

tttgtaaaaa aataagatga gcggca                                        1526
```

<210> SEQ ID NO 57
<211> LENGTH: 216
<212> TYPE: PRT
<213> ORGANISM: Human

<400> SEQUENCE: 57

```
Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
        35                  40                  45

Thr Thr Ser Asn Ser Phe Val Arg Gln Gly Ser Ala Glu Ser Tyr Thr
    50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Asp Arg Ala Cys Ala Pro Leu
    210                 215
```

<210> SEQ ID NO 58
<211> LENGTH: 1393
<212> TYPE: DNA
<213> ORGANISM: Human
<220> FEATURE:
<221> NAME/KEY: misc_feature
<222> LOCATION: (1)...(660)
<223> OTHER INFORMATION: Beta-1-5

<400> SEQUENCE: 58

```
atggtccaga agaccagcat gtcccggggc ccttacccac cctcccagga gatccccatg     60

gaggtcttcg accccagccc gcagggcaaa tacagcaaga ggaaagggcg attcaaacgg    120
```

-continued

```
tcagatggga gcacgtcctc ggataccaca tccaacagct ttgtccgcca gggctcagcg     180

gagtcctaca ccagccgtcc atcagactct gatgtatctc tggaggagga ccgggaagcc     240

ttaaggaagg aagcagagcg ccaggcatta gcgcagctcg agaaggccaa gaccaagcca     300

gtggcatttg ctgtgcggac aaatgttggc tacaatccgt ctccagggga tgaggtgcct     360

gtgcagggag tggccatcac cttcgagccc aaagacttcc tgcacatcaa ggagaaatac     420

aataatgact ggtggatcgg gcggctggtg aaggagggct gtgaggttgg cttcattccc     480

agccccgtca aactggacag ccttcgcctg ctgcaggaac agaagctgcg ccagaaccgc     540

ctcggctcca gcaaatcagg cgataactcc agttccagtc tgggagatgt ggtgactggc     600

acccgccgcc ccacaccccc tgccagtggt tacagacatg atgcagaaag ctttatttga     660

cttcttgaag catcggtttg atggcaggat ctccatcact cgtgtgacgg cagatatttc     720

cctggctaag cgctcagttc tcaacaaccc cagcaaacac atcatcattg agcgctccaa     780

cacacgctcc agcctggctg aggtgcagag tgaaatcgag cgaatcttcg agctggcccg     840

gacccttcag ttggtcgctc tggatgctga caccatcaat cacccagccc agctgtccaa     900

gacctcgctg gcccccatca ttgtttacat caagatcacc tctcccaagg tacttcaaag     960

gctcatcaag tcccgaggaa agtctcagtc caaacacctc aatgtccaaa tagcggcctc    1020

ggaaaagctg gcacagtgcc cccctgaaat gtttgacatc atcctggatg agaaccaatt    1080

ggaggatgcc tgcgagcatc tggcggagta cttggaagcc tattggaagg ccacacaccc    1140

gcccagcagc acgccaccca atccgctgct gaaccgcacc atggctaccg cagccctggc    1200

tgccagccct gcccctgtct ccaacctcca ggtacaggtg ctcacctcgc tcaggagaaa    1260

cctcggcttc tggggcgggc tggagtcctc acagcggggc agtgtggtgc cccaggagca    1320

ggaacatgcc atgtagtggg cgccctgccc gtcttccctc ctgctctggg gtcggaactg    1380

gagtgcaggg aac                                                       1393


<210> SEQ ID NO 59
<211> LENGTH: 219
<212> TYPE: PRT
<213> ORGANISM: Human

<400> SEQUENCE: 59

Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
            20                  25                  30

Lys Arg Lys Gly Arg Phe Lys Arg Ser Asp Gly Ser Thr Ser Ser Asp
        35                  40                  45

Thr Thr Ser Asn Ser Phe Val Arg Gln Gly Ser Ala Glu Ser Tyr Thr
    50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
    130                 135                 140
```

-continued

```
Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Gly Tyr Arg His Asp Ala Glu Ser Phe Ile
    210                 215

<210> SEQ ID NO 60
<211> LENGTH: 6725
<212> TYPE: DNA
<213> ORGANISM: Human
<220> FEATURE:
<221> NAME/KEY: misc_feature
<222> LOCATION: (226)...(6642)
<223> OTHER INFORMATION: Alpha-1C-2

<400> SEQUENCE: 60

ctcgaggagg cagtagtgga aaggagcagt ttttggggtt tgatgccata atgggaatca      60

ggtaatcgtc ggcggggaag aagaaacgct gcagaccacg gcttcctcga atcttgcgcg     120

aaagccgccg gcctcggagg agggattaat ccagacccgc cggggggtgt tttcacattt     180

cttcctcttc gtggctgctc ctcctattaa aaccattttt ggtccatggt caatgagaat     240

acgaggatgt acattccaga ggaaaaccac caaggttcca actatgggag cccacgcccc     300

gcccatgcca acatgaatgc caatgcggca gcggggctgg cccctgagca catccccacc     360

ccgggggctg ccctgtcgtg gcaggcggcc atcgacgcag cccggcaggc taagctgatg     420

ggcagcgctg gcaatgcgac catctccaca gtcagctcca cgcagcggaa gcggcagcaa     480

tatgggaaac ccaagaagca gggcagcacc acggccacac gcccgccccg agccctgctc     540

tgcctgaccc tgaagaaccc catccggagg gcctgcatca gcattgtcga atggaaacca     600

tttgaaataa ttattttact gactattttt gccaattgtg tggccttagc gatctatatt     660

ccctttccag aagatgattc caacgccacc aattccaacc tggaacgagt ggaatatctc     720

tttctcataa tttttacggt ggaagcgttt ttaaaagtaa tcgcctatgg actcctcttt     780

caccccaatg cctacctccg caacggctgg aacctactag attttataat tgtggttgtg     840

gggcttttta gtgcaatttt agaacaagca accaaagcag atggggcaaa cgctctcgga     900

gggaaagggg ccggatttga tgtgaaggcg ctgagggcct tccgcgtgct gcgccccctg     960

cggctggtgt ccggagtccc aagtctccag gtggtcctga attccatcat caaggccatg    1020

gtcccccctgc tgcacatcgc cctgcttgtg ctgtttgtca tcatcatcta cgccatcatc    1080

ggcttggagc tcttcatggg gaagatgcac aagacctgct acaaccagga gggcatagca    1140

gatgttccag cagaagatga cccttcccct tgtgcgctgg aaacgggcca cgggcggcag    1200

tgccagaacg gcacggtgtg caagcccggc tgggatggtc ccaagcacgg catcaccaac    1260

tttgacaact ttgccttcgc catgctcacg gtgttccagt gcatcaccat ggagggctgg    1320

acggacgtgc tgtactgggt caatgatgcc gtaggaaggg actggccctg gatctatttt    1380

gttacactaa tcatcatagg gtcatttttt gtacttaact tggttctcgg tgtgcttagc    1440

ggagagtttt ccaaagagag ggagaaggcc aaggcccggg gagatttcca gaagctgcgg    1500

gagaagcagc agctagaaga ggatctcaaa ggctacctgg attggatcac tcaggccgaa    1560
```

-continued

```
gacatcgatc ctgagaatga ggacgaaggc atggatgagg agaagccccg aaacatgagc   1620
atgcccacca gtgagaccga gtccgtcaac accgaaaacg tggctggagg tgacatcgag   1680
ggagaaaact gcggggccag gctggcccac cggatctcca agtcaaagtt cagccgctac   1740
tggcgccggt ggaatcggtt ctgcagaagg aagtgccgcg ccgcagtcaa gtctaatgtc   1800
ttctactggc tggtgatttt cctggtgttc ctcaacacgc tcaccattgc ctctgagcac   1860
tacaaccagc ccaactggct cacagaagtc caagacacgg caaacaaggc cctgctggcc   1920
ctgttcacgg cagagatgct cctgaagatg tacagcctgg gcctgcaggc ctacttcgtg   1980
tccctcttca accgctttga ctgcttcgtc gtgtgtggcg gcatcctgga gaccatcctg   2040
gtggagacca agatcatgtc cccactgggc atctccgtgc tcagatgcgt ccggctgctg   2100
aggattttca agatcacgag gtactggaac tccttgagca acctggtggc atccttgctg   2160
aactctgtgc gctccatcgc ctccctgctc cttctcctct tcctcttcat catcatcttc   2220
tccctcctgg ggatgcagct ctttggagga aagttcaact ttgatgagat gcagacccgg   2280
aggagcacat tcgataactt cccccagtcc ctcctcactg tgtttcagat cctgaccggg   2340
gaggactgga attcggtgat gtatgatggg atcatggctt atggcggccc ctcttttcca   2400
gggatgttag tctgtattta cttcatcatc ctcttcatct gtggaaacta tatcctactg   2460
aatgtgttct tggccattgc tgtggacaac ctggctgatg ctgagagcct cacatctgcc   2520
caaaaggagg aggaagagga gaaggagaga aagaagctgg ccaggactgc cagcccagag   2580
aagaaacaag agttggtgga gaagccggca gtgggggaat ccaaggagga gaagattgag   2640
ctgaaatcca tcacggctga cggagagtct ccacccgcca ccaagatcaa catggatgac   2700
ctccagccca atgaaaatga ggataagagc ccctacccca acccagaaac tacaggagaa   2760
gaggatgagg aggagccaga gatgcctgtc ggccctcgcc cacgaccact ctctgagctt   2820
caccttaagg aaaaggcagt gcccatgcca gaagccagcg cgtttttcat cttcagctct   2880
aacaacaggt ttcgcctcca gtgccaccgc attgtcaatg acacgatctt caccaacctg   2940
atcctcttct tcattctgct cagcagcatt tccctggctg ctgaggaccc ggtccagcac   3000
acctccttca ggaaccatat tctgttttat tttgatattg tttttaccac cattttcacc   3060
attgaaattg ctctgaagat gactgcttat ggggctttct tgcacaaggg ttctttctgc   3120
cggaactact tcaacatcct ggacctgctg gtggtcagcg tgtccctcat ctcctttggc   3180
atccagtcca gtgcaatcaa tgtcgtgaag atcttgcgag tcctgcgagt actcaggccc   3240
ctgagggcca tcaacagggc caaggggcta aagcatgtgg ttcagtgtgt gtttgtcgcc   3300
atccggacca tcgggaacat cgtgattgtc accaccctgc tgcagttcat gtttgcctgc   3360
atcggggtcc agctcttcaa gggaaagctg tacacctgtt cagacagttc caagcagaca   3420
gaggcggaat gcaagggcaa ctacatcacg tacaaagacg gggaggttga ccaccccatc   3480
atccaacccc gcagctggga gaacagcaag tttgactttg acaatgttct ggcagccatg   3540
atggccctct tcaccgtctc caccttcgaa gggtggccag agctgctgta ccgctccatc   3600
gactcccaca cggaagacaa gggccccatc tacaactacc gtgtggagat ctccatcttc   3660
ttcatcatct acatcatcat catcgccttc ttcatgatga acatcttcgt gggcttcgtc   3720
atcgtcacct ttcaggagca gggggagcag gagtacaaga actgtgagct ggacaagaac   3780
cagcgacagt gcgtggaata cgccctcaag gcccggcccc tgcggaggta catcccccaag  3840
aaccagcacc agtacaaagt gtggtacgtg gtcaactcca cctacttcga gtacctgatg   3900
ttcgtcctca tcctgctcaa caccatctgc ctggccatgc agcactacgg ccagagctgc   3960
```

-continued

```
ctgttcaaaa tcgccatgaa catcctcaac atgctcttca ctggcctctt taccgtggag   4020
atgatcctga agctcattgc cttcaaaccc aagcactatt tctgtgatgc atggaataca   4080
tttgacgcct tgattgttgt gggtagcatt gttgatatag caatcaccga ggtaaaccca   4140
gctgaacata cccaatgctc tccctctatg aacgcagagg aaaactcccg catctccatc   4200
accttcttcc gcctgttccg ggtcatgcgt ctggtgaagc tgctgagccg tggggagggc   4260
atccggacgc tgctgtggac cttcatcaag tccttccagg ccctgcccta tgtggccctc   4320
ctgatcgtga tgctgttctt catctacgcg gtgatcggga tgcaggtgtt tgggaaaatt   4380
gccctgaatg ataccacaga gatcaaccgg aacaacaact ttcagacctt cccccaggcc   4440
gtgctgctcc tcttcaggtg tgccaccggg gaggcctggc aggacatcat gctggcctgc   4500
atgccaggca agaagtgtgc cccagagtcc gagcccagca acagcacgga gggtgaaaca   4560
ccctgtggta gcagctttgc tgtcttctac ttcatcagct tctacatgct ctgtgccttc   4620
ctgatcatca acctctttgt agctgtcatc atggacaact ttgactacct gacaagggac   4680
tggtccatcc ttggtcccca ccacctggat gagtttaaaa gaatctgggc agagtatgac   4740
cctgaagcca agggtcgtat caaacacctg gatgtggtga ccctcctccg gcggattcag   4800
ccgccactag gttttgggaa gctgtgccct caccgcgtgg cttgcaaacg cctggtctcc   4860
atgaacatgc ctctgaacag cgacgggaca gtcatgttca atgccaccct gtttgccctg   4920
gtcaggacgg ccctgaggat caaaacagaa gggaacctag aacaagccaa tgaggagctg   4980
cgggcgatca tcaagaagat ctggaagcgg accagcatga agctgctgga ccaggtggtg   5040
ccccctgcag gtgatgatga ggtcaccgtt ggcaagttct acgccacgtt cctgatccag   5100
gagtacttcc ggaagttcaa gaagcgcaaa gagcagggcc ttgtgggcaa gccctcccag   5160
aggaacgcgc tgtctctgca ggctggcttg cgcacactgc atgacatcgg gcctgagatc   5220
cgacgggcca tctctggaga tctcaccgct gaggaggagc tggacaaggc catgaaggag   5280
gctgtgtccg ctgcttctga agatgacatc ttcaggaggg ccggtggcct gttcggcaac   5340
cacgtcagct actaccaaag cgacggccgg agcgccttcc cccagacctt caccactcag   5400
cgcccgctgc acatcaacaa ggcgggcagc agccagggcg acactgagtc gccatcccac   5460
gagaagctgg tggactccac cttcaccccg agcagctact cgtccaccgg ctccaacgcc   5520
aacatcaaca acgccaacaa caccgccctg ggtcgcctcc ctcgccccgc cggctacccc   5580
agcacggtca gcactgtgga gggccacggg ccccccttgt cccctgccat ccgggtgcag   5640
gaggtggcgt ggaagctcag ctccaacagg tgccactccc gggagagcca ggcagccatg   5700
gcgggtcagg aggagacgtc tcaggatgag acctatgaag tgaagatgaa ccatgacacg   5760
gaggcctgca gtgagcccag cctgctctcc acagagatgc tctcctacca ggatgacgaa   5820
aatcggcaac tgacgctccc agaggaggac aagagggaca tccggcaatc tccgaagagg   5880
ggtttcctcc gctctgcctc actaggtcga agggcctcct tccacctgga atgtctgaag   5940
cgacagaagg accgaggggg agacatctct cagaagacag tcctgccctt gcatctggtt   6000
catcatcagg cattggcagt ggcaggcctg agccccctcc tccagagaag ccattcccct   6060
gcctcattcc ctaggccttt tgccacccca ccagccacac ctggcagccg aggctggccc   6120
ccacagcccg tccccaccct gcggcttgag gggtcgagt ccagtgagaa actcaacagc   6180
agcttcccat ccatccactg cggctcctgg gctgagacca cccccggtgg cgggggcagc   6240
agcgccgccc ggagagtccg gcccgtctcc ctcatggtgc ccagccaggc tggggcccca   6300
```

-continued

```
gggaggcagt tccacggcag tgccagcagc ctggtggaag cggtcttgat ttcagaagga   6360

ctggggcagt ttgctcaaga tcccaagttc atcgaggtca ccacccagga gctggccgac   6420

gcctgcgaca tgaccataga ggagatggag agcgcggccg acaacatcct cagcgggggc   6480

gccccacaga gccccaatgg cgccctctta ccctttgtga actgcaggga cgcggggcag   6540

gaccgagccg ggggcgaaga ggacgcgggc tgtgtgcgcg cgcggggtcg accgagtgag   6600

gaggagctcc aggacagcag ggtctacgtc agcagcctgt agtgggcgct gccagatgcg   6660

ggcttttttt tatttgtttc aatgttccta atgggttcgt ttcagaagtg cctcactgtt   6720

ctcgt                                                               6725
```

<210> SEQ ID NO 61
<211> LENGTH: 2138
<212> TYPE: PRT
<213> ORGANISM: Human

<400> SEQUENCE: 61

```
Met Val Asn Glu Asn Thr Arg Met Tyr Ile Pro Glu Glu Asn His Gln
 1               5                  10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
```

-continued

```
    290                 295                 300

Ala Asp Val Pro Ala Glu Asp Asp Pro Ser Pro Cys Ala Leu Glu Thr
305                 310                 315                 320

Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
        355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Met
    450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
            500                 505                 510

Cys Arg Arg Lys Cys Arg Ala Ala Val Lys Ser Asn Val Phe Tyr Trp
        515                 520                 525

Leu Val Ile Phe Leu Val Phe Leu Asn Thr Leu Thr Ile Ala Ser Glu
    530                 535                 540

His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
            580                 585                 590

Cys Phe Val Val Cys Gly Gly Ile Leu Glu Thr Ile Leu Val Glu Thr
        595                 600                 605

Lys Ile Met Ser Pro Leu Gly Ile Ser Val Leu Arg Cys Val Arg Leu
    610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
            660                 665                 670

Phe Gly Gly Lys Phe Asn Phe Asp Glu Met Gln Thr Arg Arg Ser Thr
        675                 680                 685

Phe Asp Asn Phe Pro Gln Ser Leu Leu Thr Val Phe Gln Ile Leu Thr
    690                 695                 700

Gly Glu Asp Trp Asn Ser Val Met Tyr Asp Gly Ile Met Ala Tyr Gly
705                 710                 715                 720
```

-continued

```
Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
            740                 745                 750

Val Asp Asn Leu Ala Asp Ala Glu Ser Leu Thr Ser Ala Gln Lys Glu
        755                 760                 765

Glu Glu Glu Glu Lys Glu Arg Lys Lys Leu Ala Arg Thr Ala Ser Pro
    770                 775                 780

Glu Lys Lys Gln Glu Leu Val Glu Lys Pro Ala Val Gly Glu Ser Lys
785                 790                 795                 800

Glu Glu Lys Ile Glu Leu Lys Ser Ile Thr Ala Asp Gly Glu Ser Pro
                805                 810                 815

Pro Ala Thr Lys Ile Asn Met Asp Asp Leu Gln Pro Asn Glu Asn Glu
            820                 825                 830

Asp Lys Ser Pro Tyr Pro Asn Pro Glu Thr Thr Gly Glu Glu Asp Glu
        835                 840                 845

Glu Glu Pro Glu Met Pro Val Gly Pro Arg Pro Arg Pro Leu Ser Glu
    850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
                885                 890                 895

Val Asn Asp Thr Ile Phe Thr Asn Leu Ile Leu Phe Phe Ile Leu Leu
            900                 905                 910

Ser Ser Ile Ser Leu Ala Ala Glu Asp Pro Val Gln His Thr Ser Phe
        915                 920                 925

Arg Asn His Ile Leu Phe Tyr Phe Asp Ile Val Phe Thr Thr Ile Phe
    930                 935                 940

Thr Ile Glu Ile Ala Leu Lys Met Thr Ala Tyr Gly Ala Phe Leu His
945                 950                 955                 960

Lys Gly Ser Phe Cys Arg Asn Tyr Phe Asn Ile Leu Asp Leu Leu Val
                965                 970                 975

Val Ser Val Ser Leu Ile Ser Phe Gly Ile Gln Ser Ser Ala Ile Asn
            980                 985                 990

Val Val Lys Ile Leu Arg Val Leu Arg Val Leu Arg Pro Leu Arg Ala
        995                 1000                1005

Ile Asn Arg Ala Lys Gly Leu Lys His Val Val Gln Cys Val Phe Val
    1010                1015                1020

Ala Ile Arg Thr Ile Gly Asn Ile Val Ile Val Thr Thr Leu Leu Gln
1025                1030                1035                1040

Phe Met Phe Ala Cys Ile Gly Val Gln Leu Phe Lys Gly Lys Leu Tyr
                1045                1050                1055

Thr Cys Ser Asp Ser Ser Lys Gln Thr Glu Ala Glu Cys Lys Gly Asn
            1060                1065                1070

Tyr Ile Thr Tyr Lys Asp Gly Glu Val Asp His Pro Ile Ile Gln Pro
        1075                1080                1085

Arg Ser Trp Glu Asn Ser Lys Phe Asp Phe Asp Asn Val Leu Ala Ala
    1090                1095                1100

Met Met Ala Leu Phe Thr Val Ser Thr Phe Glu Gly Trp Pro Glu Leu
1105                1110                1115                1120

Leu Tyr Arg Ser Ile Asp Ser His Thr Glu Asp Lys Gly Pro Ile Tyr
                1125                1130                1135
```

-continued

```
Asn Tyr Arg Val Glu Ile Ser Ile Phe Phe Ile Ile Tyr Ile Ile Ile
            1140                1145                1150

Ile Ala Phe Phe Met Met Asn Ile Phe Val Gly Phe Val Ile Val Thr
        1155                1160                1165

Phe Gln Glu Gln Gly Glu Gln Glu Tyr Lys Asn Cys Glu Leu Asp Lys
    1170                1175                1180

Asn Gln Arg Gln Cys Val Glu Tyr Ala Leu Lys Ala Arg Pro Leu Arg
1185                1190                1195                1200

Arg Tyr Ile Pro Lys Asn Gln His Gln Tyr Lys Val Trp Tyr Val Val
                1205                1210                1215

Asn Ser Thr Tyr Phe Glu Tyr Leu Met Phe Val Leu Ile Leu Leu Asn
            1220                1225                1230

Thr Ile Cys Leu Ala Met Gln His Tyr Gly Gln Ser Cys Leu Phe Lys
        1235                1240                1245

Ile Ala Met Asn Ile Leu Asn Met Leu Phe Thr Gly Leu Phe Thr Val
    1250                1255                1260

Glu Met Ile Leu Lys Leu Ile Ala Phe Lys Pro Lys His Tyr Phe Cys
1265                1270                1275                1280

Asp Ala Trp Asn Thr Phe Asp Ala Leu Ile Val Val Gly Ser Ile Val
                1285                1290                1295

Asp Ile Ala Ile Thr Glu Val Asn Pro Ala Glu His Thr Gln Cys Ser
            1300                1305                1310

Pro Ser Met Asn Ala Glu Glu Asn Ser Arg Ile Ser Ile Thr Phe Phe
        1315                1320                1325

Arg Leu Phe Arg Val Met Arg Leu Val Lys Leu Leu Ser Arg Gly Glu
    1330                1335                1340

Gly Ile Arg Thr Leu Leu Trp Thr Phe Ile Lys Ser Phe Gln Ala Leu
1345                1350                1355                1360

Pro Tyr Val Ala Leu Leu Ile Val Met Leu Phe Phe Ile Tyr Ala Val
                1365                1370                1375

Ile Gly Met Gln Val Phe Gly Lys Ile Ala Leu Asn Asp Thr Thr Glu
            1380                1385                1390

Ile Asn Arg Asn Asn Asn Phe Gln Thr Phe Pro Gln Ala Val Leu Leu
        1395                1400                1405

Leu Phe Arg Cys Ala Thr Gly Glu Ala Trp Gln Asp Ile Met Leu Ala
    1410                1415                1420

Cys Met Pro Gly Lys Lys Cys Ala Pro Glu Ser Glu Pro Ser Asn Ser
1425                1430                1435                1440

Thr Glu Gly Glu Thr Pro Cys Gly Ser Ser Phe Ala Val Phe Tyr Phe
                1445                1450                1455

Ile Ser Phe Tyr Met Leu Cys Ala Phe Leu Ile Ile Asn Leu Phe Val
            1460                1465                1470

Ala Val Ile Met Asp Asn Phe Asp Tyr Leu Thr Arg Asp Trp Ser Ile
        1475                1480                1485

Leu Gly Pro His His Leu Asp Glu Phe Lys Arg Ile Trp Ala Glu Tyr
    1490                1495                1500

Asp Pro Glu Ala Lys Gly Arg Ile Lys His Leu Asp Val Val Thr Leu
1505                1510                1515                1520

Leu Arg Arg Ile Gln Pro Pro Leu Gly Phe Gly Lys Leu Cys Pro His
                1525                1530                1535

Arg Val Ala Cys Lys Arg Leu Val Ser Met Asn Met Pro Leu Asn Ser
            1540                1545                1550

Asp Gly Thr Val Met Phe Asn Ala Thr Leu Phe Ala Leu Val Arg Thr
```

-continued

```
        1555                1560                1565

Ala Leu Arg Ile Lys Thr Glu Gly Asn Leu Glu Gln Ala Asn Glu Glu
    1570                1575                1580

Leu Arg Ala Ile Ile Lys Lys Ile Trp Lys Arg Thr Ser Met Lys Leu
1585                1590                1595                1600

Leu Asp Gln Val Val Pro Pro Ala Gly Asp Asp Glu Val Thr Val Gly
                1605                1610                1615

Lys Phe Tyr Ala Thr Phe Leu Ile Gln Glu Tyr Phe Arg Lys Phe Lys
            1620                1625                1630

Lys Arg Lys Glu Gln Gly Leu Val Gly Lys Pro Ser Gln Arg Asn Ala
        1635                1640                1645

Leu Ser Leu Gln Ala Gly Leu Arg Thr Leu His Asp Ile Gly Pro Glu
    1650                1655                1660

Ile Arg Arg Ala Ile Ser Gly Asp Leu Thr Ala Glu Glu Glu Leu Asp
1665                1670                1675                1680

Lys Ala Met Lys Glu Ala Val Ser Ala Ala Ser Glu Asp Asp Ile Phe
                1685                1690                1695

Arg Arg Ala Gly Gly Leu Phe Gly Asn His Val Ser Tyr Tyr Gln Ser
            1700                1705                1710

Asp Gly Arg Ser Ala Phe Pro Gln Thr Phe Thr Thr Gln Arg Pro Leu
        1715                1720                1725

His Ile Asn Lys Ala Gly Ser Ser Gln Gly Asp Thr Glu Ser Pro Ser
    1730                1735                1740

His Glu Lys Leu Val Asp Ser Thr Phe Thr Pro Ser Ser Tyr Ser Ser
1745                1750                1755                1760

Thr Gly Ser Asn Ala Asn Ile Asn Asn Ala Asn Asn Thr Ala Leu Gly
                1765                1770                1775

Arg Leu Pro Arg Pro Ala Gly Tyr Pro Ser Thr Val Ser Thr Val Glu
            1780                1785                1790

Gly His Gly Pro Pro Leu Ser Pro Ala Ile Arg Val Gln Glu Val Ala
        1795                1800                1805

Trp Lys Leu Ser Ser Asn Arg Cys His Ser Arg Glu Ser Gln Ala Ala
    1810                1815                1820

Met Ala Gly Gln Glu Glu Thr Ser Gln Asp Glu Thr Tyr Glu Val Lys
1825                1830                1835                1840

Met Asn His Asp Thr Glu Ala Cys Ser Glu Pro Ser Leu Leu Ser Thr
                1845                1850                1855

Glu Met Leu Ser Tyr Gln Asp Asp Glu Asn Arg Gln Leu Thr Leu Pro
            1860                1865                1870

Glu Glu Asp Lys Arg Asp Ile Arg Gln Ser Pro Lys Arg Gly Phe Leu
        1875                1880                1885

Arg Ser Ala Ser Leu Gly Arg Arg Ala Ser Phe His Leu Glu Cys Leu
    1890                1895                1900

Lys Arg Gln Lys Asp Arg Gly Gly Asp Ile Ser Gln Lys Thr Val Leu
1905                1910                1915                1920

Pro Leu His Leu Val His His Gln Ala Leu Ala Val Ala Gly Leu Ser
                1925                1930                1935

Pro Leu Leu Gln Arg Ser His Ser Pro Ala Ser Phe Pro Arg Pro Phe
            1940                1945                1950

Ala Thr Pro Pro Ala Thr Pro Gly Ser Arg Gly Trp Pro Pro Gln Pro
        1955                1960                1965

Val Pro Thr Leu Arg Leu Glu Gly Val Glu Ser Ser Glu Lys Leu Asn
    1970                1975                1980
```

-continued

Ser Ser Phe Pro Ser Ile His Cys Gly Ser Trp Ala Glu Thr Thr Pro
1985 1990 1995 2000

Gly Gly Gly Gly Ser Ser Ala Ala Arg Arg Val Arg Pro Val Ser Leu
2005 2010 2015

Met Val Pro Ser Gln Ala Gly Ala Pro Gly Arg Gln Phe His Gly Ser
2020 2025 2030

Ala Ser Ser Leu Val Glu Ala Val Leu Ile Ser Glu Gly Leu Gly Gln
2035 2040 2045

Phe Ala Gln Asp Pro Lys Phe Ile Glu Val Thr Thr Gln Glu Leu Ala
2050 2055 2060

Asp Ala Cys Asp Met Thr Ile Glu Glu Met Glu Ser Ala Ala Asp Asn
2065 2070 2075 2080

Ile Leu Ser Gly Gly Ala Pro Gln Ser Pro Asn Gly Ala Leu Leu Pro
2085 2090 2095

Phe Val Asn Cys Arg Asp Ala Gly Gln Asp Arg Ala Gly Gly Glu Glu
2100 2105 2110

Asp Ala Gly Cys Val Arg Ala Arg Gly Arg Pro Ser Glu Glu Glu Leu
2115 2120 2125

Gln Asp Ser Arg Val Tyr Val Ser Ser Leu
2130 2135

<210> SEQ ID NO 62
<211> LENGTH: 2970
<212> TYPE: DNA
<213> ORGANISM: Human
<220> FEATURE:
<221> NAME/KEY: misc_feature
<222> LOCATION: (502)...(2316)
<223> OTHER INFORMATION: Beta-2C

<400> SEQUENCE: 62
cagcagcgtg ctaagaagca gtcacataaa cagcagcagg agtaggcctc ctgcttttca 60
aaagcagagt actgcagggt cgcgaaatgc aagacactca gatgtttgaa aatctcccga 120
gttgagaatg gctactgtaa aagcgtcacc aagaaactct gacgatctgg acagtcctaa 180
ctctgtgtta gcaatactta cttccggaaa attaatgcta cttcttgtag atttttgcaa 240
ataggaaacc cccttgaaga agatctcaaa ttacgccccc cacccccaaa aaaagacaaa 300
caggggagaa caaagttttg gcatgcctgc aggaacggtg gctttttttag aaactaccta 360 ggaggcagaa gctaagtgat ttgctcatgc ctcttacctg ggagtagaag gtgggaagaa 420
atggaccgag gctgtgacga gaagacaagg cacagtgcag cttggtgaag ccacacgctg 480
actgcgttct gccccctctt catgcagtgc tgcgggctgg tgcatcgccg gcgagtacgg 540
gtgtcctatg gttcggcaga ctcctacact agccgtccat ccgattccga tgtatctctg 600
gaggaggacc gggaggcagt gcgcagagaa gcggagcggc aggcccaggc acagttggaa 660
aaagcaaaga caaagcccgt tgcatttgcg gttcggacaa atgtcagcta cagtgcggcc 720
catgaagatg atgttccagt gcctggcatg gccatctcat tcgaagcaaa agattttctg 780
catgttaagg aaaaatttaa caatgactgg tggataggggc gattggtaaa agaaggctgt 840
gaaatcggat tcattccaag cccagtcaaa ctagaaaaca tgaggctgca gcatgaacag 900
agagccaagc aagggaaatt ctactccagt aaatcaggag gaaattcatc atccagtttg 960
ggtgacatag tacctagttc cagaaaatca acacctccat catctgctat agacatagat 1020
gctactggct tagatgcaga agaaaatgat attccagcaa accaccgctc ccctaaaccc 1080

-continued

```
agtgcaaaca gtgtaacgtc accccactcc aaagagaaaa gaatgccctt ctttaagaag   1140

acagagcaca ctcctccgta tgatgtggta ccttccatgc gaccagtggt cctagtgggc   1200

ccttctctga agggctacga ggtcacagat atgatgcaaa aagcgctgtt tgattttta   1260

aaacacagat ttgaagggcg gatatccatc acaagggtca ccgctgacat ctcgcttgcc   1320

aaacgctcgg tattaaacaa tcccagtaag cacgcaataa tagaaagatc caacacaagg   1380

tcaagcttag cggaagttca gagtgaaatc gaaaggattt ttgaacttgc aagaacattg   1440

cagttggtgg tccttgacgc ggatacaatt aatcatccag ctcaactcag taaaacctcc   1500

ttggccccta ttatagtata tgtaaagatt tcttctccta aggttttaca aaggttaata   1560

aaatctcgag ggaaatctca agctaaacac ctcaacgtcc agatggtagc agctgataaa   1620

ctggctcagt gtcctccaga gctgttcgat gtgatcttgg atgagaacca gcttgaggat   1680

gcctgtgagc accttgccga ctatctggag gcctactgga aggccaccca tcctcccagc   1740

agtagcctcc ccaaccctct ccttagccgt acattagcca cttcaagtct gcctcttagc   1800

cccaccctag cctctaattc acagggttct caaggtgatc agaggactga tcgctccgct   1860

cctatccgtt ctgcttccca agctgaagaa gaacctagtg tggaaccagt caagaaatcc   1920

cagcaccgct cttcctcctc agccccacac cacaaccatc gcagtgggac aagtcgcggc   1980

ctctccaggc aagagacatt tgactcggaa acccaggaga gtcgagactc tgcctacgta   2040

gagccaaagg aagattattc ccatgaccac gtggaccact atgcctcaca ccgtgaccac   2100

aaccacagag acgagaccca cgggagcagt gaccacagac acagggagtc ccggcaccgt   2160

tcccgggacg tggatcgaga gcaggaccac aacgagtgca acaagcagcg cagccgtcat   2220

aaatccaagg atcgctactg tgaaaaggat ggagaagtga tatcaaaaaa acggaatgag   2280

gctggggagt ggaacaggga tgtttacatc ccccaatgag ttttgccctt ttgtgttttt   2340

ttttttttt ttttgaagtc ttgtataact aacagcatcc ccaaaacaaa aagtctttgg   2400

ggtctacact gcaatcatat gtgatctgtc ttgtaatatt ttgtattatt gctgttgctt   2460

gaatagcaat agcatggata gagtattgag atactttttc ttttgtaagt gctacataaa   2520

ttggcctggt atggctgcag tcctccggtt gcatactgga ctcttcaaaa actgttttgg   2580

gtagctgcca cttgaacaaa atctgttgcc acccaggtga tgttagtgtt ttaagaaatg   2640

tagttgatgt atccaacaag ccagaatcag cacagataaa aagtggaatt tcttgtttct   2700

ccagattttt aatacgttaa tacgcaggca tctgatttgc atattcattc atggaccact   2760

gtttcttgct tgtacctctg gctgactaaa tttggggaca gattcagtct tgccttacac   2820

aaaggggatc ataaagttag aatctatttt ctatgtacta gtactgtgta ctgtatagac   2880

agtttgtaaa tgttatttct gcaaacaaac acctccttat tatatataat atatatatat   2940

atatcagttt gatcacacta ttttagagtc                                    2970
```

<210> SEQ ID NO 63
<211> LENGTH: 605
<212> TYPE: PRT
<213> ORGANISM: Human

<400> SEQUENCE: 63

```
Met Gln Cys Cys Gly Leu Val His Arg Arg Arg Val Arg Val Ser Tyr
 1               5                  10                  15

Gly Ser Ala Asp Ser Tyr Thr Ser Arg Pro Ser Asp Ser Asp Val Ser
            20                  25                  30

Leu Glu Glu Asp Arg Glu Ala Val Arg Arg Glu Ala Glu Arg Gln Ala
```

-continued

```
        35                  40                  45

Gln Ala Gln Leu Glu Lys Ala Lys Thr Lys Pro Val Ala Phe Ala Val
    50                  55                  60

Arg Thr Asn Val Ser Tyr Ser Ala Ala His Glu Asp Asp Val Pro Val
65                  70                  75                  80

Pro Gly Met Ala Ile Ser Phe Glu Ala Lys Asp Phe Leu His Val Lys
                85                  90                  95

Glu Lys Phe Asn Asn Asp Trp Trp Ile Gly Arg Leu Val Lys Glu Gly
            100                 105                 110

Cys Glu Ile Gly Phe Ile Pro Ser Pro Val Lys Leu Glu Asn Met Arg
        115                 120                 125

Leu Gln His Glu Gln Arg Ala Lys Gln Gly Lys Phe Tyr Ser Ser Lys
    130                 135                 140

Ser Gly Gly Asn Ser Ser Ser Ser Leu Gly Asp Ile Val Pro Ser Ser
145                 150                 155                 160

Arg Lys Ser Thr Pro Pro Ser Ser Ala Ile Asp Ile Asp Ala Thr Gly
                165                 170                 175

Leu Asp Ala Glu Glu Asn Asp Ile Pro Ala Asn His Arg Ser Pro Lys
            180                 185                 190

Pro Ser Ala Asn Ser Val Thr Ser Pro His Ser Lys Glu Lys Arg Met
        195                 200                 205

Pro Phe Phe Lys Lys Thr Glu His Thr Pro Pro Tyr Asp Val Val Pro
    210                 215                 220

Ser Met Arg Pro Val Val Leu Val Gly Pro Ser Leu Lys Gly Tyr Glu
225                 230                 235                 240

Val Thr Asp Met Met Gln Lys Ala Leu Phe Asp Phe Leu Lys His Arg
                245                 250                 255

Phe Glu Gly Arg Ile Ser Ile Thr Arg Val Thr Ala Asp Ile Ser Leu
            260                 265                 270

Ala Lys Arg Ser Val Leu Asn Asn Pro Ser Lys His Ala Ile Ile Glu
        275                 280                 285

Arg Ser Asn Thr Arg Ser Ser Leu Ala Glu Val Gln Ser Glu Ile Glu
    290                 295                 300

Arg Ile Phe Glu Leu Ala Arg Thr Leu Gln Leu Val Val Leu Asp Ala
305                 310                 315                 320

Asp Thr Ile Asn His Pro Ala Gln Leu Ser Lys Thr Ser Leu Ala Pro
                325                 330                 335

Ile Ile Val Tyr Val Lys Ile Ser Ser Pro Lys Val Leu Gln Arg Leu
            340                 345                 350

Ile Lys Ser Arg Gly Lys Ser Gln Ala Lys His Leu Asn Val Gln Met
        355                 360                 365

Val Ala Ala Asp Lys Leu Ala Gln Cys Pro Pro Glu Leu Phe Asp Val
    370                 375                 380

Ile Leu Asp Glu Asn Gln Leu Glu Asp Ala Cys Glu His Leu Ala Asp
385                 390                 395                 400

Tyr Leu Glu Ala Tyr Trp Lys Ala Thr His Pro Pro Ser Ser Ser Leu
                405                 410                 415

Pro Asn Pro Leu Leu Ser Arg Thr Leu Ala Thr Ser Ser Leu Pro Leu
            420                 425                 430

Ser Pro Thr Leu Ala Ser Asn Ser Gln Gly Ser Gln Gly Asp Gln Arg
        435                 440                 445

Thr Asp Arg Ser Ala Pro Ile Arg Ser Ala Ser Gln Ala Glu Glu Glu
    450                 455                 460
```

-continued

```
Pro Ser Val Glu Pro Val Lys Lys Ser Gln His Arg Ser Ser Ser Ser
465                 470                 475                 480

Ala Pro His His Asn His Arg Ser Gly Thr Ser Arg Gly Leu Ser Arg
                485                 490                 495

Gln Glu Thr Phe Asp Ser Glu Thr Gln Glu Ser Arg Asp Ser Ala Tyr
            500                 505                 510

Val Glu Pro Lys Glu Asp Tyr Ser His Asp His Val Asp His Tyr Ala
        515                 520                 525

Ser His Arg Asp His Asn His Arg Asp Glu Thr His Gly Ser Ser Asp
    530                 535                 540

His Arg His Arg Glu Ser Arg His Arg Ser Arg Asp Val Asp Arg Glu
545                 550                 555                 560

Gln Asp His Asn Glu Cys Asn Lys Gln Arg Ser Arg His Lys Ser Lys
                565                 570                 575

Asp Arg Tyr Cys Glu Lys Asp Gly Glu Val Ile Ser Lys Lys Arg Asn
            580                 585                 590

Glu Ala Gly Glu Trp Asn Arg Asp Val Tyr Ile Pro Gln
        595                 600                 605


<210> SEQ ID NO 64
<211> LENGTH: 2712
<212> TYPE: DNA
<213> ORGANISM: Human
<220> FEATURE:
<221> NAME/KEY: misc_feature
<222> LOCATION: (23)...(2061)
<223> OTHER INFORMATION: Beta-2E

<400> SEQUENCE: 64

agtgtgtgtt ttcagcccct cctggaatgg gaaaataaga atctccctgg atgggagtcc     60

tctggggcag ggagtgaaag ccccggaggc agaaagggac ggagaacagg ggcttgccca    120

gagcatggat aggaaaggag ctggggttct ccggggctca gcgcgcactg agaacctgtg    180

cccggggctg cagctgcgga cgataaaggc gctgtctggc tcatgaaggc cacctggatc    240

aggcttctga aaagagccaa gggaggaagg ctgaagaatt ctgatatctg tggttcggca    300

gactcctaca ctagccgtcc atccgattcc gatgtatctc tggaggagga ccgggaggca    360

gtgcgcagag aagcggagcg gcaggcccag gcacagttgg aaaaagcaaa gacaaagccc    420

gttgcatttg cggttcggac aaatgtcagc tacagtgcgg cccatgaaga tgatgttcca    480

gtgcctggca tggccatctc attcgaagca aaagattttc tgcatgttaa ggaaaaattt    540

aacaatgact ggtggatagg gcgattggta aaagaaggct gtgaaatcgg attcattcca    600

agcccagtca aactagaaaa catgaggctg cagcatgaac agagagccaa gcaagggaaa    660

ttctactcca gtaaatcagg aggaaattca tcatccagtt tgggtgacat agtacctagt    720

tccagaaaat caacacctcc atcatctgct atagacatag atgctactgg cttagatgca    780

gaagaaaatg atattccagc aaaccaccgc tcccctaaac ccagtgcaaa cagtgtaacg    840

tcaccccact ccaaagagaa aagaatgccc ttctttaaga agacagagca cactcctccg    900

tatgatgtgg taccttccat gcgaccagtg gtcctagtgg gcccttctct gaagggctac    960

gaggtcacag atatgatgca aaaagcgctg tttgattttt taaaacacag atttgaaggg   1020

cggatatcca tcacaagggt caccgctgac atctcgcttg ccaaacgctc ggtattaaac   1080

aatcccagta agcacgcaat aatagaaaga tccaacacaa ggtcaagctt agcggaagtt   1140

cagagtgaaa tcgaaaggat tttgaactt gcaagaacat tgcagttggt ggtccttgac    1200
```

```
gcggatacaa ttaatcatcc agctcaactc agtaaaacct ccttggcccc tattatagta   1260

tatgtaaaga tttcttctcc taaggtttta caaaggttaa taaaatctcg agggaaatct   1320

caagctaaac acctcaacgt ccagatggta gcagctgata aactggctca gtgtcctcca   1380

gagctgttcg atgtgatctt ggatgagaac cagcttgagg atgcctgtga gcaccttgcc   1440

gactatctgg aggcctactg gaaggccacc catcctccca gcagtagcct ccccaaccct   1500

ctccttagcc gtacattagc cacttcaagt ctgcctctta gccccaccct agcctctaat   1560

tcacagggtt ctcaaggtga tcagaggact gatcgctccg ctcctatccg ttctgcttcc   1620

caagctgaag aagaacctag tgtggaacca gtcaagaaat cccagcaccg ctcttcctcc   1680

tcagccccac accacaacca tcgcagtggg acaagtcgcg gcctctccag gcaagagaca   1740

tttgactcgg aaacccagga gagtcgagac tctgcctacg tagagccaaa ggaagattat   1800

tcccatgacc acgtggacca ctatgcctca caccgtgacc acaaccacag agacgagacc   1860

cacgggagca gtgaccacag acacagggag tcccggcacc gttcccggga cgtggatcga   1920

gagcaggacc acaacgagtg caacaagcag cgcagccgtc ataaatccaa ggatcgctac   1980

tgtgaaaagg atggagaagt gatatcaaaa aaacggaatg aggctgggga gtggaacagg   2040

gatgtttaca tcccccaatg agttttgccc ttttgtgttt tttttttttt ttttttgaag   2100

tcttgtataa ctaacagcat ccccaaaaca aaaagtcttt ggggtctaca ctgcaatcat   2160

atgtgatctg tcttgtaata ttttgtatta ttgctgttgc ttgaatagca atagcatgga   2220

tagagtattg agatactttt tcttttgtaa gtgctacata aattggcctg gtatggctgc   2280

agtcctccgg ttgcatactg gactcttcaa aaactgtttt gggtagctgc cacttgaaca   2340

aaatctgttg ccacccaggt gatgttagtg ttttaagaaa tgtagttgat gtatccaaca   2400

agccagaatc agcacagata aaaagtggaa tttcttgttt ctccagattt ttaatacgtt   2460

aatacgcagg catctgattt gcatattcat tcatggacca ctgtttcttg cttgtacctc   2520

tggctgacta aatttgggga cagattcagt cttgccttac acaaagggga tcataaagtt   2580

agaatctatt ttctatgtac tagtactgtg tactgtatag acagtttgta aatgttattt   2640

ctgcaaacaa acacctcctt attatatata atatatatat atatatcagt ttgatcacac   2700

tattttagag tc                                                       2712

<210> SEQ ID NO 65
<211> LENGTH: 612
<212> TYPE: PRT
<213> ORGANISM: Human

<400> SEQUENCE: 65

Met Lys Ala Thr Trp Ile Arg Leu Leu Lys Arg Ala Lys Gly Gly Arg
 1               5                  10                  15

Leu Lys Asn Ser Asp Ile Cys Gly Ser Ala Asp Ser Tyr Thr Ser Arg
            20                  25                  30

Pro Ser Asp Ser Asp Val Ser Leu Glu Glu Asp Arg Glu Ala Val Arg
        35                  40                  45

Arg Glu Ala Glu Arg Gln Ala Gln Ala Gln Leu Glu Lys Ala Lys Thr
    50                  55                  60

Lys Pro Val Ala Phe Ala Val Arg Thr Asn Val Ser Tyr Ser Ala Ala
65                  70                  75                  80

His Glu Asp Asp Val Pro Val Pro Gly Met Ala Ile Ser Phe Glu Ala
                85                  90                  95
```

-continued

```
Lys Asp Phe Leu His Val Lys Glu Lys Phe Asn Asn Asp Trp Trp Ile
            100                 105                 110

Gly Arg Leu Val Lys Glu Gly Cys Glu Ile Gly Phe Ile Pro Ser Pro
        115                 120                 125

Val Lys Leu Glu Asn Met Arg Leu Gln His Glu Gln Arg Ala Lys Gln
    130                 135                 140

Gly Lys Phe Tyr Ser Ser Lys Ser Gly Gly Asn Ser Ser Ser Ser Leu
145                 150                 155                 160

Gly Asp Ile Val Pro Ser Ser Arg Lys Ser Thr Pro Pro Ser Ser Ala
                165                 170                 175

Ile Asp Ile Asp Ala Thr Gly Leu Asp Ala Glu Glu Asn Asp Ile Pro
            180                 185                 190

Ala Asn His Arg Ser Pro Lys Pro Ser Ala Asn Ser Val Thr Ser Pro
        195                 200                 205

His Ser Lys Glu Lys Arg Met Pro Phe Phe Lys Lys Thr Glu His Thr
    210                 215                 220

Pro Pro Tyr Asp Val Val Pro Ser Met Arg Pro Val Val Leu Val Gly
225                 230                 235                 240

Pro Ser Leu Lys Gly Tyr Glu Val Thr Asp Met Met Gln Lys Ala Leu
                245                 250                 255

Phe Asp Phe Leu Lys His Arg Phe Glu Gly Arg Ile Ser Ile Thr Arg
            260                 265                 270

Val Thr Ala Asp Ile Ser Leu Ala Lys Arg Ser Val Leu Asn Asn Pro
        275                 280                 285

Ser Lys His Ala Ile Ile Glu Arg Ser Asn Thr Arg Ser Ser Leu Ala
    290                 295                 300

Glu Val Gln Ser Glu Ile Glu Arg Ile Phe Glu Leu Ala Arg Thr Leu
305                 310                 315                 320

Gln Leu Val Val Leu Asp Ala Asp Thr Ile Asn His Pro Ala Gln Leu
                325                 330                 335

Ser Lys Thr Ser Leu Ala Pro Ile Ile Val Tyr Val Lys Ile Ser Ser
            340                 345                 350

Pro Lys Val Leu Gln Arg Leu Ile Lys Ser Arg Gly Lys Ser Gln Ala
        355                 360                 365

Lys His Leu Asn Val Gln Met Val Ala Ala Asp Lys Leu Ala Gln Cys
    370                 375                 380

Pro Pro Glu Leu Phe Asp Val Ile Leu Asp Glu Asn Gln Leu Glu Asp
385                 390                 395                 400

Ala Cys Glu His Leu Ala Asp Tyr Leu Glu Ala Tyr Trp Lys Ala Thr
                405                 410                 415

His Pro Pro Ser Ser Ser Leu Pro Asn Pro Leu Leu Ser Arg Thr Leu
            420                 425                 430

Ala Thr Ser Ser Leu Pro Leu Ser Pro Thr Leu Ala Ser Asn Ser Gln
        435                 440                 445

Gly Ser Gln Gly Asp Gln Arg Thr Asp Arg Ser Ala Pro Ile Arg Ser
    450                 455                 460

Ala Ser Gln Ala Glu Glu Glu Pro Ser Val Glu Pro Val Lys Lys Ser
465                 470                 475                 480

Gln His Arg Ser Ser Ser Ser Ala Pro His His Asn His Arg Ser Gly
                485                 490                 495

Thr Ser Arg Gly Leu Ser Arg Gln Glu Thr Phe Asp Ser Glu Thr Gln
            500                 505                 510

Glu Ser Arg Asp Ser Ala Tyr Val Glu Pro Lys Glu Asp Tyr Ser His
```

-continued

```
        515                 520                 525

Asp His Val Asp His Tyr Ala Ser His Arg Asp His Asn His Arg Asp
    530                 535                 540

Glu Thr His Gly Ser Ser Asp His Arg His Arg Glu Ser Arg His Arg
545                 550                 555                 560

Ser Arg Asp Val Asp Arg Glu Gln Asp His Asn Glu Cys Asn Lys Gln
                565                 570                 575

Arg Ser Arg His Lys Ser Lys Asp Arg Tyr Cys Glu Lys Asp Gly Glu
            580                 585                 590

Val Ile Ser Lys Lys Arg Asn Glu Ala Gly Glu Trp Asn Arg Asp Val
        595                 600                 605

Tyr Ile Pro Gln
    610
```